United States Patent
Caldwell et al.

(10) Patent No.: US 6,498,161 B1
(45) Date of Patent: Dec. 24, 2002

(54) PYRROLIDINE MODULATORS OF CHEMOKINE RECEPTOR ACTIVITY

(75) Inventors: Charles G. Caldwell, Scotch Plains, NJ (US); Kevin T. Chapman, Scotch Plains, NJ (US); Jeffrey Hale, Westfield, NJ (US); Dooseop Kim, Westfield, NJ (US); Christopher Lynch, Scotch Plains, NJ (US); Malcolm MacCoss, Freehold, NJ (US); Sander G. Mills, Scotch Plains, NJ (US); Christopher Willoughby, Clark, NJ (US); Scott Berk, Maplewood, NJ (US); Ronald M. Kim, Hoboken, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/543,019

(22) Filed: Apr. 4, 2000

Related U.S. Application Data

(60) Provisional application No. 60/128,172, filed on Apr. 6, 1999.

(51) Int. Cl.[7] .................... A61K 31/165; C07D 207/04; C07D 207/12; C07D 211/04; C07D 211/06

(52) U.S. Cl. ............... 514/252.03; 514/89; 514/255.05; 514/316; 514/318; 514/321; 514/326; 544/238; 544/332; 544/336; 544/337; 546/22; 546/24; 546/187; 546/194; 546/198; 546/208; 546/209; 546/210

(58) Field of Search .................... 546/187, 194, 546/198, 208, 209, 210; 544/238, 332, 336, 337; 514/252.03, 255.05, 316, 318, 321, 326

(56) References Cited

U.S. PATENT DOCUMENTS

| | | | |
|---|---|---|---|
| 5,468,469 A | 11/1995 | Aszalos et al. | 514/150 |
| 5,684,032 A | 11/1997 | Elliott et al. | 514/414 |
| 5,776,954 A | 7/1998 | de Laszlo et al. | 514/340 |
| 6,166,037 A | * 12/2000 | Budhu et al. | 514/326 |
| 6,248,755 B1 | * 6/2001 | Chapman et al. | 514/320 |
| 6,265,434 B1 | * 7/2001 | Caldwell et al. | 514/429 |

FOREIGN PATENT DOCUMENTS

| WO | WO 99/09984 | 3/1999 |
|---|---|---|

OTHER PUBLICATIONS

Mandell, HIV and The Acquired Immunodeficiency Syndrome, Cecil Textbook of Medicine, 20th Edition, vol. 2, pp. 1837–1855, 1996.*

Aleman et al., PubMed Abstract (Antivir. Ther. 4(2): 109–15) ,1999.*

Farber, PubMed Abstract (Braz. J. Med. Biol. 31(1): 11–7), 1998.*

McFadden et al., New Strategies for Chemokine Inhibition and Modulation, Biochem. Pharmacol., vol. 54, No. 12, pp. 1271–1280, 1997.*

C. Dorn et al, "Discovery of Potent Human CCR5 Antagonists for the Treatment of HIV–I Infection", Abstract 117, 219th National Meeting of the American Chemical Society, San Francisco, CA, Mar. 2000.

L. Meurer et al, "Discovery of Potent Human CCR5 Antagonists for the Treatment of HIV–II Infection", Abstract 118, 219th National Meeting of the American Chemical Society, San Francisco, CA, Mar. 2000.

P. Finke et al, "Discovery of Potent Human CCR5 Antagonists for the Treatment of HIV–III Infection", Abstract 119, 219th National Meeting of the American Chemical Society, San Francisco, CA, Mar. 2000.

C. Caldwell et al, "Discovery of Potent Human CCR5 Antagonists for the Treatment of HIV–IV Infection", Abstract 120, 219th National Meeting of the American Chemical Society, San Francisco, CA, Mar. 2000.

J. J. Gomez–Reino et al., "Association of Rheumatoid Arthritis with a Functional Chemokine Receptor, CCR5", Arthritis & Rheumatism, vol. 42, No. 5, May 1999, pp. 989–992.

H. Hotoda, "Small–molecule inhibitors of HIV–1 entry via chemokine receptors", Drugs of the Future, vol. 24, No. 12, 1999, pp. 1355–1362.

T. J. Schall, "Biology of the Rantes/sis Cytokine Family", Cytokine, vol. 3, No. 3, May 1991, pp. 165–183.

P. M. Murphy, "The Molecular Biology of Leukocyte Chenoattractant Receptors", Annual Review of Immunology, vol. 12, 1994, pp. 593–633.

H. Deng et al., "Identification of a mojor co–receptor for primary isolates of HIV–1", Nature, vol. 381, Jun. 1996, pp. 661–666.

(List continued on next page.)

*Primary Examiner*—Deepak R. Rao
(74) *Attorney, Agent, or Firm*—Kenneth R. Walton; Melvin Winokur; J. Eric Thies

(57) ABSTRACT

The present invention is directed to pyrrolidine compounds of the formula I:

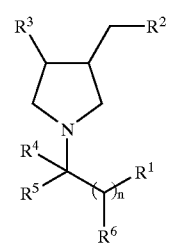

I (wherein $R^1$, $R^2$, $R^3$, $R^4$, $R^5$, $R^6$ and n are defined herein) which are useful as modulators of chemokine receptor activity. In particular, these compounds are useful as modulators of the chemokine receptors CCR-5 and/or CCR-3.

43 Claims, No Drawings

OTHER PUBLICATIONS

R. Horuk, "Molecular properties of the chemokine receptor family", Trends Pharm. Science, vol. 15, 1994, pp. 159–165.

A. Ben–Baruch et al., "Monocyte Chemotactic Protein–3 (MCP3) Interacts with Multiple Leukocyte Receptors", J. Biol. Chem., vol. 270, No. 38, Sep. 1995, pp. 22123–22128.

K. Neote et al., "Molecular Cloning, Functional Expression, and Signaling Characteristics of C–C Chemokine Receptor", Cell, vol. 72, Feb. 1993, pp. 415–425.

C. Combadiere et al., "Cloning and Functional Expression of a Human Eosinophil CC Chemokine Receptor", J. Biol. Chem., vol. 270, No. 27, Jul. 1995, pp. 16491–16494.

C. A. Power et al., "Molecular Cloning and Functional Expression of a Novel Cc Chemokine Receptor cDNA from a Human Basophilic Line", J. Biol. Chem., vol. 270, No. 33, Aug. 1995, pp. 19495–19500.

M. Samson et al., "Molecular Cloning and Functional Expression of a New Human CC–Chemokine Receptor Gene", Biochemistry, vol. 35, 1996, pp. 3362–3367.

A. Chaudhuri et al., "Expression of the Duffy Antigen in K562 Cells,", J. Biol. Chem., vol. 269, No. 11, Mar. 1994, pp. 7835–7838.

H. Kita et al., "Chemokines Active on Eosinophils: Potential Roles in Allergic Inflammation", J. Exp. Med., vol. 183, Jun. 1996, pp. 2421–2426.

D. Smith et al., "Blocking of HIV–1 Infectivity by a Soluable, Secreted Form of the CD4 Antigen", Science, vol. 238, 1987, pp. 1704–1707.

J. A. Levy, "Infection by Human Immunodeficiency Virus —DC4 is not Enough", N. Eng. J. Med., vol. 335, No. 20, Nov. 1996), pp. 1528–1530.

T. Dragic et al., "HIV–1 entry into CD4+ cells is mediated by the chemokine receptor CC–CKR5", Nature, vol. 381, Jun. 1996, pp. 667–673.

L. Wu et al., "CD4–induced interaction of primary HIV–1 gp120 glycoproteins with the chemokine receptor CCR–5", Nature, vol. 384, Nov. 1996, pp. 179–183.

A. Trkola et al., "CD4–dependent, antibody–sensitive interactions between HIV–1 and its co–receptor CCR–5", Nature, vol. 384, Nov. 1996, pp. 184–187.

M. Samson et al., "Resistance to HIV–1 infection in caucasian individuals bearing mutant alleles of the CCR–5 cehmokine receptor gene", Nature, vol. 382, Aug. 1996, pp. 722–725.

C. M. Hill et al., "Natural resistence to HIV?", Nature, vol. 382, Aug. 1996, pp. 668–669.

Y. Huang et al., "The Role of a mutant CCR5 allele in HIV–1 transmission and disease progression", Nature Medicine, vol. 2, No. 11, Nov. 1996, pp. 1240–1243.

L. Zhang et al., "HIV–1 subtype and second–receptor use", Nature, vol. 383, Oct. 1996, p. 768.

W. S. Blair et al., "HIV–1 entry—an expanding portal for drug discovery", DDT, vol. 5, May 2000, pp. 183–194.

M. Baba et al., "A small–molecule, nonpeptide CCR5 antagonist with highly potent and selective anti HIV–1 activity", Proc. Natl. Acad. Sci., vol. 96, May 1999, pp. 5698–5703.

R. Horuk et al., "Chemokine Receptor Antagonists", Med. Res. Rev., vol. 20, No. 2, 2000, pp. 155–168.

M. Shiraishi et al., "Discovery of Novel, Potent , and Selective Small–Molecule CCR5 Antagonists as Anti–HIV–1 Agents: Synthesis and Biological Evaluation of Anilide Derivatives with a Quanternary Ammonium Moiety", J. Med. Chem., vol. 43, 2000, pp. 2049–2063.

* cited by examiner

PYRROLIDINE MODULATORS OF CHEMOKINE RECEPTOR ACTIVITY

This application claims the benefit of U.S. Provisional Application No. 60/128,172, filed Apr. 6, 1999, the disclosure of which is hereby incorporated by reference in its entirety.

BACKGROUND OF THE INVENTION

Chemokines are chemotactic cytokines that are released by a wide variety of cells to attract macrophages, T cells, eosinophils, basophils and neutrophils to sites of inflammation (reviewed in Schall, *Cytokine*, 3, 165–183 (1991) and Murphy, *Rev. Immun.*, 12, 593–633 (1994)). There are two classes of chemokines, C-X-C ($\alpha$) and C-C ($\beta$), depending on whether the first two cysteines are separated by a single amino acid (C-X-C) or are adjacent (C-C). The $\alpha$-chemokines, such as interleukin-8 (IL-8), neutrophil-activating protein-2 (NAP-2) and melanoma growth stimulatory activity protein (MGSA) are chemotactic primarily for neutrophils, whereas $\beta$-chemokines, such as RANTES, MIP-1$\alpha$, MIP-1$\beta$, monocyte chemotactic protein-1 (MCP-1), MCP-2, MCP-3 and eotaxin are chemotactic for macrophages, T-cells, eosinophils and basophils (Deng, et al., *Nature*, 381, 661–666 (1996)).

The chemokines bind specific cell-surface receptors belonging to the family of G-protein-coupled seven-transmembrane-domain proteins (reviewed in Horuk, *Trends Pharm. Sci.*, 15, 159–165 (1994)) which are termed "chemokine receptors." On binding their cognate ligands, chemokine receptors transduce an intracellular signal though the associated trimeric G protein, resulting in a rapid increase in intracellular calcium concentration. There are at least sixteen human chemokine receptors that bind or respond to $\beta$-chemokines with the following characteristic pattern: CCR-1 (or "CKR-1" or "CC-CKR-1") [MIP-1$\alpha$, MIP-1$\beta$, MCP-3, RANTES] (Ben-Barruch, et al., *J. Biol. Chem.*, 270, 22123–22128 (1995); Beote, et al, *Cell*, 72, 415–425 (1993)); CCR-2A and CCR-2B (or "CKR-2A"/ "CKR-2A" or "CC-CKR-2A"/"CC-CKR-2A") [MCP-1, MCP-3, MCP-4]; CCR-3 (or "CKR-3" or "CC-CKR-3") [eotaxin, RANTES, MCP-3] (Combadiere, et al., *J. Biol. Chem.*, 270, 16491–16494 (1995); CCR4 (or "CKR-4" or "CC-CKR-4") [MIP-1$\alpha$, RANTES, MCP-1] (Power, et al., *J. Biol. Chem.*, 270, 19495–19500 (1995)); CCR-5 (or "CKR-5" or "CC-CKR-5") [MIP-1$\alpha$, RANTES, MIP-1$\beta$] (Sanson, et al., *Biochemistry*, 35, 3362–3367 (1996)); and the Duffy blood-group antigen [RANTES, MCP-1] (Chaudhun, et al., *J. Biol. Chem.*, 269, 7835–7838 (1994)). The $\beta$-chemokines include eotaxin, MIP ("macrophage inflammatory protein"), MCP ("monocyte chemoattractant protein") and RANTES ("regulation-upon-activation, normal T expressed and secreted").

Chemokine receptors, such as CCR-1, CCR-2, CCR-2A, CCR-2B, CCR-3, CCR-4, CCR-5, CXCR-3, CXCR-4, have been implicated as being important mediators of inflammatory and immunoregulatory disorders and diseases, including asthma, rhinitis and allergic diseases, as well as autoimmune pathologies such as rheumatoid arthritis and atherosclerosis. A review of the role of chemokines in allergic inflammation is provided by Kita, H., et al., *J. Exp. Med.* 183, 2421–2426 (1996). Accordingly, agents which modulate chemokine receptors would be useful in such disorders and diseases. Compounds which modulate chemokine receptors would be especially useful in the treatment and prevention of atopic conditions including allergic rhinitis, dermatitis, conjunctivitis, and particularly bronchial asthma.

A retrovirus designated human immunodeficiency virus (HIV-1) is the etiological agent of the complex disease that includes progressive destruction of the immune system (acquired immune deficiency syndrome; AIDS) and degeneration of the central and peripheral nervous system. This virus was previously known as LAV, HTLV-III, or ARV.

Certain compounds have been demonstrated to inhibit the replication of HIV, including soluble CD4 protein and synthetic derivatives (Smith, et al., *Science*, 238, 1704–1707 (1987)), dextran sulfate, the dyes Direct Yellow 50, Evans Blue, and certain azo dyes (U.S. Pat. No. 5,468,469). Some of these antiviral agents have been shown to act by blocking the binding of gp120, the coat protein of HIV, to its target, the CD4 glycoprotein of the cell.

Entry of HIV-1 into a target cell requires cell-surface CD4 and additional host cell cofactors. Fusin has been identified as a cofactor required for infection with virus adapted for growth in transformed T-cells, however, fusin does not promote entry of macrophagetropic viruses which are believed to be the key pathogenic strains of HIV in vivo. It has recently been recognized that for efficient entry into target cells, human immunodeficiency viruses require a chemokine receptors, most probably CCR-5 or CXCR-4, as well as the primary receptor CD4 (Levy, *N. Engl. J. Med.*, 335(20), 1528–1530 (Nov. 14, 1996). The principal cofactor for entry mediated by the envelope glycoproteins of primary macrophage-trophic strains of HIV-1 is CCR5, a receptor for the $\beta$-chemokines RANTES, MIP-1$\alpha$ and MIP-1$\beta$ (Deng, et al., *Nature*, 381, 661–666 (1996)). HIV attaches to the CD4 molecule on cells through a region of its envelope protein, gp120. It is believed that the CD-4 binding site on the gp120 of HIV interacts with the CD4 molecule on the cell surface, and undergoes conformational changes which allow it to bind to another cell-surface receptor, such as CCR5 and/or CXCR-4. This brings the viral envelope closer to the cell surface and allows interaction between gp41 on the viral envelope and a fusion domain on the cell surface, fusion with the cell membrane, and entry of the viral core into the cell. It has been shown that $\beta$-chemokine ligands prevent HIV-1 from fusing with the cell (Dragic, et al., *Nature*, 381, 667–673 (1996)). It has further been demonstrated that a complex of gp120 and soluble CD4 interacts specifically with CCR-5 and inhibits the binding of the natural CCR-5 ligands MIP-1$\alpha$ and MIP-1$\beta$, (Wu, et al., *Nature*, 384, 179–183 (1996); Trkola, et al., *Nature*, 384, 184–187 (1996)).

Humans who are homozygous for mutant CCR-5 receptors which do not serve as co-receptors for HIV-1 in vitro appear to be unusually resistant to HIV-1 infection and are not immuno-compromised by the presence of this genetic variant (*Nature*, 382, 722–725 (1996)). Absence of CCR-5 appears to confer substantial protection from HIV-1 infection (*Nature*, 382, 668–669 (1996)). Other chemokine receptors may be used by some strains of HIV-1 or may be favored by non-sexual routes of transmission. Although most HIV-1 isolates studied to date utilize CCR-5 or fusin, some can use both as well as the related CCR-2B and CCR-3 as co-receptors (*Nature Medicine*, 2(11), 1240–1243 (1996)). Nevertheless, drugs targeting chemokine receptors may not be unduly compromised by the genetic diversity of HIV-1 (Zhang, et al., *Nature*, 383, 768 (1996)). Accordingly, an agent which could block chemokine receptors in humans who possess normal chemokine receptors should prevent infection in healthy individuals and slow or halt viral progression in infected patients. By focusing on the host's cellular immune response to HIV infection, better therapies towards all subtypes of HIV may be provided. These results indicate that inhibition of chemokine receptors presents a viable method for the prevention or treatment of infection by HIV and the prevention or treatment of AIDS.

The peptides eotaxin, RANTES, MIP-1α, MIP-1β, MCP-1, and MCP-3 are known to bind to chemokine receptors. As noted above, the inhibitors of HIV-1 replication present in supernatants of CD8+ T cells have been characterized as the β-chemokines RANTES, MIP-1α and MIP-1β.

SUMMARY OF THE INVENTION

The present invention is directed to compounds which inhibit the entry of human immunodeficiency virus (HIV) into target cells and are of value in the prevention of infection by HIV, the treatment of infection by HIV and the prevention and/or treatment of the resulting acquired immune deficiency syndrome (AIDS). The present invention also relates to pharmaceutical compositions containing the compounds and to a method of use of the present compounds and other agents for the prevention and treatment of AIDS and viral infection by HIV.

The present invention is further directed to compounds which are modulators of chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

DETAILED DESCRIPTION OF THE INVENTION

The present invention is directed to compounds of formula I;

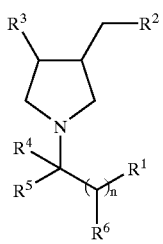

I wherein:
$R^1$ is selected from:
  (1) —$CO_2H$,
  (2) —$NO_2$,
  (3) -tetrazolyl,
  (4) -hydroxyisoxazole,
  (5) —$SO_2NH$—($C_{0-3}$ alkyl)—$R^9$, wherein $R^9$ is independently selected from: hydrogen, $C_{1-6}$ alkyl, $C_{5-6}$ cycloalkyl, benzyl or phenyl, which is unsubstituted or substituted with 1–3 substituents where the substituents are independently selected from: halo, $C_{1-3}$ alkyl, $C_{1-3}$ alkoxy and trifluoromethyl,
  (6) —$SO_2NHCO$—($C_{0-3}$ alkyl)—$R^9$, wherein $R^9$ is independently selected from: hydrogen, $C_{1-6}$ alkyl, $C_{5-6}$ cycloalkyl, benzyl or phenyl, which is unsubstituted or substituted with 1–3 substituents where the substituents are independently selected from: halo, $C_{1-3}$ alkyl, $C_{1-3}$ alkoxy and trifluoromethyl, and
  (7) —$P(O)(OH)_2$;
$R^2$ is selected from the group consisting of;

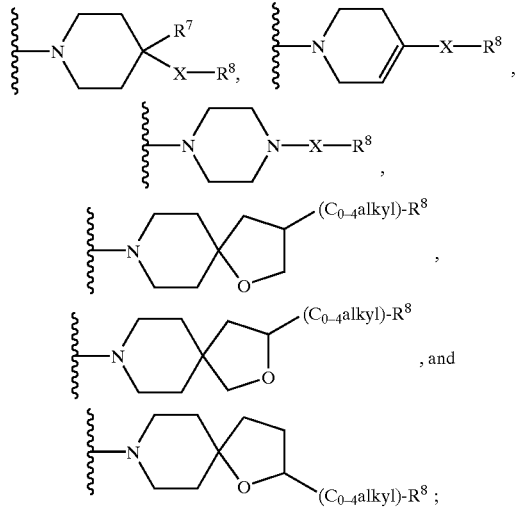

wherein $R^7$ is selected from:
  (1) hydrogen,
  (2) $C_{1-6}$ alkyl, which is unsubstituted or substituted with 1–4 substituents where the substituents are independently selected from: hydroxy, cyano, and halo,
  (3) cyano,
  (4) hydroxy, and
  (5) halo;
wherein X is —($C_{0-6}$ alkyl)—Y—($C_{0-6}$ alkyl)-,
  where the alkyl is unsubstituted or substituted with 1–7 substituents where the substituents are independently selected from:
    (a) halo,
    (b) hydroxy,
    (c) —O—$C_{1-3}$ alkyl, and
    (d) trifluoromethyl,
  and where Y is selected from:
    —$SO_2$—, —$NR^{10}$—, —S—, —O—, —SO—, —$SO_2N(R^{10})$—, —$N(R^{10})SO_2$—, and —$PO_2$;
  and where $R^{10}$ is independently selected from: hydrogen, $C_{1-6}$ alkyl, benzyl, phenyl, (CO)$C_{1-6}$ alkyl, —$SO_2$—$C_{1-6}$ alkyl, —$SO_2$-phenyl, —$SO_2$-heterocycle, and $C_{1-6}$ alkyl-$C_{3-6}$ cycloalkyl,
    which is unsubstituted or substituted with 1–3 substituents where the substituents are independently selected from: halo, $C_{1-3}$ alkyl, $C_{1-3}$ alkoxy and trifluoromethyl;
or X is

and wherein $R^8$ is selected from:
  t-butyl, cyclohexyl, phenyl, naphthyl, biphenyl, and heterocycle, which is unsubstituted or substituted with 1–7 of $R^{11}$ where $R^{11}$ is independently selected from:

(a) halo,
(b) cyano,
(c) hydroxy,
(d) $C_{1-6}$ alkyl, which is unsubstituted or substituted with 1–5 of $R^{12}$ where $R^{12}$ is independently selected from: halo, cyano, hydroxy, $C_{1-6}$ alkoxy, $—CO_2H$, $—CO_2(C_{1-6}$ alkyl$)$, phenyl, trifluoromethyl, and $—NR^9R^{10}$,
(e) $—O—C_{1-6}$ alkyl, which is unsubstituted or substituted with 1–5 of $R^{12}$,
(f) $—CF_3$,
(g) $—CHF_2$,
(h) $—CH_2F$,
(i) $—NO_2$,
(j) phenyl,
(k) $—CO_2R^9$,
(l) tetrazolyl,
(m) $—NR^9R^{10}$,
(n) $—NR^9—COR^{10}$,
(o) $—NR^9—CO_2R^{10}$,
(p) $—CO—NR^9R^{10}$,
(q) $—OCO—NR^9R^{10}$,
(r) $—NR^9CO—NR^9R^{10}$,
(s) $—S(O)_m—R^9$, wherein m is an integer selected from 0, 1 and 2,
(t) $—S(O)_2—NR^9R^{10}$,
(u) $—NR^9S(O)_2—R^{10}$, and
(v) $—NR^9S(O)_2—NR^9R^{10}$;

$R^3$ is selected from the group consisting of:
phenyl and heterocycle,
which is unsubstituted or substituted with 1–7 substituents where the substituents are independently selected from:
(a) halo,
(b) trifluoromethyl,
(c) hydroxy,
(d) $C_{1-3}$ alkyl,
(e) $—O—C_{1-3}$ alkyl,
(f) $—CO_2R^9$,
(g) $—NR^9R^{10}$, and
(h) $—CONR^9R^{10}$, $R^4$ is selected from:
$C_{1-10}$ alkyl, $C_{3-8}$ cycloalkyl, $—(C_{1-3}$ alkyl$)$—$C_{3-8}$ cycloalkyl, $C_{2-10}$ alkenyl, $C_{2-10}$ alkynyl, phenyl, $—(C_{1-6}$ alkyl$)$-phenyl, naphthyl, biphenyl, heterocycle, hydrogen, cyclohexenyl, dihydronaphthyl, tetrahydronaphthyl, and octahydronaphthyl,
which is unsubstituted or substituted with 1–7 of $R^{11}$ where $R^{11}$ is independently as defined above;

$R^5$ is selected from:
hydrogen or $C_{1-6}$ alkyl, wherein the alkyl is unsubstituted or substituted with 1–7 substituents where the substituents are independently selected from:
(a) halo,
(b) trifluoromethyl,
(c) hydroxy,
(d) $C_{1-3}$ alkyl,
(e) $—O—C_{1-3}$ alkyl,
(f) $—CO_2R^9$,
(g) $—NR^9R^{10}$, and
(h) $—CONR^9R^{10}$, or where $R^4$ and $R^5$ may be joined together to form a $C_{3-8}$ cycloalkyl ring which may be unsubstituted or substituted with 1–7 of $R^{11}$;

$R^6$ is independently selected from:
hydrogen or $C_{1-6}$ alkyl, wherein the alkyl is unsubstituted or substituted with 1–7 substituents where the substituents are independently selected from:
(a) halo,
(b) trifluoromethyl,
(c) hydroxy,
(d) $C_{1-3}$ alkyl,
(e) $—O—C_{1-3}$ alkyl,
(f) $—CO_2R^9$,
(g) $—NR^9R^{10}$, and
(h) $—CONR^9R^{10}$;

n is an integer selected from 0, 1, 2 and 3;
and pharmaceutically acceptable salts thereof and individual diastereomers thereof.

In one embodiment, the present invention is directed to compounds of formula I, wherein:
$R^1$ is selected from:
(1) $—CO_2H$,
(2) $—NO_2$,
(3) -tetrazolyl,
(4) -hydroxyisoxazole,
(5) $—SO_2NH—(C_{0-3}$ alkyl$)$—$R^9$, wherein $R^9$ is independently selected from: hydrogen, $C_{1-6}$ alkyl, $C_{5-6}$ cycloalkyl, benzyl or phenyl, which is unsubstituted or substituted with 1–3 substituents where the substituents are independently selected from: halo, $C_{1-3}$ alkyl, $C_{1-3}$ alkoxy and trifluoromethyl, and
(6) $—P(O)(OH)_2$;

$R^2$ is selected from the group consisting of:

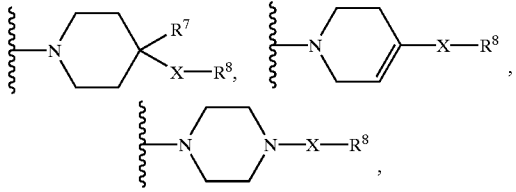

wherein $R^7$ is selected from:
(1) hydrogen,
(2) $C_{1-6}$ alkyl, which is unsubstituted or substituted with 1–4 substituents where the substituents are independently selected from: hydroxy, cyano, and halo,
(3) cyano,
(4) hydroxy, and
(5) halo, wherein X is $—(C_{0-6}$ alkyl$)$—Y—$(C_{0-6}$ alkyl$)$-,
where the alkyl is unsubstituted or substituted with 1–7 substituents where the substituents are independently selected from:
(a) halo,
(b) hydroxy,
(c) $—O—C_{1-3}$ alkyl, and
(d) trifluoromethyl, and where Y is selected from:
$—SO_2—$, $—NR^{10}—$, $—S—$, $—O—$, and $—SO—$,
and where $R^{10}$ is independently selected from:
hydrogen, $C_{1-6}$ alkyl, benzyl, phenyl, $(CO)C_{1-6}$ alkyl, $—SO_2—C_{1-6}$ alkyl, $—SO_2$-phenyl, $—SO_2$-heterocycle, and $C_{1-6}$ alkyl-$C_{3-6}$ cycloalkyl,
which is unsubstituted or substituted with 1–3 substituents where the substituents are independently selected from: halo, $C_{1-3}$ alkyl, $C_{1-3}$ alkoxy and trifluoromethyl, and and wherein $R^8$ is selected from:
  phenyl, naphthyl, biphenyl, and heterocycle,
    which is unsubstituted or substituted with 1–7 of $R^{11}$
      where $R^{11}$ is independently selected from:
        (a) halo,
        (b) cyano,
        (c) hydroxy,
        (d) $C_{1-6}$ alkyl, which is unsubstituted or substituted with 1–5 of $R^{12}$ where $R^{12}$ is independently selected from: halo, cyano, hydroxy, $C_{1-6}$ alkoxy, —$CO_2H$, —$CO_{2(C1-6}$ alkyl), phenyl, trifluoromethyl, and —$NR^9R^{10}$,
        (e) —O—$C_{1-6}$ alkyl, which is unsubstituted or substituted with 1–5 of $R^{12}$,
        (f) —$CF_3$,
        (g) —$CHF_2$,
        (h) —$CH_2F$,
        (i) —$NO_2$,
        (j) phenyl,
        (k) —$CO_2R^9$,
        (l) tetrazolyl,
        (m) —$NR^9R^{10}$,
        (n) —$NR^9$—$COR^{10}$,
        (o) —$NR^9$—$CO_2R^{10}$,
        (p) —CO—$NR^9R^{10}$,
        (q) —OCO—$NR^9R^{10}$,
        (r) —$NR^9$CO—$NR^9R^{10}$,
        (s) —$S(O)_m$—$R^9$, wherein m is an integer selected from 0, 1 and 2,
        (t) —$S(O)_2$—$NR^9R^{10}$,
        (u) —$NR^9S(O)_2$—$R^{10}$, and
        (v) —$NR^9S(O)_2$—$NR^9R^{10}$;
$R^3$ is selected from the group consisting of:
  phenyl and heterocycle,
    which is unsubstituted or substituted with 1–7 substituents where the substituents are independently selected from:
      (a) halo,
      (b) trifluoromethyl,
      (c) hydroxy,
      (d) $C_{1-3}$ alkyl,
      (e) —O—$C_{1-3}$ alkyl,
      (f) —$CO_2R^9$,
      (g) —$NR^9R^{10}$, and
      (h) —$CONR^9R^{10}$;
$R^4$ is selected from:
  $C_{1-10}$ alkyl, $C_{3-8}$ cycloalkyl, —($C_{1-3}$ alkyl)—$C_{3-8}$ cycloalkyl, $C_{2-10}$ alkenyl, $C_{2-10}$ alkynyl, phenyl, —($C_{1-6}$ alkyl)-phenyl, naphthyl, biphenyl, heterocycle, hydrogen, cyclohexenyl, dihydronaphthyl, tetrahydronaphthyl, and octahydronaphthyl,
    which is unsubstituted or substituted with 1–7 of $R^{11}$
      where $R^{11}$ is independently as defined above;
$R^5$ is selected from:
  hydrogen or $C_{1-6}$ alkyl, wherein the alkyl is unsubstituted or substituted with 1–7 substituents where the substituents are independently selected from:
    (a) halo,
    (b) trifluoromethyl,
    (c) hydroxy,
    (d) $C_{1-3}$ alkyl,
    (e) —O—$C_{1-3}$ alkyl,
    (f) —$CO_2R^9$,
    (g) —$NR^9R^{10}$, and
    (h) —$CONR^9R^{10}$, or where $R^4$ and $R^5$ may be joined together to form a $C_{3-8}$ cycloalkyl ring which may be unsubstituted or substituted with 1–7 of $R^{11}$;
$R^6$ is independently selected from:
  hydrogen or $C_{1-6}$ alkyl, wherein the alkyl is unsubstituted or substituted with 1–7 substituents where the substituents are independently selected from:
    (a) halo,
    (b) trifluoromethyl,
    (c) hydroxy,
    (d) $C_{1-3}$ alkyl,
    (e) —O—$C_{1-3}$ alkyl,
    (f) —$CO_2R^9$,
    (g) —$NR^9R^{10}$, and
    (h) —$CONR^9R^{10}$;
n is an integer selected from 0, 1, 2 and 3;
and pharmaceutically acceptable salts thereof and individual diastereomers thereof.

Preferred compounds of the present invention include those of formula Ia:

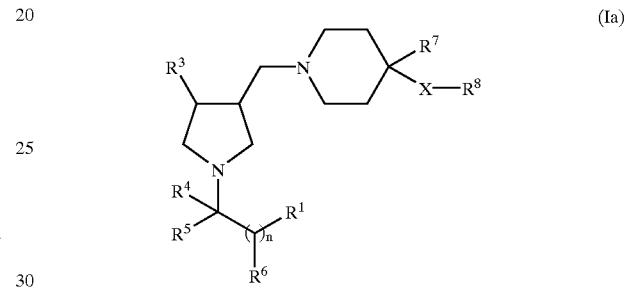

(Ia)

wherein $R^1$, $R^3$, $R^4$, $R^5$, $R^6$, $R^7$, $R^8$, X and n are defined herein;
and pharmaceutically acceptable salts and individual diastereomers thereof.

More preferred compounds of the present invention include those of formula Ic:

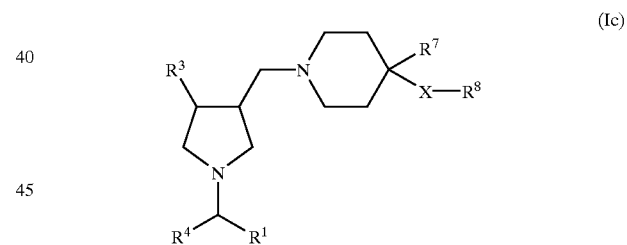

(Ic)

wherein $R^1$, $R^3$, $R^4$, $R^7$, $R^8$ and X are defined herein;
and pharmaceutically acceptable salts and individual diastereomers thereof.

Highly preferred compounds of the present invention include those of formula Id:

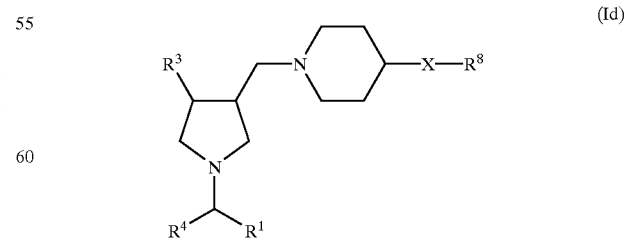

(Id)

wherein $R^1$, $R^3$, $R^4$, $R^8$ and X are defined herein;
and pharmaceutically acceptable salts and individual diastereomers thereof.

More highly preferred compounds of the present invention include those of formula Ie:

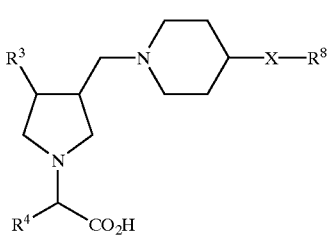

(Ie)

wherein $R^3$, $R^4$, $R^8$ and X are defined herein;
and pharmaceutically acceptable salts and individual diastereomers thereof.

In the present invention it is preferred that $R^1$ is selected from:
(1) —$CO_2H$,
(2) —$P(O)(OH)_2$, and
(3) -tetrazolyl.

In the present invention it is more preferred that $R^1$ is selected from:
(1) —$CO_2H$, and
(2) -tetrazolyl.

In the present invention it is even more preferred that $R^1$ is —$CO_2H$.

In the present invention it is preferred that $R^2$ is

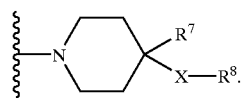

In the present invention it is more preferred that $R^2$ is

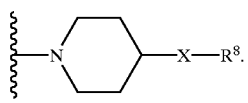

In the present invention it is preferred that $R^3$ is selected from the group consisting of:
phenyl and thienyl,
which may be unsubstituted or substituted with 1–5 substituents where the substituents are independently selected from:
(a) halo,
(b) trifluoromethyl,
(c) hydroxy,
(d) $C_{1-3}$ alkyl, and
(e) —O—$C_{1-3}$ alkyl.

In the present invention it is more preferred that $R^3$ is selected from the group consisting of:
phenyl and thienyl,
which may be unsubstituted or substituted with 1–5 substituents where the substituents are independently selected from:
(a) fluoro,
(b) chloro,
(c) trifluoromethyl,
(d) hydroxy, and
(e) $C_{1-3}$ alkyl.

In the present invention it is even more preferred that $R^3$ is selected from the group consisting of:
phenyl, which may be unsubstituted or substituted with 1–5 substituents where the substituents are independently selected from:
(a) fluoro, and
(b) chloro; and
unsubstituted thienyl.

In the present invention it is most preferred that $R^3$ is unsubstituted phenyl, (3-fluoro)phenyl or 3-thienyl.

In the present invention it is preferred that $R^4$ is $C_{1-10}$ alkyl, $C_{3-8}$ cycloalkyl, or —($C_{1-3}$ alkyl)—$C_{3-8}$ cycloalkyl,
which is unsubstituted or substituted with 1–5 substituents where the substituents are independently selected from:
(a) halo,
(b) hydroxy,
(c) —$C_{1-6}$ alkyl, which is unsubstituted or substituted with halo, cyano, —$CO_2H$, hydroxy or trifluoromethyl,
(d) —O—$C_{1-6}$ alkyl, which is unsubstituted or substituted halo, cyano, —$CO_2H$, hydroxy or trifluoromethyl,
(e) —$CF_3$,
(f) —$CHF_2$,
(g) —$CH_2F$, and
(h) —$CO_2H$.

In the present invention it is more preferred that $R^4$ is selected from: isopropyl, isobutyl, sec-butyl, t-butyl, cyclohexyl, cyclopentyl, cyclobutyl, cyclopropyl, —$CH_2$-cyclohexyl, —$CH_2$-cyclopentyl, —$CH_2$-cyclobutyl, and —$CH_2$-cyclopropyl. In an aspect of this embodiment, in the present invention it is more preferred that $R^4$ is selected from: isopropyl, isobutyl, sec-butyl, cyclohexyl, cyclopentyl, cyclobutyl, cyclopropyl, —$CH_2$-cyclohexyl, —$CH_2$-cyclopentyl, —$CH_2$-cyclobutyl, and —$CH_2$-cyclopropyl.

In the present invention it is even more preferred that $R^4$ is selected from: isopropyl, sec-butyl, t-butyl, cyclohexyl, cyclopentyl, cyclobutyl, cyclopropyl, —$CH_2$-cyclobutyl, and —$CH_2$-cyclopropyl. In an aspect of this embodiment, in the present invention it is more preferred that that $R^4$ is selected from: isopropyl, cyclohexyl, cyclopentyl, cyclobutyl, cyclopropyl, —$CH_2$-cyclobutyl, and —$CH_2$-cyclopropyl.

In the present invention it is most preferred that $R^4$ is selected from: cyclohexyl, isopropyl, sec-butyl, t-butyl, —$CH_2$-cyclobutyl and —$CH_2$-cyclopropyl. In an aspect of this embodiment, in the present invention it is most preferred that $R^4$ is selected from: cyclohexyl, isopropyl, —$CH_2$-cyclobutyl and —$CH_2$-cyclopropyl.

In the present invention it is preferred that $R^5$ is hydrogen.

In the present invention it is preferred that $R^6$ is hydrogen or unsubstituted $C_{1-6}$ alkyl.

In the present invention it is more preferred that $R^6$ is hydrogen.

In the present invention it is preferred that $R^7$ is hydrogen, fluoro, hydroxy or $C_{1-6}$ alkyl.

In the present invention it is more preferred that $R^7$ is hydrogen or fluoro.

In the present invention it is even more preferred that $R^7$ is hydrogen.

In the present invention it is preferred that X is:
—($C_{0-4}$ alkyl)—Y—($C_{0-4}$ alkyl)-,
where the alkyl is unsubstituted or substituted with 1–4 substituents where the substituents are independently selected from:
(a) halo,
(b) hydroxy, (c) —O—$C_{1-3}$ alkyl, and
(d) trifluoromethyl,
and where Y is selected from:
—$SO_2$—, —$NR^{10}$—, —S—, —O—, and —SO—,
and where $R^{10}$ is independently selected from: hydrogen, unsubstituted $C_{1-6}$ alkyl, and unsubstituted $C_{1-6}$ alkyl-$C_{3-6}$ cycloalkyl.

In the present invention it is more preferred that X is:
—($C_{0-2}$ alkyl)—Y—($C_{0-2}$ alkyl)-, where the alkyl is unsubstituted,
and where Y is selected from:
—$SO_2$—, —SO—, —$NR^{10}$—, —S—, and —O—,
and where $R^{10}$ is independently selected from: unsubstituted $C_{1-4}$ alkyl, and unsubstituted $C_{1-3}$ alkyl-$C_{3-6}$ cycloalkyl.

In the present invention it is even more preferred that X is selected from:
—($C_{0-2}$ alkyl)—$SO_2$—($C_{0-2}$ alkyl)-,
—($C_{0-2}$ alkyl)—SO—($C_{0-2}$ alkyl)-,
—($C_{0-2}$ alkyl)—S—($C_{0-2}$ alkyl)-,
—($C_{0-2}$ alkyl)—O—($C_{0-2}$ alkyl)-, and
—($C_{0-2}$ alkyl)—$NR^{10}$—($C_{0-2}$ alkyl)-,
where $R^{10}$ is independently selected from: unsubstituted $C_{2-4}$ alkyl, and unsubstituted $C_{1-2}$ alkyl-$C_3$ cycloalkyl.

In the present invention it is most preferred that X is selected from:
(1) —$CH_2CH_2$—$SO_2$—,
(2) —$CH_2CH_2$—SO—,
(3) —$CH_2CH_2$—S—,
(4) —$CH_2$—O—$CH_2$—,
(5) —N($CH_2CH_3$)—,
(6) —N($CH_2CH_2CH_3$)—, and
(7) —N($CH_2$-cyclopropyl)-.

In the present invention it is preferred that $R^8$ is selected from:
phenyl, naphthyl, benzoimidazolyl, benzofurazanyl, isoxazolyl, pyrazinyl, pyridazinyl, pyridyl, pyrimidyl, and tetrazolopyridyl,
which is unsubstituted or substituted with 1–7 substituents where the substituents are independently selected from:
(a) halo,
(b) cyano,
(c) hydroxy,
(d) $C_{1-6}$ alkyl, which is unsubstituted or substituted with 1–5 of $R^{12}$ where $R^{12}$ is independently selected from: halo, cyano, hydroxy, $C_{1-6}$ alkoxy, —$CO_2H$, phenyl, —$CO_2$($C_{1-6}$ alkyl), trifluoromethyl, and —$NR^9R^{10}$, wherein $R^9$ and $R^{10}$ are independently selected from: hydrogen, $C_{1-6}$ alkyl, $C_{5-6}$ cycloalkyl, benzyl or phenyl, which is unsubstituted or substituted with 1–3 substituents where the substituents are independently selected from: halo, $C_{1-3}$ alkyl, $C_{1-3}$ alkoxy and trifluoromethyl;
(e) —O—$C_{1-6}$ alkyl, which is unsubstituted or substituted with 1–5 of $R^{12}$,
(f) —$CF_3$,
(g) —$CHF_2$,
(h) —$CH_2F$,
(i) —$NO_2$,
(j) phenyl,
(k) —$CO_2R^9$,
(l) tetrazolyl,
(m) —$NR^9R^{10}$,
(n) —$NR^9$—$COR^{10}$,
(o) —$NR^9$—$CO_2R^{10}$,
(p) —CO—$NR^9R^{10}$,
(q) —OCO—$NR^9R^{10}$,
(r) —$NR^9CO$—$NR^9R^{10}$,
(s) —$S(O)_m$—$R^9$, wherein m is an integer selected from 0, 1 and 2,
(t) —$S(O)_2$—$NR^9R^{10}$,
(u) —$NR^9S(O)_2$—$R^{10}$, and
(v) —$NR^9S(O)_2$—$NR^9R^{10}$.

In the present invention it is more preferred that $R^8$ is selected from: phenyl, benzofurazanyl, pyridyl, pyrimidyl, pyrazyl, and pyridazyl;
which is unsubstituted or substituted with 1–5 substituents where the substituents are independently selected from:
(a) halo,
(b) cyano,
(c) —$NO_2$,
(d) —$CF_3$,
(e) —$CHF_2$,
(f) —$CH_2F$,
(g) tetrazolyl,
(h) $C_{1-6}$ alkyl, which is unsubstituted or substituted with phenyl, and
(i) —O—$C_{1-6}$ alkyl.

In the present invention it is even more preferred that $R^8$ is selected from: phenyl, benzofurazanyl, pyridyl, pyrimidyl, pyrazyl, and pyridazyl;
which is unsubstituted or substituted with 1–3 substituents where the substituents are independently selected from:
(a) fluoro,
(b) chloro,
(c) cyano,
(d) —$NO_2$, and
(e) —$CF_3$.

In the present invention it is most preferred that $R^8$ is selected from: phenyl, benzofurazanyl, pyridyl, pyrimidyl, pyrazyl, and pyridazyl.

In the present invention it is preferred that n is an integer selected from 0 and 1.

In the present invention it is more preferred that n is an integer which is 0.

It is to be understood that embodiments of the present invention include, but are not limited to, compounds of formula I wherein $R^1$, $R^2$, $R^3$, $R^4$, $R^5$, $R^6$, $R^7$, $R^8$, X, and n are defined in accordance with one of the embodiments or aspects thereof as set forth above. Any and all possible combinations of preferred, more preferred, even more preferred, highly preferred, more highly preferred, and/or most preferred definitions of these variables are within the scope of the present invention.

The compounds of the instant invention have at least two asymmetric centers at the ring junction of the substituents bearing $R^2$ and $R^3$. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The relative configurations of the more preferred compounds of this invention are of the trans orientation, i.e. as depicted:

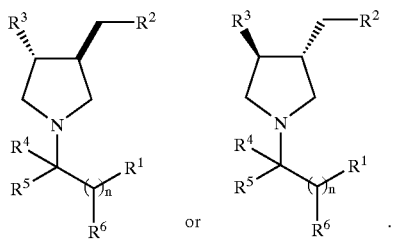

The relative configurations of the most preferred compounds of this invention with respect to the configuration of the substituent on the pyrrolidine nitrogen are of the orientation as depicted:

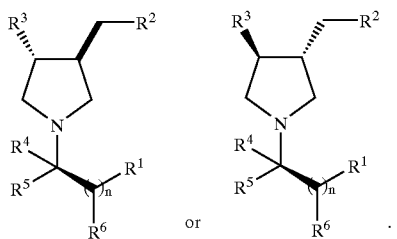

A preferred aspect of the present invention is a compound of formula (II):

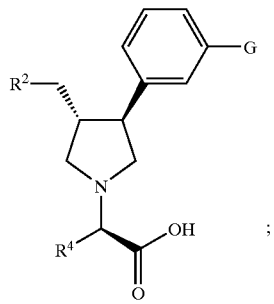
(II)

wherein $R^2$ is selected from the group consisting of

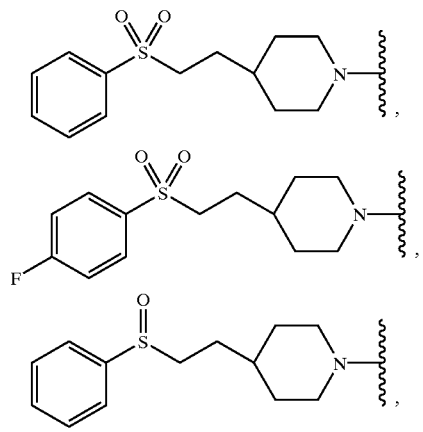

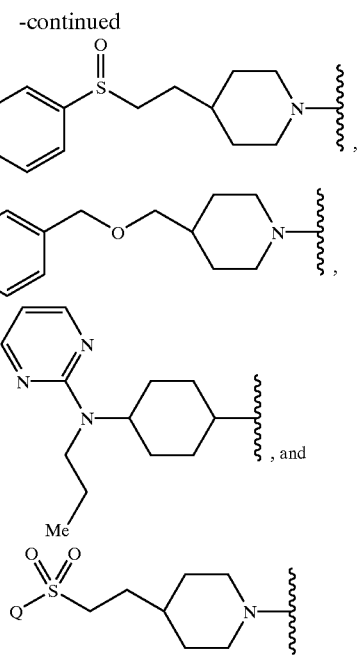

$R^4$ is selected from the group consisting of

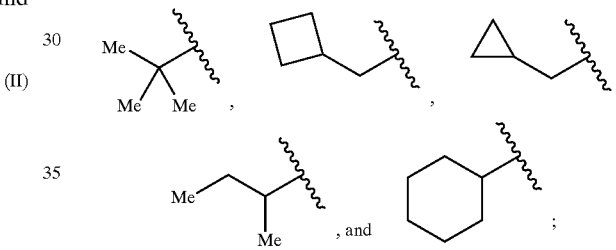

Q is pyridyl, pyrazinyl, pyrimidinyl, or thienyl, any one of which is unsubstituted or substituted with methyl or trifluoromethyl; and G is hydrogen or fluoro;

and pharmaceutically acceptable salts thereof and individual diastereomers thereof.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

As appreciated by those of skill in the art, halo or halogen as used herein are intended to include chloro, fluoro, bromo and iodo. Similarly, $C_{1-8}$, as in $C_{1-8}$ alkyl is defined to identify the group as having 1, 2, 3, 4, 5, 6, 7 or 8 carbons in a linear or branched arrangement, such that $C_{1-8}$ alkyl specifically includes methyl, ethyl, propyl, butyl, pentyl, hexyl, heptyl and octyl. Likewise, $C_0$, as in $C_0$ alkyl is defined to identify the presence of a direct covalent bond.

As with "$C_{1-8}$ alkyl", the term "$C_{1-6}$ alkyl" means linear or branched chain alkyl groups having from 1 to 6 carbon atoms and includes all of the hexyl alkyl, pentyl alkyl, etc. isomers.

The term "$C_3$–$C_8$ cycloalkyl" refers to a cyclic ring selected from cyclopropyl, cyclobutyl, cyclopentyl, cyclohexyl, cycloheptyl, and cyclooctyl. The term "$C_3$–$C_6$ cycloalkyl" refers to a cyclic ring selected from cyclopropyl, cyclobutyl, cyclopentyl, and cyclohexyl. Similar terms (e.g., "$C_4$–$C_6$ cycloalkyl") have analogous meanings.

The term "$C_{1-6}$ alkoxy" means an —O-alkyl group wherein alkyl is $C_{1-6}$ alkyl as defined above. Suitable alkoxy groups include, but are not limited to, methoxy, ethoxy, n-propoxy, isopropoxy, n-butoxy, isobutoxy, tert-butoxy, and sec-butoxy.

The term "heterocycle" (which may alternatively be referred to as "heterocyclic") refers to a 4- to 8-membered monocyclic ring, a 7- to 11-membered bicyclic system, or a 10 to 15-membered tricyclic ring system, any ring of which is saturated or unsaturated (partially or totally), and which consists of carbon atoms and one or more heteroatoms (e.g., from 1 to 4 heteroatoms) selected from N, O and S, and wherein the nitrogen and sulfur heteroatoms may optionally be oxidized, the nitrogen heteroatom may optionally be quaternized, and a ring carbon may optionally be oxidized (i.e., is substituted with oxo). The heterocyclic ring may be attached at any heteroatom or carbon atom, provided that attachment results in the creation of a stable structure. A preferred heterocycle is a 4- to 8-membered monocyclic ring or a 7- to 11-membered bicyclic system, as defined and described above.

The term "heterocycle" as used herein is intended to include the following groups: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzyl, tetrahydrofuranyl, and tetrahydrothienyl, and N-oxides thereof.

The term "heterocycle" as used herein is also intended to include, but is not limited to, the following groups: methylenedioxyphenyl, imidazopyridyl, imidazopyrimidinyl, imidazopyridazinyl, imidazopyrazinyl, imidazotriazinyl, imidazothipheyl, pyrazolopyridyl, pyrazolopyrimidinyl, pyrazolopyridazinyl, pyrazolopyrazinyl, pyrazolotriazinyl, pyrazolothiophenyl, triazolopyridyl, triazolopyrimidinyl, triazolopyridazinyl, triazolopyrazinyl, triazolothiophenyl, tetrahydroimidazopyridinyl, tetrahydropyrazolopyridinyl, tetrahydrotriazopyridinyl, tetrahydrotriazolopyridazinyl, and tetrahydroindazolyl.

The term "heterocycle" as used herein is also intended to include, but is not limited to, the following groups: tetrahydroimidazopyrimidyl, tetrahydroimidazopyrazinyl, tetrahydroimidazopyridazinyl, tetrahydrotriazolopyrimidyl, tetrahydrotriazolopyrazinyl, tetrahydropyrazolopyrimidyl, tetrahydropyrazolopyrazinyl, imidazothiazolyl, and imidazothiadiazolyl.

The term "heterocycle" as used herein is also intended to include, but is not limited to, oxopyridinyl (e.g., 2-oxopyridinyl), oxopiperidinyl, and oxopyrazolyl.

The terms "thiophenyl" and "thienyl" have the same meaning herein and are used interchangeably. Similarly, the following pairs of terms are used interchangeably: "indazolyl" and "benzopyrazolyl"; "pyridinyl" and "pyridyl".

In the expression " . . . which is unsubstituted or substituted with . . . ", "which" is intended to refer back to all preceding chemical groups in the particular definition in which the expression appears, unless a contrary meaning is expressed or is implied by the context. Furthermore, the term "substituted" in the expression includes mono- and poly-substitution by a named substituent to the extent such single and multiple substitution is chemically allowed in any of the named chemical groups. Thus, for example, the expression "is independently selected from: hydrogen, $C_{1-6}$ alkyl, $C_{5-6}$ cycloalkyl, benzyl or phenyl, which is unsubstituted or substituted with 1–3 substituents . . . ", encompasses hydrogen, $C_{1-6}$ alkyl, $C_{5-6}$ cycloalkyl, benzyl, phenyl, mono- and di- and tri-substituted $C_{1-6}$ alkyl, mono- and di- and tri-substituted $C_{5-6}$ cycloalkyl, mono- and di- and tri-substituted benzyl and mono- and di- and tri-substituted phenyl.

Exemplifying the invention is the use of the compounds disclosed in the Examples and herein.

Specific compounds within the present invention include a compound which is selected from the group consisting of:

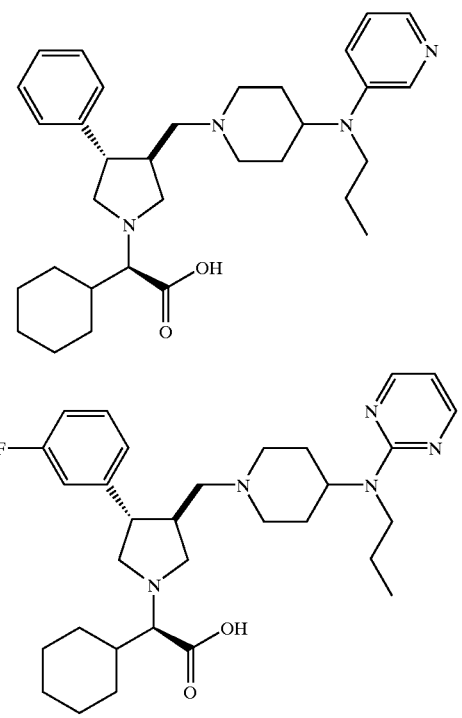

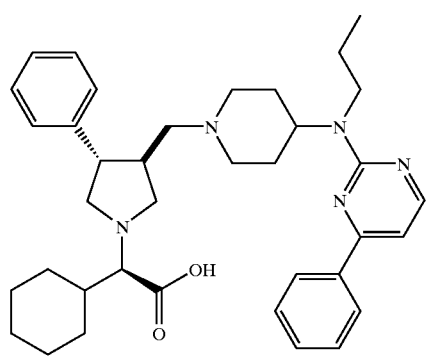
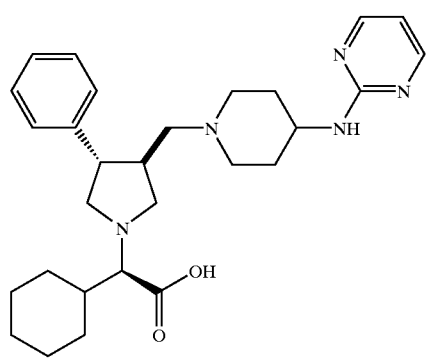
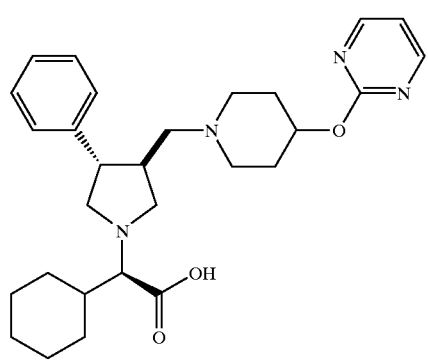
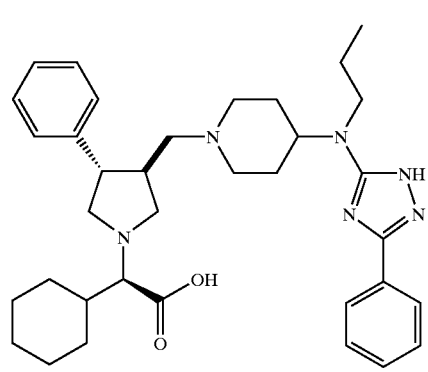
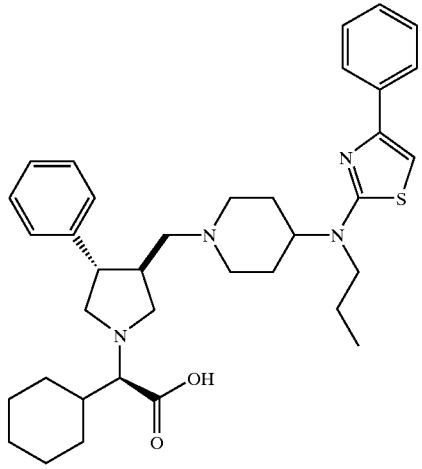
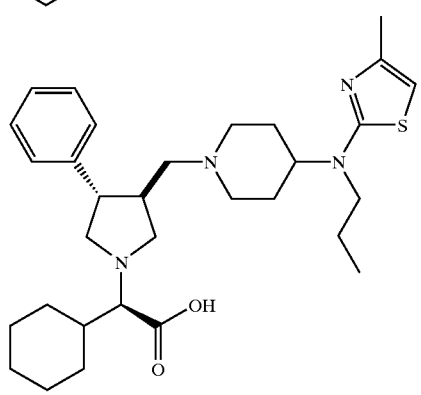
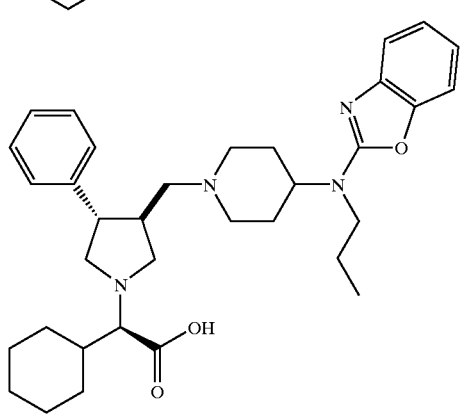
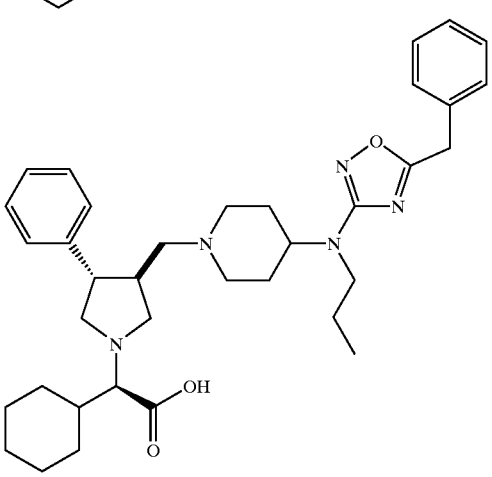

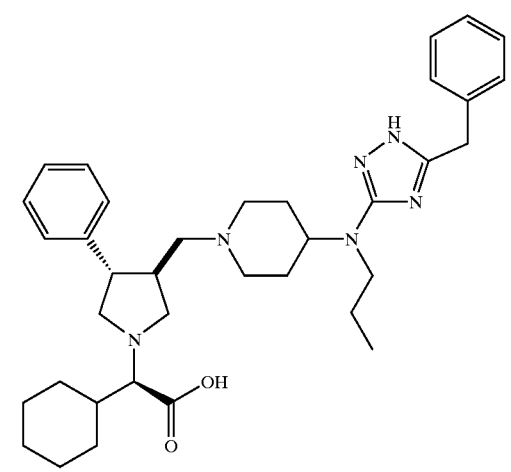
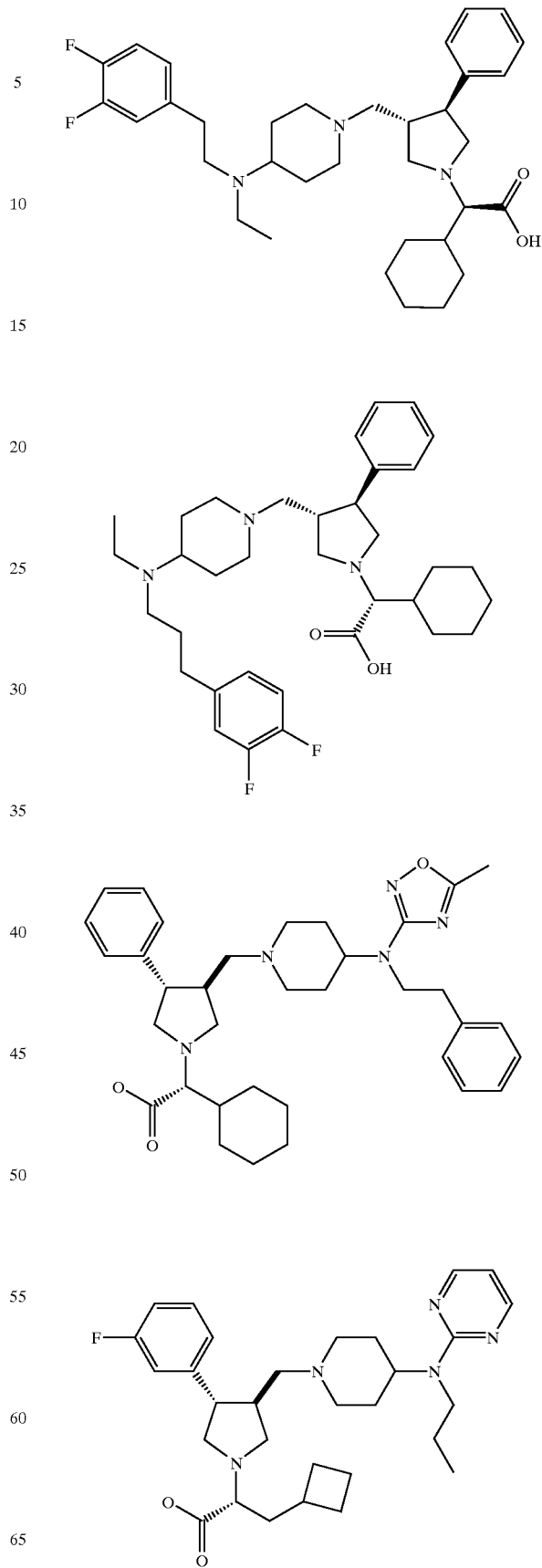

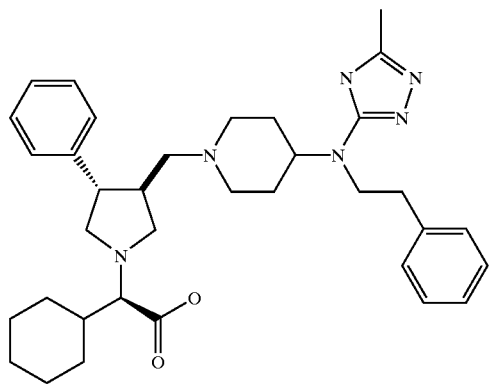
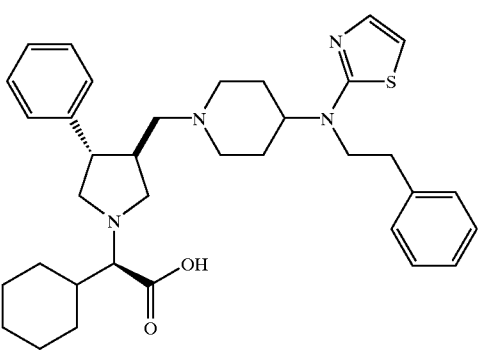
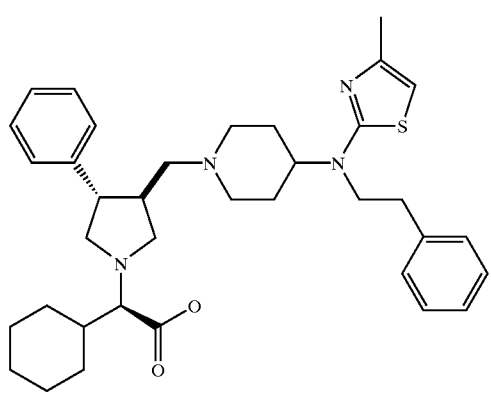
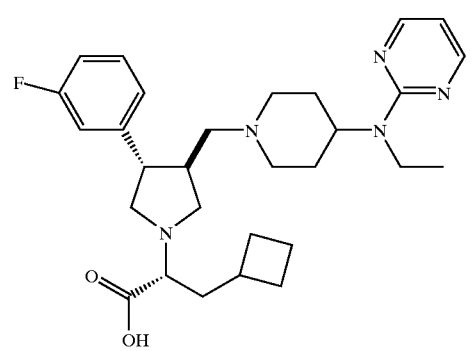
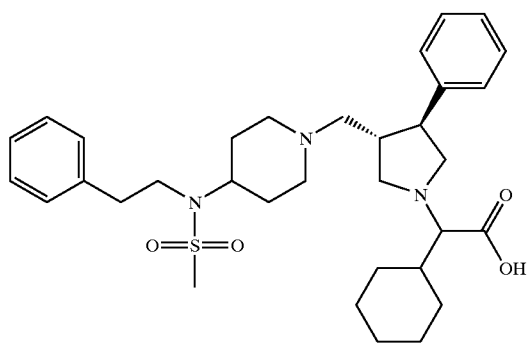
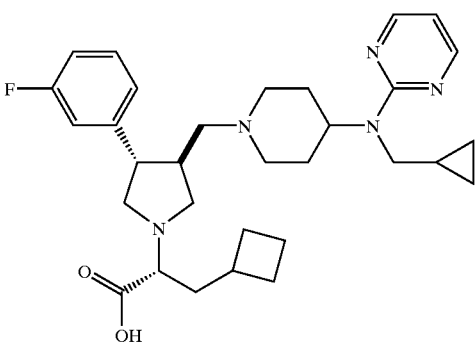
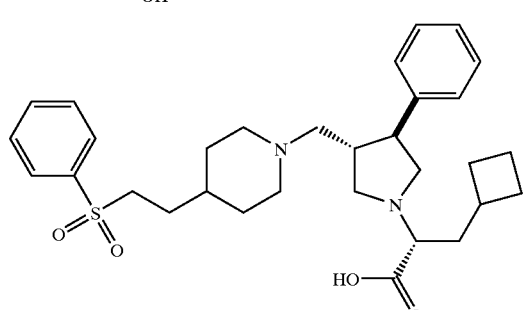
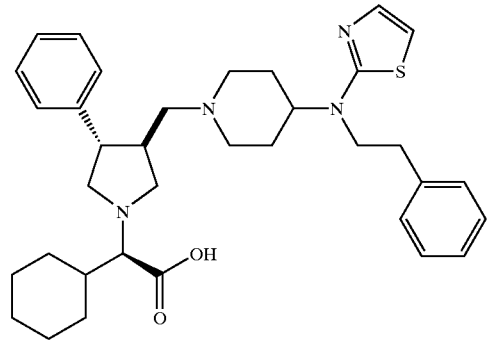
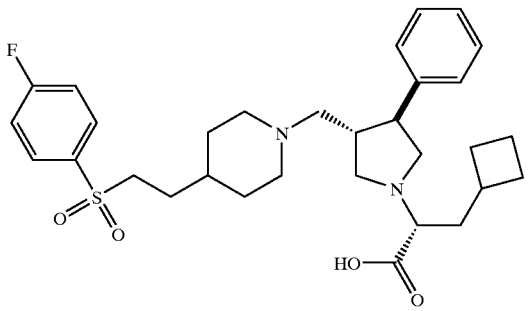

23
-continued
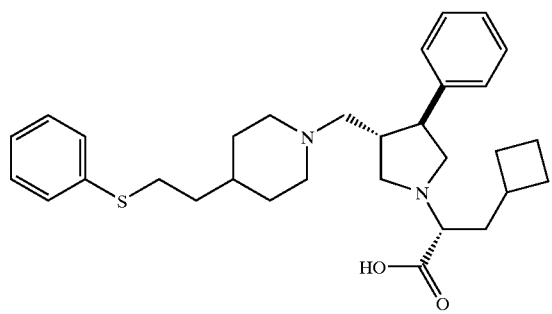
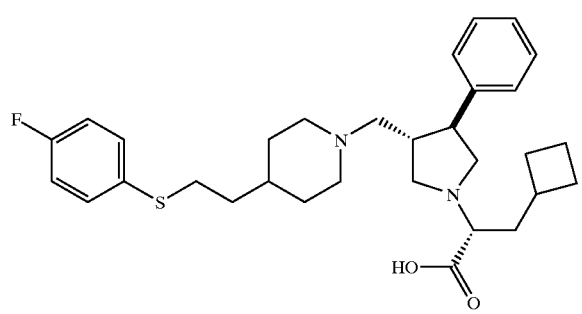
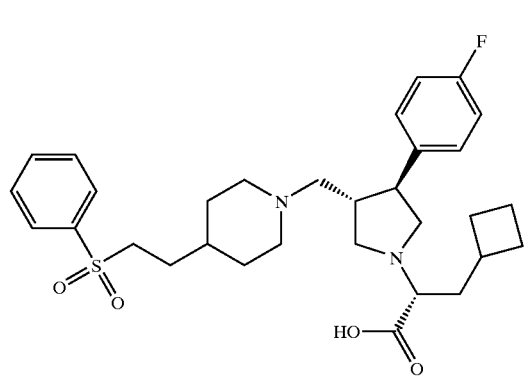
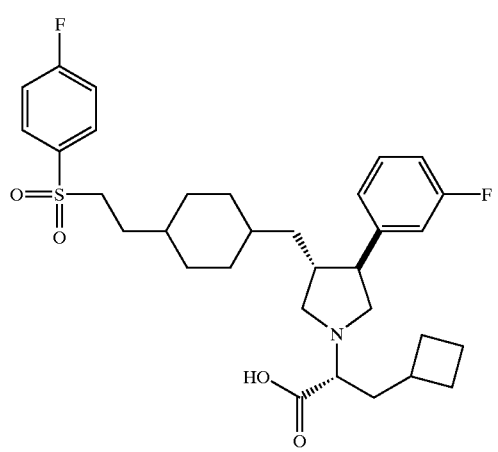
24
-continued
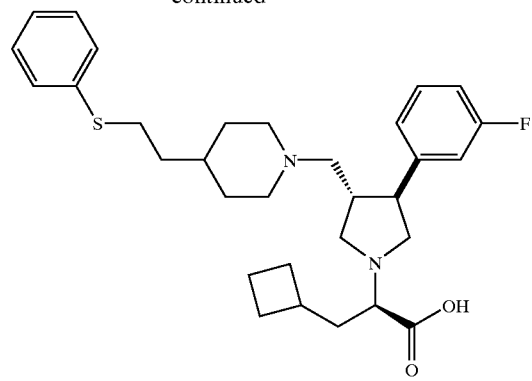
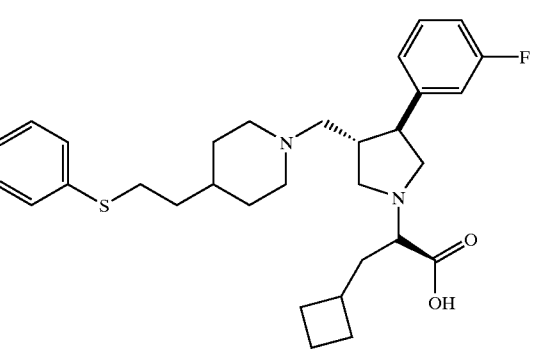
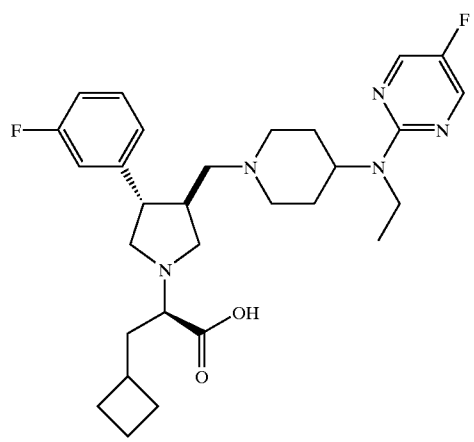
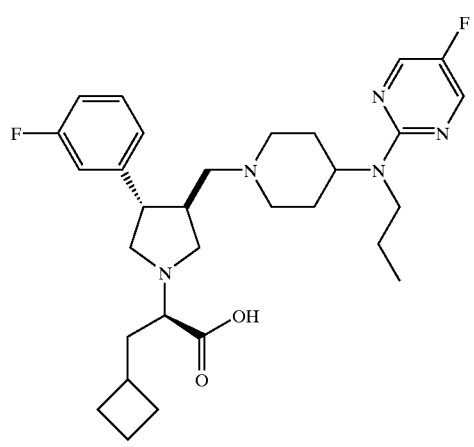

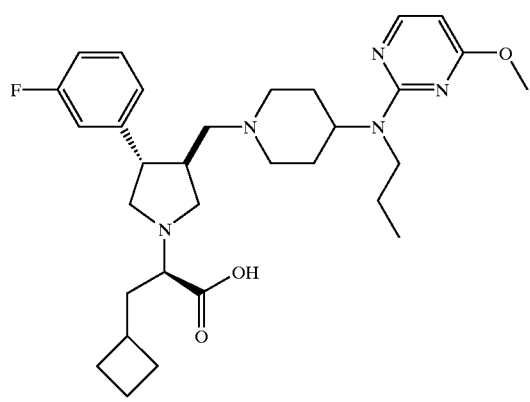
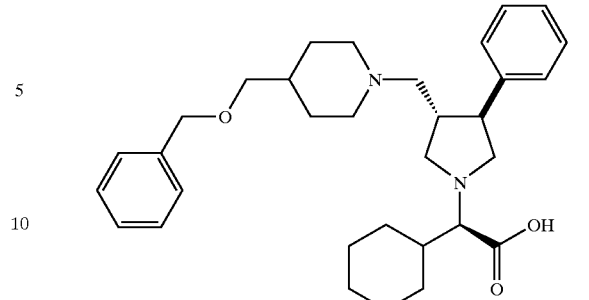
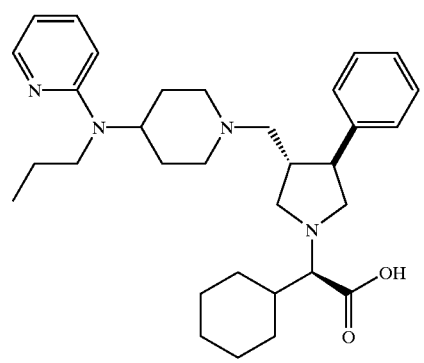
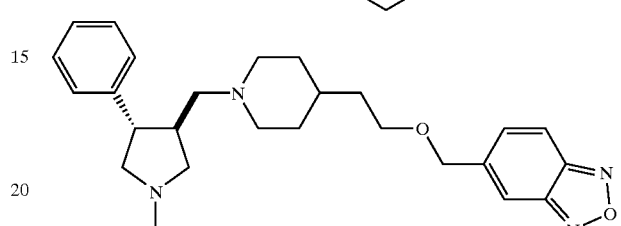
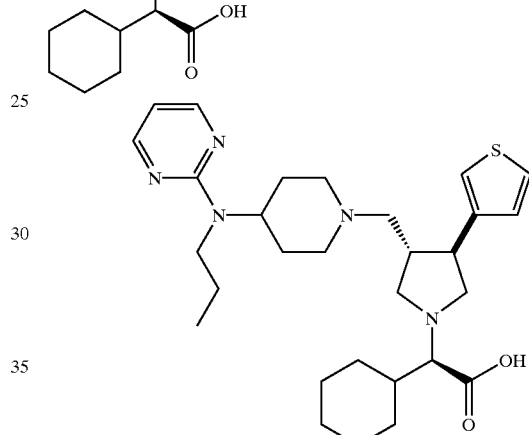
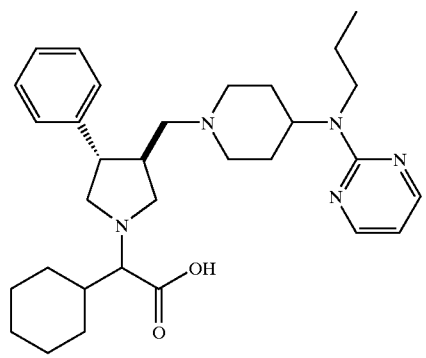
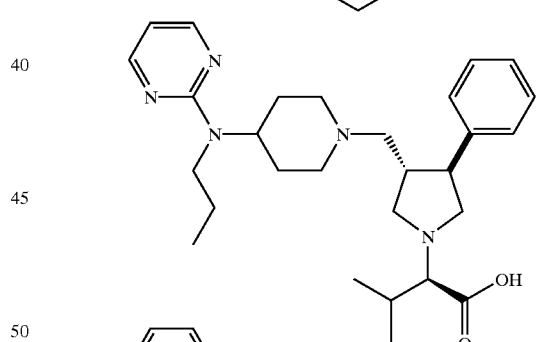
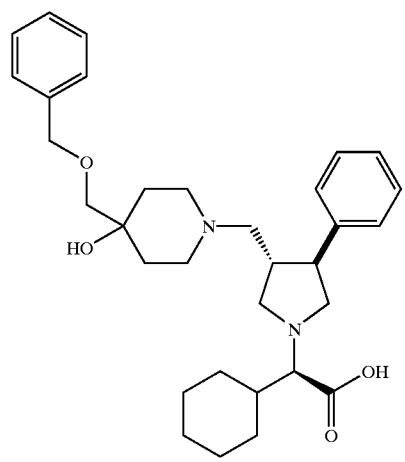
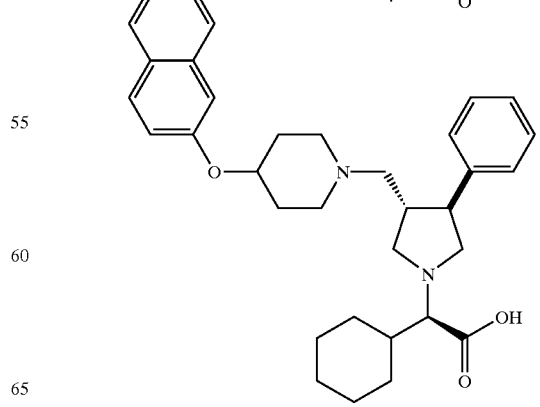

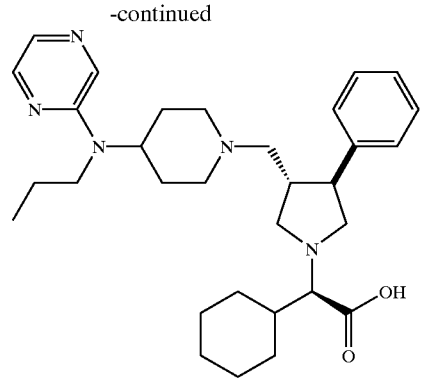
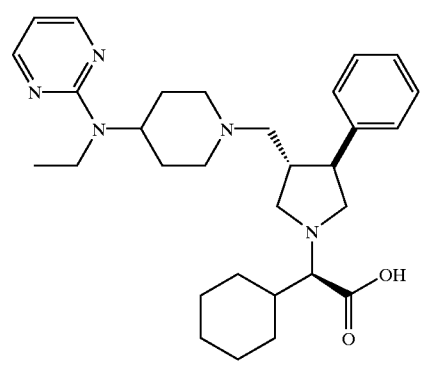
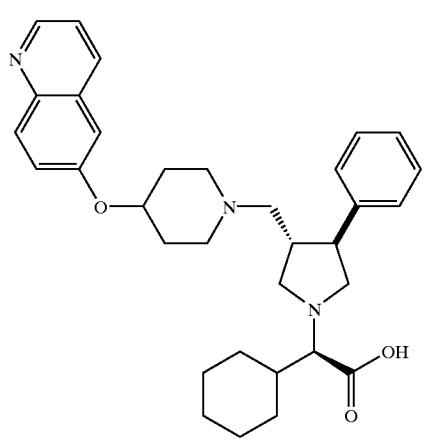
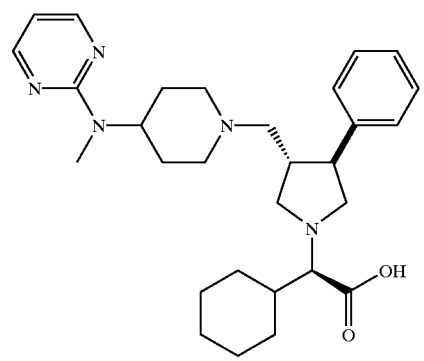
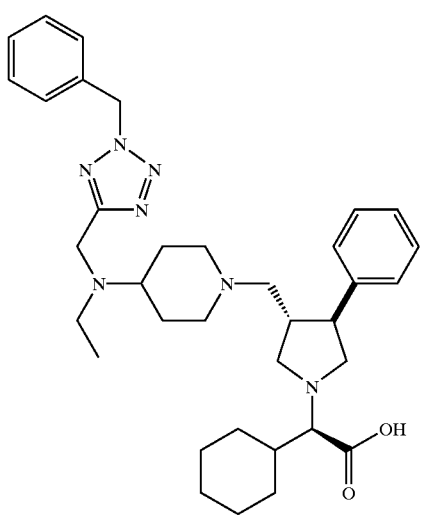
and pharmaceutically acceptable salts thereof and individual diastereomers thereof.
Specific compounds within the present invention also include compounds selected from the group consisting of:
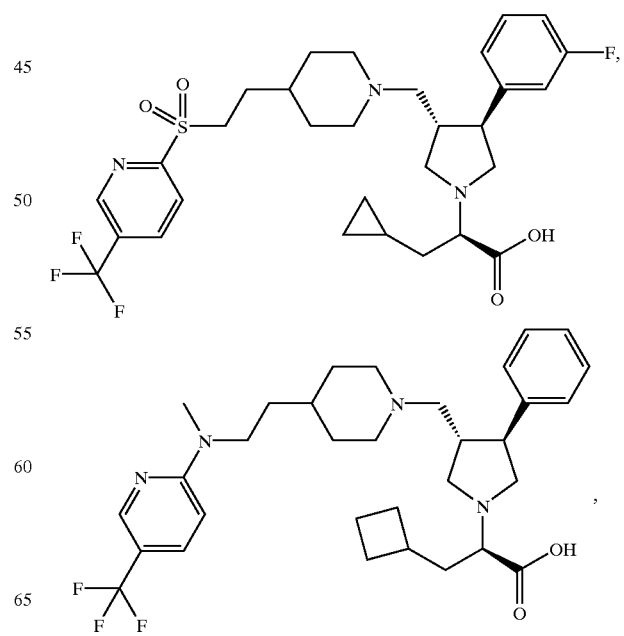

-continued
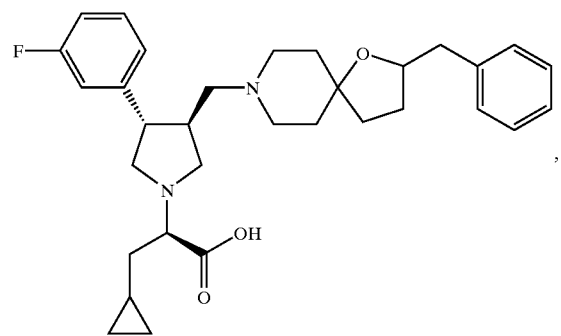
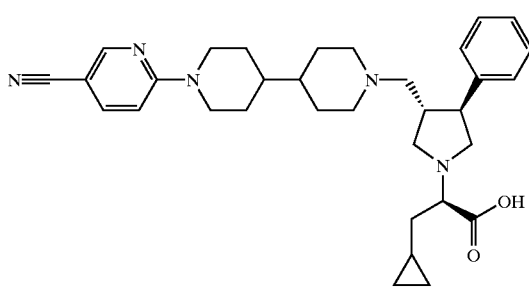
lp;2p
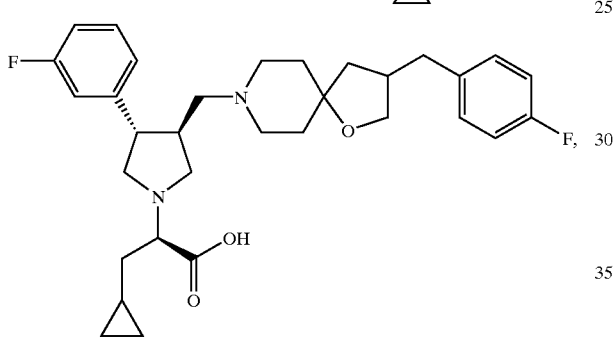
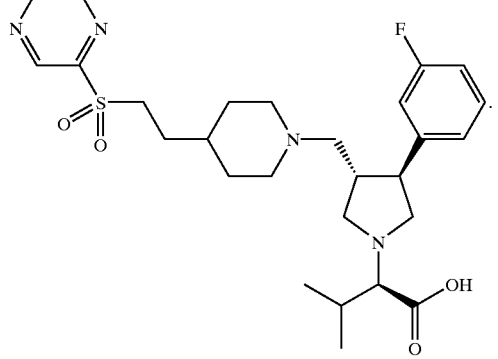
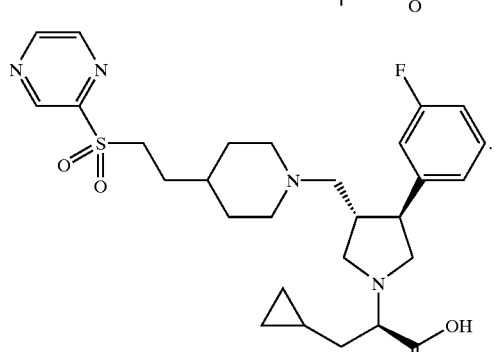
-continued
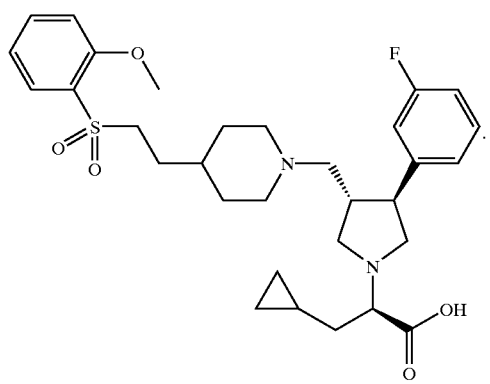
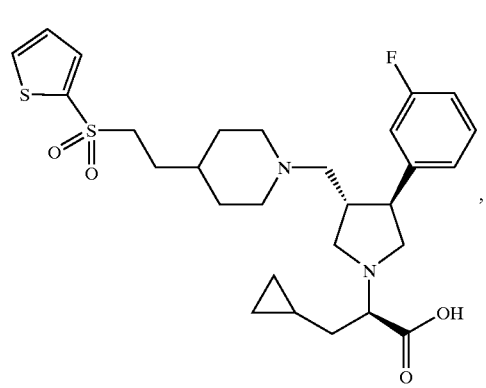
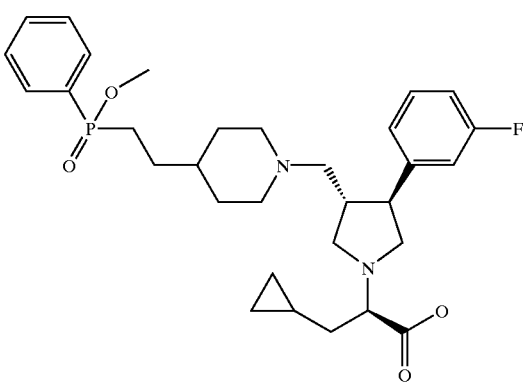
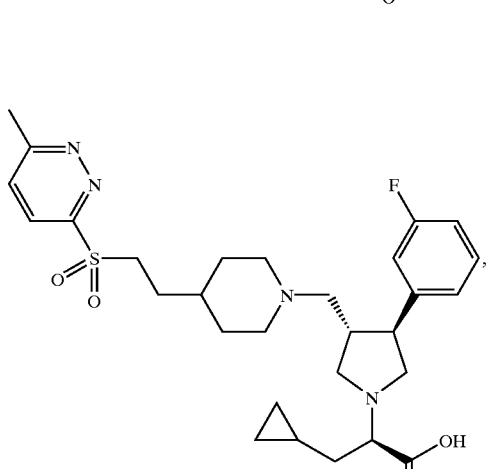

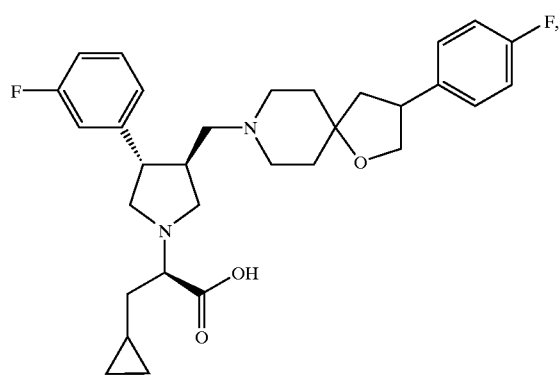
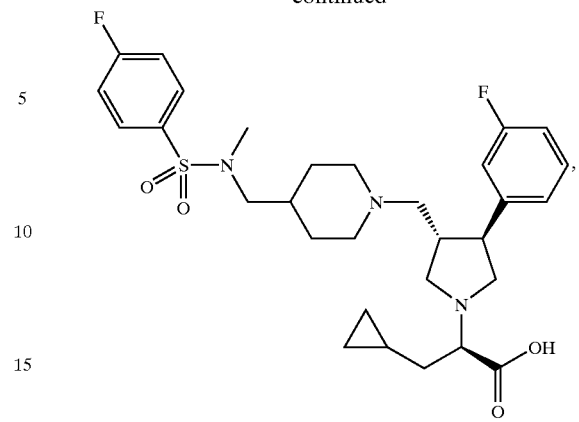
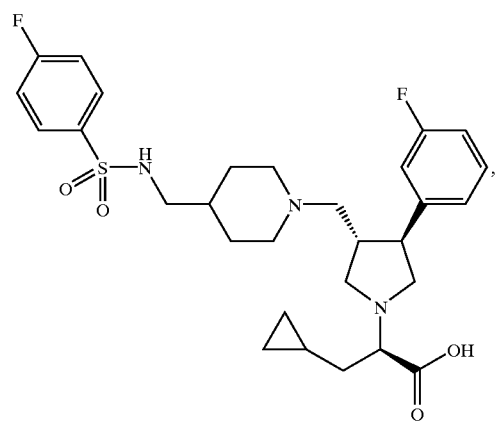
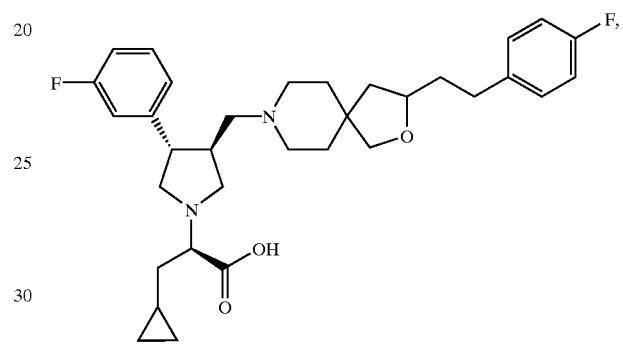
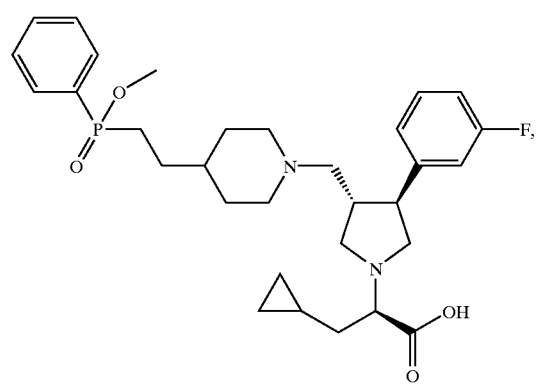
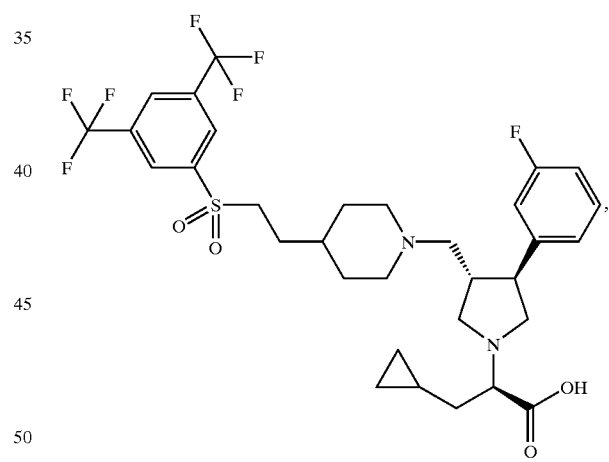
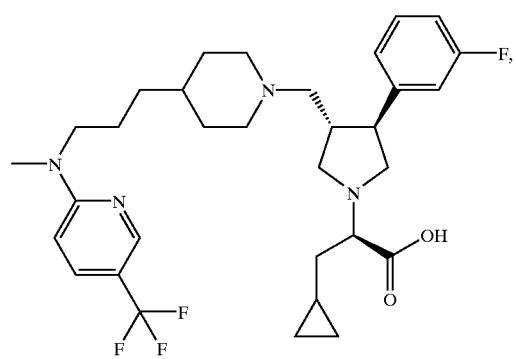
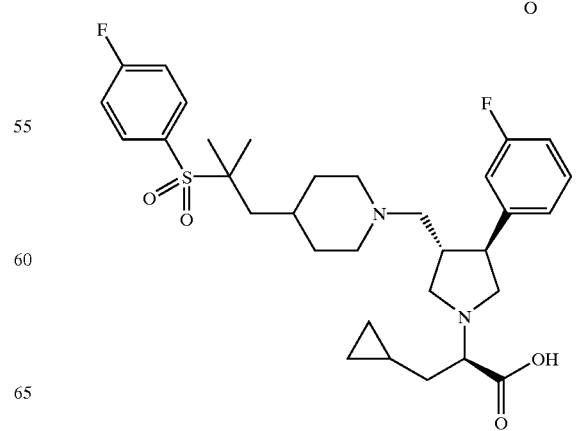

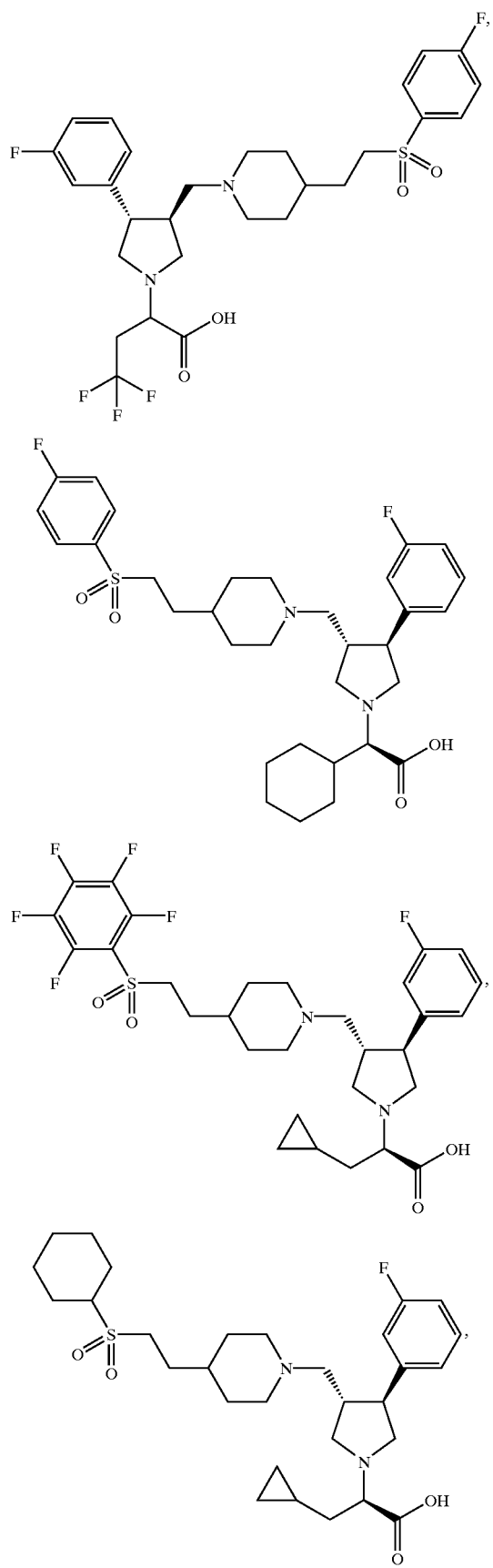
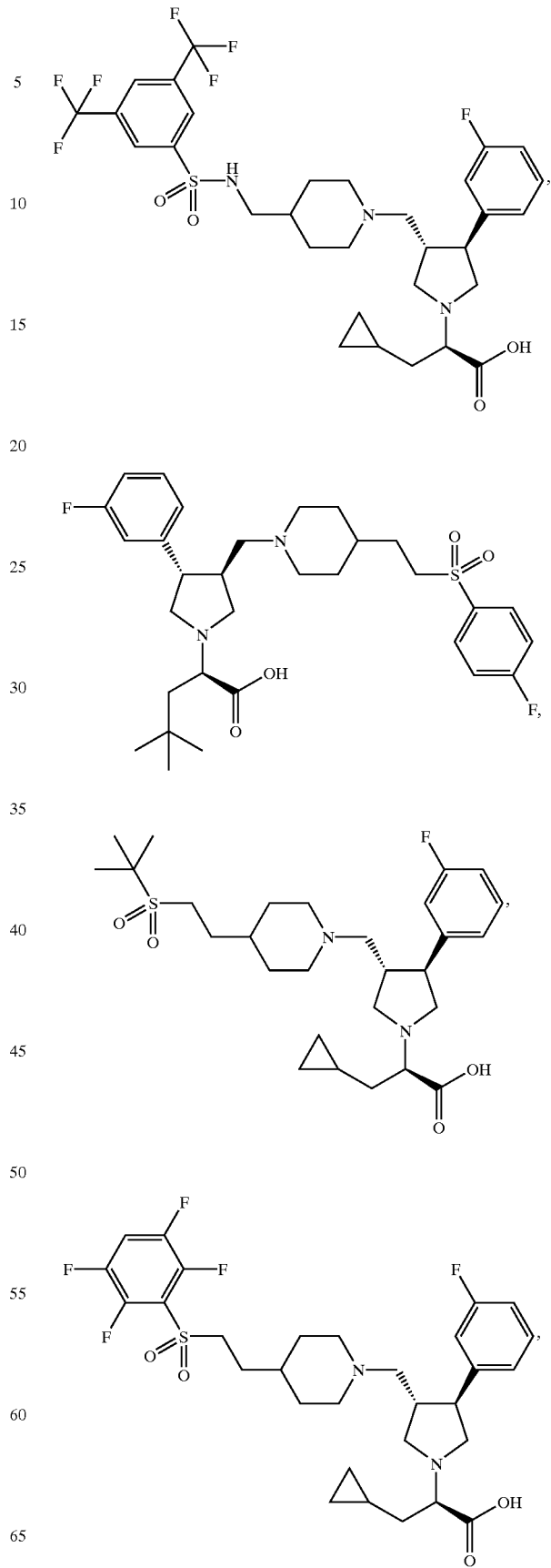

-continued

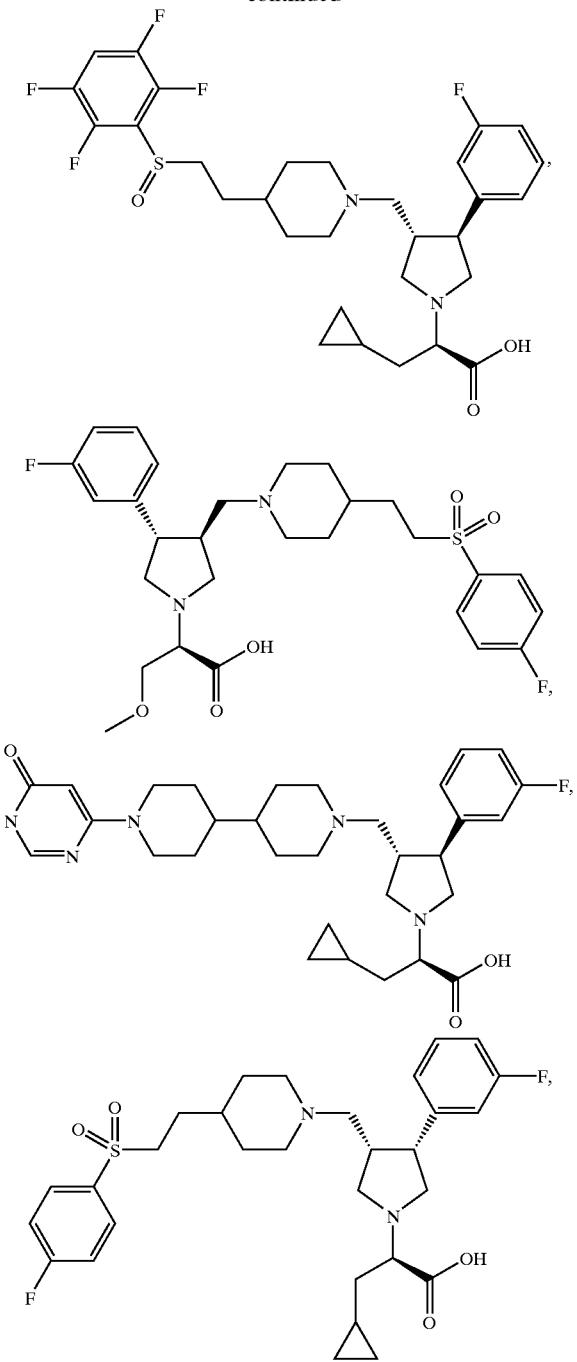

and pharmaceutically acceptable salts thereof and individual diastereomers thereof.

The subject compounds are useful in a method of modulating chemokine receptor activity in a patient in need of such modulation comprising the administration of an effective amount of the compound.

The present invention is directed to the use of the foregoing compounds as modulators of chemokine receptor activity. In particular, these compounds are useful as modulators of the chemokine receptors, including CCR-5 and/or CCR-3.

The utility of the compounds in accordance with the present invention as modulators of chemokine receptor activity may be demonstrated by methodology known in the art, such as the assay for chemokine binding as disclosed by Van Riper, et al., *J. Exp. Med.*, 177, 851–856 (1993) which may be readily adapted for measurement of CCR-5 binding, and the assay for CCR-3 binding as disclosed by Daugherty, et al., *J. Exp. Med.*, 183, 2349–2354 (1996). Cell lines for expressing the receptor of interest include those naturally expressing the receptor, such as EOL-3 or THP-1, or a cell engineered to express a recombinant receptor, such as CHO, RBL-2H3, HEK-293. For example, a CCR3 transfected AML14.3D10 cell line has been placed on restricted deposit with American Type Culture Collection in Rockville, Md. as ATCC No. CRL-12079, on Apr. 5, 1996. The utility of the compounds in accordance with the present invention as inhibitors of the spread of HIV infection in cells may be demonstrated by methodology known in the art, such as the HIV quantitation assay disclosed by Nunberg, et al., *J. Virology*, 65 (9), 4887–4892 (1991).

In particular, the compounds of the following examples had activity in binding to the CCR-5 or the CCR-3 receptor in the aforementioned assays, generally with an $IC_{50}$ of less than about 1 μM. Such a result is indicative of the intrinsic activity of the compounds in use as modulators of chemokine receptor activity.

Mammalian chemokine receptors provide a target for interfering with or promoting eosinophil and/or lymphocyte function in a mammal, such as a human. Compounds which inhibit or promote chemokine receptor function, are particularly useful for modulating eosinophil and/or lymphocyte function for therapeutic purposes. Accordingly, the present invention is directed to compounds which are useful in the prevention and/or treatment of a wide variety of inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited. For example, eosinophilic infiltration to inflammatory sites (e.g., in asthma) can be inhibited according to the present method.

Similarly, an instant compound which promotes one or more functions of a mammalian chemokine receptor (e.g., a human chemokine) is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, eosinophils can be recruited to combat parasitic infections.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the method of the present invention. In a preferred embodiment, the disease or condition is one in which the actions of eosinophils and/or lymphocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, particularly bronchial asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersentitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with promoters of chemokine receptor function, include, but are not limited to: immunosuppression, such as that in individuals with immunodeficiency syndromes such as AIDS, individuals undergoing radiation therapy, chemotherapy, therapy for autoimmune disease or other drug therapy (e.g., corticosteroid therapy), which causes immunosuppression; immunosuppression due congenital deficiency in receptor function or other causes; and infectious diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, *Taeniasis saginata*, Cysticercosis); visceral worms, visceral larva migrans (e.g., Toxocara), *eosinophilic gastroenteritis* (e.g., Anisaki spp., Phocanema ssp.), cutaneous larva migrans (*Ancylostona braziliense, Ancylostoma caninum*).

The compounds of the present invention are accordingly useful in the prevention and treatment of a wide variety of inflammatory and immunoregulatory disorders and diseases, allergic conditions, atopic conditions, as well as autoimmune pathologies.

In another aspect, the instant invention may be used to evaluate putative specific agonists or antagonists of chemokine receptors, including CCR-5 and/or CCR-3. Accordingly, the present invention is directed to the use of these compounds in the preparation and execution of screening assays for compounds which modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors, including CCR-5 and/or CCR-3. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating chemokine receptor activity in humans and animals comprising combining a compound of the present invention with a pharmaceutical carrier or diluent.

The present invention is further directed to the use of these compounds in the prevention or treatment of infection by a retrovirus, in particular, the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

In a preferred aspect of the present invention, a subject compound may be used in a method of inhibiting the binding of a chemokine to a chemokine receptor, such as CCR-5 or CCR-3, of a target cell, which comprises contacting the target cell with an amount of the compound which is effective at inhibiting the binding of the chemokine to the chemokine receptor.

The subject treated in the methods above is a mammal, preferably a human being, male or female, in whom modulation of chemokine receptor activity is desired. "Modulation" as used herein is intended to encompass antagonism, agonism, partial antagonism, inverse agonism and/or partial agonism. In a preferred aspect of the present invention, modulation refers to antagonism of chemokine receptor activity. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

Combined therapy to modulate chemokine receptor activity and thereby prevent and treat inflammatory and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in the treatment or prevention of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compounds of the pressent invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) VLA-4 antagonists such as those described in U.S. Pat. No. 5,510,332, WO95/15973, WO96/01644, WO96/06108, WO96/20216, WO96/22966, WO96/31206, WO96/4078 1, WO97/03094, WO97/02289, WO 98/42656, WO98/53814, WO98/53817, WO98/53818, WO98/54207, and WO98/58902; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (HI-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CXCR4, CCR-1, CCR-2, CCR-3 and CCR-5; (j) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), α-glucosidase inhibitors (acarbose) and glitazones (troglitazone and pioglitazone); (l) preparations of interferon beta (interferon beta-1α, interferon beta-1β); (m) other compounds such as 5-aminosalicylic acid and prodrugs thereof, antimetabolites such as azathioprine and 6-mercaptopurine, and cytotoxic cancer chemotherapeutic agents. The weight ratio of the compound of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

The present invention is further directed to combinations of the present compounds with one or more agents useful in the prevention or treatment of AIDS. For example, the compounds of this invention may be effectively administered, whether at periods of pre-exposure and/or post-exposure, in combination with effective amounts of the AIDS antivirals, immunomodulators, anti-infectives, or vaccines known to those of ordinary skill in the art.

| Drug Name | Manufacturer | Indication |
|---|---|---|
| ANTIVIRALS | | |
| 097 | Hoechst/Bayer | HIV infection, AIDS, ARC (non-nucleoside reverse transcriptase inhibitor) |
| 141 W94 | Glaxo Wellcome | HIV infection, AIDS, ARC (protease inhibitor) |

-continued

| Drug Name | Manufacturer | Indication |
|---|---|---|
| 1592U89 | Glaxo Wellcome | HIV infection, AIDS, ARC |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which neutralizes pH labile alpha aberrant Interferon | Advanced Biotherapy Concepts (Rockville, MD) | AIDS, ARC |
| AR177 | Aronex Pharm | HIV infection, AIDS, ARC |
| beta-fluoro-ddA | Nat'l Cancer Institute | AIDS-associated diseases |
| (−) 6-Chloro-4(S)-cyclopropy-lethynyl-4(S)-tri-fluoro-methyl-1,4-dihydro-2H-3,1-benzoxazin-2-one | Merck | HIV infection, AIDS, ARC (non-nucleoside reverse transcriptase inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus immune globin | MedImmune | CMV retinitis |
| Cytovene Ganciclovir | Syntex | sight threatening CMV peripheral CMV retinitis |
| Delaviridine | Pharmacia-Upjohn | HIV infection, AIDS, ARC (protease inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| EL10 | Elan Corp, PLC (Gainesville, GA) | HIV infection |
| Efavirenz (DMP 266) (−) 6-Chloro-4(S)-cyclopropy-lethynyl-4(S)-tri-fluoro-methyl-1,4-dihydro-2H-3,1-benzoxazin-2-one, | DuPont (SUSTIVA ®), Merck (STOCRIN ®) | HIV infection, AIDS, ARC (non-nucleoside RT inhibitor) |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| GW 141 | Glaxo Welcome | HIV infection, AIDS, ARC (protease inhibitor) |
| GW 1592 | Glaxo Welcome | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| Compound A | Merck | HIV infection, AIDS, ARC, asymptomatic HIV positive |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (protease inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphono-formate | Astra Pharm. Products, Inc | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydro-deoxythymidine | Bristol-Myers Squibb | HIV infection, AIDS, ARC |
| T-20 | Trimeris | HIV infection, AIDS, ARC |
| Valaciclovir | Glaxo Wellcome | genital HSV & CMV infections |
| Virazole Ribavirin | Viratek/ICN (Costa Mesa, CA) | asymptomatic HIV positive, LAS, ARC |
| Amprenivir VX-478 | Vertex | HIV infection, AIDS, ARC |
| Zalcitabine | Hoffman-La Roche | HIV infection, AIDS, ARC, with AZT |

-continued

| Drug Name | Manufacturer | Indication |
|---|---|---|
| Zidovudine; AZT | Glaxo Wellcome | HIV infection, AIDS, ARC, Kaposi's sarcoma, in combination with other therapies |
| ABT-378 | Abbott | HIV infection, AIDS, ARC (protease inhibitor) |
| JE2147/AG1776 | Agouron | HIV infection, AIDS, ARC (protease inhibitor) |
| T-20 T-1249 | Trimeris | HIV infection, AIDS, ARC (fusion inhibitor) |
| BMS 232632 | Bristol-Myers-Squibb | HIV infection, AIDS, ARC (protease inhibitor) |
| IMMUNO-MODULATORS | | |
| AS-101 | Wyeth-Ayerst | AIDS |
| Bropirimine | Pharmacia Upjohn | advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute | HIV infection |
| Tumor Necrosis Factor; TNF | Genentech | ARC, in combination w/gamma Interferon |
| etanercept | Immunex Corp (Enbrel ®) | rheumatoid arthritis |
| infliximab | Centocor (Remicade ®) | rheumatoid arthritis and Crohn's disease |
| ANTI-INFECTIVES | | |
| Clindamycin with Primaquine | Pharmacia Upjohn | PCP |
| Fluconazole | Pfizer | cryptococcal meningitis, candidiasis |
| Pastille Nystatin Pastille | Squibb Corp. | prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | cryptosporidial diarrhea |
| Intraconazole-R51211 | Janssen Pharm. | histoplasmosis; cryptococcal meningitis |
| Trimetrexate | Warner-Lambert | PCP |
| OTHER | | |
| Daunorubicin | NeXstar, Sequus | Karposi's sarcoma |
| Recombinant Human Erythropoietin | Ortho Pharm. Corp. | severe anemia assoc. with AZT therapy |
| Recombinant Human Growth Hormone | Serono | AIDS-related wasting, cachexia |
| Leukotriene B4 Receptor Antagonist | — | HIV infection |
| Megestrol Acetate | Bristol-Myers Squibb | treatment of anorexia assoc. w/AIDS |
| Soluble CD4 Protein and Derivatives | — | HIV infection |
| Testosterone | Alza, Smith Kline | AIDS-related wasting |
| Total Enteral Nutrition | Norwich Eaton Pharmaceuticals | diarrhea and malabsorption related to AIDS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Preferred combinations are simultaneous or alternating treatments with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. Preferred agents for combination therapy include: Zidovudine, Lamivudine, Stavudine, Efavirenz, Ritonavir, Nelfinavir, Abacavir, Indinavir, 141-W94 (4-amino-N-((2 syn,3S)-2-hydroxy-4-phenyl-3-((S)-tetrahydrofuran-3-yloxycarbonylamino)-butyl)-N-isobutyl-benzenesulfonamide), N-(2(R)-hydroxy-1(S)-15 indanyl)-2(R)-phenylmethyl-4-(S)-hydroxy-5-(1-(4-(2-benzo[b]furanylmethyl)-2(S)-N'(t-butylcarbox-amido)-piperazinyl))-pentaneamide, and Delavirdine. A preferred inhibitor of HIV protease is indinavir, which is the sulfate salt of N-(2(R)-hydroxy-1(S)-indanyl)-2(R)-phenylmethyl-4-(S)-hydroxy-5-(1 -(4-(3-pyridyl-methyl)-2(S)-N'-(t-butylcarbo-xamido)-piperazinyl))-pentane-amide ethanolate, and is synthesized according to U.S. Pat. No. 5,413,999. Indinavir is generally administered at a dosage of 800 mg three times a day. Other preferred inhibitors of HIV protease include nelfinavir and ritonavir. Preferred non-nucleoside inhibitors of HIV reverse transcriptase include (−) 6-chloro-4(S)-cyclopropylethynyl-4(S)-trifluoromethyl-1,4-dihydro-2H-3,1-benzoxazin-2-one, which may be prepared by methods disclosed in EP 0,582,455. The preparation of ddC, ddI and AZT are also described in EPO 0,484,071. These combinations may have unexpected effects on limiting the spread and degree of infection of HIV. Preferred combinations with the compounds of the present invention include the following: (1) Zidovudine and Lamivudine; (2) Stavudine and Lamivudine; (3) Efavirenz; (4) Ritoavir; (5) Nelfinavir; (6) Abacavir; (7) Indinavir; (8) 141-W94; and (9) Delavirdine. Preferred combinations with the compounds of the present invention further include the following (1) indinavir, with efavirenz or (−) 6-chloro-4(S)-cyclopropylethynyl-4(S)-trifluoromethyl- 1,4-dihydro-2H-3,1-benzoxazin-2-one, and, optionally, AZT and/or 3TC and/or ddI and/or ddC; (2) indinavir, and any of AZT and/or ddI and/or ddC.

Compound A in the foregoing Table is N-(2(R)-hydroxy-1(S)-indanyl)-2(R)-phenylmethyl-4(S)-hydroxy-5-(1-(4-(2-benzo[b]furanylmethyl)-2(S)-N'-(t-butylcarboxamido)-piperazinyl))pentaneamide, preferably administered as the sulfate salt. Compound A can be prepared as described in U.S. Pat. No. 5,646,148.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally- occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In the treatment or prevention of conditions which require chemokine receptor modulation an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made from known procedures or as illustrated.

SCHEME 1

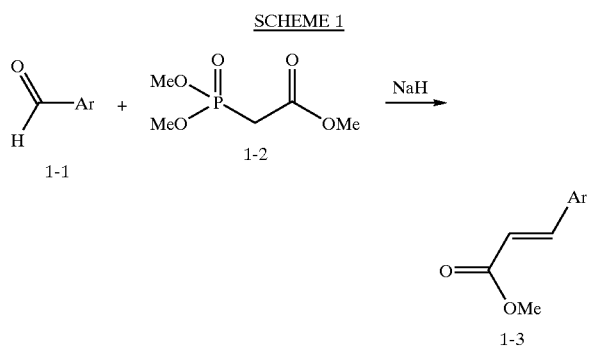

The preparation of cinnamate esters such as 1-3 as intermediates that can be used for the synthesis of compounds within the scope of the instant invention is detailed in Scheme 1. Cinnamate esters of structure 1-3 can be obtained commercially or can be synthesized by reacting a suitable aromatic aldehyde 1-1 with 5 a phosphonoacetate such as 1-2 or a stabilized Wittig reagent in the presence of sodium hydride or other bases such as sodium, lithium or potassium hexamethyldisilazide, potassium t-butoxide, and the like. The aldehyde 1-1 can be obtained commercially or can be prepared in a variety of ways from commercial materials (see March J. "Advanced Organic Chemistry", 4th ed., John Wiley & Sons, New York, pp. 1270–1271 (1992)).

SCHEME 2

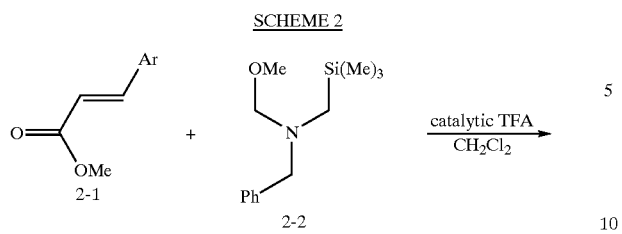

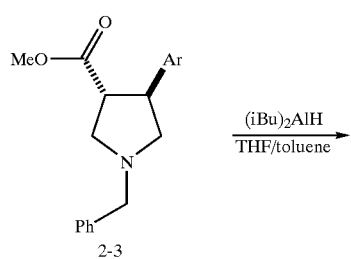

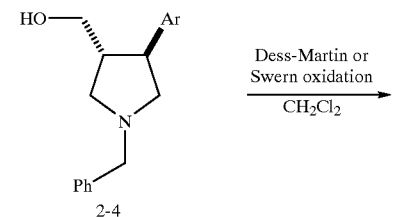

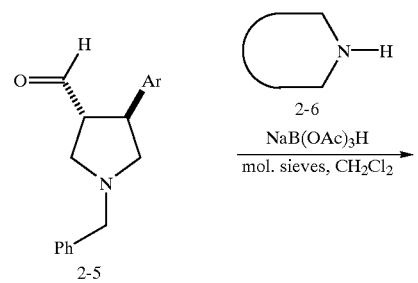

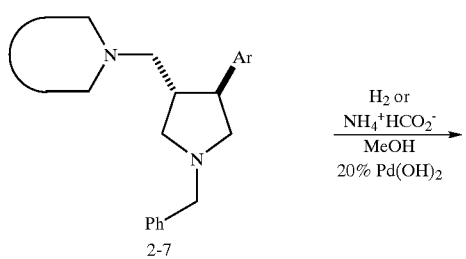

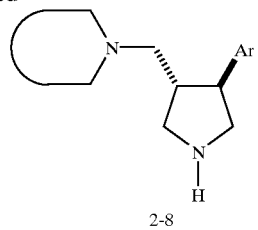

-continued

The preparation of compounds within the scope of the instant invention which bear a 1,3,4-trisubstituted pyrrolidine framework is detailed in Scheme 2. Treatment of a trans-cinnamic ester such as 2-1 with commercially available N-benzyl-N-methoxymethyl-N-(trimethylsilyl)-methylamine (2-2) in the presence of a substoichiometric amount of an acid such as TFA, titanium tetrafluoride, lithium fluoride or cesium fluoride, according to the procedure of Padwa et al (*J. Org. Chem.* 1987, 52, 235) preferentially affords the 3,4-trans pyrrolidine 2-3. Executing this sequence starting from the cis-cinnamic ester results in preferential formation of the 3,4-cis pyrrolidine. Reduction of ester 2-3, for example, with diisobutylaluminum hydride, lithium aluminium hydride, or sodium bis(2-methoxyethoxy)aluminum hydride, provides the primary alcohol 2-4. Oxidation to the aldehyde 2-5 can be carried out under numerous conditions, such as with the Dess-Martin periodinane, with DMSO and oxalyl chloride at low temperature, followed by triethylamine (Swern oxidation), or with various chromium trioxide-based reagents (see March J. "Advanced Organic Chemistry", 4th ed., John Wiley & Sons, New York, pp. 1167–1171 (1992)). Reductive amination with cyclic amine 2-6 then provides diamine 2-7, which can itself be a chemokine receptor modulator. Alternatively, the N-benzyl group is cleaved in a hydrogen atmosphere or with ammonium formate in the presence of 20% palladium hydroxide to provide the secondary amine 2-8.

SCHEME 3

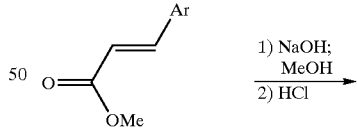

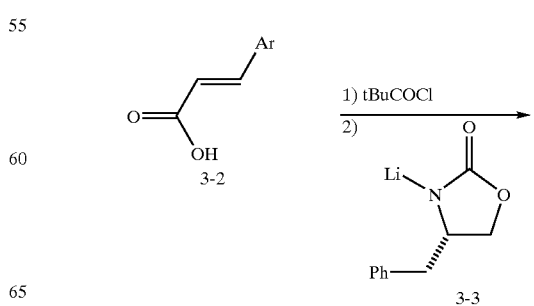

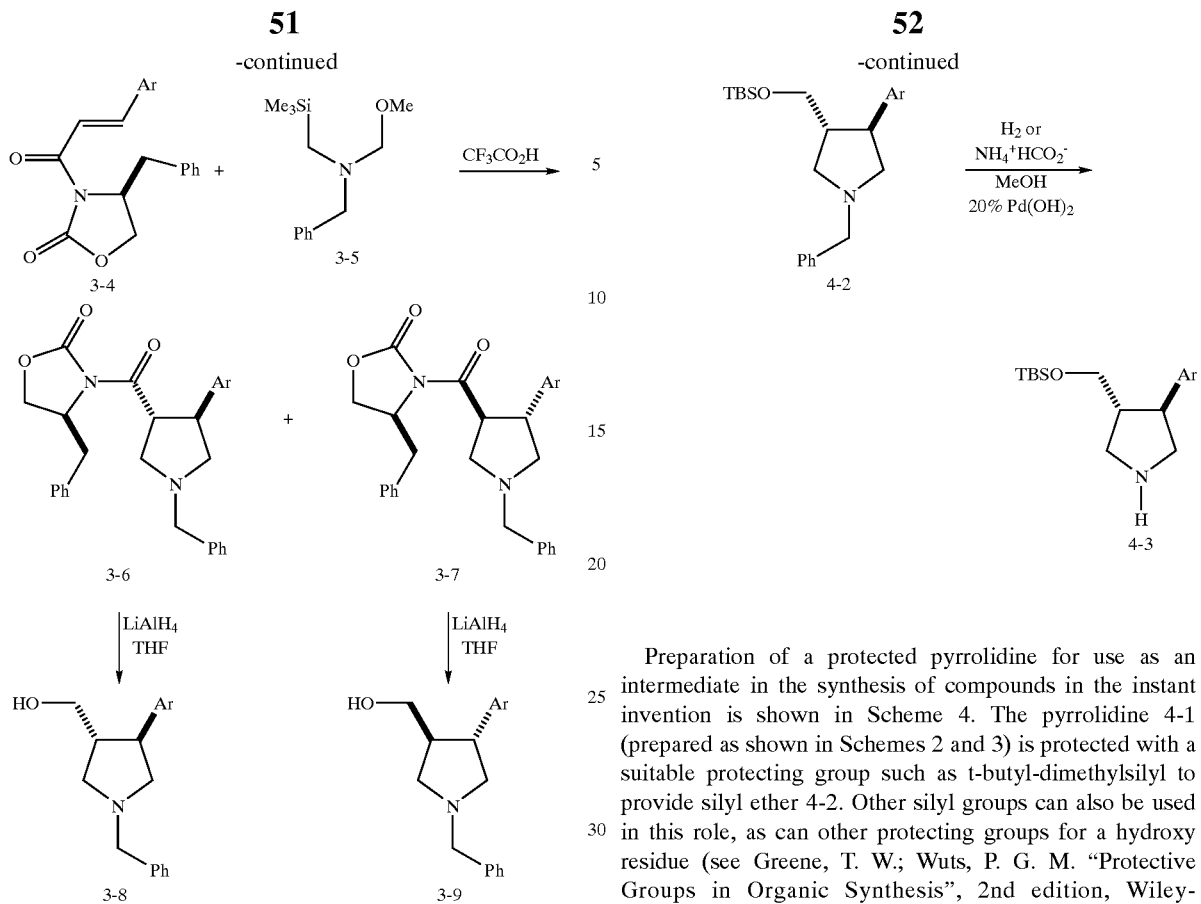

Scheme 3 shows the preparation of optically pure pyrrolidine intermediates. Hydrolysis of unsaturated ester 3-1 provided acid 3-2, which is converted to diacyl derivative 3-4 by activation of the acid group, for example by formation of a mixed anhydride with pivaloyl chloride, followed by reaction with the lithium salt of 4-(S)-benzyloxazolidin-2-one (3-3). Treatment of 3-4 with commercially available N-benzyl-N-methoxymethyl-N-(trimethylsilyl)-methylamine (2-2) in the presence of a substoichiometric amount of an acid such as TFA, titanium tetrafluoride, lithium fluoride or cesium fluoride according to the procedure of Padwa et al (*J. Org. Chem.* 1987, 52, 235) affords the diastereomeric pyrrolidines 3-6 and 3-7, which can be separated by flash chromatography, preparative thin layer chromatography, medium pressure liquid chromatography, high pressure liquid chromatography, fractional crystallization, or similar methods known in the art. The separated products are then individually reduced, for example with lithium alumum hydride (LAH) or other strong hydride reducing agents, to provide pyrrolidines 3-8 and 3-9 in optically enriched form.

Preparation of a protected pyrrolidine for use as an intermediate in the synthesis of compounds in the instant invention is shown in Scheme 4. The pyrrolidine 4-1 (prepared as shown in Schemes 2 and 3) is protected with a suitable protecting group such as t-butyl-dimethylsilyl to provide silyl ether 4-2. Other silyl groups can also be used in this role, as can other protecting groups for a hydroxy residue (see Greene, T. W.; Wuts, P. G. M. "Protective Groups in Organic Synthesis", 2nd edition, Wiley-Interscience, New York, pp. 10–143 (1991)), subject to the group being stable to conditions used to remove the benzyl group and being removable under conditions that would not adversely affect the remainder of the molecule. Removal of the benzyl group on nitrogen is then carried out by hydrogenolysis, for example by transfer hydrogenation with ammonium formate in the presence of 20% palladium hydroxide or with catalytic hydrogenation with 10% palladium on carbon under one or more atmospheres of hydrogen. Alternatively, compound 4-1 can be debenzylated first under the conditions noted above and then silylated on the hydroxy group, to provide 4-3.

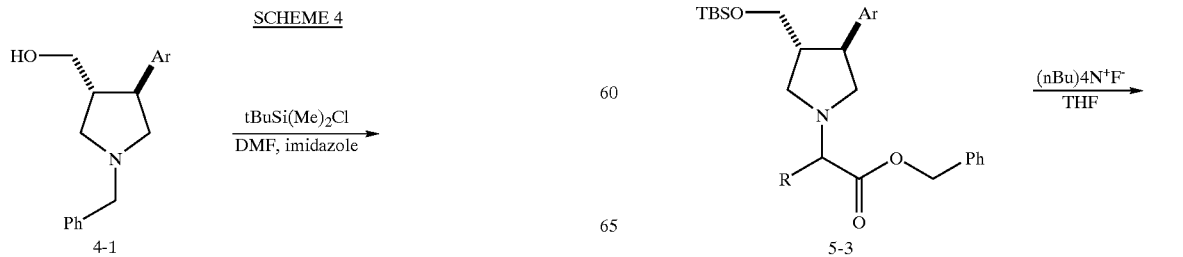

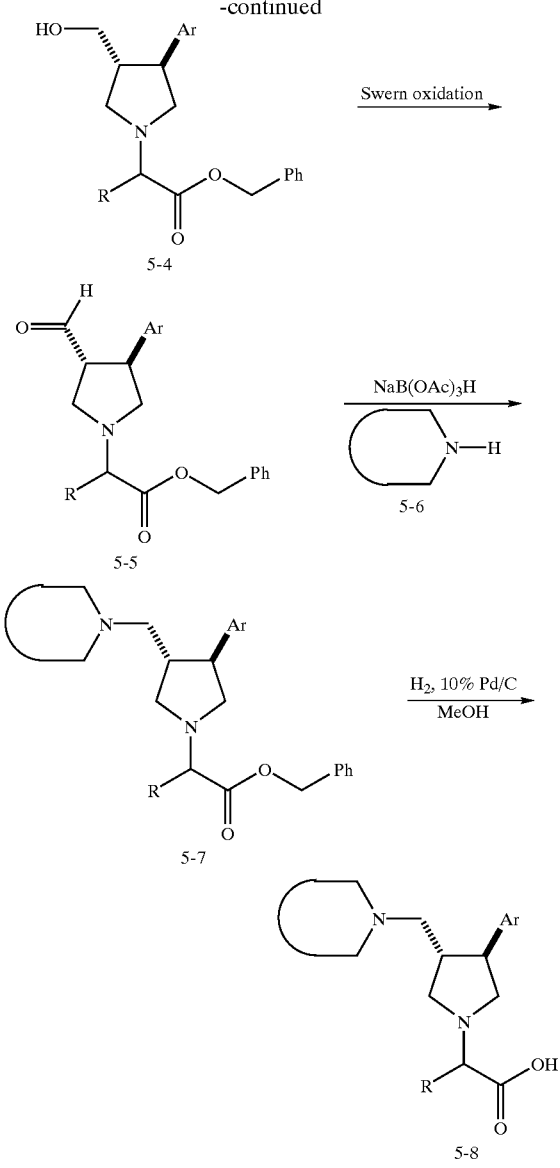

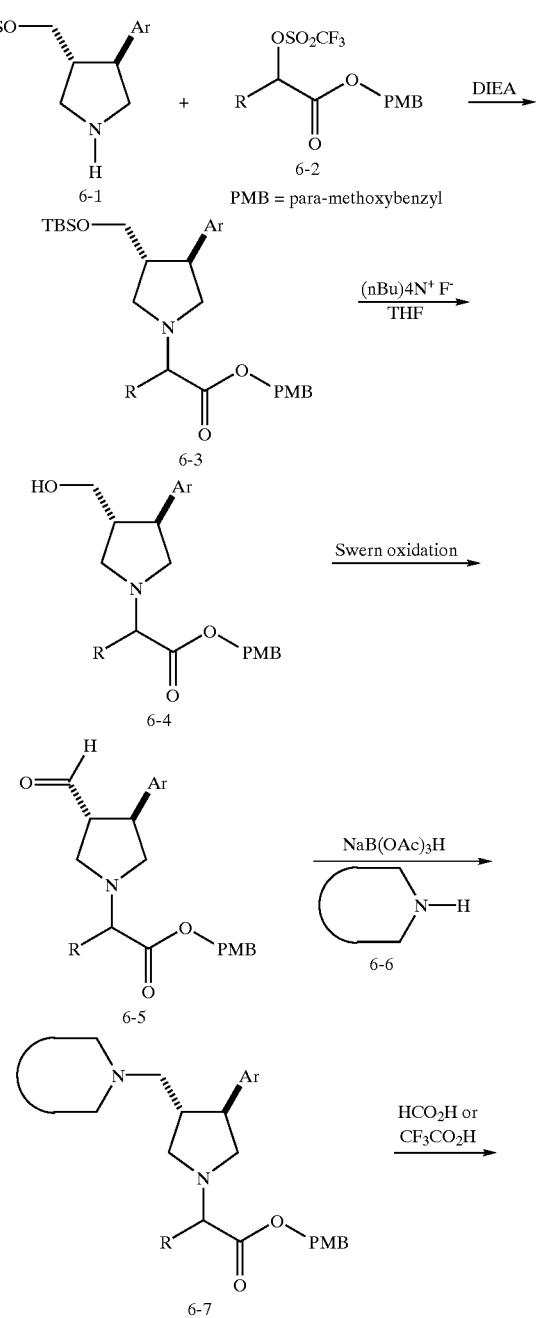

oxidation conditions. Other methods for oxidizing a primary hydroxy group to an aldehyde can also be used, for example the Dess-Martin periodinane, or with various chromium trioxide-based reagents (see March J. "Advanced Organic Chemistry", 4th ed., John Wiley & Sons, New York, pp. 1167–1171 (1992)). Reductive amination with cyclic amine 5-6 then provides diamine 5-7, which can itself be a chemokine receptor antagonist. Cleavage of the benzyl group with catalytic hydrogenation, for example under an atmosphere of hydrogen in the presence of 10% palladium on carbon as catalyst in methanol or ethanol as solvent, provides acid 5-8. Alternatively, the benzyl ester can be cleaved by treatment with strong aqueous base if the remainder of the molecule is stable to those conditions.

Preparation of some 1,3,4-trisubstituted pyrrolidines within the scope of the instant invention is given in Scheme 5. Alkylation of pyrrolidine 5-1 with the trifluoromethanesulfonate (triflate) ester of a suitable alpha-hydroxy ester derivative 5-2 in the presence of a hindered base such as DIEA ((N,N-(diisopropyl)ethylamine) or a sparingly soluble base such as potassium carbonate provides the N-substituted product 5-3. Triflate ester 5-2 is prepared by treating the parent alpha-hydroxy ester with triflic anhydride in the presence of a suitable hindered tertiary amine, such as DIEA, 2,6-lutidine or 2,6-di-t-butyl-4-methylpyridine at or below room temperature in a suitable inert solvent such as dichloromethane or 1,2-dichloroethane. Alternatively, other leaving groups can be employed to activate the alpha-position on ester 5-2 instead of a triflate, such as chloride, bromide, iodide, methanesulfonate, p-toluenesulfonate, etc. Deprotection of silyl ether 5-3 is carried out with tetrabutylammonium fluoride in THF, to afford alcohol 5-4. Alternatively, acidic conditions can be used to remove the silyl group, for example aqueous trifluoroacetic acid, hydrogen fluoride in pyridine, hydrochloric acid, etc. Oxidation of 5-4 to the aldehyde 5-5 is accomplished using the Swern

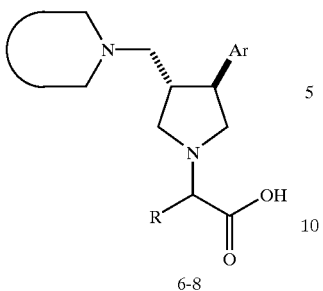

Preparation of 1,3,4-trisubstituted pyrrolidines with in the scope of the instant invention wherein the carboxylic acid protecting group is cleavable under mild acidic conditions is given in Scheme 6. Alkylation of pyrrolidine 6-1 with the triflate ester of a suitable alpha-hydroxy ester derivative 6-2 in the presence of a hindered bas e such as DIEA or a sparingly soluble base such as potassium carbonate provides the N-substituted product 6-3 (PMB=para-methoxybenzyl). Triflate ester 6-2 is prepared by treating the parent alpha-hydroxy ester with triflic anhydride in the presence of a suitable hindered tertiary amine, such as DIEA, 2,6-lutidine or 2,6-di-t-butyl-4-methylpyridine at or below room temperature in a suitable inert solvent such as dichloromethane or 1,2-dichloroethane. Alternatively, other leaving groups can be employed to activate the alpha-position on ester 6-2 instead of a triflate, such as chloride, bromide, iodide, methanesulfonate, p-toluenesulfonate, etc. Deprotection of silyl ether 6-3 is carried out with tetrabutylammonium fluoride in THF, to afford alcohol 6-4. Alternatively, mildly acidic conditions in some cases can be used to selectively remove the silyl group, for example aqueous trifluoroacetic acid, hydrogen fluoride in pyridine, hydrochloric acid, etc. Oxidation of 6-4 to the aldehyde 6-5 is accomplished using the Swern oxidation conditions. Other methods for oxidizing a primary hydroxy group to an aldehyde can also be used, for example the Dess-Martin periodinane, or with various chromium trioxide-based reagents (see March J. "Advanced Organic Chemistry", 4th ed., John Wiley & Sons, New York, pp. 1167–1171 (1992)). Reductive amination with cyclic amine 6-6 then provides diamine 6-7, which can itself be a chemokine receptor antagonist. Cleavage of the PMB group with acid, for example with formic acid or trifluoroacetic acid plus anisole, provides acid 6-8. Alternatively, the ester can be cleaved by treatment with strong aqueous base or by catalytic hydrogenation if the remainder of the molecule is stable to those conditions.

SCHEME 7

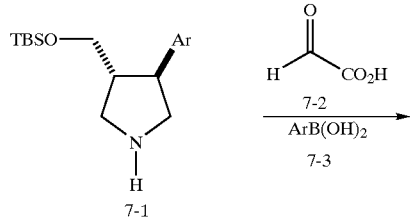

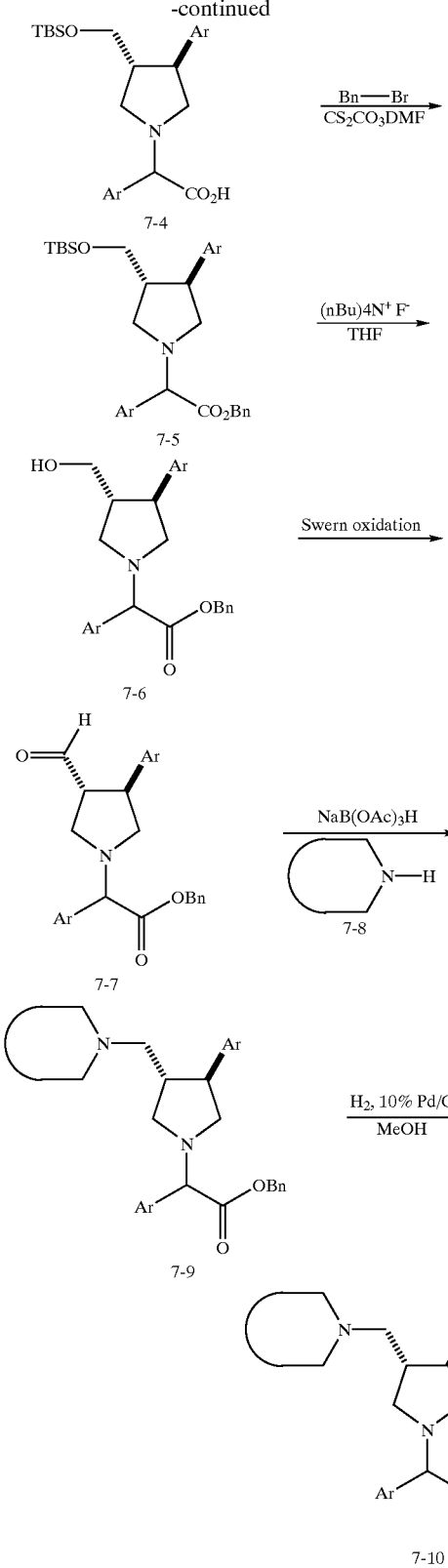

An alternative route for the synthesis of pyrrolidines with a 1-(α-arylacetic acid) substituent is given in Scheme 7. Reaction of the protected pyrrolidine 7-1 with glyoxylic acid in the presence of an aryl boronic acid 7-3 provides the N-aralkylated product 7-4 (see Petasis, N. A.; Goodman, A.;

Zavialov, I. A. *Tetrahedron* 1997, 53, 16463–16470; and PCT Int. Appl. WO 9800398). Protection of the acid by alkylation with benzyl bromide in DMF in the presence of cesium carbonate provides ester 7-5. Deprotection of the silyl group with tetrabutylammonium fluoride in THF, or with mild acid such as aqueous trifluoroacetic acid, then provides alcohol 7-6. Alternatively, simultaneous removal of the silyl group of 7-4 and formation of the ester can be carried out by heating 7-4 in an anhydrous solution of the esterifying alcohol in the presence of acid, such as toluenesulfonic acid, triflic acid, hydrochloric acid, and the like. The alcohol 7-6 is oxidized to aldehyde 7-7 using the Swern oxidation conditions. Other methods for oxidizing a primary hydroxy group to an aldehyde can also be used, for example the Dess-Martin periodinane, or with various chromium trioxide-based reagents (see March J. "Advanced Organic Chemistry", 4th ed., John Wiley & Sons, New York, pp. 1167–1171 (1992)). Reductive amination with cyclic amine 7-8 then provides diamine 7-9, which can itself be a chemokine receptor antagonist. Deprotection of the benzyl ester is carried out with catalytic hydrogenation, for example under an atmosphere of hydrogen in the presence of 10% palladium on carbon as catalyst in methanol or ethanol as solvent, provides acid 7-10. Alternatively, the benzyl ester can be cleaved by treatment with strong aqueous base if the remainder of the molecule is stable to those conditions.

SCHEME 8

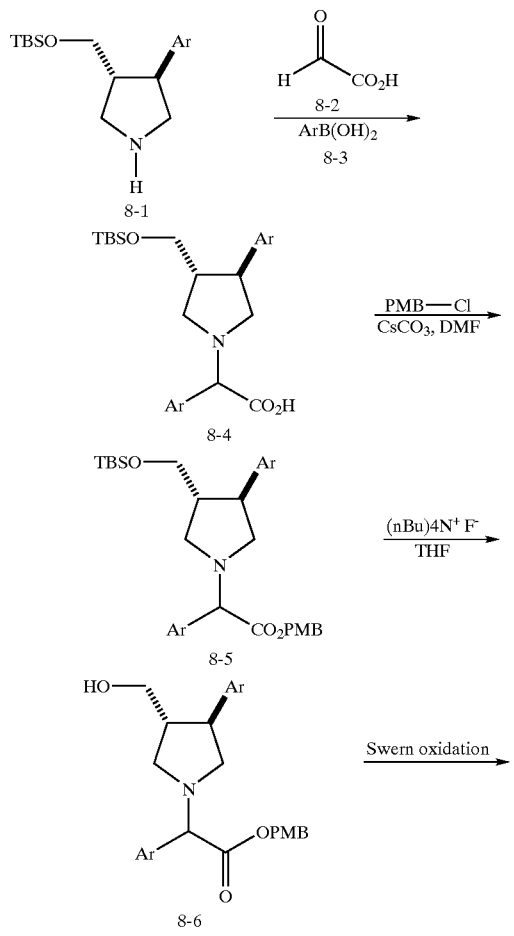

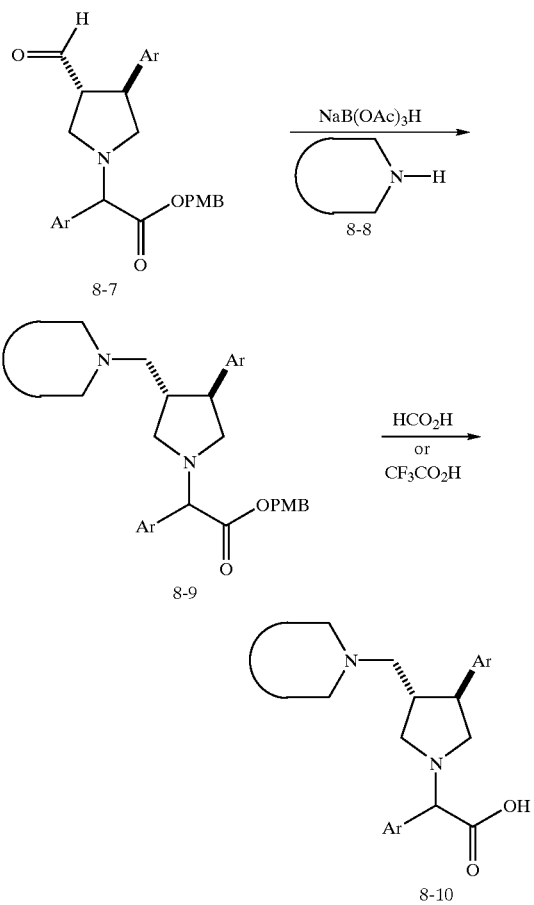

An alternative route for the synthesis of pyrrolidines with a 1-(α-arylacetic acid) substituent, wherein the carboxylic acid protecting group can be cleaved in mild acid, is given in Scheme 8. Reaction of the protected pyrrolidine 8-1 with glyoxylic acid in the presence of an arylboronic acid 8-3 provides the N-aralkylated product 8-4, according to the procedure of Petasis, N. A.; Goodman, A.; Zavialov, I. A. *Tetrahedron* 1997, 53, 16463–16470 (see also PCT Int. Appl. WO 9800398). Protection of the acid by alkylation with para-methoxybenzyl chloride in DMF in the presence of cesium carbonate provides ester 8-5. Deprotection of the silyl group with tetrabutylammonium fluoride in THF, provides alcohol 8-6. The alcohol 8-6 is oxidized to aldehyde 8-7 using the Swern oxidation conditions. Other methods for oxidizing a primary hydroxy group to an aldehyde can also be used, for example the Dess-Martin periodinane, or with various chromium trioxide-based reagents (see March J. "Advanced Organic Chemistry", 4th ed., John Wiley & Sons, New York, pp. 1167–1171 (1992)). Reductive amination with cyclic amine 8-8 then provides diamine 8-9, which can itself be a chemokine receptor antagonist. Deprotection of the p-methoxybenzyl ester is carried out by treatment with formic acid, trifluroacetic acid plus anisole, or other moderate acids, at temperatures from 0 degrees C to 120 degrees C, to provide the chemokine receptor antagonist 8-10.

SCHEME 9

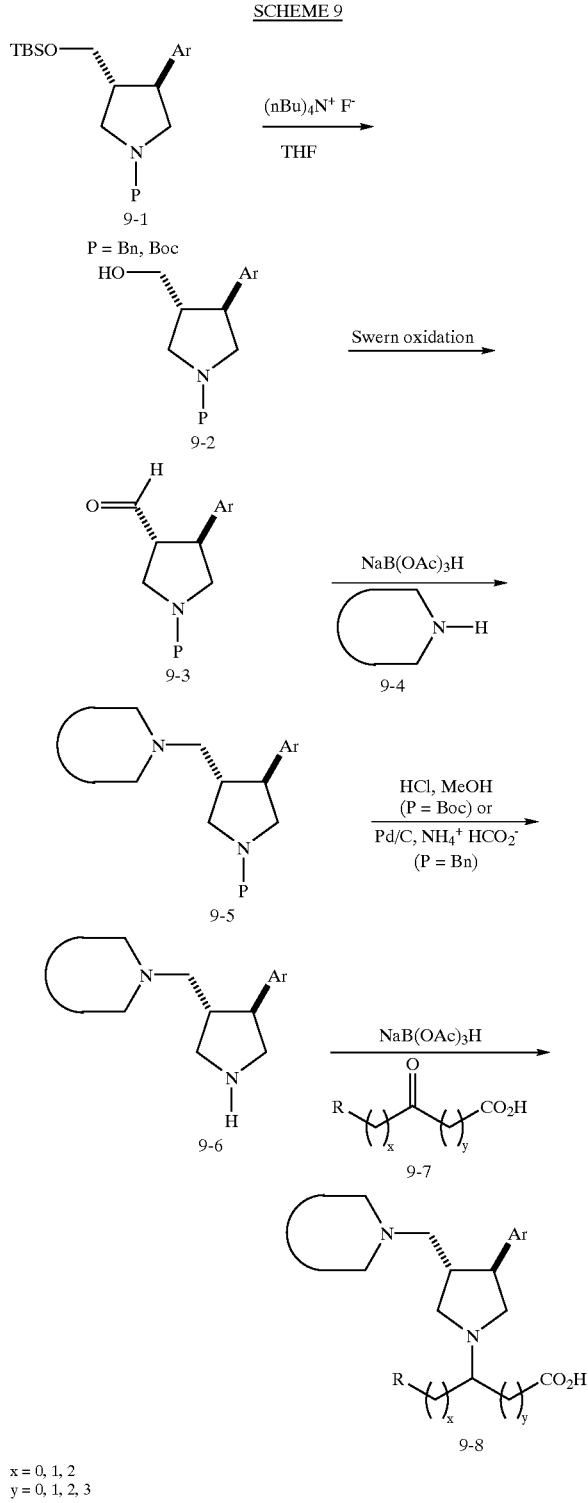

x = 0, 1, 2
y = 0, 1, 2, 3

Another method of preparing compounds within the scope of the instant invention is given in Scheme 9. Doubly protected pyrrolidine 9-1 (obtained either as shown in Scheme 4 for 4-2 when P=benzyl or by protection of 4-3 with Boc anhydride in THF/water in the presence of triethylamine when P=Boc) is desilylated with tetrabutylammonium fluoride in THF to provide alcohol 9-2. Oxidation of 9-2 to 9-3 is carried out using Swern's oxidation conditions. Other methods for oxidizing a primary hydroxy group to an aldehyde can also be used, for example the Dess-Martin periodinane, or with various chromium trioxide-based reagents (see March J. "Advanced Organic Chemistry", 4th ed., John Wiley & Sons, New York, pp. 1167–1171 (1992)). Reductive amination with cyclic amine 9-4 then provides diamine 9-5, which can itself be a chemokine receptor antagonist. Deprotection of the pyrrolidine nitrogen, when P=Boc, can be carried out with HCl in methanol or with trifluoroacetic acid and anisole in dichloromethane, to give secondary amine 9-6. When P=benzyl, debenzylation is carried out in the presence of palladium on carbon as a catalyst, using either hydrogen gas or ammonium formate to effect transfer hydrogenation. Reductive amination with keto-acid 9-7 then provides pyrrolidine 9-8.

SCHEME 10

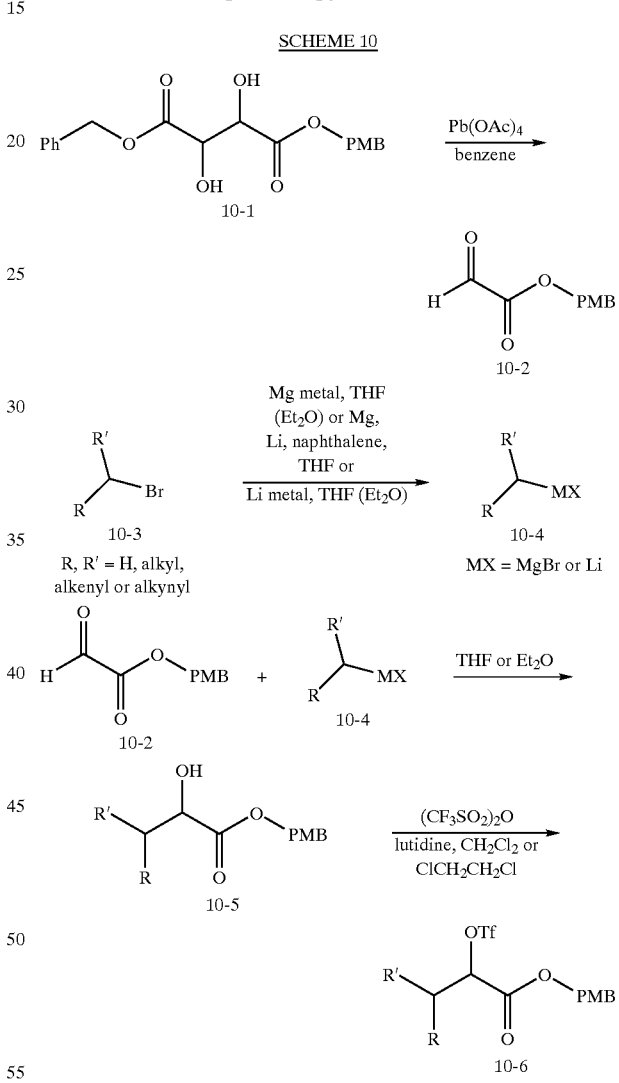

Scheme 10 illustrates preparation of intermediate 2-alkyl-2-trifluoromethanesulfonoxyacetic acid derivatives when the 1-alkyl-1-hydroxyacetic acid is not commerically available. Treatment of the para-methoxybenzyl ester of tartaric acid with lead tetraacetate in benzene provides the glyoxylic ester 10-2. Separately, a commercially available alkyl bromide (such as cyclobutylmethyl bromide) is treated with magnesium metal (in the absence or presence of lithium/naphthalene) or with lithium metal to provide the organometallic intermediate 10-4. Adding 10-4 to the aldehyde 10-2 provides the 2-hydroxy-ester 10-5. Formation of the trifluoromethanesulfonate ester is carried out under standard conditions (for example, with trifluoromethansulfonic anhydride in the presence of a hindered base such as 2,6-lutidine or DIEA in a halogenated solvent at between −78 degrees C to room temperature, preferably near 0 degrees C, to give 10-6, which is then employed as described above.

SCHEME 11

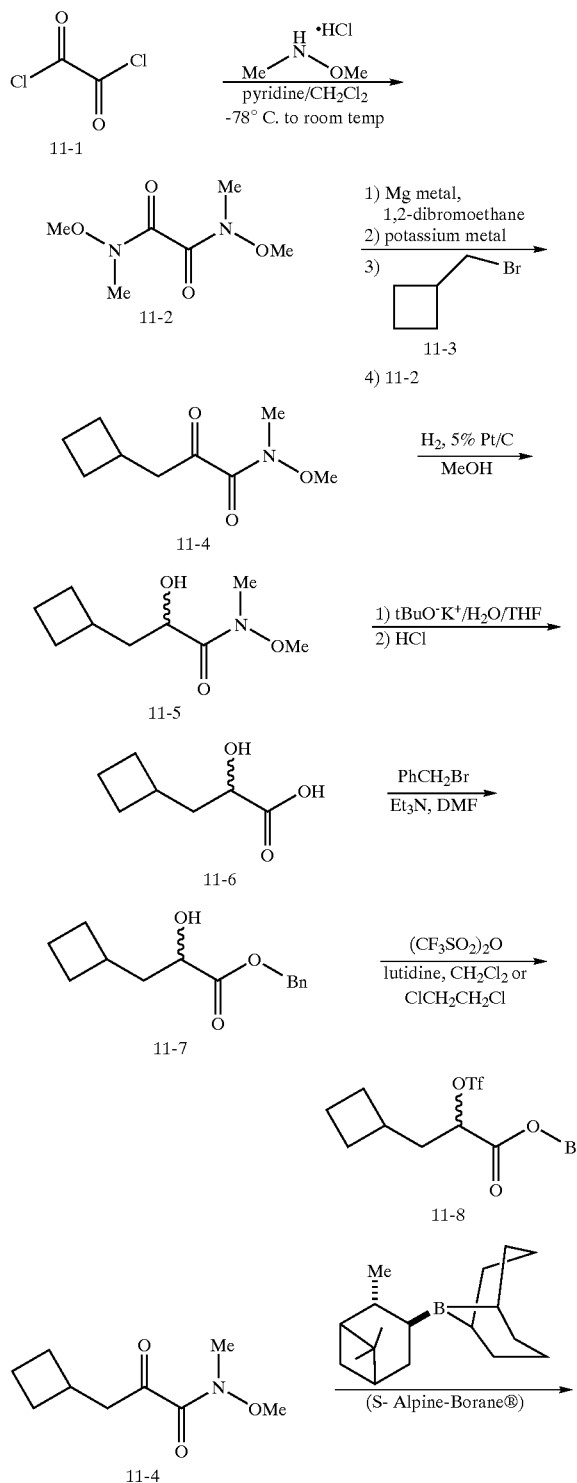

-continued

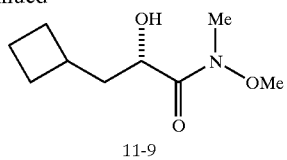

11-9

Scheme 11 illustrates an alternate preparation of intermediate 2-alkyl-2-trifluoromethanesulfonoxyacetic acid derivatives; in this example, the side chain is exemplified by a cyclobutylmethyl subunit. Treatment of oxalyl chloride (11-1) with N-methyl-N-methoxyamine hydrochloride in the presence of pyridine yields the bis amide 11-2 (also called the bis-Weinreb amide). In a separate vessel, formation of magnesium dibromide in THF, followed by addition of potassium metal, forms a very reactive grade of magnesium metal. Addition of a suitable aliphatic bromide or iodide, for example cyclobutylmethyl bromide (11-3), provides the desired organomagnesium reagent in situ. Addition of bis-amide 11-2, followed by suitable workup, affords the keto-ester 11-4. This compound is reduced by hydrogenation in the presence of 5% platinum on carbon and triethylamine to the racemic alcohol 11-5. Hydrolysis with potassium t-butoxide in THF/water followed by acidification yields the hydroxy acid 11-6. Acid 11-6 is then protected, for example as the benzyl ester, by treatment with benzyl bromide and triethylamine in DMF, to provide 11-7. This ester is then activated with triflic anhydride (or other triflating agents) under the usual conditions. Alternatively, keto-ester 11-4 can be reduced enantioselectively, for example with B-isopinocampheyl-9-borabicyclo[3.3.1]nonane (also known as S-Alpine-borane® to provide S-hydroxy derivative 11-9, which can be carried through the rest of the sequence as for 11-5.

SCHEME 12

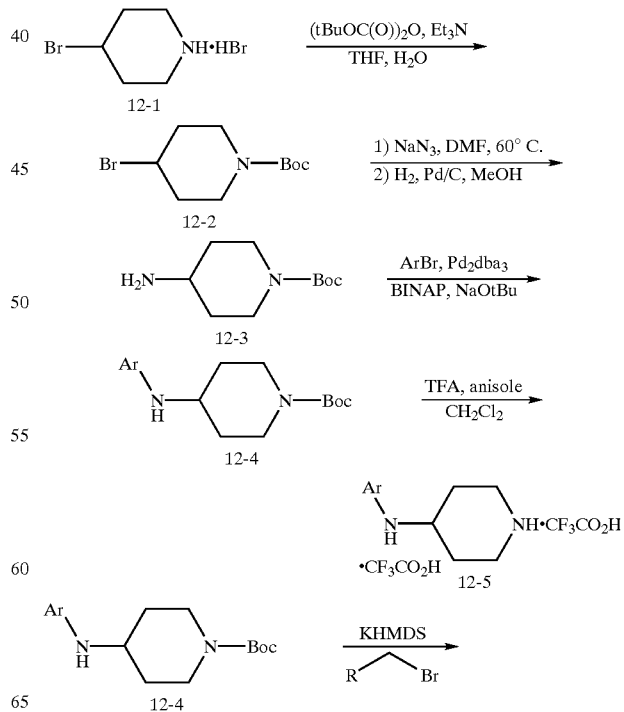

-continued

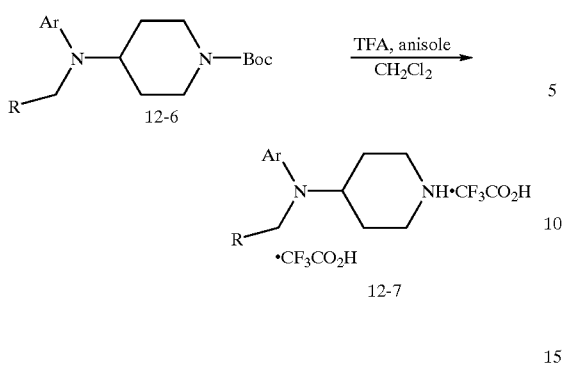

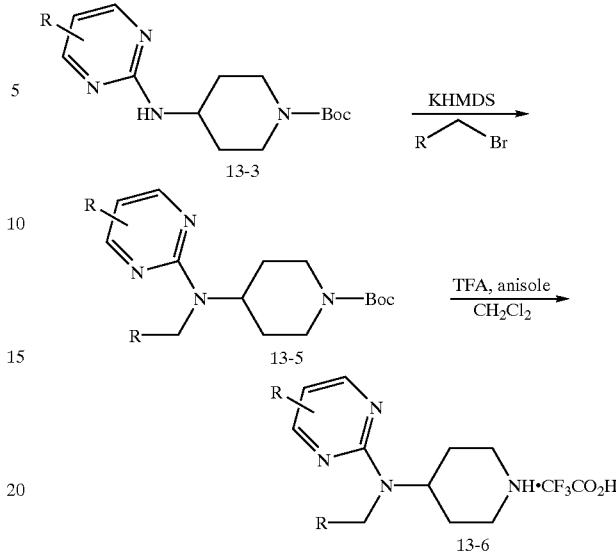

Procedures for synthesizing certain CCR5 receptor modulators containing 4-(heteroarylamino)piperidine functionality are shown in Scheme 12. After protecting commercially available 4-bromopiperidine, the bromide is diplaced with sodium azide, and the azide is reduced, for example by catalytic reduction, to provide aminopiperidine 12-3. Treatment of 12-3 with an aryl or heteroaryl halide (the halide preferably being bromide) in the presence of a palladium catalyst, sodium t-butoxide and a suitable bidentate ligand (such as BINAP), according to the conditions of Buchwald et al., provides arylamine 12-4. Direct acidic deprotection of 12-4 may be carried out to provide secondary amine 12-5. Alternatively, amine 12-4 may be alkylated with a suitable alkyl, alkenyl or alkynyl halide (wherein the halide is bromo or iodo in the case of an alkyl group and chloro or bromo in the case of allylic or propargylic functionality) in the presence of a strong base, such as potassium hexamethyldisilazide, to provide trisubstituted amine 12-6. Acidic deprotection, for example, trifluoroacetic acid and anisole in dichloromethane, or methanolic hydrochloric acid, then provides the bis ammonium salt, which in the case of trifluoroacetic acid deprotection, is compound 12-7. The secondary piperidines 12-5 and 12-7 are then utilized as the cyclic secondary amine component as shown above in Scheme 2 and in Schemes 5-9.

SCHEME 13

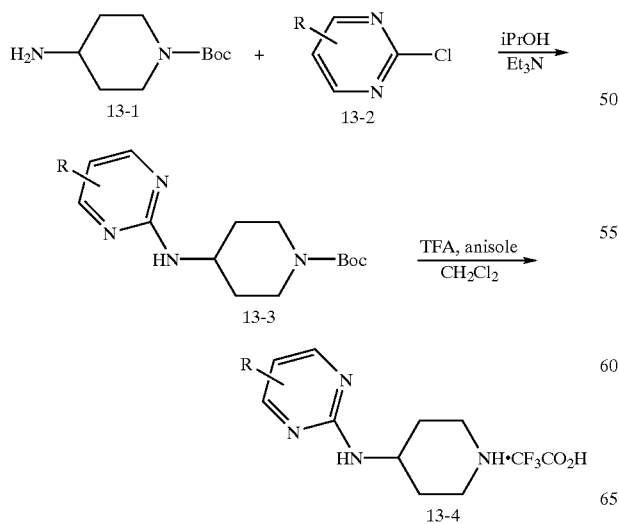

For certain aminoheterocycles, direct displacement of a halogen may provide improved access to the desired intermediates. For example, as shown in Scheme 13, unsubstituted and substituted 2-chloropyrimidines 13-2 may be coupled directly to amine 13-1 in the presence of a suitable base, such as triethylamine, to provide aminopyrimidine 13-3. Acidic deprotection then affords 13-4. Alternatively, 13-3 may be alkylated in the presence of a strong base to provide 13-5, which upon deprotection gives intermediate 13-6. The secondary piperidines 13-4 and 13-6 are then utilized as the cyclic secondary amine component as shown above in Scheme 2 and in Schemes 5-9.

SCHEME 14

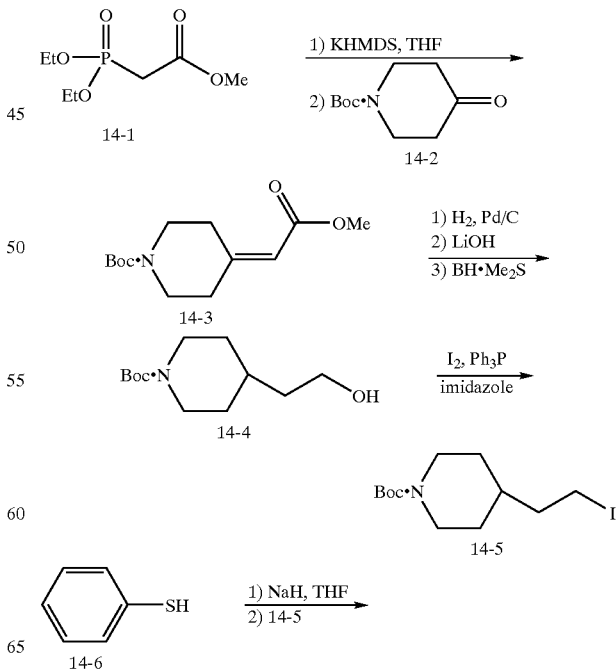

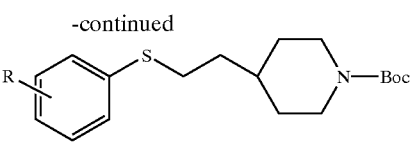

14-7

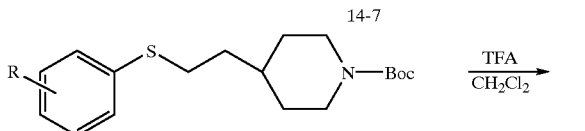

14-7

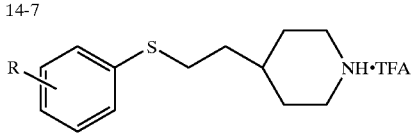

14-8

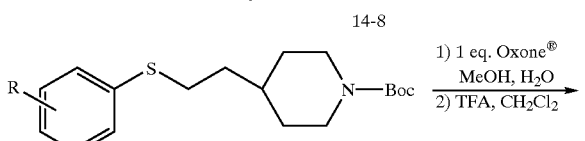

14-7

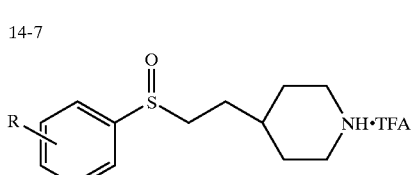

14-9

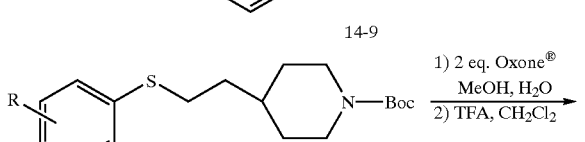

14-7

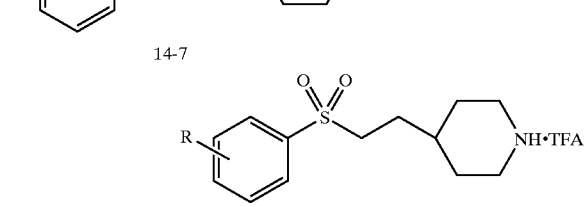

14-10

Procedures for synthesizing the present compounds containing 4-(2-(arylthio)ethyl)piperidine functionality are shown in Scheme 14. Treatment of phosphonoacetate 14-1 with KHMDS followed by addition of commercially available N-Boc-4-piperidone 14-2 provides unsaturated ester 14-3. Hydrogenation of 14-3 followed by hydrolysis to the acid and then reduction with boranemethyl sulfide then affords primary alcohol 14-4. Treatment with iodine and triphenylphosphine under standard conditions yields iodide 14-5. Reaction of the anion of a suitable aryl sulfide 14-6 with iodide 14-5 affords 4-(2-(arylthio)ethyl)-piperidine derivative 14-7. Sulfide can be deprotected directly under acidic conditions to give piperidine 14-8. Alternatively, the sulfur may be oxidized with one or two equivalents of a mild oxidizing agent such as Oxone® or mCPBA (m-chloroperoxybenzoic acid) to provide the corresponding sulfoxide or sulfone, respectively. In each case, the Boc group can be removed to provide sulfoxide 14-9 and sulfone 14-10. Each of these N-unsubstituted piperidines are then utilized as the cyclic secondary amine component as shown above in Scheme 2 and in Schemes 5-9.

In some cases the order of carrying out the foregoing reaction schemes may be varied to facilitate the reaction or to avoid unwanted reaction products. The following examples are provided for the purpose of further illustration only and are not intended to be limitations on the disclosed invention.

GENERAL

Concentration of solutions was carried out on a rotary evaporator under reduced pressure. Flash chromatography was carried out on silica gel (230–400 mesh). NMR spectra were obtained in CDCl$_3$ solution unless otherwise noted. Coupling constants (J) are in hertz (Hz). Abbreviations: diethyl ether (ether), triethylamine (TEA), N,N-diisopropylethylamine (DIEA) saturated aqueous (sat'd), room temperature (rt), hour(s) (h), minute(s) (min).

HPLC CONDITIONS

HPLC A. Retention time using the following conditions: Column: YMC ODS A, 5$\mu$, 4.6×50 mm; Gradient Eluant: 10:90 to 90:10 v/v CH$_3$CN/H$_2$O+0.5% TFA over 4.5 min, hold 30 sec; Detection: PDA, 210–400 nm; Flow Rate: 2.5 mL/min.

HPLC B. Retention time using the following conditions: Column: Analytical Sales & Services Advantage HL C18 5$\mu$ 4.6×100 mm column; Gradient Eluant: 10:90 to 90:10 v/v CH$_3$CN/H$_2$O+0.5% TFA over 10 min, hold 2 min; Detection: PDA, 200–400 nm; Flow Rate: 2.25 mL/min.

PYRROLIDINE 1

3-(R)-(t-Butyldimethylsilyloxymethyl)-4-(S)-phenylpyrrolidine

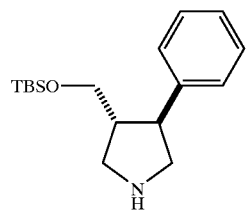

Step A: 3-((E)-Cinnamoyl)-4-(S)-benzyl Oxazolidin-2-one

A solution of 222 g (1.5 mol) of trans-cinnamic acid and 250 mL (1.77 mol) of TEA in 3 L of THF at −78° C. was treated with 200 mL of trimethylacetyl chloride maintaining the internal temperature at less than −65° C. The resulting mixture was warmed to 0° C., then cooled to −78° C.

In a separate flask, a solution of 4-(S)-benzyl-oxazolidin-2-one in 2.05 L of THF at −20° C. was treated with 660 mL of 2.5 M n-butyllithium in hexanes over 45 min. The resulting turbid mixture was cooled to −78° C. and then transferred via cannula to the flask containing the mixed anhydride. The resulting mixture was allowed to warm to rt and was stirred for 20 h. The reaction was quenched with 300 mL of sat'd NH$_4$Cl; the resulting mixture was partitioned between EtOAc and H$_2$O and the layers were separated. The organic layer was dried over MgSO$_4$. The aqueous layer was extracted with 2×EtOAc; the extracts were dried and all of the organic extracts were combined. Partial concentration in vacuo caused precipitation of a solid; the mixture was diluted with hexanes and allowed to stand at rt for 1.5 h. The precipitate was filtered and dried to afford 402.2 g (87%) of the title compound: $^1$H NMR (500 MHz) δ 2.86 (dd, J=13.5, 9.5, 1H), (3.38, J=13.5, 3.5, 1H), 4.20–4.27 (m, 2H), 4.78–4.83 (m, 1H), 7.24–7.42 (5H), 7.63–7.65 (m, 1H), 7.92 (app d, J=2.5, 1H).

Step B: 3-(1-Benzyl-4-(S)-phenylpyrrolidine-3-(R)-carbonyl)-4-(S)-benzyl Oxazolidin-2-one and 3-(1-Benzyl-4-(R)-phenyl-pyrrolidine-3-(S)-carbonyl)-4-(S)-benzyl Oxazolidin-2-one A solution of 402 g (1.3 mol) of 3-((E)-cinnamoyl)4-(S)-benzyl oxazolidin-2-one (from Step A) and 474 g (2.0 mol) of N-methoxymethyl-N-trimethylsilylmethyl benzyl amine in 4 L of CH$_2$Cl$_2$ at −10° C. was treated with 6 mL of trifluoroacetic acid. The resulting mixture was stirred cold for 4 h and then was treated with an additional 4 mL of trifluoroacetic acid. The reaction mixture was warmed to rt and stirred for 20 h. The reaction was quenched with 2 L of sat'd NaHCO$_3$ and the layers were separated. The organic layer was washed with 1 L of sat'd NaCl and concentrated. Chromatography on 10 kg of silica gel using 4:1 v/v hexanes/EtOAc (24 L), then 7:3 v/v hexanes/EtOAc (36 L), then 3:2 v/v hexanes/EtOAc (32 L) afforded 260.9 g (45%) of 3-(1-benzyl-4-(S)-phenylpyrrolidine-3-(R)-carbonyl)-4-(S)-benzyl oxazolidin-2-one and 247.5 g (43%) of 3-(1-benzyl-4-(R)-phenyl-pyrrolidine-3-(S)-carbonyl)-4-(S)-benzyl oxazolidin-2-one. For 3-(1-benzyl-4-(S)-phenylpyrrolidine-3-(R)-carbonyl)-4-(S)-benzyl oxazolidin-2-one: $^1$H NMR (500 MHz) δ 2.66 (t, J=8.0, 1H), 2.78 (dd, J=13.0, 9.0, 1H), 2.87 (dd, J=9.0, 4.5, 1H), 3.21–3.27 (m, 2H), 3.64 (d, J=11.5, 1H), 3.77 (d, J=11.5, 1H), 4.10–4.15 (m, 2H), 4.61–4.65 (m, 1H), 7.16–7.38 (15H). For 3-(1-benzyl-4-(R)-phenylpyrrolidine-3-(S)-carbonyl)-4-(S)-benzyl oxazolidin-2-one: $^1$H NMR (500 MHz) δ 2.69–2.76 (m, 2H), 2.82 (dd, J=9.5, 5.5, 1H), 3.14–3.22 (3H), 3.64 (d, J=13.0, 1H), 3.74 (d, J=13.0, 1H), 4.07–4.12 (m, 2H), 4.16 (t, J=9.0, 1H), 4.26–4.30 (m, 1H), 4.65–4.69 (m, 1H), 7.03–7.40 (15H).

Step C: 1-Benzyl-3-(R)-hydroxymethyl-4-(S)-phenylpyrrolidine

A solution of 3-(1-benzyl-4-(S)-phenylpyrrolidine-3-(R)-carbonyl)-4-(S)-benzyl oxazolidin-2-one (from Step B) in 2.5 L of THF at 10° C. was treated with 1.18 L of 1.0 M lithium aluminum hydride solution in THF over a period of 2 h. The resulting mixture was warmed to rt and stirred for 20 h. The reaction was quenched by adding 40 mL of H$_2$O, then 40 mL of 2.0 N NaOH, then 115 mL of H$_2$O and then was stirred at rt for 1.5 h. The mixture was filtered and the filtrate was concentrated. Chromatography on 4 kg of silica using 4:1 hexanes/acetone (14 L), then 7:3 hexanes/acetone as the eluant to afford 108.4 g (69%) of the title compound: $^1$H NMR (400 MHz) δ 2.38–2.46 (m, 2H), 2.78–2.88 (3H), 3.20–3.26 (2H), 3.65 (dd, J=12.0, 4.0, 1H), 3.66 (app s, 2H), 3.74 (dd, J=12.0, 4.0, 1H), 7.18–7.34 (10H); ESI-MS 268 (M+H); HPLC A: 2.35 min.

Step D: 1-Benzyl-3-(R)-(t-butyldimethylsilyloxymethyl)-4-(S)-phenylpyrrolidine

A solution of 82.0 g (0.31 mol) of 1-benzyl-3-(R)-hydroxymethyl-4-(S)-phenyl pyrrolidine (from Step C) and 46.5 g (0.36 mol) of N,N-diisopropylethylamine in 1 L of CH$_2$Cl$_2$ was treated with 54.2 g (0.36 mol) of t-butyldimethylsilyl chloride and the resulting mixture was stirred at rt for 20 h. The reaction was quenched with 750 mL of sat'd NaHCO3 and the layers were separated. The organic layer was combined with 150 g of silica gel and aged for 45 min. The mixture was filtered and the filtrate was concentrated to afford 117 g (100%) of the title compound.

Step E: 3-(R)-(t-Butyldimethylsilyloxymethyl)-4-(S)-phenylpyrrolidine

A mixture of 117 g (0.31 mol) of 1-benzyl-3-(R)-(t-butyldimethylsilyloxymethyl)-4-(S)-phenyl pyrrolidine (from Step D), 31.5 g (0.50 mol) ammonium formate, 20.0 g of 20% palladium hydroxide on carbon in 1.5 L of MeOH was heated at 55° C. for 2.5 h. The mixture was cooled and filtered through a pad of Celite. The filtrate was concentrated. The residue was dissolved in 1 L of CH$_2$Cl$_2$, washed with 300 mL of 10% NH4OH solution, 200 mL of sat'd NaCl, dried over MgSO4 and concentrated to afford 89.2 g (99%) of the title compound: $^1$H NMR (400 MHz) δ −0.09 (s, 3H), −0.08 (s, 3H), 0.77 (s, 9H), 2.25–2.30 (m, 1H), 2.84–2.96 (4H), 3.18 (dd, J=11.2, 3.2, 1H), 3.29–3.36 (m, 1H), 3.44 (dd, J=10.0, 6.0), 3.56 (dd, J=10.0, 4.4, 1H); ESI-MS 292 (M+H); HPLC A: 3.44 min.

PYRROLIDINE 2

3-(R)-(t-Butyldimethylsilyloxymethyl)-4-(S)-(3-fluoro)phenylpyrrolidine

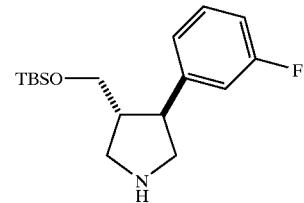

The title compound was prepared using procedures analogous to those described to prepare Pyrrolidine 1, except that trans-(3-fluoro)cinnamic acid was substituted for trans-cinnamic acid in Step A. For the title compound: $^1$H NMR (400 MHz): δ 0.013 (s, 3H), 0.016 (s, 3H), 0.87 (s, 9H), 2.09 (br s, 1H), 2.30–2.37 (m, 1H), 2.88–2.90 (3H), 2.23 (dd, J=8.0, 11.2, 1H), 3.39 (dd, J=6.8, 10.0. 1H), 3.56 (dd, J=6.0, 10.0, 1H), 3.64 (dd, J=5.2, 10.0), 6.86–6.91 (m, 1H), 6.95 (dt, J=12.0, 2.4, 1H), 7.01 (d, J=7.6, 1H), 7.22–7.27 (m, 1H); ESI-MS 310 (M+H); HPLC A: 3.05 min.

PYRROLIDINE 3

(3-(R)-((t-Butyldimethylsilyloxy)methyl)-4-(S)-(3-thienyl)pyrrolidine

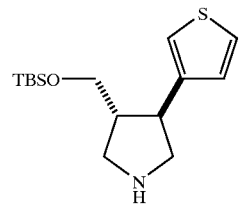

Step A: 1-(Prop-2-enyl)-3-(R)-(hydroxymethyl)-4-(S)-(3-thienyl)pyrrolidine

The title compound was prepared using procedures analogous to those used to prepare 1-benzyl-3-(R)-(hydroxymethyl)-4-(S)-phenylpyrroldine (Pyrrolidine 1, Step C), except that trans-3-(3-thienyl)acrylic was substituted for trans-cinnamic acid in Step A and N-methoxymethyl-N-trimethylsilylmethyl(prop-2-enyl) amine was substituted for N-methoxymethyl-N-trimethylsilylmethyl benzyl amine in Step B. For the title compound: $^1$H NMR (500 MHz) δ 2.30–2.34 (m, 1H), 2.44 (t, J=8.5, 1H), 2.67 (t, J=9.0, 1H), 2.77 (dd, J=5.0, 9.0, 1H), 3.02–3.15 (4H), 3.53 (dd, J=7.5, 10.0, 1H), 3.64 (dd, J=5.0, 10.0, 1H), 5.07 (d, J=10.0, 1H), 5.17 (d, J=17.5, 1H), 5.83–5.91 (m, 1H), 6.97–6.99 (2H), 7.20–7.22 (m, 1H); ESI-MS 224 (M+H).

Step B: 1-(Prop-2-enyl)-3-(R)-(t-butyldimethylsilyloxymethyl)-4-(S)-(3-thienyl)pyrrolidine A solution of 1.06 g (4.75 mmol) of 1-(prop-2-enyl)-(3-(R)-(hydroxymethyl))-4-(S)-(3-thienyl)pyrrolidine (from Step A) in 12.0 mL of $CH_2Cl_2$ at 0° C. was treated with 0.99 mL (5.7 mmol) of N,N-diisopropylethylamine and 855 mg (5.6 mmol) of t-butyldimethylsilyl chloride. After warming to rt and stirring for 20 h, the solution was partitioned between 100 mL of ether and 100 mL of $H_2O$. After separating the phases, the aqueous layer was extracted with 100 mL of ether. The combined organic phases were dried over $MgSO_4$ and concentrated. The residue was purified by flash chromatography eluting with 3:1 v/v hexanes/EtOAc to yield 1.24 g (77%) of the title compound: $R_F$: 0.54 (3:2 v/v hexanes/EtOAc); $^1$HNMR (300 Mhz) δ 0.0 (s, 6H), 0.86 (s, 9H), 2.35 (m, 1H), 2.52–2.71 (m, 3H), 2.97–3.20 (m, 4H), 3.54–3.66 (m, 2H), 5.06–5.21 (m, 2H), 5.89 (m, 1H). 6.98–7.02 (m, 2H), 7.22 (m, 1H).

Step C: 3-(R)-(t-Butyldimethylsilyloxymethyl)-4-(S)-(3-thienyl)pyrrolidine

A solution of 3.7 g (11.0 mmol) of 1-(prop-2-enyl)-3-(R)-(t-butyldimethylsilyloxymethyl)-4-(S)-(3-thienyl)pyrrolidine (from Step B) in 16% aqueous acetonitrile (degassed with nitrogen) was treated with 540 mg (0.58 mmol) of chlorotris(triphenylphosphine)rhodium. The reaction was warmed to reflux and the propanal that formed was removed via azeotropic distillation with the solvents. Additional solvent was added periodically to maintain a constant reaction volume. After 6 h, TLC indicated the absence of starting material. The reaction was cooled to rt and concentrated. The residue was purified by flash chromatography eluting with a gradient of 97:2:1 v/v/v $CH_2Cl_2$/MeOH/$NH_4OH$, then 94:5:1 v/v/v $CH_2Cl^2$/MeOH/$NH_4OH$, then 89:10:1 v/v/v $CH_2Cl_2$/MeOH/$NH_4OH$ to yield 2.76 g (84%) of the title compound: $R_F$: 0.26 (97:2:1 v/v/v $CH_2Cl_2$/MeOH/$NH_4OH$); $^1$HNMR (300 MHz) δ 0.0 (s, 6H), 0.86 (s, 9H), 2.36 (m, 1H), 2.93–3.70 (m, 7H), 6.99–7.06 (m, 2H), 7.28 (m, 1H).

HYDROXY ESTER 1

2-(S)-Hydroxy-3-(cyclopropyl)propanoic Acid, (4-Methoxy)benzyl Ester

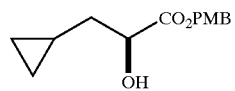

Step A: 2-(S)-Hydroxy-3-cyclopropyl Propanoic Acid

A 1 L, 3-neck flask was equipped with two dropping funnels, one containing 21.3 mL of 2.0 N $H_2SO_4$ and the other containing 21.3 mL of 2.0 N $NaNO_2$. A mixture of 5.00 g (38.7 mmol) of 2-(S)-amino-3-cyclopropyl propanoic acid in 28 mL of $H_2O$ at 0° C. was treated with a sufficient amount of the acid solution to dissolve the solids. The remaining $H_2SO_4$ solution and the $NaNO_2$ solution were added maintaing the internal temperature at less than 5° C. The resulting mixture was stirred cold for 3 h, then warmed to rt and stirred for 20 h. The reaction mixture was saturated with NaCl and extracted with 4×100 mL of EtOAc. The extracts were dried over $MgSO_4$ and concentrated to afford 4.30 g (85%) of the title compound: $^1$H NMR (300 MHz): δ 0.13–0.18 (m, 2H), 0.48–0.54 (m, 2H), 0.89 (m, 1H), 1.67–1.76 (m, 2H), 4.37 (dd, J=6.4, 4.7 Hz, 1H).

Step B: 2-(S)-Hydroxy-3-(cyclopropyl)propanoic Acid, 4-(Methoxy)benzyl Ester

A solution of 4.30 g (33 mmol) of 2-(S)-hydroxy-3-(cyclopropyl)propanoic acid (from Step A), 6.40 mL (46 mmol) of TEA and 5.90 mL (44 mmol) of 4-(methoxy)benzyl chloride in 40 mL of DMF was stirred at rt for 2 h. The mixture was partitioned between 500 mL of ether and 300 mL of $H_2O$ and the layers were separated. The organic layer was washed with 300 mL of 2.0 N HCl, 300 mL of sat'd $NaHCO_3$, 2×300 mL of $H_2O$, 300 mL of sat'd NaCl, dried over $MgSO_4$ and concentrated. Flash chromatography on 500 g of silica gel using 5:1 v/v hexanes/EtOAc as the eluant afforded 4.30 g (52%, 97.5% ee) of the title compound: $R_F$: 0.20 (4:1 v/v hexanes/EtOAc); $^1$H NMR (300 MHz): δ 0.01–0.09 (m, 2H), 0.40–0.45 (m, 2H), 0.84 (m, 1H), 1.55–1.67 (m, 2H), 2.82 (br m, 1H), 3.81 (s, 3H), 4.25 (br m, 1H), 5.14 (ABq, J=11.8, 2H), 6.90 (d, J=8.7, 2H), 7.29 (d, J=8.7, 2H). HPLC: Chiracel OB 4.6×250 mm column, 65:35 v/v hexanes/EtOH, 0.5 mL/min, 220 nm. Retention times: (S)-enantiomer, 20.4 min; (R)-enantiomer, 17.3 min.

HYDROXY ESTER 2

2-(S)-Hydroxy-3-(cyclobutyl)propanoic Acid, Benzyl Ester

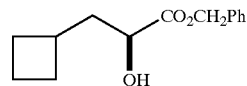

Step A: N,N'-Dimethyl-N,N'-dimethoxy Oxamide

A mixture of 48.0 g (0.49 mol) of N,O-dimethylhydroxylamine.HCl in 250 mL of 3:2 v/v $CH_2Cl_2$/pyridine was cooled to −78° C. and was treated with 17.4 mL (0.2 mol) of oxalyl chloride maintaining the internal temperature at less than −70° C. The resulting mixture was allowed to warm to rt and stirred for 20 h. The reaction was quenched with 250 mL of sat'd NaCl and the quenched mixture was extracted with 3×400 mL of $CH_2Cl_2$. The extracts were combined, dried over $MgSO_4$ and concentrated. Recrystallization from 250 mL of MTBE afforded 24.28 g (69%) of the title compound: $^1$H NMR (500 MHz) δ 3.25 (s, 6H), 3.75 (s, 6H).

Step B: N-Methyl-N-methoxy2-oxo-3-cyclobutyl Propanamide

A suspension of 4.86 g (0.20 mol) of magnesium turnings in 250 mL of THF was treated with 2.0 mL (0.022 mol) of 1,2-dibromoethane and then was warmed until gas evolution from the surface of the Mg was visible. 15.2 mL (0.178 mol) of 1,2-dibromoethane was added at rate to maintain a gentle reflux. After the addition, the resulting mixture was heated at reflux for 30 min, then cooled to rt. Potassium (15.6 g, 0.40 mol) was added in ~1 g portions; the mixture was warmed until the potassium started to react and a fine black precipitate formed. This was repeated until all of the potassium was added to the reaction mixture. The resulting suspension of Mg was cooled to 0° C.

The finely divided Mg was treated with 22.5 mL (0.20 mol) of bromomethylcyclobutane maintaining the internal temperature at <5° C. The resulting mixture was stirred cold for 1 h, then was treated with 26.40 g (0.15 mol) of N,N'-dimethyl-N,N'-dimethoxy oxamide (from Step A) in portions as a solid. The resulting mixture was stirred at 0° C. for 16 h. The reaction was poured onto a mixture of 100 mL conc. HCl and 500 g of ice under $N_2$ atmosphere. The quenched mixture was extracted with 1.5 L of EtOAc. The extract was washed with 500 mL of sat'd NaCl, dried over $MgSO_4$ and concentrated. Flash chromatography on 500 g of silica gel using 3:1 v/v hexanes/EtOAc as the eluant afforded 22.3 g (80%) of the title compound: $^1$H NMR (500

MHz) δ 1.66–1.76 (m, 2H), 1.82–1.98 (m, 2H), 2.12–2.22 (m, 2H), 2.74–2.84 (3H), 3.20 (s, 3H), 3.66 (s, 3H).

Step C: N-Methyl-N-methoxy2-(S)-hydroxy-3-cyclobutyl Propanamide

A mixture of 11.40 g (61.5 mmol) of N-methyl-N-methoxy 2-oxo-3-cyclobutyl propanamide (from Step B) and 250 mL 0.5 N (R)-Alpine Borane® solution in THF was concentrated and stirred at rt for 5 days. The mixture was cooled to 0° C. and quenched with 6.8 mL (75.0 mmol) of isobutyraldehyde. The resulting mixture was diluted with 200 mL of ether and treated with 7.5 mL (125 mmol) of ethanolamine. The precipitate that formed was filtered and the filtrate was concentrated. Flash chromatography on 500 g of silica gel using 9:1 v/v $CH_2Cl_2$ as the eluant afforded 11.48 g (99%, 91% ee) of the title compound: $^1$H NMR (500 MHz) δ 1.59–1.70 (m, 2H), 1.67 (s, 1H), 1.77–1.83 (m, 2H), 1.82–1.92 (m, 1H), 2.03–2.13 (m, 2H), 2.53–2.60 (m, 1H), 3.23 (s, 3H), 3.72 (s, 3H), 4.31 (app d, J=5.5, 1H); HPLC: Chiralpak AS 4.6×250 mm column, 75/25 hexanes/iPrOH, 0.5 mL/min, 210 nm. Retention Times: (S)-Enantiomer, 13.3 min; (R)-enantiomer, 17.2 min.

Step D: 2-(S)-Hydroxy-3-(cyclobutyl)propanoic Acid

A suspension of 33.66 g (0.3 mol) of potassium t-butoxide in 50 mL of THF was treated with 5.40 mL (0.3 mol) of $H_2O$. The resulting mixture was treated with a solution of 11.48 g (0.061 mol) of N-methyl-N-methoxy 2-(S)-hydroxy-3-cyclobutyl propanamide (from Step C) in 20 mL of THF and stirred at rt for 20 h. The mixture was concentrated and the residue was partitioned between 300 mL of ether and 200 mL of $H_2O$ and the layers were separated. The pH of the aqueous layer was adjusted to 2 with concentrated HCl and extracted with 300 mL of EtOAc. The extract was washed with 100 mL of sat'd NaCl, dried over $MgSO_4$ and concentrated to afford 7.50 g (85%) of the title compound: $^1$H NMR (500 MHz) δ 1.66–1.76 (m, 2H), 1.78–1.98 (4H), 2.06–2.16 (m, 2H), 2.51–2.61 (m, 1H), 4.20 (dd, J=8.0, 4.0, 1H).

Step E: 2-(S)-Hydroxy-3-(cyclobutyl)propanoic Acid, Benzyl Ester

A mixture of 1.05 g (7.3 mmol) of 2-(S)-hydroxy-3-(cyclobutyl)propanoic acid (from Step D), 40 mL (10.0 mmol) of TEA and 1.20 mL (10.0 mmol) of benzyl bromide in 8 mL of DMF was stirred at rt for 2 h. The mixture was partitioned between 200 mL of ether and 100 mL of $H_2O$ and the layers were separated. The organic layer was washed with 100 mL of 2.0 N HCl, 100 mL of sat'd $NaHCO_3$, 2×100 mL of $H_2O$, 100 mL of sat'd NaCl, dried over $MgSO_4$ and concentrated. Flash chromatography on 60 g of silica gel using 4:1 v/v hexanes/ether as the eluant afforded 1.20 g (70%) of the title compound: $^1$H NMR (500 MHz) δ 1.58–1.70 (m, 2H), 1.72–1.82 (m, 2H), 1.84–1.92 (m, 2H), 1.98–2.10 (m, 2H), 2.46–2.58 (m, 1H), 2.63 (br s, 1H), 4.15 (dd, J=7.5, 3.0), 7.33–7.40 (m, 5H).

HYDROXY ESTER 3

2-(S)-Hydroxy-3-(cyclopentyl)propanoic Acid, Benzyl Ester

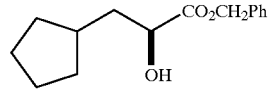

Step A: N-Methoxy-N-methyl-cyclopentylacetamide

A solution of 2.0 mL (15.9 mmol) of cyclopentylacetic acid in 80 mL of $CH_2Cl_2$ at 0° C. was treated with 3.7 mL (33.6 mmol) of N-methyl-morpholine and 2.2 mL (16.9 mmol) of isobutyl chloroformate. After stirring for 20 min, 1.61 g (16.5 mmol) of N,O-dimethyl-hydroxylamine.HCl was added. The reaction was warmed to rt and stirred for 3 h. The reaction was partitioned between 200 mL of EtOAc and 200 mL 2.0 N HCl. After separating the phases, the organic layer was washed with 200 mL of 1.0 N $NaHCO_3$, dried over $Na_2SO_4$ and concentrated. Flash chromatography on silica gel using 4:1 v/v hexanes/EtOAc afforded 2.28 g (83%) of the title compound as a colorless oil. $R_F$: 0.27 (4:1 v/v hexanes/EtOAc). $^1$H NMR (300 MHz): δ 1.12–1.23 (m, 2H), 1.51–1.89 (m, 6H), 2.28 (m, 1H), 2.44 (d, J=7.5, 2H), 3.18 (s, 3H), 3.67 (s, 3H).

Step B: Cyclopentylmethylene Phenyl Ketone

A solution of 1.98 g (11.5 mmol) of N-methoxy-N-methyl-cyclopentylacetamide (from Step A) in 115 mL of THF at 0° C. was treated with 13.0 mL of 1.8 M phenyl-lithium in cyclohexane/diethylether over 40 min. After stirring for 1 h, the reaction was quenched with 2.0 N HCl and warmed to rt. The quenched reaction was partitioned between 200 mL of ether and 200 mL 2.0 N HCl and the layers were separated. The organic layer was washed with 200 mL of 1.0 N $NaHCO_3$, dried over $Na_2SO_4$ and concentrated. Flash chromatography on silica gel using 9:1 v/v hexanes/EtOAc afforded 1.57 g (72%) of the title compound: $R_F$: 0.66 (4:1 v/v hexanes/EtOAc); $^1$H NMR (300 MHz): δ 1.14–1.22 (m, 2H), 1.52–1.67 (m, 4H), 1.82–1.92 (m, 2H), 2.37 (m, 1H), 2.98 (d, J=7.1, 2H), 7.26–7.61 (m, 5H).

Step C: (S)-2-Cyclopentyl-1-phenylethanol

A solution of 2.7 mL of 1.0 M (R)-2-methyl-CBS-oxazaborolidine solution in toluene in 4 mL of $CH_2Cl_2$ at –25° C. was treated with 1.4 mL of 2.0 M borane methyl sulfide complex in THF and stirred cold for 10 min. A solution of 501 mg (2.66 mmol) of cyclopentylmethylene phenyl ketone (from Step B) in 2 mL of $CH_2Cl_2$ was added over 25 min and the resulting mixture was stirred cold for an additional 45 min. The reaction was quenched by pouring it into cold (–25° C.) MeOH. The quenched reaction was warmed to rt and stirred for 45 min until gas evolution ceased. The mixture was concentrated and the residue dissolved in 20 mL of MeOH and concentrated again. Flash chromatography on silica gel using 17:3 v/v hexanes/EtOAc afforded 413 mg (81%) of the title compound: $R_F$: 0.53 (4:1 v/v hexanes/ EtOAc); $^1$H NMR (300 MHz): δ 1.10–1.17 (m, 2H), 1.47–1.89 (m, 9H), 4.69 (m, 1H), 7.25–7.35 (m, 5H).

Step D: Acetic Acid, (S)-2-Cyclopentyl-1-phenylethyl Ester

A solution of 406 mg (2.13 mmol) of (S)-2-cyclopentyl-1-phenylethanol (from Step C) in 9 mL of pyridine was treated with 1 mL of acetic anhydride. After stirring for 6 h, the reaction was concentrated. Flash chromatography on silica gel using 93:7 v/v hexanes/EtOAc afforded 495 mg (100%) of the title compound: $R_F$: 0.75 (4:1 v/v hexanes/ EtOAc); $^1$H NMR (300 MHz): δ 1.10–1.21 (m, 2H), 1.44–2.04 (m, 9H), 2.05 (s, 3H), 5.75 (dd, J=8.0, 6.1, 1H), 7.25–7.34 (m, 5H).

Step E: (S)-2-Acetoxy-3-(cyclopentyl)propanoic Acid

A solution of 479 mg (2.0 mmol) of acetic acid, (S)-2-cyclopentyl-1-phenylethyl ester (from Step D) in 14 mL of 2:2:3 v/v/v $CCl_4/CH_3CN/H_2O$ was treated with 6.59 g (28.9 mmol) of periodic acid and 7.8 mg (0.037 mmol) of $RuCl_3.H_2O$. The reaction was warmed to 33° C. and stirred for 4 h. After cooling to 0° C., 100 mL of ether was added. After stirring for 10 min and separating the phases, the aqueous layer was extracted with 2×100 mL of ether. The combined organic layers were dried over $Na_2SO_4$ and concentrated to give 395 mg (95%) of the title compound: $R_F$: 0.62 (90:10:1 v/v/v $CH_2Cl_2$/MeOH/HOAc); $^1$H NMR (300 MHz): δ 1.09–1.98 (m, 11H), 2.14 (s, 3H), 5.03 (dd, J=8.8, 4.3, 1H), 8.9 (br, 1H).

Step F: 2-(S)-Hydroxy-3-(cyclopentyl)propanoic Acid

A solution of 395 mg (1.97 mmol) of 2-(S)-acetoxy-3-(cyclopentyl)propanoic acid (from Step E) in 10 mL MeOH and 1 mL of $H_2O$ was treated with 1.29 g (9.33 mmol) of $K_2CO_3$ and stirred at rt for 30 h. The volatiles were removed under reduced pressure. The crude product was partitioned between 100 mL of ether and 100 mL of $H_2O$ and the layers were separated. The aqueous layer was acidified to pH 1–2 using 2.0 N HCl and extracted with 3×150 mL of EtOAc. The combined organic layers were dried over $Na_2SO_4$ and concentrated to give 287 mg (92%) of the title compound: $^1H$ NMR (300 MHz) δ 1.11–2.15 (m, 11H), 4.27 (dd, J=8.1, 4.7, 1H), 6.5 (br, 1H).

Step G: 2-(S)-Hydroxy-3-(cyclopentyl)propanoic Acid, Benzyl Ester

A solution of 287 mg (1.81 mmol) of 2-(S)-hydroxy-3-(cyclopentyl)propanoic acid (from Step F) in 8 mL of DMF was treated with 0.38 mL (2.72 mmol) of TEA and 0.33 mL (2.77 mmol) of benzyl bromide and stirred at rt for 22 h. The reaction was diluted with 200 ml of ether and washed with 200 mL of $H_2O$, 200 mL of 2.0 N HCl, 200 mL of 1.0 N $NaHCO_3$, 200 mL of $H_2O$ and 200 mL of sat'd NaCl. The organic layer was dried over $MgSO_4$ and concentrated. Flash chromatography on silica gel using 17:3 v/v hexanes/EtOAc afforded 102 mg (22%, 95.5% ee) of the title compound: $R_F$: 0.40 (4:1 v/v hexanes/EtOAc); $^1H$ NMR (300 MHz): δ 1.04–1.17 (m, 2H), 1.46–1.87 (m, 8H), 1.99 (m, 1H), 2.65 (m, 1H), 4.22 (dd, J=7.8, 4.8, 1H), 5.23 (ABq, J=12.3, 2H), 7.32–7.41 (m, 5H). HPLC: Chirapak AS 4.6×250 mm column, 17:3 v/v hexanes/iPrOH, 0.5 mL/min, 220 nm. Retention times: (S)-Enantiomer, 12.2 min; (R)-enantiomer, 15.3 min.

The following α-hydroxy benzyl and (4-methoxy)benzyl esters were prepared from the corresponding α-hydroxy acids (obtained from commercial sources or prepared as above) using esterification conditions analogous to those described above:

HYDROXY ESTER 4

2-(S)-Hydroxy-3-(cyclobutyl)propanoic Acid, (4-Methoxy)benzyl Ester

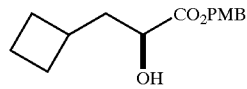

$^1H$ NMR (500 MHz) δ 1.56–1.94 (6H), 1.98–2.12 (m, 2H), 2.44–2.56 (m, 1H), 2.64 (br s, 1H), 3.82 (s, 3H), 4.11–4.13 (m, 1H), 5.19 (ABq, J=25.0, 2H), 6.90 (d, J=9.0, 2H), 7.30 (d, J=9.0, 2H).

HYDROXY ESTER 5

2-(S)-Hydroxy-2-(cyclohexyl)acetic Acid, Benzyl Ester

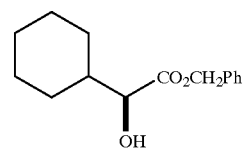

$R_F$: 0.37 (4:1 v/v hexanes/EtOAc); $^1H$ NMR (300MHz) δ 1.11–1.38 (m, 11H), 2.65 (d, J=6.3 Hz, 1H), 4.06 (dd, J=6.3, 3.5 Hz, 1H), 5.22 (s, 2H), 7.30–7.39 (m, 5H).

HYDROXY ESTER 6

2-(S)-Hydroxy-2-(cyclohexyl)acetic Acid, (4-Methoxy)benzyl Ester

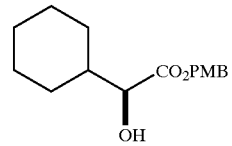

$^1H$ NMR (500 MHz) δ 1.10–1.80 (11H), 2.68 (t, J=5.7 Hz, 1H), 3.83 (s, 3H), 4.06 (dd, J=6.1, 3.6 Hz, 1H), 5.17 (s, 2H), 6.91 (d, J=8.6 Hz, 1H), 7.31 (d, J=8.6 Hz, 1H).

HYDROXY ESTER 7

2-(S)-Hydroxy-3-methylbutanoic Acid, Benzyl Ester

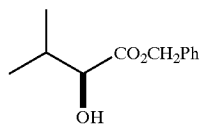

$R_F$: 0.39 (4:1 v/v hexanes/EtOAc); $^1H$ NMR (300 MHz) δ 0.83 (d, J=7.0, 3H), 1.01 (d, J=7.0, 3H), 2.08 (m, 1H), 2.67 (d, J=6.3, 1H), 4.08 (dd, J=6.0, 3.6, 1H), 5.22 (ABq, J=12.1, 2H), 7.34–7.39 (m, 5H).

HYDROXY ESTER 8

2-(S)-Hydroxy-3-methylbutanoic Acid, (4-Methoxy)benzyl Ester

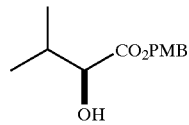

$^1H$ NMR (500 MHz, $CDCl_3$): δ 7.30~7.33 (m, 2H), 6.90~6.93 (m, 2H), 5.20 (AB d, 11.9 Hz, 1H), 5.15 (AB d, 11.9 Hz, 1H), 4.07 (d, 3.4 Hz, 1H), 3.83 (s, 3H), 2.68 (br s, 1H), 2.04~2.13 (m, 1H), 1.01 (d, 7.0 Hz, 3H), 0.83 (d, 6.9 Hz, 3H).

HYDROXY ESTER 9

2-(S)-Hydroxy-3-(S)-methylpentanoic Acid, Benzyl Ester $R_F$: 0.67 (2:1 v/v hexanes/EtOAc); $^1H$ NMR (500 MHz) δ 7.35~7.42 (m, 5H), 5.26 (AB d, J=12.1 Hz, 1H), 5.22 (AB d, J=12.2 Hz, 1H), 4.14 (br s, 1H), 2.71 (br s, 1H), 1.81~1.89 (m, 1H), 1.30~1.38 (m, 1H), 1.20~1.29 (m, 1H), 0.99 (d, J=7.1 Hz, 3H), 0.88 (t, J=7.5 Hz, 3H).

HYDROXY ESTER 10

2-(S)-Hydroxy-3-(R)-methylpentanoic Acid, Benzyl Ester $R_F$: 0.64 (2:1 v/v hexanes/EtOAc); $^1H$ NMR (500 MHz) δ 7.35~7.42 (m, 5H), 5.26 (AB d, J=12.2 Hz, 1H), 5.23 (AB d, J=12.2 Hz, 1H), 4.25 (dd, J=2.8 & 5.6 Hz, 1H), 2.70 (br d, J=~3.8 Hz, 1H), 1.82~1.89 (m, 1H), 1.51~1.60 (m, 1H), 1.29~1.38 (m, 1H), 0.96 (t, J=7.5 Hz, 3H), 0.80 (d, J=6.9 Hz, 3H).

HYDROXY ESTER 11

2-(S)-Hydroxy-3-(S)-methylpentanoic Acid, (4-Methoxy)benzyl Ester $R_F$: 0.38 (4:1 v/v hexanes/EtOAc); $^1$H NMR (500 MHz) δ 7.30~7.33 (m, 2H), 6.89~6.92 (m, 2H), 5.19 (AB d, J=11.9 Hz, 1H), 5.15 (AB d, J=11.9 Hz, 1H), 4.10 (dd, J=3.7 & 6.0 Hz, 1H), 3.83 (s, 3H), 2.71 (d, J=5.9 Hz, 1H), 1.78~1.86 (m, 1H), 1.18~1.36 (m, 2H), 0.97 (d, J=7.1 Hz, 3H), 0.87 (t, J=7.3 Hz, 3H).

HYDROXY ESTER 12

2-(S)-Hydroxy-3-(cyclopropyl)propanoic Acid, Benzyl Ester

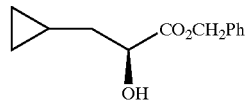

$^1$H NMR (300 MHz, CDCl$_3$): δ 7.33~7.47 (m, 5H), 5.21 (s, 2H), 4.28~4.37 (m, 1H), 2.80~2.90 (m, 1H), 1.60~1.72 (m, 2H), 0.79~0.0.91 (m, 1H), 0.40~0.53 (m, 2H), 0.00~0.14 (m, 2H).

ALDEHYDE 1

2-(R)-(3-(R)-Formyl-4-(S)-phenylpyrrolidin-1-yl)-3-(cyclobutyl)propionic Acid, Benzyl Ester

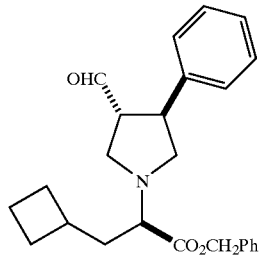

Step A: 2-(R)-(3-(R)-(t-Butyldimethylsilyloxymethyl)-4-(S)-phenylpyrrolidin-1-yl)-3-(cyclobutyl)propionic Acid, Benzyl Ester A solution of 1.84 g (7.8 mmol) of 2-(S)-hydroxy-3-(cyclobutyl)propionic acid, benzyl ester (Hydroxy Ester 2) in 30 mL of CH$_2$Cl$_2$ at −5° C. was treated with 1.40 mL (8.4 mmol) of trifluoromethanesulfonic anhydride maintaining the internal temperature at less than 0° C. The resulting mixture was stirred cold for 2 min, then treated with 1.10 mL (9.6 mmol) of 2,6-lutidene, maintaining the internal temperature at less than 0° C. The resulting mixture was stirred cold for 30 min, then treated with a solution of 2.65 g (9.5 mmol) of 3-(R)-(t-butyldimethylsilyloxymethyl)-4-(S)-phenylpyrrolidine (Pyrroldine 1) in 10 mL of CH$_2$Cl$_2$ and 3.00 mL (31.2 mmol) of DIEA. The resulting mixture was warmed to rt and stirred for 20 h. The reaction was quenched with 50 mL of sat'd NaHCO$_3$ and the quenched mixture was extracted with 200 mL of ether. The ether extract was dried over MgSO$_4$ and concentrated. Flash chromtography on 150 g of silica gel using 20:1 v/v hexanes/ether as the eluant afforded 3.23 g (81 % based on Hydroxy Ester 2) of the title compound: $^1$H NMR (300 MHz) δ −0.25 (s, 3H), −0.21 (s, 3H), 0.84 (s, 9H), 1.57–2.07 (8H), 2.29–2.39 (2H), 2.66–2.77 (m, 2H), 2.93 (q, J=7.8, 1H), 3.06 (t, J=8.4, 1H), 3.19 (t, J=8.4, 1H), 3.26 (dd, J=2.1, 6.3, 1H), 3.45–3.60 (m, 2H), 5.15 (s, 2H), 7.17–7.38 (10H).

Step B: 2-(R)-(3-(R)-Hydroxymethyl-4-(S)-phenylpyrrolidin-1-yl)-3-(cyclobutyl)propionic Acid, Benzyl Ester A solution of 3.20 g (6.3 mmol) of 2-(R)-(3-(R)-(t-butyldimethylsilyloxymethyl)-4-(S)-phenylpyrrolidin-1-yl)-3-(cyclobutyl) propionic acid, benzyl ester (from Step A) in 40 mL of THF at 0° C. was treated with 10 mL of 1.0 M tetrabutylammonium fluoride solution in THF. The resulting mixture was warmed to rt and stirred for 2.5 h. The reaction mixture was partitioned between 200 mL of ether and 100 mL of 50% sat'd NaHCO$_3$ and the layers were separated. The organic layer was dried over MgSO4 and concentrated. Flash chromatography on 100 g of silica gel using 2:1 v/v hexanes/ether as the eluant afforded 2.34 g (94%) of the title compound: $^1$H NMR (500 MHz) δ 1.56–2.07 (8H), 2.15 (br s, 1H), 2.27–2.37 (2H), 2.64 (t, J=11.0, 1H), 2.80 (dd, J=6.5, 11.0), 3.04–3.11 (2H), 3.23–3.30 (2H), 3.56 (dd, J=7.5, 13.0, 1H), 3.68 (dd, J=5.5, 13.0, 1H), 5.15 (ABq, J=20.0, 2H), 7.17–7.40 (10H).

Step C: 2-(R)-(3-(R)-Formyl-4-(S)-phenylpyrrolidin-1-yl)-3-(cyclobutyl)propionic Acid, Benzyl Ester A solution of 1.29 mL (14.8 mmol) of oxalyl chloride in 15 mL of CH$_2$Cl$_2$ at −78° C. was treated with 2.10 mL (29.7 mmol) of DMSO maintaining the temperature at less than −60° C. The resulting mixture was stirred cold for 5 min. A solution of 2.33 g (5.9 mmol) of 2-(R)-(3-(R)-(hydroxymethyl)4-(S)-phenylpyrrolidin-1-yl)-3-(cyclobutyl)propionic acid, benzyl ester (from Step B) in 10 mL of CH$_2$Cl$_2$ was added maintaining the temperature at less than −60° C. The resulting mixture was stirred cold for 30 min. The mixture was treated with 10.3 mL (59.3 mmol) of DIEA maintaining the temperature at less than −60° C. The reaction was warmed to 0° C., stirred for 20 min and quenched with H$_2$O. The mixture was partitioned between 250 mL of CH$_2$Cl$_2$ and 100 mL of H$_2$O and the layers were separated. The aqueous layer was extracted with 250 mL of CH$_2$Cl$_2$. The combined organic phases were dried over Na$_2$SO$_4$ and concentrated. Flash chromatography on 100 g of silica gel using 4:1 v/v hexanes/ether as the eluant afforded 2.30 g (97%) of the title compound: $^1$H NMR (300 MHz) δ 1.54–2.08 (m, 8H), 2.31 (m, 1H), 2.75 (t, J=8.6 Hz, 1H), 2.96 (m, 1H), 3.11–3.35 (m, 4H), 3.56 (q, J=7.9 Hz, 1H), 5.16 (s, 2H), 7.19–7.39 (m, 10H), 9.63 (d, J=2.2 Hz, 1H).

The following 1,3,4-trisubstituted pyrrolidine aldehydes were prepared from the appropriate α-hydroxy ester and 3,4-disubstituted pyrroldine using procedures analogous to those described for the preparation of Aldehyde 1.

ALDEHYDE 2

2-(R)-(3-(R)-Formyl-4-(S)-(3-fluorophenyl)pyrrolidin-1-yl)-3-(cyclobutyl)propionic Acid, Benzyl Ester

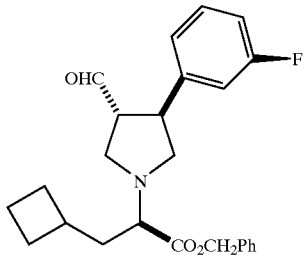

The title compound was prepared from α-Hydroxy Ester 2 and Pyrrolidine 2: $R_F$: 0.60 (7:3 v/v hexane/EtOAc); $^1$H NMR (300 MHz) δ 1.57–2.08 (m, 8H), 2.29 (m, 1H), 2.73 (br t, 1H), 2.92 (m, 1H), 3.14–3.34 (m, 4H), 3.56 (br q, 1H), 5.16 (s, 2H), 6.88–6.99 (m, 3H), 7.20–7.39 (m, 6H), 9.62 (d, J=2.0, 1H).

ALDEHYDE 3

2-(R)-(3-(R)-Formyl-4-(S)-phenylpyrrolidin-1-yl)-3-(cyclobutyl)propionic Acid, (4-methoxy)benzyl Ester

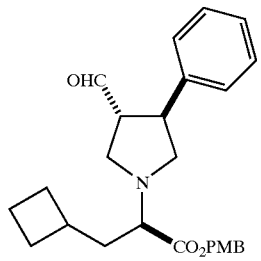

The title compound was prepared from α-Hydroxy Ester 4 and Pyrrolidine 1.

ALDEHYDE 4

2-(R)-(3-(R)-Formyl-4-(S)-phenylpyrrolidin-1-yl)-2-(cyclohexyl)acetic Acid, Benzyl Ester

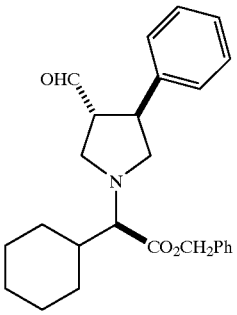

The title compound was prepared from α-Hydroxy Ester 5 and Pyrrolidine 1: $R_F$: 0.50 (4:1 v/v hexanes/EtOAc); $^1$H NMR (500 MHz) δ 0.94–1.03 (m, 2H), 1.05–1.29 (4H), 1.59 (app d, J=12.5, 1H), 1.67–1.84 (3H), 1.96 (app d, J=12.5, 1H), 2.71 (t, J=8.5, 1H), 2.93–2.96 (m, 1H), 3.17–3.22 (3H), 3.32 (t, J=8.5, 1H), 3.55 (q, J=8.0, 1H), 5.19 (app s, 2H), 7.19–7.41 (10H), 9.64 (d, J=2.0, 1H).

ALDEHYDE 5

2-(R)-(3-(R)-Formyl-4-(S)-phenylpyrrolidin-1-yl)-2-(cyclohexyl)acetic Acid, (4-methoxy)benzyl Ester

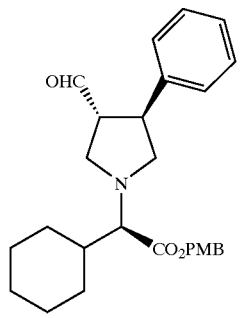

The title compound was prepared from α-Hydroxy Ester 6 and Pyrrolidine 1: $^1$H NMR (500 MHz) δ 0.95–1.98 (10H), 2.68 (t, J=8.6, 1H), 2.91–2.95 (m, 1H), 3.16–3.23 (3H), 3.29 (t, J=8.3, 1H), 3.48–3.56 (2H), 3.83 (s, 3H), 5.12 (s, 2H), 6.88–6.91 (2H), 7.17–7.35 (7H), 9.63 (d, J=2.3, 1H).

ALDEHYDE 6

2-(R)-(3-(R)-Formyl-4-(S)-(3-fluorophenyl)pyrrolidin-1-yl)-2-(cyclohexyl)acetic Acid, Benzyl Ester

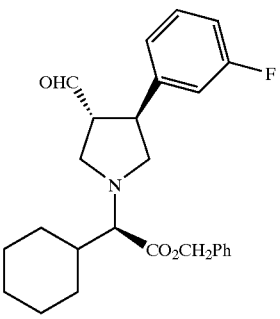

The title compound was prepared from α-Hydroxy Ester 5 and Pyrrolidine 2.

ALDEHYDE 7

2-(R)-(3-(R)-Formyl-4-(S)-(3-fluorophenyl)
pyrrolidin-1-yl)-2-(cyclohexyl)acetic Acid, (4-
Methoxy)benzyl Ester

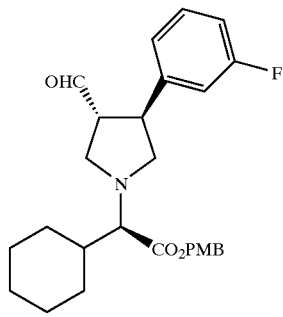

The title compound was prepared from α-Hydroxy Ester 6 and Pyrrolidine 2.

ALDEHYDE 8

2-(R)-(3-(R)-Formyl-4-(S)-phenylpyrrolidin-1-yl)-3-
methyl Butanonic Acid, Benzyl Ester

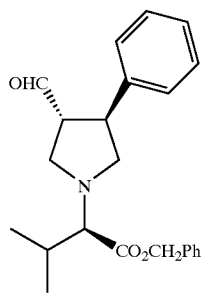

The title compound was prepared from α-Hydroxy Ester 7 and Pyrrolidine 1: $R_F$: 0.77 (3:2 v/v hexanes/EtOAc); $^1$H NMR (300 MHz) δ 0.89 (d, J=6.8, 3H), 1.00 (d, J=6.8, 3H), 2.08 (m, 1H), 2.66 (dd, J=8.9, 8.0, 1H), 2.92 (m, 1H), 3.08 (d, J=10.0, 1H), 3.17 (d, J=6.6, 1H), 3.28 (t, J=8.4, 1H), 3.53 (m, 1H), 5.17 (s, 2H), 7.16–7.38 (m, 10H), 9.63 (d, J=2.1, 1H).

ALDEHYDE 9

2-(R)-(3-(R)-Formyl-4-(S)-phenylpyrrolidin-1-yl)-3-
methyl Butanonic Acid, (4-Methoxy)benzyl Ester

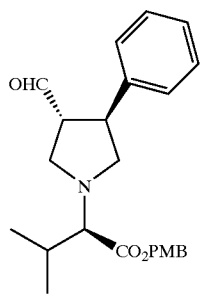

The title compound was prepared from α-Hydroxy Ester 8 and Pyrrolidine 1.

ALDEHYDE 10

2-(R)-(3-(R)-Formyl-4-(S)-(3-fluorophenyl)
pyrrolidin-1-yl)-3-methyl Butanonic Acid, Benzyl
Ester

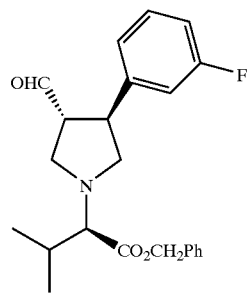

The title compound was prepared from α-Hydroxy Ester 7 and Pyrrolidine 2.

ALDEHYDE 11

2-(R)-(3-(R)-Formyl-4-(S)-(3-fluorophenyl)
pyrrolidin-1-yl)-3-methyl Butanonic Acid, (4-
Methoxy)benzyl Ester

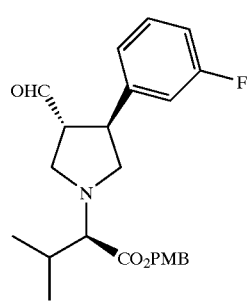

The title compound was prepared from α-Hydroxy Ester 8 and Pyrrolidine 2: $^1$H NMR (500 MHz) δ 0.91 (d, J=6.5, 3H), 1.00 (d, J=6.5, 3H), 2.04–2.09 (m, 1H), 2.68 (t, J=8.5, 1H), 2.88–2.92 (m, 1H), 3.06 (d, J=10.0, 1H), 3.14–3.19 (2H), 3.26 (t, J=8.5, 1H), 3.55 (q, J=7.5, 1H), 3.82 (s, 3H), 5.13 (app s, 2H), 6.88–6.97 (4H), 7.18–7.34 (5H), 9.64 (d, J=1.5, 1H).

ALDEHYDE 12

2-(R)-(3-(R)-Formyl-4-(S)-(3-fluorophenyl)
pyrrolidin-1-yl)-3-(cyclopropyl)propionic Acid, (4-
Methoxy)benzyl Ester

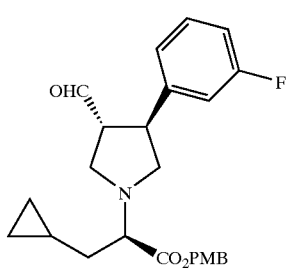

The title compound was prepared from α-Hydroxy Ester 1 and Pyrrolidine 2: $R_F$: 0.40 (7:3 v/v hexanes/EtOAc); $^1$H NMR (300 MHz) δ 0.01–0.10 (m, 2H), 0.36–0.49 (m, 2H), 0.69 (m, 1H), 1.54–1.76 (m, 2H), 2.64–3.61 (m, 7H), 3.80 (s, 3H), 5.12 (s, 2H), 6.84–7.04 (m, 5H), 7.21–7.34 (m, 3H) 9.63 (d, J=1.9, 1H).

ALDEHYDE 13

2-(R)-(3-(R)-Formyl-4-(S)-(3-thienyl)pyrrolidin-1-yl)-3-(cyclobutyl)propionic Acid, (4-Methoxy) benzyl Ester

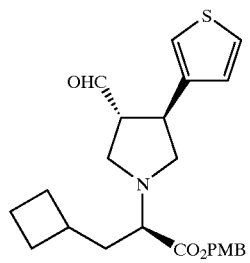

The title compound was prepared from α-Hydroxy Ester 2 and Pyrrolidine 3: $R_F$: 0.56 (4:1 v/v hexanes/EtOAc); $^1$H NMR (300 Mhz) δ 1.56–2.05 (m, 8H), 2.27 (m, 1H), 2.69 (br t, 1H), 2.89 (m, 1H), 3.06–3.31 (m, 4H), 3.63 (br q, 1H), 3.81 (s, 3H), 5.09 (s, 2H), 6.86–6.96 (m, 4H), 7.25–7.33 (m, 3H), 9.63 (d, J=2.2, 1H).

ALDEHYDE 14

2-(R)-(3-(R)-Formyl-4-(S)-(3-fluorophenyl) pyrrolidin-1-yl)-3-(S)-methylpentanoic Acid, Benzyl Ester Step A: 2-(S)-Trifluoromethanesulfonyl-3-(S)-methylpentanoic Acid, Benzyl Ester A solution of 1.887 g triflic anhydride (6.69 mmole) in 5 mL DCM was cooled in a ice acetone bath at about −13° C. To this was added a solution of 1.416 g (6.37 mmole) 2-(S)-hydroxy-3-(S)-methylpentanoic acid, benzyl ester (Hydroxy acid 9), 0.751 g 2,6-lutidine in 10 mL DCM dropwise with stirring under nitrogen over 10 minutes. After stirring in the cold bath for one hour, the reaction mixture was transferred into a separatory funnel with 150 mL ether. It was washed with 60 mL water (3×) and brine (1×), dried over sodium sulfate, and concentrated to give the crude product (2.248 g). FC (0~35% ethyl acetate in hexanes) gave the title compound (1.764 g) as a colorless oil. $R_f$: 0.77 (30% ethyl acetate in hexanes). $^1$H NMR (500 MHz) δ 7.36~7.42 (m, 5H), 5.30 (AB d, J=11.9 Hz, 1H), 5.26 (AB d, J=12.1 Hz, 1H), 5.06 (d, 3.9 Hz, 1H), 2.12~2.19 (m, 1H), 1.41~1.49 (m, 1H), 1.26~1.35 (m, 1H), 1.05 (d, J=6.8 Hz, 3H), 0.90 (t, J=7.6 Hz, 3H).

Step B: 2-(R)-(3-(R)-(t-Butyldimethylsilyloxymethyl)-4-(S)-(3-fluorophenyl)pyrrolidin-1-yl)-3-(S)-methylpentanoic Acid, Benzyl Ester A solution of 1.02 g DIEA (7.891 mmole) and 1.437 g (4.642 mmole) 3-(R)-(t-butyldimethylsilyloxymethyl)-4-(S)-(3-fluorophenyl)pyrrolidine (Pyrrolidine 2) in 5 mL DCM. was treated with a solution of 1.645 g (4.642 mmole) 2-(S)-trifluoromethane-sulfonyl-3-(S)-methylpentanoic acid, benzyl ester (from Step A above) in 10 mL DCM. After stirring over night at room temperature, the reaction mixture was transferred into a separatory funnel with 125 mL ether. It was washed with 75 mL 2% sodium bicarbonate, water (2×) and brine, dried over sodium sulfate, and concentrated to give the crude product (2.59 g). FC (5~105% ethyl acetate in hexanes with 1% triethylamine) gave the title compound (2.378 g) as a colorless oil. $R_f$: 0.70 (5% ethyl acetate in hexanes with 1% triethylamine). $^1$H NMR (500 MHz) δ 7.33~7.41 (m, 5H), 7.20~7.24 (m, 1H), 6.98 (d, J=7.5 Hz, 1H), 6.94 (d, J=10.3 Hz, 1H), 6.87~6.90 (m, 1H), 5.18 (s, 2H), 3.55 (dd, J=5.5 & 9.8 Hz, 1H), 3.50 (dd, J=7.1 & ~9.9 Hz, 1H), 3.14~3.20 (m, 2H), 3.08~3.12 (m, 1H), 2.91~2.96 (m, 1H), 2.70~2.73 (m, 1H), 2.62~2.65 (m, 1H), 2.28~2.34 (m, 1H), 1.83~1.90 (m, 1H), 1.41~1.48 (m, 1H), 1.06~1.12 (m, 1H), 1.01 (d, J=6.7 Hz, 3H), 0.90 (t, J=7.4 Hz, 3H), 0.87 (s, 9H), 0.01 (s, 6H).

Step C: 2-(R)-(3-(R)-(Hydroxymethyl)-4-(S)-(3-fluorophenyl)pyrrolidin-1-yl)-3-(S)-methylpentanoic Acid, Benzyl Ester The product from Step B above in 20 mL THF was treated with 10 mL 1 N tetrabutylammonium fluoride in THF overnight. The reaction mixture was partitioned between 300 mL of ether and 150 mL icy water. The organic layer was washed with 75 mL 5% NaHCO$_3$ (3×) and saturated brine. The organic layer was dried over Na$_2$SO$_4$ and concentrated. Flash chromatography on 100 g of silica gel using 15~50% ethyl acetate in hexanes with 1% triethylamine afforded 1.587 g of the title compound as a colorless oil: $^1$H NMR (500 MHz) δ 7.33~7.42 (m, 5H), 7.22~7.26 (m, 1H), 6.98 (d, J=7.8 Hz, 1H), 6.88~6.94 (m, 2H), 5.19 (s, 2H), 3.67 (dd, J=4.8 & 10.5 Hz, 1H), 3.55~3.58 (m, 1H), 3.06~3.30 (m, 4H), 2.75~2.79 (m, 1H), 2.63~2.67 (m, 1H), 2.31~2.36 (m, 1H), 1.97 (br s, ~1H, OH?), 1.87~1.91 (m, 1H), 1.43~1.51 (m, 1H), 1.05~1.14 (m, 1H), 1.02 (d, J=6.6 Hz, 3H), 0.90 (t, J=7.3 Hz, 3H).

Step D: 2-(R)-(3-(R)-Formyl-4-(S)-(3-fluorophenyl) pyrrolidin-1-yl)-3-(S)-methylpentanoic Acid, Benzyl Ester After cooling 0.605 g (4.767 mmole) oxalyl chloride in 30 mL DCM in a dry ice acetone bath under nitrogen, 0.748 g (9.569 mmole) DMSO in 5 mL DCM was added over 5 minutes. After stirring for 15 minutes, a solution of the alcohol (1.587 g, 3.987 mmole) from Step C above in 30 mL DCM was added over 20 minutes. After an additional 20 minutes, a solution of 2.017 g (19.935 mmole) triethylamine in 5 mL DCM was added over 5 minutes. The cooling bath was allowed to warm up overnight. The reaction mixture was transferred into a separatory funnel with ether and was washed with 1 N NaOH, water, and saturated brine. The organic layer was dried over sodium sulfate and concentrated to give 1.63 g crude product. FC on silica gel (5~40% ethyl acetate in hexanes) gave 1.257 g title compound as a colorless oil. $R_f$: 0.44 (20% ethyl acetate in hexanes). $^1$H NMR (500 MHz) δ 9.64 (d, J=2.1 Hz, 1H), 7.33~7.41 (m, 5H), 7.24~7.27 (m, 1H), 6.90~6.98 (m, 3H), 5.21 (AB d, J=12.2 Hz, 1H), 5.18 (AB d, J=12.2 Hz, 1H), 3.54~3.58 (m, 1H), 3.26~3.29 (m, 1H), 3.14~3.22 (m, 3H), 2.89~2.93 (m, 1H), 2.68~2.71 (m, 1H), 1.86~1.93 (m, 1H), 1.39~1.47 (m, 1H), 1.04~1.15 (m, 1H), 0.99 (d, J=6.7 Hz, 3H), 0.91 (t, J=7.5 Hz, 3H). Some starting material was also recovered (0.298 g). $R_f$: 0.13 (20% ethyl acetate in hexanes).

ALDEHYDE 15

2-(R)-(3-(R)-Formyl-4-(S)-(3-fluorophenyl) pyrrolidin-1-yl)-3-(R)-methylpentanoic Acid, Benzyl Ester Step A: 2-(S)-Trifluoromethanesulfonyl-3-(R)-methylpentanoic Acid, Benzyl Ester A solution of 1.334 g triflic anhydride (6.00 mmole) in 5 mL DCM was cooled in a ice acetone bath at about −13° C. A solution of 1.777 g (6.3 mmole) 2-(S)-hydroxy-3-(R)-methylpentanoic acid, benzyl ester (Hydroxy acid 10), 0.707 g 2,6-lutidine in 50 mL DCM was added dropwise with stirring under nitrogen over 15 minutes. After stirring in the cold bath for half an hour and without cooling for another half an hour, the reaction mixture was transferred into a separatory funnel with 150 mL ether. It was washed with 60 mL water (3x) and brine (1x), dried over sodium sulfate, and concentrated to give the crude product (2.187 g). FC (0~25% ethyl acetate in hexanes) gave the title compound (1.29 g) as a colorless oil. $R_f$: 0.83 (30% ethyl acetate in hexanes). $^1$H NMR (500 MHz) δ 7.35~7.43 (m, 5H), 5.30 (AB d, J=11.9 Hz, 1H), 5.28 (AB d, J=11.9 Hz, 1H), 5.14 (d, J=3.0 Hz, 1H), 2.09~2.17 (m, 1H), 1.48~1.57 (m, 1H), 1.32~1.41 (m, 1H), 0.98 (t, J=7.4 Hz, 3H), 0.945 (d, J=6.8 Hz, 3H).

Step B: 2-(R)-(3-(R)-(t-Butyldimethylsilyloxymethyl)-4-(S)-(3-fluorophenyl)pyrrolidin-1-yl)-3-(R)-methylpentanoic Acid, Benzyl Ester A solution of 0.708 g DIEA (5.476 mmole) and 0.997 g (3.221 mmole) 3-(R)-(t-butyldimethylsilyloxymethyl)-4-(S)-(3-fluorophenyl)pyrrolidine (Pyrrolidine 2) in 5 mL DCM. was treated with a solution of 1.141 g (3.221 mmole) 2-(S)-trifluoromethane-sulfonyl-3-(R)-methylpentanoic acid, benzyl ester (from Step A above) in 5 mL DCM. After stirring over night at room temperature, the reaction mixture was transferred into a separatory funnel with 125 mL ether. It was washed with 75 mL 2% sodium bicarbonate, water (2x) and brine, dried over sodium sulfate, and concentrated to give the crude product (1.813 g). FC (5~105% ethyl acetate in hexanes with 1% triethylamine) gave the title compound (1.666 g) as a colorless oil. $R_f$: 0.70 (5% ethyl acetate in hexanes with 1% triethylamine). $^1$H NMR (500 MHz) δ 7.33~7.42 (m, 5H), 7.20~7.24 (m, 1H), 6.98 (d, J=7.5 Hz, 1H), 6.95 (d, J=10.0 Hz, 1H), 6.87~6.90 (m, 1H), 5.19 (s, 2H), 3.56 (dd, J=5.5 & 9.8 Hz, 1H), 3.50 (dd, J=7.1 & ~10.8 Hz, 1H), 3.14~3.20 (m, 2H), 3.08~3.11 (m, 1H), 2.91~2.96 (m, 1H), 2.68~2.72 (m, 1H), 2.61~2.65 (m, 1H), 2.29~2.33 (m, 1H), 1.84~1.90 (m, 1H), 1.68~1.76 (m, 1H), 1.16~1.23 (m, 1H), 0.89~0.94 (t & d, 6H), 0.87 (s, 9H), 0.01 (s, 6H).

Step C: 2-(R)-(3-(R)-(Hydroxymethyl)-4-(S)-(3-fluorophenyl)pyrrolidin-1-yl)-3-(R)-methylpentanoic Acid, Benzyl Ester The product from Step B above in 15 mL THF was treated with 7 mL 1 N tetrabutylammonium fluoride in THF overnight. The reaction mixture was partitioned between 300 mL of ether and 150 mL icy water. The organic layer was washed with 75 mL 5% NaHCO$_3$ (3x) and saturated brine. The organic layer was dried over Na$_2$SO$_4$ and concentrated. Flash chromatography on 100 g of silica gel using 20~40% ethyl acetate in hexanes with 1% triethylamine afforded 1.24 g of the title compound as a colorless oil: $^1$H NMR (500 MHz) δ 7.33~7.42 (m, 5H), 7.21~7.26 (m, 1H), 6.98 (d, J=7.6 Hz, 1H), 6.88~6.95 (m, 2H), 5.19 (s, 2H), 3.66~3.69 (m, 1H), 3.55~3.60 (m, 1H), 3.24~3.28 (m, 1H), 3.18 (d, J=9.2 Hz, 1H), 3.05~3.12 (m, 2H), 2.72 (dd, J=5.0 & 9.1 Hz, 1H), 2.60 (dd, J=7.7 & 9.0 Hz, 1H), 2.28~2.34 (m, 1H), 1.99~2.02 (m, 1H, OH?), 1.84~1.91 (m, 1H), 1.61~1.69 (m, ~1H), 1.16~1.25 (m, 1H), 0.92 (t, J=7.6 Hz, 3H), 0.91 (d, J=7.6 Hz, 3H).

Step D: 2-(R)-(3-(R)-Formyl-4-(S)-(3-fluorophenyl)pyrrolidin-1-yl)-3-(R)-methylpentanoic Acid, Benzyl Ester The title compound (1.031 g) was obtained from the alcohol in Step C above using the same procedure as described in Aldehyde 14 Step D. $R_f$: 0.47 (20% ethyl acetate in hexanes). $^1$H NMR (500 MHz) δ 9.64 (s, 1H), 7.34~7.42 (m, 5H), 7.24~7.28 (m, 1H), 6.91~6.99 (m, 3H), 5.20 (s, 2H), 3.53~3.58 (m, 1H), 3.12~3.29 (m, 4H), 2.89~2.94 (m, 1H), 2.66~2.71 (m, 1H), 1.88~1.93 (m, 1H), 1.63~1.70 (m, 1H), 1.15~1.21 (m, 1H), 0.89~0.93 (m, 6H).

ALDEHYDE 16

2-(R)-(3-(R)-Formyl-4-(S)-(3-fluorophenyl)pyrrolidin-1-yl)-3-(S)-methylpentanoic Acid, (4-Methoxy)benzyl Ester Step A: 2-(S)-Trifluoromethanesulfonyl-3-(S)-methylpentanoic Acid, (4-Methoxy)benzyl Ester The title compound was obtained from Hydroxyester 11 using the same procedure as described in Aldehyde 14 Step A for its benzyl analog. $^1$H NMR (500 MHz) δ 7.31~7.34 (m, 2H), 6.89~6.93 (m, 2H), 5.24 (AB d, J=11.7 Hz, 1H), 5.19 (AB d, J=11.9 Hz, 1H), 5.03 (d, 4.2 Hz, 1H), 3.83 (s, 3H), 2.09~2.17 (m, 1H), 1.41~1.49 (m, 1H), 1.39~1.47 (m, 1H), 1.24~1.33 (m, 1H), 1.03 (d, J=6.9 Hz, 3H), 0.89 (t, J=7.5 Hz, 3H).

Step B: 2-(R)-(3-(R)-(t-Butyldimethylsilyloxymethyl)-4-(S)-(3-fluorophenyl)pyrrolidin-1-yl)-3-(S)-methylpentanoic Acid, (4-Methoxy)benzyl Ester The title compound was obtained from triflate (Step A above) using the same procedure as described in Aldehyde 14 Step B for its benzyl analogue. $R_f$: 0.26 (1:15 ethyl acetate and hexanes). $^1$H NMR (500 MHz) δ 7.31~7.34 (m, 2H), 7.19~7.24 (m, 1H), 6.86~6.97 (m, 5H), 5.11 (s, 2H), 3.83 (s, 3H), 3.55 (dd, J=5.6 & 10.0 Hz, 1H), 3.495 (dd, J=7.0 & 9.9 Hz, 1H), 3.12~3.16 (m, 2H), 3.06~3.10 (m, 1H), 2.90~2.94 (m, 1H), 2.695 (dd, J=7.2 & 9.0 Hz, 1H), 2.62~2.65 (dd, J=6.6 & 9.0 Hz, 1H), 2.27~2.33 (m, 1H), 1.82~1.88 (m, 1H), 1.41~1.46 (m, 1H), 1.04~1.10 (m, 1H), 1.00 (d, J=6.7 Hz, 3H), 0.89 (t, J=7.3 Hz, 3H), 0.86 (s, 9H), 0.00 (s, 6H).

Step C: 2-(R)-(3-(R)-(Hydroxymethyl)-4-(S)-(3-fluorophenyl)pyrrolidin-1-yl)-3-(S)-methylpentanoic Acid, (4-Methoxy)benzyl Ester The title compound was obtained from triflate from Step B above using the same procedure as described in Aldehyde 14 Step C for its benzyl analogue. $^1$H NMR (500 MHz) δ 7.32~7.35 (m, 2H), 7.21~7.26 (m, 1H), 6.88~6.97 (m, 5H), 5.13 (s, 2H), 3.82 (s, 3H), 3.67 (dd, J=4.8 & 10.3 Hz, 1H), 3.57 (dd, J=6.2 & 10.3 Hz, 1H), 3.22~3.26 (m, 1H), 3.15 (d, J=9.3 Hz, 1H), 3.09~3.12 (m, 1H), 3.03~3.08 (m, 1H), 2.73 (dd, J=4.9 & 9.3 Hz, 1H), 2.61 (dd, J=7.7 & 9.1 Hz, 1H), 2.27~2.33 (m, 1H), 1.84~1.89 (m, 1H), 1.41~1.49 (m, 1H), 1.03~1.10 (m, 1H), 1.00 (d, J=6.6 Hz, 3H), 0.89 (t, J=7.3 Hz, 3H).

Step D: 2-(R)-(3-(R)-Formyl-4-(S)-(3-fluorophenyl)pyrrolidin-1-yl)-3-(S)-methylpentanoic Acid, (4-Methoxy)benzyl Ester The title compound was obtained from the alcohol (Step C above) using the same procedure as described in Aldehyde 14 Step D for its benzyl analogue. $^1$H NMR (500 MHz) δ 9.64 (d, J=2.1 Hz, 1H), 7.32~7.35 (m, 2H), 7.23~7.27 (m, 1H), 6.88~6.96 (m, 5H), 5.14 (AB d, J=11.9 Hz, 1H), 5.11 (AB d, J=11.9 Hz, 1H), 3.82 (s, 3H), 3.52~3.57 (m, 1H), 3.24~3.27 (m, 1H), 3.12~3.20 (m, 3H), 2.88~2.92 (m, 1H), 2.68 (dd, J=7.8 & 8.9 Hz, 1H), 1.84~1.91 (m, 1H), 1.38~1.45 (m, 1H), 1.05~1.13 (m, 1H), 0.98 (d, J=6.7 Hz, 3H), 0.90 (t, J=7.3 Hz, 3H).

ALDEHYDE 17

α-(R)-(3-(R)-Formyl-4-(S)-(3-fluorophenyl)pyrrolidin-1-yl)-tert-butylacetic Acid, Benzyl Ester

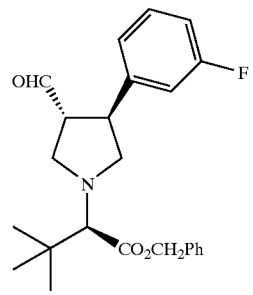

Step A: 3,3-Dimethyl-2-(S)-hydroxybutyric Acid Benzyl Ester (S)-3,3-dimethyl-2-hydroxybutyric acid (2.1 grams, 15.9 mmol) and triethylamine (3.3 mL, 23.8 mmoL) were dissolved in 15 mL DMF. Benzylbromide (2.8 mL, 23.8 mmol) was added and the mixture was stirred overnight. Ethyl acetate was added and the mixture was washed with water (3×) and sat'd NaCl then dried over sodium sulfate and concentrated. Flash chromatography (150 g silica, 7/1Hexane/EtOAc) afforded 3.4 grams (96%) of the title compound. $^1$H NMR (300 MHz, CDCl$_3$). δ 0.98 (s, 9H), 2.75 (d, 1H), 3.85 (d, 1H), 5.23, (s, 2H), 7.27–7.3 (m, 5H).

Step B: 3,3-Dimethyl-2-(S)-trifluoromethanesulfonylbutyric Acid Benzyl Ester

A solution of 3,3-dimethyl-2-(S)-hydroxybutyric acid benzyl ester (3.4 grams, 15.3 mmol, from Step A) in 60 mL dichloromethane was cooled to −78 C under nitrogen. 2,6-lutidine (2.3 mL, 19.9 mmol) then trifluoromethanesulfonic anhydride (3.1 mL, 18.4 mmol) were added dropwise via syringe. The mixture was warmed to room temperature and stirred for 1 h. Water was added and the mixture was extracted with ethyl acetate. The organic layer was dried over sodium sulfate and concentrated. Flash chromatography (150 g silica, 20/1 Hexane/EtOAc) afforded 3.3 grams (61%) of the desired triflate. $^1$H NMR (400 MHz, CDCl$_3$). δ 1.05 (s, 9H), 4.8, (s, 1H), 5.25 (dd, 2H), 7.3–7.4 (m, 5H).

Step C: α-(R)-((3-(R)-(tert Butyldimethylsilyloxy)methyl)-4-(S)-(3-fluorophenyl)pyrrolidin-1-yl)-tert-butylacetic Acid A dry flask was charged 10 mL DMF and 3,3-dimethyl-2-(S)-trifluoromethanesulfonylbutyric acid benzyl ester, (2.2 grams, 6.4 mmol). The vessel was purged with nitrogen and 3-(R)-(t-butyldimethylsilyloxymethyl)-4-(S)-(3-fluoro)phenyl pyrrolidine (2.7 grams, 8.9 mmol, Pyrrolidine 2) then diisopropylethyl amine (1.8 mL, 10.2 mmol) were added. The mixture was heated to 50 C overnight. Water (200 mL) was added and the mixture was extracted with ether (2×150 mL). The combined organics were dried over sodium sulfate and concentrated. Flash chromatography (150 g silica, 30/1 Hexane/EtOAc) afforded 2.0 grams (61%) of product. $^1$H NMR (400 MHz, CDCl$_3$). δ 0 (s, 6H), 0.84 (s, 9H), 1.05 (s, 9H), 2.25–2.35 (m, 1H), 2.8–2.94 (m, 3H), 3.1–3.22 (m, 3H), 3.45–3.58 (m, 2H), 5.1–5.25 (dd, 2H), 6.83–6.99 (m, 3H), 7.19–7.24 (m, 1H), 7.3–7.42 (m, 5H).

Step D: α-(R)-(3-(R)-Formyl-4-(S)-(3-fluorophenyl)pyrrolidin-1-yl)-tert-butylacetic Acid, Benzyl Ester The title compound was prepared in two steps from A-(R)-(3-(S)-tert butyldimethylsilyloxy)methyl)-4-(S)-(3-fluorophenyl)pyrrolidin-1-yl)-tert-butylacetic acid (Step C) using procedures analogous to those in for Aldehyde 1 Steps B and C. $^1$H NMR (400 MHz, CDCl$_3$). δ 1.05 (s, 9H), 2.88–2.96 (m, 2H), 3.2–3.35 (m, 4H), 3.48–4.53 (q, 1H), 5.11–5.25 (dd, 2H), 6.89–6.99 (m, 3H, 7.21–7.26 (m, 1H). 7.35–7.45 (m, 5H), 9.61 (s, 1H).

ALDEHYDE 18

α-(R)-(3-(R)-Formyl-4-(S)-(3-fluorophenyl)pyrrolidin-1-yl)-tert-butylacetic Acid, 4-Methoxybenzyl Ester

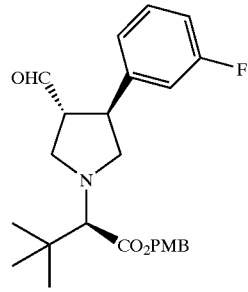

The title compound was prepared in an analagous fashion to aldehyde 17 except that in Step A 4-methoxybenzyl chloride was used rather than benzyl bromide. $^1$H NMR (400 MHz, CDCl$_3$). δ 1.05 (s, 9H), 2.85–2.96 (m, 2H), 3.18–3.36 (m, 4H), 3.45–4.53 (q, 1H), 3.82, (s, 3H), 5.05–5.22 (dd, 2H), 6.89–6.99 (m, 5H), 7.21–7.26 (m, 1H). 7.35–7.45 (m, 2H), 9.61 (s, 1H).

ALDEHYDE 19

2-(R)-(3-(R)-Formyl-4-(S)-(3-fluorophenyl)pyrrolidin-1-yl)-3-(cyclopropyl)propionic Acid, Benzyl Ester

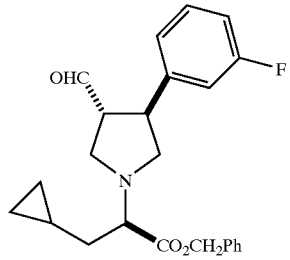

The title compound was prepared from α-Hydroxy Ester 12 and Pyrrolidine 2: $^1$H NMR (400 MHz) δ 0.03–0.12 (m, 2H), 0.40–0.52 (m, 2H), 0.70–0.80 (m, 1H), 1.59–1.67 (m, 1H), 1.73–1.81 (m, 1H), 2.77–2.82 (m, 1H), 2.94–3.00 (m, 1H), 3.18–3.23 (m, 2H), 3.26–3.34 (m, 1H), 3.50–3.57 (m, 1H), 3.58–3.63 (m, 1H), 5.20 (s, 2H), 6.90–7.02 (m, 3H), 7.22–7.30 (m, 1H), 7.34–7.42 (m, 5H), 9.67 (s, 1H); ESI-MS. M/z; (M+H)=396.1.

EXAMPLE 1

2-(R)-(3-(S)-((4-(N-(prop-1-yl)-N-(Pyrimid-2-yl)amino)piperidin-1-yl)methyl)-4-(S)-(3-fluorophenyl)pyrrolidin-1-yl)-3-cyclobutanepropionic Acid Step A: 4-Amino-1-tert-butoxycarbonylpiperidine 1-tert-butoxycarbonylpiperid-4-one (20 grams, 100 mmol), benzylamine (11 mL, 100 mmol) and sodium triacetoxyborohydride (32 grams, 150 mmol) were stirred together in 400 mL 1,2-dicloroethane for 3 h. The resulting mixture was diluted with 1 L of EtOAc and washed with 1M aqueous NaOH (500 mL) followed by sat'd aqueous NaCl (500 mL). The organic phase was dried over $Na_2SO_4$ and concentrated to afford 30.1 grams of 4-N-benzylamino-1-tert-butoxycarbonyl piperidine as a viscous oil. The oil was dissolved in 400 mL MeOH and ammonium formate (39 grams, 600 mmol) was added. The vessel was purged with nitrogen and 6.5 grams 10% palladium on carbon (6 mmol) was added. The mixture was refluxed for 1 h then filtered through celite and concentrated. Drying under vaccum afforded 20 grams (100% yield) of the title compound. $^1$H NMR (300 MHz, $CDCl_3$). δ 1.15–1.3 (m, 2H), 1.43 (s, 9H), 1.7–1.9 (m, 4H), 2.65–2.72 (m, 3H), 3.95–4.1 (m, 2H).

Step B: 4-N-(Pyrimid-2-yl)amino-1-tert-butoxycarbonylpiperidine 4-amino-1-tert-butoxycarbonylpiperidine (1.9 grams, 9.5 mmol, from Step A), 2-chloropyrimidine (1.1 grams, 9.5 mmol) and N,N-diisopropylethylamine (3.3 mL, 19 mmol) were combined in 10 mL isopropanol and the mixture was refluxed for 24 h. The mixture was cooled, diluted with 100 mL $CH_2Cl_2$ and washed with water and sat'd aqueous NaCl. The organic phase was dried over $MgSO_4$ and concentrated. Flash chromatography (60 grams silica, 1/1 hexane/EtOAc eluent) afforded 0.97 grams (37%) of the title compound. $^1$H NMR (300 MHz, $CDCl_3$). δ 1.31–1.45 (m, 2H), 1.44 (s, 9H), 2.0–2.1 (m, 2H), 2.9–3.0 (m, 2H), 3.9–4.1 (m, 3H), 5.0–5.05 (m, 1H), 6.5–6.58, (t 1H), 8.15–8.2 (d, 2H).

Step C: 4-(N-(Pyrimid-2-yl)-N-allyl)amino-1-tert-butoxylcarbonylpiperidine

A solution of 4-N-(pyrimid-2-yl)amino-1-tert-butoxycarbonyl-piperidine (528 mg, 1.9 mmol, from Step B) in 5 mL dry THF was cooled to −78° C. and a solution of sodium hexamethyldisilazide (2.8 mL, 1.0 M in THF, 2.8 mmol) was added via syringe. The mixture was stirred cold for 20 min then allylbromide (0.23 mL, 2.7 mmol) was added. The mixture was then warmed to room temp and stirred for 1.5 h at which time tlc showed very little starting material. The solution was poured into 100 mL sat'd ammonium chloride/100 mL $CH_2Cl_2$. The layers were separated and the organic phase was dried over $Na_2SO_4$ and concentrated. Flash chromatography (25 grams silica, 4/1 hexane/EtOAc eluent) afforded 367 mg (61%) of 4-N-(pyrimid-2-yl)-N-allylamino-1-tert-butoxycarbonylpiperidine. $^1$H NMR (300 MHz, $CDCl_3$). δ 1.45 (s, 9H), 1.6–1.8 (m, 4H), 2.75–2.85 (m, 2H), 4.1–4.3 (m, 4H), 4.7–4.8 (m, 1H), 5.05–5.17 (m, 2H), 5.92–5.98 (m, 1H), 6.45–6.5 (t, 1H), 8.3–8.35 (d, 2H).

Step D: 4-(N-(Pyrimid-2-yl)-N-prop-1-yl)aminopiperidine Dihydrochloride

In a round bottom flask purged with nitrogen 4-N-(pyrimid-2-yl)-4-N-allylamino-1-tert-butoxylcarbonylpiperidine (461 mg, 1.45 mmol, from Step C) was dissolved in 4 mL methanol and 150 mg (0.14 mmol) 10% palladium on carbon was added. The mixture was stirred under 1 atm of hydrogen using a balloon for 1.5 h. The mixture was filtered through celite and concentrated. Flash chromatography (20 grams silica, 3/1 hexane/EtOAc eluent) afforded 280 mg (60%) of 4-N-(pyrimid-2-yl)-4-N-prop-1-yl)amino-1-tert-butoxylcarbonylpiperidine. $^1$H NMR (400 MHz, $CDCl_3$). δ 0.9–1.0 (t, 3H, J=7 Hz), 1.5 (s, 9H), 1.6–1.8 (m, 6H), 2.8–2.9 (m, 2H), 3.33–3.4 (m, 2H), 4.2–4.27 (m, 2H), 4.7–4.8 (m, 1H), 6.42–6.45 (t, 1H), 8.3–8.35 (d, 2H). This material was dissolved in 2% conc. HCl/MeOH and heated to 50° C. for 2 h. Removal of solvent and drying under vacuum afforded the title compound as a white solid.

Step E: 2-(R)-(3-(S)-((4-(N-(prop-1-yl)-N-(Pyrimid-2-yl)-amino)-piperidin-1-yl)methyl)-4-(S)-(3-fluorophenyl)pyrrolidin-1-yl)-3-cyclobutanepropionic Acid A solution of 2-(R)-((3-(R)-formyl)-4-(S)-3-fluorophenylpyrrolidinyl-yl)-3-cyclobutanepropionic acid, benzyl ester (25 mg, 0.061 mmol; prepared above as Aldehyde 2) in 2 mL MeOH was stirred with 15 mg (0.014 mmol) 10% palladium on carbon under 1 atm of hydrogen using a balloon. After 1 hour the mixture was filtered through celite, concentrated and redissolved in 1 mL 1,2-dichloroethane. 4-(N-(pyrimid-2-yl)-4-N-prop-1-yl)aminopiperidine dihydrochloride (20 mg, 0.067 mmol from Step D), sodium triacetoxy borohydride (26 mg, 0.122 mmol) and triethylamine (0.024 mL, 0.171 mmol) were added and the mixture was stirred for 12 h. Solid di-tert-butyldicarbonate (25 mg, 0.11 mmol) was added and stirring was continued for 3 h. The solvent was removed and the product was purified by flash chromatography (3 grams silica 19/1 $CH_2Cl_2$/MeOH→19/1/0.2 $CH_2Cl_2$/MeOH/$NH_4OH$) to give 19.1 mg (60% yield). $^1$H NMR (500 MHz, $CDCl_3$). δ 0.92–0.95 (t, 3H, J=7 Hz), 1.55–3.5 (29H), 3.8–3.9 (m, 1H), 4.5–4.6 (m, 1H), 6.4–6.43 (t, 1H, J=4.8 Hz), 6.92–6.9 (t, 1H, J=6.4 Hz) 7.04–7.11 (m, 2H), 7.25–7.3 (m, 1H), 8.25–8.3 (d, 2H, J=4.8 Hz): ESI-MS. M/z; (M+H)=524.4 (obs), 524.3 (calc.).

EXAMPLE 2

2-(R)-(3-(S)-((4-(N-(prop-1-yl)-N-(Pyrimid-2-yl)amino)piperidin-1-yl)methyl)-4-(S)-(3-fluorophenyl)pyrrolidin-1-yl)cyclohexylacetic Acid Step A: 4-(N-(Pyrimid-2-yl)-N-allyl)aminopiperidine Dihydrochloride A solution of 4-(N-(pyrimid-2-yl)-N-allyl)amino-1-tertbutoxylcarbonylpiperidine (100 mg, 0.31 mmol; from material obtained in Example 1 Step C) in 2% conc. HCl/MeOH was heated to 50° C. for 2 h. Removal of solvent followed by drying under vacuum afforded the title compound (90 mg, 99%).

Step B: 2-(R)-(3-(S)-((4-(N-Allyl-N-(pyrimid-2-yl)amino)-piperidin-1-yl)methyl)-4-(S)-(3-fluorophenyl)pyrrolidin-1-yl)-cyclohexylacetic Acid, Benzyl Ester The title compound was prepared from 2-(R)-(3-(S)-formyl-4-(S)-(3-fluorophenyl)pyrrolidin-1-yl)-cyclohexaneacetic acid, benzyl ester 83 mg, 0.195 mmol; prepared above as Aldehyde 6), 4-(N-allyl-N-(pyrimid-2-yl)-amino)piperidine dihydrochloride (64 mg, 0.219mmol, from Step A), 104 mg (0.49 mmol) $NaHB(OAc)_3$, and 0.035 ml (0.25 mmol) triethylamine in 3 ml dichloromethane. The mixture was stirred overnight at room temperature. The reaction was diluted with 100 ml EtOAc and washed with 1M NaOH and saturated NaCl. The organic phase was dried over $Na_2SO_4$ and concentrated under reduced pressure. The material was purified using flash chromatography (5% EtOAc in hexane) to provide 83 mg of the title compound. $R_F$: 0.3 (5% EtOAc/hexane). HPLC (Zorbax SB-C8 column, 4.6 mm×7.5 cm, Gradient: 90 $H_2O$:10 $CH_3CN$ to 0 $H_2O$:100 $CH_3CN$ over 7.5 minutes then hold at 100 $CH_3CN$:0 $H_2O$ for 45 seconds, 2.25 mL/min, 220 nm): Retention Time: 4.6 minutes.

Step C: α-(R)-(3-(S)-((4-(N-(prop-1-yl)-N-(Pyrimid-2-yl)-amino)-piperidin-1-yl)methyl)-4-(S)-(3-fluorophenyl)pyrrolidin-1-yl)-cyclohexylacetic Acid A solution of 80 mg (0.12 mmol) of 2-(R)-(3-(S)-((4-(N-allyl-N-(pyrimid-2-yl)-amino)-piperidin-1-yl)methyl)-4-(S)-(3-fluorophenyl)-pyrrolidin-1-yl)-cyclohexylacetic acid, benzyl ester from Step B, in 3.0 mL of MeOH was hydrogenated using 20 mg (0.018 mmol) of 10% palladium on carbon under one atmosphere of hydrogen gas. After TLC indicated the absence of the starting benzylester, the reaction was filtered through a 0.45 micron nylon membrane polypropylene filter and concentrated under reduced pressure to give 60 mg of the title compound as a white solid. HPLC (Zorbax SB-C8 column, 4.6 mm×7.5 cm, Gradient: 90 $H_2O$:10 $CH_3CN$ to 0 $H_2O$:100 $CH_3CN$ over 7.5 minutes then hold at 100 $CH_3CN$:0 $H_2O$ for 45 seconds, 2.25 mL/min, 220 nm): Retention Time: 3.4 minutes. ESI-MS: 538.0 (M+1). $^1$H NMR (500 MHz, $CDCl_3$): δ 0.89–0.92 (t, J=7.4 Hz, 3H), 1.20–3.42 (25H), 3.87 (1H), 4.59 (1H), 6.42–6.43 (t, J=4.8 Hz, 1H), 6.91–6.95 (t, J=6.4 Hz, 1H), 7.03–7.09 (m, 2H), 7.24–7.31 (m, 1H), 8.24–8.25 (d, J=4.6 Hz, 2H).

EXAMPLE 3

2-(R)-(3-(S)-((4-(N-(prop-1-yl)-N-(Pyrid-3-yl)amino)piperidin-1-yl)methyl)-4-(S)-phenylpyrrolidin-1-yl)cyclohexaneacetic Acid Step A: 4-N-(Pyrid-3-yl)amino-1-tert-butoxycarbonylpiperidine 3-bromopyridine (0.096 mL, 1 mmol), 4-amino-1-tert-butoxycarbonylpiperidine (240 mg, 1.2 mmol from Example 1 Step A), sodium tert-butoxide (135 mg, 1.4 mmol), tris-dibenzylidine acetone dipalladium (18 mg, 0.02 mmol) and 2,2'-bis(diphenylphosphino)-1,1'-binaphthyl (25 mg, 0.04 mmol) were combined in 9 mL dry toluene under nitrogen. The mixture was heated to 70° C. for 2 h then cooled to room temperature and diluted with 50 mL EtOAc. The solution was washed with water and sat'd aq. NaCl then dried over $Na_2SO_4$ and concentrated. Flash chromatography (15 grams silica, 2/1 hexane/EtOAc eluent) afforded 257 mg (93%) of the title compound.

Step B: 4-N-(Pyrid-3-yl)-4-(N-allylamino)piperidine Dihydrochloride

4-N-(pyrid-3-yl)amino-1-tert-butoxycarbonyl-piperidine (200 mg, 0.72 mmol, from Step A) was allylated according to the procedure in Example 1 Step C to give pure product after workup. The Boc group was removed by heating in 2% conc. HCl/MeOH @ 50° C. for 2 h. Concentration and drying under vacuum provided 207 mg of the title compound.

Step C: 2-(R)-(3-(S)-((4-(N-(Allyl)-N-(pyrid-3-yl)-amino)-piperidin-1-yl)methyl)-4-(S)-phenylpyrrolidin-1-yl)-cyclohexaneacetic Acid Benzyl Ester A solution of 2-(R)-(3-(R)-formyl-4-(S)-phenylpyrrolidin-1-yl)cyclohexaneacetic acid, benzyl ester (35 mg, 0.086 mmol; prepared above as Aldehyde 4), 4-(N-(pyrid-3-yl)-N-allylamino)piperidine dihydrochloride (28 mg, 0.103 mmol, from Step B), sodium triacetoxyborohydride (44 mg, 0.206 mmol) and triethylamine (0.03 mL, 0.206 mmol) were stirred in 2 mL 1,2-dichloroethane for 12 h. The mixture was diluted with 25 mL EtOAc and washed with water and sat'd aq. NaCl. The organic phase was dried over $Na_2SO_4$ and concentrated. Flash chromatography (5 grams silica, 0→2% MeOH/$CH_2Cl_2$ eluent) afforded 37 mg (70%) of the title compound. M/z; (M+H)=607.4 (obs), 607.4 (calc.).

Step D: 2-(R)-(3-(S)-((4-(N-(prop-1-yl)-N-(Pyrid-3-yl)-amino)-piperidin-1-yl)methyl)-4-(S)-phenylpyrrolidin-1-yl)-cyclohexaneacetic Acid A solution of 2-(R)-(3-(S)-((4-(N-(allyl)-N-(pyrid-3-yl)-amino)-piperidin-1-yl)methyl)-4-(S)-phenylpyrrolidin-1-yl)-cyclohexaneacetic acid benzyl ester (37 mg, 0.061 mmol from Step C) in 2 mL MeOH was stirred with 13 mg (0.012 mmol) 10% palladium on carbon under 1 atm of hydrogen using a balloon. After 2 h the mixture was filtered and concentrated to provide 30 mg of the title compound. $^1$H NMR (500 MHz, $CDCl_3$) δ 0.90–0.93 (t, 3H, J=7.5 Hz), 1.1–3.4 (m, 33H), 6.91–6.93 (d, 1H, J=8 Hz), 7.07–7.1 (m, 1H), 7.2–7.35 (m, 5H), 7.92–7.93 (d, 1H, J=4 Hz), 8.08–8.09 (d, 1H, J=2 Hz). ESI-MS. M/z; (M+H)=519.4 (obs), 519.36 (calc.).

EXAMPLE 4

2-(R)-(3-(S)-((4-(N-(Pyrimid-2-yl)amino)piperidin-1-yl)methyl)-4-(S)-(3-fluorophenyl)pyrrolidin-1-yl)cyclohexaneacetic Acid Step A: 4-N-(Pyrimid-2-yl)aminopiperidine Dihydrochloride A solution of 4-N-(pyrimid-2-yl)amino-1-tert-butoxycarbonyl-piperidine (40 mg, 0.199 mmol from Example 1 Step B) in 2% HCl/MeOH was heated to 50° C. for 2 h then concentrated and dried under vacuum to provide the title compound.

Step B: 2-(R)-(3-(S)-((4-(N-(Pyrimid-2-yl)amino)piperidin-1-yl)methyl)-4-(S)-phenylpyrrolidin-1-yl)cyclohexaneacetic Acid A solution of 2-(R)-(3-(R)-formyl-4-(S)-phenylpyrrolidin-1-yl)-cyclohexaneacetic acid, benzyl ester (30 mg, 0.074 mmol; prepared above as Aldehyde 4), 4-N-(pyrimid-2-yl)aminopiperidine dihydrochloride (26 mg, 0.103 mmol from Step A), sodium triacetoxyborohydride (31 mg, 0.146 mmol) and triethylamine (0.03 mL, 0.206 mmol) were stirred in 1 mL 1,2-dichloroethane for 4 h. The product was purified by preparative tlc (12/1 $CH_2Cl_2$/MeOH eluent) then dissolved in 1 mL MeOH and stirred with 25 mg (0.023 mmol) 10% palladium on carbon under 1 atm hydrogen. After 3 h LC/MS showed both desired and over-reduced product. The catalyst was filtered off and the solvent was removed. The desired compound was purified by preparative HPLC (column: Zorbax SB-C8 9.5×250 mm, gradient: 5% acetonitrile/water w/0.1% TFA for 5 min then ramp to 50% acetonitrile/water w/0.1% TFA over 30 min, flow: 10 mL/min) to afford 12 mg (34%) of the title compound. $^1$H NMR (500 MHz, $CD_3OD$). δ 01.16–1.39 (m, 5H), 1.45–1.52 (m, 3H), 1.67–1.7 (m, 1H), 1.78–1.96 (m, 7H), 2.15–2.2 (m, 1H), 2.33–2.37 (m, 1H), 2.48–2.52 (m, 1H), 2.71–2.91 (m, 3H), 3.17–3.18 (m, 1H), 3.29–3.70 (m, 6H), 6.54–6.56 (t, 1H, J=5 Hz), 7.29–7.32 (m, 1H), 7.35–7.39 (m, 4H), 8.21–8.22 (d, 2H, J=5 Hz). ESI-MS. M/z; (M+H)=478.5 (obs), 478.31 (calc.)

EXAMPLE 5

2-(R)-(3-(S)-((4-(N-(4-Methylthiazol-2-yl)-N-(propy-1-yl)amino)piperidin-1-yl)methyl)-4-(S)-phenylpyrrolidin-1-yl)cyclohexaneacetic Acid Step A: 4-N-(prop-1-yl)Amino-1-tert-butoxycarbonylpiperidine A solution of 1-tert-butoxycarbonylpiperid-4-one (5 grams, 25 mmol), N-propylamine (3.69 mL, 45 mmol), acetic acid (1.43 mL, 25 mmol), and sodium triacetoxyborohydride (7.95 grams, 37.5 mmol) in dichloromethane (100 mL) was stirred for 16 h. The mixture was washed with water (50 mL) was then sat'd sodium bicarbonate. The aqueous layer was extracted with 20 mL dichloromethane and the combined organic phases were dried over $MgSO_4$ and concentrated to provide 6 grams (95%) of the title compound.

Step B: N-(prop-1-yl)-N-(4-(1-tert-Butoxycarbonyl)piperidyl)thiourea

4-N-(prop-1-yl)amino-1-tert-butoxycarbonyl-piperidine (2.42 grams, 10 mmol, from Step A) and N-benzoylisothiocyanate (1.48 mL, 11 mmol) were stirred in dichloromethane (20 mL) overnight. The mixture was concentrated and 50 mL hexane was added which caused precipitation of a white solid. The solid was washed with 25 mL hexane and dried to give 3.4 grams of material. The material so isolated was dissolved in 50 mL dioxane and 8.4 mL hydrazine was added. After 1 h tlc showed complete reaction. The mixture was concentrated and the product was purified by flash chromatography (50/1 $CH_2Cl_2$/MeOH) to give 2.4 grams (96%) of the title compound.

Step C: 4-(N-(4-Methylthiazol-2-yl)-N-(propy-1-yl)amino)-1-tert-butoxycarbonylpiperidine A solution of N-(prop-1-yl)-N-(4-(1-tert-butoxycarbonyl)-piperidyl)thiourea (60 mg, 0.2 mmol, from Step B) and 2-chloroacetone (0.016 mL) were heated together in 0.5 mL DMF at 86° C. for 16 h. The mixture was concentrated and flash chromatography (5.5/1 hexane/EtOAc) afforded 44 mg of the title compound.

Step D: 4-N-(4-Methylthiazol-2-yl)-(N-(propy-1-yl)amino) piperidine

4-N-(4-methylthiazol-2-yl)-(N-(propy-1-yl)amino)-1-tert-butoxycarbonylpiperidine (44 mg from Step G) was dissolved in 2 mL 1/1 TFA/$CH_2Cl_2$ and stirred for 30 min. The mixture was diluted with 5 mL $CH_2Cl_2$ and washed with sat'd aqueous $NaHCO_3$ (3×). The organic phase was dried dried over $Na_2SO_4$ and concentrated to give 32 mg of the title compound.

Step E: 2-(R)-(3-(S)-((4-(N-(4-Methylthiazol-2-yl)-N-(propy-1-yl)-amino)piperidin-1-yl)methyl)-4-(S)-phenylpyrrolidin-1-yl)-cyclohexaneacetic Acid A solution of 2-(R)-(3-(R)-Formyl-4-(S)-phenylpyrrolidin-1-yl)-cyclohexaneacetic acid, para-methoxybenzyl ester (35 mg, 0.086 mmol; prepared above as Aldhyde 5), 4-(N-(4-methylthiazol-2-yl)-N-(propy-1-yl)-amino)piperidine (24 mg, 0.098 mmol from Step D) and sodium triacetoxyborohydride, 32 mg (0.15 mmol) in 0.7 mL 1,2-dichloroethane was stirred for 12 h. The solvent was removed and the product was purified by preparative HPLC (column: YMC Combiprep ODS-A 20×50 mm, gradient: 5% acetonitrile/water w/0.1% TFA for 1 min then ramp to 100% acetonitrile/water w/0.1% TFA over 6 min, flow: 20 mL/min). The so isolated material was stirred in 3 mL formic acid for 16 h. After removal of solvent the residue was purified by ion exchange chromatography (3 grams SCX resin, 100% MeOH→2.0 M $NH_3$/MeOH) to give 17 mg (42%) of the title compound. $^1$H NMR (500 MHz, $CD_3OD$). δ 0.90–0.93 (t, 3H, J=7 Hz), 1.15–2.0 (m, 18H), 2.1–2.15 (m, 1H), 2.15 (s, 3H), 2.25–2.3 (m, 1H), 2.5–2.6 (m, 1H), 2.8–2.9 (m, 2H), 3.0–3.1 (m, 1H), 3.14–3.25 (m, 3H), 3.43–3.85 (m, 6H), 6.1 (s, 1H), 7.29–7.32 (m, 1H), 7.35–7.39 (m, 4H), ESI-MS. M/z; (M+H)=539.5 (obs), 539.33 (calc.).

EXAMPLE 6

2-(R)-(3-(S)-((4-(N-(5-Benzyltriazol-2-yl)-N-(prop-1-yl)amino)piperidin-1-yl)methyl)-4-(S)-phenylpyrrolidin-1-yl)cyclohexaneacetic Acid Step A 4-N-(5-Methyl-1,3,4-triazol-2-yl)-(N-propylamino) piperidine The title compound was prepared using a procedure analogous to that described in Example 21, Steps A to E, below, except that in Step A, n-propylamine was used instead of 2-phenethylamine; in Step B, 2-phenylacetyl chloride was used instead of acetyl chloride and in Step D, $NH_2NH_2$ was used instead of $NH_2OH$.

Step B: 2-(R)-(3-(S)-((4-(N-(5-Benzyltriazol-2-yl)-N-(prop-1-yl)amino)piperidin-1-yl)methyl)-4-(S)-phenylpyrrolidin-1-yl)cyclohexaneacetic Acid The title compound was prepared according to the procedure in Example 5 from of 2-(R)-(3-(R)-Formyl-4-(S)-phenyl-pyrrolidin-1-yl)cyclohexaneacetic acid, para-methoxybenzyl ester (33 mg, 0.075 mmol; prepared above as Aldehyde 5) and 4-(N-(5-benzyltriazol-2-yl)-N-(propy-1-yl)-amino)piperidine (29 mg, 0.098 mmol, from Step A). 11.2 mg (25%) was obtained. $^1$H NMR (500 MHz, $CD_3OD$). δ 0.88–0.91 (t, 3H, J=7.5 Hz), 1.15–1.95 (m 19H), 2.1–2.2 (m, 1H), 2.3–2.4 (m, 1H), 2.7–2.85 (m, 2H), 2.95–3.22 (m, 4H), 3.43–3.75 (m, 6H), 4.84 (s, 2H), 7.16–7.35 (m, 10H), ESI-MS. M/z; (M+H)=599.5 (obs), 599.4 (calc.).

EXAMPLES 7–13

Examples 7–13 in Table 1 were prepared according to the procedure given in Example 5 Step E, the procedure given in Example 1 Step E or the procedure given below for Examples 14–20. The piperidine derivatives were prepared in a fashion analogous to that shown above for the specific examples.

TABLE 1

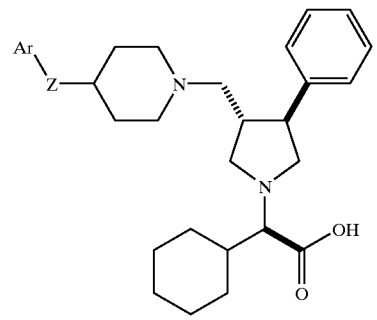

| EXAMPLE # | Ar | Z | ESI-MS M/z (M + 1) |
|---|---|---|---|
| 7 | 4-phenylpyrimidin-2-yl | N-ethyl | 596.5 |

TABLE 1-continued

| EXAMPLE # | Ar | Z | ESI-MS M/z (M + 1) |
|---|---|---|---|
| 8 | pyrimidin-2-yl | –O–CH2– | 479.4 |
| 9 | 5-phenyl-1H-1,2,4-triazol-3-yl | –N(CH2CH2Me)– | 585.5 |
| 10 | benzoxazol-2-yl | –N(CH2CH2Me)– | 559.5 |
| 11 | 5-benzyl-1,2,4-oxadiazol-3-yl | –N(CH2CH2Me)– | 600.5 |
| 12 | 5-phenyl-1,2,4-oxadiazol-3-yl | –N(CH2CH2Me)– | 586.5 |
| 13 | 4-(4-fluorobenzyl)-5-methylthiazol-2-yl | –N(CH2CH2Me)– | 647.6 |

EXAMPLES 14–20

Examples 14–20 in Table 2 were prepared according to the following procedure: A solution of 2-(R)-((3-(R)-Formyl)-4-(S)-(3-fluorophenyl)pyrrolidin-1-yl)-3-cyclobutanepropionic acid, benzyl ester (32 mg, 0.078 mmol; prepared above as Aldehyde 2), the appropriate piperidine derivative (0.09 mmol), sodium triacetoxyborohydride (32 mg, 0.152 mmol) and triethylamine (0.032 mL, 0.227 mmol) was stirred for 3–4 h until no aldehyde remained by HPLC. The crude mixture was filtered through a pad of silica (3 grams) eluting with 19/1 CH$_2$Cl$_2$/MeOH. The solvent was removed and the residue was dissolved in 2 mL MeOH and stirred over palladium on carbon (0.015 mmol) under 1 atm of hydrogen using a balloon. After complete reaction the catalyst was filtered off and the product was purified by flash chromatography (3 grams silica 19/1 CH$_2$Cl$_2$/MeOH→19/1/0.2 CH$_2$Cl$_2$/MeOH/NH$_4$OH) to give the pure compounds.

The piperidine derivatives were prepared in a fashion analogous to that shown above for the specific examples.

TABLE 2

| EXAMPLE # | Ar | R | ESI-MS M/z (M + 1) |
|---|---|---|---|
| 14 | F$_3$C-pyrimidin-2-yl | propyl (Me) | 592.3 |
| 15 | pyrimidin-2-yl | propyl (Me) | 510.3 |
| 16 | pyrimidin-2-yl | CH$_2$-cyclopropyl | 536.3 |
| 17 | F-pyrimidin-2-yl | propyl (Me) | 528.4 |
| 18 | F-pyrimidin-2-yl | propyl (Me) | 542.4 |
| 19 | MeO-pyrimidin-2-yl | propyl (Me) | 554.3 |

TABLE 2-continued

| EXAMPLE # | Ar | R | ESI-MS M/z (M + 1) |
|---|---|---|---|
| 20 | F$_3$C-pyrimidin-2-yl | propyl (Me) | 592.3 |

EXAMPLE 21

2-(R)-(3-(S)-((4-(N-(5-Methyl-1,2,4-oxadiazol-3-yl)-N-(2-phenethyl)amino)piperidin-1-yl)methyl)-4-(S)-phenylpyrrolidin-1-yl)-cyclohexaneacetic Acid Step A: 4-(N-(2-Phenylethyl)amino)-1-(tert-butoxycarbonyl)piperidine To a solution of tert-butyl-4-oxo-1-piperidinecarboxylate in methylene chloride was added 2-phenethylamine, NaBH(OAc)$_3$ and HOAc. The mixture was stirred at ambient temperature for 16 hours and quenched by addition of H$_2$O. The aqueous layer was neutralized with NaHCO$_3$ and extracted with CH$_2$Cl$_2$. The combined organic layer was washed with saturated NaHCO$_3$ and brine and dried over MgSO$_4$. Evaporation of solvent gave an off-white solid. This material was used without further purification. ESI-MS 305 (M+H); HPLC A: 2.54 min.

Step B: 1-Acetyl-3-(1-tert-butoxycarbonylpiperidin-4-yl)-3-(2-phenethyl)thiourea To a suspension of NaSCN in acetone was added acetyl chloride at ambient temperature. The mixture was stirred for 2 hours and a solution of 4-(N-(2-phenylethyl)amino)-1-(tert-butoxycarbonyl)piperidine was added. The reaction was stirred for 2 hours at ambient temperature, and then refluxed for 1.5 hours. After extractive work up, a yellow solid was afforded. This material was used without further purification. ESI-MS 350 (M-t-Bu+H); HPLC A: 3.39 min.

Step C: 1-Acetyl-3-(1-tert-butoxycarbonylpiperidin-4-yl)-3-(2-phenethyl)-2-methyl-2-thiopseudourea To a methanol solution of 1-acetyl-3-(1-tert-butoxycarbonylpiperidin-4-yl)-3-(2-phenethyl)thiourea was added methyl iodide and DIEA. After stirring for 3 hours, the solvent was removed in vacuo and the reaction mixture was purified by flash chromatography on silica. The product appeared as a clear oil. ESI-MS 420 (M+H); HPLC A: 3.19 min.

Step D: 1-tert-Butoxycarbonyl-4-(N-(5-methyl-1,2,4-oxadiazol-3-yl)-N-(2-phenethyl)amino)piperidine To an ethanol solution of 1-acetyl-3-(1-tert-butoxycarbonylpiperidin-4-yl)-3-(2-phenethyl)-2-methyl-2-thiopseudourea was added NH$_2$OH. The reaction mixture was refluxed for 16 hours before ethanol was removed in vacuo. Purification by flash chromatography on silica afforded the product as a clear oil. ESI-MS 387 (M+H); HPLC A: 3.79 min.

Step E: 4-(N-(5-Methyl-1,2,4-oxadiazol-3-yl)-N-(2-phenethyl)amino)piperidine 1-tert-Butoxycarbonyl-4-(N-(5-methyl-1,2,4-oxadiazol-3-yl)-N-(2-phenethyl)amino)piperidine was dissolved in a mixture of 1:1 TFA/CH$_2$Cl$_2$. The mixture was allowed to stand for 30 minutes at ambient temperature before the solvents were removed in vacuo. The residue was washed with saturated NaHCO$_3$. The resulting suspension was extracted with ethyl acetate. The combined organic layer was dried over MgSO$_4$. Evaporation of solvent resulted a clear oil. ESI-MS 287 (M+H); HPLC A: 2.04 min.

Step F: 2-(R)-(3-(S)-((4-(N-(5-Methyl-1,2,4-oxadiazol-3-yl)-N-(2-phenethyl)amino)piperidin-1-yl)methyl)-4-(S)-phenylpyrrolidin-1-yl)-cyclohexaneacetic Acid, Benzyl Ester To a solution of 4-N-(5-methyl-1,2,4-oxadiazol-3-yl)-(N-(2-phenethyl)amino)piperidine and 2-(R)-(3-(R)-formyl-4-(S)-phenylpyrrolidin-1-yl)-cyclohexaneacetic acid, benzyl ester (prepared above as Aldehyde 4) in CH$_2$Cl$_2$ was added NaHB(OAc)$_3$ and HOAc. The reaction mixture was stirred for 16 hours. After extractive work up, the crude product was purified by flash chromatography on silica. ESI-MS 676 (M+H); HPLC A: 3.21 min.

Step G: 2-(R)-(3-(S)-((4-(N-(5-Methyl-1,2,4-oxadiazol-3-yl)-N-(2-phenethyl)amino)piperidin-1-yl)methyl)-4-(S)-phenylpyrrolidin-1-yl)-cyclohexaneacetic Acid To a solution of 2-(R)-(3-(S)-((4-(N-(5-methyl-1,2,4-oxadiazol-3-yl)-N-(2-phenethyl)amino)piperidin-1-yl)methyl)-4-(S)-phenylpyrrolidin-1-yl)-cyclohexaneacetic acid, benzyl ester in methanol was added 10% Pd/C, the reaction mixture was vigorously stirred for 45 minutes under 1 atm of hydrogen. The mixture was filtered and methanol removed in vacuo. The crude product was purified by reverse phase HPLC. ESI-MS 586 (M+H); HPLC A: 2.54 min.

EXAMPLE 22

2-(R)-(3-(S)-((4-(N-(5-Methyl-1,3,4-triazol-2-yl)-N-(2-phenethyl)amino)piperidin-1-yl)methyl)-4-(S)-phenylpyrrolidin-1-yl)-cyclohexaneacetic Acid Step A: 4-(N-(5-Methyl-1,3,4-triazol-2-yl)-N-(2-phenethyl)amino)piperidine The title compound was prepared from 1-acetyl-3-(1-tert-butoxycarbonylpiperidin-4-yl)-3-(2-phenethyl)-2-methyl-2-thiopseudourea (From Example 21, Step C) using a procedure analogous to that described in Example 21, Steps D to E, employing NH$_2$NH$_2$ instead of NH$_2$OH. ESI-MS 286 (M+H); HPLC A: 1.28 min.

Step B: 2-(R)-(3-(S)-((4-(N-(5-Methyl-1,3,4-triazol-2-yl)-N-(2-phenethyl)amino)piperidin-1-yl)methyl)-4-(S)-phenylpyrrolidin-1-yl)-cyclohexaneacetic Acid The title compound was prepared by using procedures analogous to that described in Example 21, Step F to G. ESI-MS 585 (M+H); HPLC A: 2.00 min.

EXAMPLE 23

2-(R)-(3-(S)-((4-(N-(1,3-Thiazol-2-yl)-N-(2-phenethyl)amino)piperidin-1-yl)methyl)-4-(S)-phenylpyrrolidin-1-yl)-cyclohexaneacetic Acid STEP A: 1-(1-tert-Butoxycarbonylpiperidin-4-yl)-1-(2-phenethyl)thiourea To a solution of 1-acetyl-3-(1-tert-butoxycarbonylpiperidin-4-yl)-3-(2-phenethyl)thiourea (From Example 21, Step B) in methanol was added NH$_2$NH$_2$. The mixture was refluxed for 35 minutes. The solvent was removed and the crude product was purified by flash chromatography on silica. ESI-MS 364 (M+H); HPLC A: 3.31 min.

Step B: 1-tert-Butoxycarbonyl-4-(N-(1,3-thiazol-2-yl)-N-(2-phenethyl)amino)piperidine To a solution of 1-(1-tert-butoxycarbonylpiperidin-4-yl)-1-(2-phenethyl)thiourea in ethanol was added DIEA and chloroacetaldehyde. The mixture was heated at 90° C. for 1.5 hours. After evaporating the solvent, the crude product was purified by flash chromatography on silica. ESI-MS 388 (M+H); HPLC A: 2.82 min.

Step C: 4-(N-(1,3,-Thiazol-2-yl)-N-(2-phenethyl)amino)piperidine

The title compound was prepared using a procedure analogous to that described in Example 21, Step E. The compound was purified by reverse phase HPLC. ESI-MS 288 (M+H); HPLC A: 1.52 min.

Step D: 2-(R)-(3-(S)-((4-(N-(1,3,-Thiazol-2-yl)-N-(2-phenethyl)amino)piperidin-1-yl)methyl)-4-(S)-phenylpyrrolidin-1-yl)-cyclohexaneacetic Acid, 4-Methoxybenzyl Ester The title compound was prepared from 4-(N-(1,3,-thiazol-2-yl)-N-(2-phenethyl)amino)piperidine using a procedure analogous to that described in Example 21, Step F. 2-(R)-(3-(R)-formyl-4-(S)-phenylpyrrolidin-1-yl)-cyclohexaneacetic acid, 4-methoxybenzyl ester (prepared above as Aldehyde 5) was used instead of 2-(R)-(3-(R)-formyl-4-(S)-phenylpyrrolidin-1-yl)cyclohexaneacetic acid, benzyl ester. ESI-MS 707 (M+H); HPLC A: 3.09 min.

Step E: 2-(R)-(3-(S)-((4-(N-(1,3,-Thiazol-2-yl)-N-(2-phenethyl)amino)-piperidin-1-yl)methyl)-4-(S)-phenylpyrrolidin-1-yl)-cyclohexaneacetic Acid The title compound was prepared by dissolving 2-(R)-(3-(S)-((4-(N-(1,3,-thiazol-2-yl)-N-(2-phenethyl)amino)piperidin-1-yl)methyl)-4-(S)-phenylpyrrolidin-1-yl)-cyclohexaneacetic acid, 4-methoxybenzyl ester in neat formic acid, the solution was allowed to stand for 16 hours before the formic acid was removed in vacuo. The crude product was purified by reverse phase HPLC and ESI-MS 587 (M+H); HPLC A: 2.23 min.

EXAMPLE 24

2-(R)-(3-(S)-((4-(N-(4-Methyl-1,3-Thiazol-2-yl)-N-(2-phenethyl)amino)piperidin-1-yl)methyl)-4-(S)-phenylpyrrolidin-1-yl)-cyclohexaneacetic Acid The title compound was prepared using a procedure analogous to that described in Example 23, Steps A to E, except in Step B bromoacetone was used instead of chloroacetaldehyde and the compound was purified by flash chromatography on silica. ESI-MS 601 (M+H); HPLC A: 2.22 min.

EXAMPLE 25

2-(R)-(3-(S)-((4-(N-(prop-1-yl)-N-(pyrimid-2-yl)-amino)-piperidin-1-yl)methyl)-4-(S)-(3-fluorophenyl)pyrrolidin-1-yl)-cyclohexylacetic Acid Step A 2-(R)-(3-(S)-((4-(N-(prop-1-yl)-N-(Pyrimid-2-yl)-amino)-piperidin-1-yl)methyl)-4-(S)-(3-fluorophenyl)pyrrolidin-1-yl)cyclohexylacetic Acid, Benzyl Ester The title compound was prepared using 2-(R)-((3-(R)-formyl-4-(S)-(3-fluorophenyl)pyrrolidin-1-yl)-cyclohexaneacetic acid, benzyl ester (83 mg, 0.196 mmol; prepared above as Aldehyde 6), 4-(N-allyl-N-(pyrimid-2-yl)amino)piperidine hydrochloride (64 mg, 0.25 mmol) from Example 2, Step A, NaHB(OAc)$_3$, (104 mg, 0.49 mmol) and triethylamine (0.035 ml, 1.3 mmol) in 3 ml dichloromethane. The mixture was stirred overnight at room temperature. The reaction was diluted with 100 ml EtOAc and washed with 1M NaOH and saturated NaCl. The organic phase was dried over Na₂SO₄ and concentrated under reduced pressure. The material was purified using flash chromatography (5% EtOAc in hexane) to provide 83 mg (70%) of the desired compound. $R_F$: 0.3 (5% EtOAc in hexane). HPLC (Zorbax SB-C8 column, 4.6 mm×7.5 cm, Gradient: 90 H₂O:10 CH₃CN to 0 H₂O:100 CH₃CN over 7.5 minutes then hold at 100 CH₃CN:0 H₂O for 45 seconds, 2.25 mL/min, 220 nm): Retention Time: 4.6 minutes.

Step B  2-(R)-(3-(S)-((4-(N-(prop-1-yl)-N-(Pyrimid-2-yl)-amino)piperidin-1-yl)methyl)-4-(S)-(3-fluorophenyl)pyrrolidin-1-yl)cyclohexylacetic Acid A solution of 2-(R)-(3-(S)-((4-(N-(prop-1-yl)-N-(pyrimid-2-yl)amino)-piperidin-1-yl)methyl)-4-(S)-(3-fluorophenyl)pyrrolidin-1-yl)cyclohexylacetic acid, benzyl ester (80 mg, 0.13 mmol) from Example 25 Step A, in 3.0 mL of MeOH was hydrogenated using 10% palladium on carbon (20 mg, 0.026 mmol) under one atmosphere of hydrogen gas. After TLC indicated the absence of the starting benzyl ester, the reaction was filtered through a 0.45 micron nylon membrane polypropylene filter and concentrated under reduced pressure to give 60 mg (80%) of the title compound as a white solid. HPLC (Zorbax SB-C8 column, 4.6 mm×7.5 cm, Gradient: 90 H₂O:10 CH₃CN to 0 H₂O:100 CH₃CN over 7.5 minutes then hold at 100 CH₃CN:0 H₂O for 45 seconds, 2.25 mL/min, 220 nm): Retention Time: 3.4 minutes. ESI-MS: 538.0 (M+1). ¹H NMR (500 MHz, CDCl₃): δ 0.89–0.92 (t, J=7.4 Hz, 3H), 1.20–3.42 (25H), 3.87 (1H), 4.59 (1H), 6.42–6.43 (t, J=4.8 Hz, 1H), 6.91–6.95 (t, J=6.4 Hz, 1H), 7.03–7.09 (m, 2H), 7.24–7.31 (m, 1H), 8.24–8.25 (d, J=4.6 Hz, 2H).

EXAMPLE 26

2-(R)-(3-(S)-((4-(N-(prop-1-yl)-N-(Pyrimid-2-yl)-amino)-piperidin-1-yl)methyl)-4-(S)-phenylpyrrolidin-1-yl)-cyclohexylacetic Acid Step A  2-(R)-(3-(S)-((4-(N-(prop-1-yl)-N-(Pyrimid-2-yl)-amino)piperidin-1-yl)methyl)-4-(S)-(phenylpyrrolidin-1-yl)cyclohexylacetic Acid, Benzyl Ester The title compound was prepared using 2-(R)-(3-(R)-formyl-4-(S)-phenylpyrrolidin-1-yl)-cyclohexaneacetic acid, benzyl ester using (75 mg, 0.185 mmol; prepared above as Aldehyde 4), 4-(N-allyl-N-(pyrimid-2-yl)amino)piperidine hydrochloride (61 mg, 0.24 mmol) from Example 2, Step A, NaHB(OAc)₃, (97 mg, 0.46 mmol) and triethylamine (0.026 ml, 0.24 mmol) in 3 ml dichloromethane. The mixture was stirred overnight at room temperature. The reaction was diluted with 100 ml EtOAc and washed with 1M NaOH and saturated NaCl. The organic phase was dried over Na₂SO₄ and concentrated under reduced pressure. The material was purified using flash chromatography (5% EtOAc in hexane) to provide 80 mg (71%) of the title compound. HPLC (Zorbax SB-C8 column, 4.6 mm×7.5 cm, Gradient: 90 H₂O:10 CH₃CN to 0 H₂O:100 CH₃CN over 7.5 minutes then hold at 100 CH₃CN:0 H₂O for 45 seconds, 2.25 mL/min, 220 nm): Retention Time: 4.4 minutes.

Step B  2-(R)-(3-(S)-((4-(N-(prop-1-yl)-N-(Pyrimid-2-yl)-amino)piperidin-1-yl)methyl)-4-(S)-(phenyl)pyrrolidin-1-yl)cyclohexylacetic Acid A solution of 2-(R)-(3-(S)-((4-(N-(prop-1-yl)-N-(pyrimid-2-yl)amino)-piperidin-1-yl)methyl)-4-(S)-phenylpyrrolidin-1-yl)-cyclohexylacetic acid, benzyl ester (0.026 ml, 0.24 mmol) from Step A), in 3.0 mL of MeOH was hydrogenated using 10% palladium on carbon (28 mg, 0.026 mmol) under one atmosphere of hydrogen gas. After TLC indicated the absence of the starting benzylester, the reaction was filtered through a 0.45 micron nylon membrane polypropylene filter and concentrated under reduced pressure to give 50 mg (74%) of the title compound as a white solid. HPLC (Zorbax SB-C8 column, 4.6 mm×7.5 cm, Gradient: 90 H₂O:10 CH₃CN to 0 H₂O:100 CH₃CN over 7.5 minutes then hold at 100 CH₃CN:0 H₂O for 45 seconds, 2.25 mL/min, 220 nm): Retention Time: 3.28 minutes. ESI-MS: 520 (M+1).

EXAMPLES 27–29

Examples 27–29 in Table 3 were prepared in a fashion analogous to that shown above for the specific examples. The piperidine derivatives were prepared in a fashion analogous to that shown above for specific examples.

TABLE 3

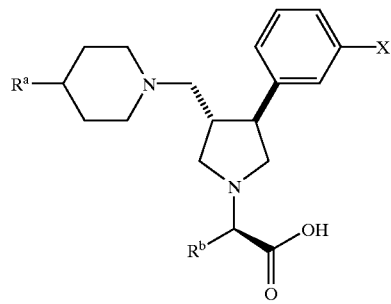

| EXAMPLE # | Ra | Rb | X | ESI-MS M/z (M + 1) |
|---|---|---|---|---|
| 27 | 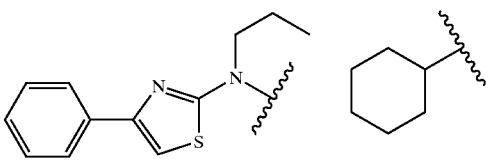 | | H | 601 |

TABLE 3-continued

| EXAMPLE # | Ra | Rb | X | ESI-MS M/z (M + 1) |
|---|---|---|---|---|
| 28 | (thiazol-2-yl-N-propyl) | (butyl) | F | 543 |
| 29 | (benzofurazan-CH2-O-CH2CH2-) | (cyclohexyl-CH-) | H | 561 |

EXAMPLE 30

2-(R)-(3-(S)-(4-(2-((4-Fluorophenyl)sulfonyl)-1-ethyl)piperidin-1-yl)methyl-4-(S)-(3-fluorophenyl)-pyrrolidin-1-yl)-3-cyclobutylpropionic Acid, Trifluoroacetate Step A: 4-(2-Hydroxy-1-ethyl)-1-piperidine Acetate Combined 4-(2-hydroxy-1-ethyl)pyridine (25 g, 0.2 mol) and platinum oxide (1 g, 4.4 mmol) in 400 mL acetic acid. Placed under 45 psi hydrogen at 60° C. for 24 hours. Decanted, then filtered through Celite and removed the solvent to afford 38 g (100%) of the crude product, which was used without further purification.

Step B: 4-(2-Hydroxy-1-ethyl)-1-tert-butoxycarbonyl-piperidine

Dissolved sodium bicarbonate (134 g, 1.6 mol) and 4-(2-hydroxy-1-ethyl)-1-piperidine acetate (38 g, 0.2 mol, from Step A) in 500 mL of 50% tetrahydrofuran in water. Added di-tert-butyl dicarbonate (35 g, 0.2 mol) and stirred at r.t. overnight. Diluted with ethyl acetate and extracted the aq. layer with 2×300 mL of ethyl acetate. Washed the combined organic layers with 2×300 mL of 1 N HCl and brine. Dried over MgSO₄ and concentrated to afford 37.4 g (81%) of the title compound. ESI-MS: 230 (M+H); HPLC A: 2.76 min.

Step C: 4-(2-Iodo-1-ethyl)-1-tert-butoxycarbonyl-piperidine

Combined 4-(2-hydroxy-1-ethyl)-1-tert-butoxycarbonyl-piperidine (37.4 g, 0.16 mol, from Step B), triphenylphosphine (55 g, 0.21 mol) and imidazole (14 g, 0.21 mol) in 800 mL of 33% acetonitrile in ether. Cooled to 0° C. and added iodine (56 g, 0.22 mol) portionwise. Diluted with 1 L of ether. Washed organic layer with 2×500 mL each of sat. aq. Na₂S₂O₃, sat. aq. CuSO₄ and brine. Dried over MgSO₄, filtered and concentrated. Triphenylphosphine oxide precipitates. Added ether and filtered the slurry through a plug of silica gel. Purified a portion of the crude material by flash chromatography (5% ethyl acetate in hexane eluent) to afford the title compound. ¹H-NMR (400 Mhz, CDCl₃): δ 4.10 (br s, 2H), 3.23 (t, 2H, J=7.2 Hz), 2.72 (br t, 2H, 12.3 Hz), 1.79 (q, 2H, J=7 Hz), 1.67 (br d, 2H, 14 Hz), 1.61 (m, 1H), 1.47 (s, 9H), 1.14 (qd, 2H, J=4.3, 12 Hz); ESI-MS: 340 (M+H); HPLC A: 3.74 min.

Step D: 4-(2-((4-Fluorophenyl)thio)-1-ethyl)-1-tert-butoxycarbonyl-piperidine

To a slurry of sodium hydride (47 mg, 60% in mineral oil, 1.2 mmol) in tetrahydrofuran at 0° C. was added 4-fluorothiophenol (0.1 mL, 0.94 mmol). The reaction mixture was warmed to r.t. for 20 min, followed by addition of 4-(2-iodo-1-ethyl)-1-tert-butoxycarbonyl-piperidine (265 mg, 0.78 mmol, from Step C). The reaction was then heated to reflux for 10 min, cooled and diluted with ether. The organic layer was washed with 1 N NaOH, dried over MgSO₄ and concentrated to provide 252 mg (95%) of the title compound. ESI-MS: 340.0 (M+H); HPLC A: 4.07 min.

Step E: 4-(2-((4-Fluorophenyl)sulfonyl)-1-ethyl)piperidine Trifluoroacetate

Added a solution of oxone (1.14 g, 1.86 mmol) in water to a solution of 4-(2-((4-fluorophenyl)thio)-1-ethyl)-1-tert-butoxycarbonyl-piperidine (252 mg, 0.74 mmol, from Step D) in methanol at 0° C. Warmed to r.t. After 90 min., added an additional 0.5 g of oxone. After 3 hours, the reaction mixture was diluted with methylene chloride and washed with 1 N NaOH containing sodium bisulfite. The aq. layer was extracted twice with methylene chloride, and the combined organic layers were dried over MgSO₄. The solution was concentrated and dissolved in 5% trifluoroacetic acid in methylene chloride for 1 hour. The solvent was evaporated to afford 297 mg (100%) of the title compound. ESI-MS: 239.8 (M+H); HPLC A: 2.54 min.

Step F: 2-(R)-(3-(S)-(4-(2-((4-Fluorophenyl)sulfonyl)-1-ethyl)piperidin-1-yl)methyl-4-(S)-(3-fluorophenyl)-pyrrolidin-1-yl)-3-cyclobutylpropionic Acid, Trifluoroacetate Dissolved 2-(R)-(3-(R)-formyl-4-(S)-(3-fluorophenyl)-pyrrolidin-1-yl)-3-cyclobutylpropionic acid, benzyl ester (25 mg, 0.06 mmol; prepared above as Aldehyde 2) in 3 mL of methanol. Added 10% palladium on carbon (20 mg, 0.019 mmol) and placed the reaction mixture under 1 atm of hydrogen using a balloon. After vigorous stirring for 3 hours, filtered through Celite, concentrated and redissolved in 0.5 mL of 1,2-dichloroethane. Added a solution of diisopropylethylamine (0.038 mL, 0.22 mmol) and 4-(2-((4-fluorophenyl)sulfonyl)-1-ethyl)piperidine trifluoromethylacetate (39 mg, 0.1 mmol, from Step E) in 0.5 mL of 1,2-dichloroethane. Added a slurry of sodium triacetoxyborohydride (36 mg, 0.17 mmol) in 0.5 mL of 1,2-dichloroethane, shook well and let stand at r.t. for 16 hours. Solid di-tert-butyldicarbonate (28 mg, 0.12 mmol) was added and stirring was continued for 3 h. The solvent was removed and the product was purified by preprative HPLC (column: YMC Combiprep ODS-A 20×50 mm, gradient: 10% acetonitrile/water w/0.1% TFA for 1.5 min then ramp to 90% acetonitrile/water w/0.1% TFA over 7.5 min, flow: 20 mL/min) to give 13 mg (31%) of the title compound. ESI-MS: 575.2 (M+H); HPLC A: 3.38 min.

EXAMPLE 31

2-(R)-(3-(S)-(4-(2-((4-Fluorophenyl)thio)-1-ethyl)piperidin-1-yl)methyl-4-(S)-(3-fluorophenyl)-pyrrolidin-1-yl)-3-cyclobutylpropionic Acid Trifluoroacetate Dissolved 2-(R)-(3-(R)-formyl-4-(S)-(3-fluorophenyl)-pyrrolidin-1-yl)-3-cyclobutylpropionic acid, benzyl ester (25 mg, 0.06 mmol; prepared above as Aldehyde 2) in 3 mL of methanol. Added 10% palladium on carbon (20 mg, 0.019 mmol) and placed the reaction mixture under 1 atm of hydrogen using a balloon. After vigorous stirring for 3 hours, filtered through Celite, concentrated and redissolved in 0.5 mL of 1,2-dichloroethane. Added a solution of diisopropylethylamine (0.038 mL, 0.22 mmol) 4-(2-((4-fluorophenyl)thio)-1-ethyl)-1-tert-butoxycarbonyl-piperidine (35 mg, 0.1 mmol, from Example 30, Step D) in 0.5 mL of 1,2-dichloroethane. Added a slurry of sodium triacetoxyborohydride (36 mg, 0.17 mmol) in 0.5 mL of 1,2-dichloroethane, shook well and let stand at r.t. for 16 hours. Solid di-tert-butyldicarbonate (28 mg, 0.12 mmol) was added and stirring was continued for 3 h. The solvent was removed and the product was purified by preprative HPLC (column: YMC Combiprep ODS-A 20×50 mm, gradient: 10% acetonitrile/water w/0.1% TFA for 1.5 min then ramp to 90% acetonitrile/water w/0.1% TFA over 7.5 min, flow: 20 mL/min) to give 4 mg (13%) of the title compound. ESI-MS: 543.2 (M+H); HPLC A: 3.54 min.

EXAMPLES 32–34

Examples 32–34 in Table 4 were prepared by reductive amination of the appropriate amine with α-(R)-(3-(R)-Formyl-4-(S)-phenyl-pyrrolidin-1-yl)cyclohexaneacetic acid, para-methoxybenzyl ester (prepared above as Aldehyde 5) followed by purification by preparative HPLC and generation of the free acid by treatment with formic acid.

TABLE 4

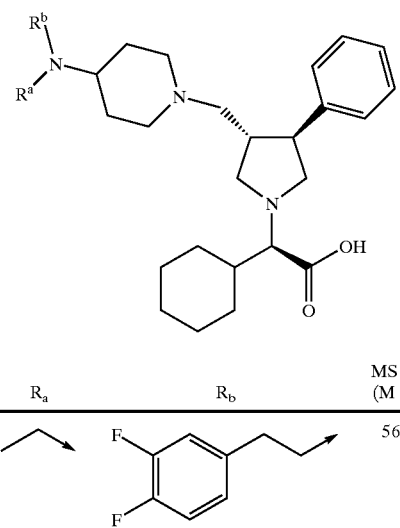

| EXAMPLE # | $R_a$ | $R_b$ | MS m/Z (M + 1) | HPLC A (min.) |
|---|---|---|---|---|
| 32 | 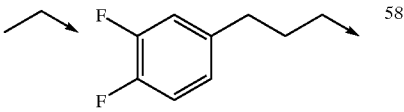 | | 568.2 | 2.07 |
| 33 | | | 582.2 | 2.16 |
| 34 | 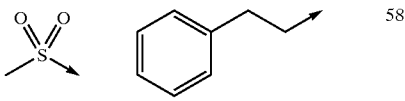 | | 582.3 | 2.41 |

EXAMPLES 35–40

Examples 35–40 in Table 5 were prepared according to the general procedure given in Examples 30 and 31, employing the appropriate commercially available thiophenols in Step D and the appropriate aldehyde whose syntheses are described above.

TABLE 5

| EXAMPLE # | $R_a$ | $R_b$ | MS m/Z (M + 1) | HPLC A (min.) |
|---|---|---|---|---|
| 35 | H→ | phenylsulfonyl | 539.2 | 3.20 |
| 36 | H→ | 4-fluorophenylsulfonyl | 557.2 | 3.19 |
| 37 | H→ | phenylthio | 507.2 | 3.62 |
| 38 | H→ | 4-fluorophenylthio | 525.3 | 3.66 |
| 39 | F→ | phenylsulfonyl | 557.2 | 3.32 |
| 40 | F→ | phenylthio | 525.2 | 3.67 |

EXAMPLE 41

2-(R)-(3-(S)-(4-(N-Pyrimidin-2-yl-N-ethyl) aminopiperidin-1-yl)methyl-4-(S)-phenylpyrrolidin-1-yl)-2-(cyclohexyl)acetic Acid Step A: 1-(t-Butoxycarbonyl)-4-(N-pyrimidin-2-yl-N-ethyl) amino Piperidine A solution of 150 mg (0.54 mmol) of 1-(t-butoxycarbonyl)-4-(N-pyrimidin-2-yl)aminopiperidine (from Example 1, Step C) in 3 mL of 2:1 v/v DMF/ethyl iodide at 0° C. was treated with 25 mg (0.62 mmol) of NaH (60% in mineral oil). The resulting mixture was warmed to rt and stirred for 1 h. The mixture was partitioned between 50 mL of ether and 50 mL of $H_2O$ and the layers were separated. The organic layer was washed with 3×50 mL of $H_2O$, 50 mL of 5% $Na_2S_2O_3$, 50 mL of sat'd NaCl, dried over $MgSO_4$ and concentrated. Flash chromatography on 10 g of silica gel using 3:1 v/v hexanes/ether as the eluant afforded 117 mg (71%) of the title compound: $^1$H NMR (300 MHz) δ 1.18 (t, J=6.9, 3H), 1.48 (s, 9H), 1.65–1.74 (4H), 2.79–2.88 (m, 2H), 3.49 (q, J=6.9, 2H), 4.19–4.26 (m, 2H), 4.71–4.80 (m, 1H), 6.45 (app t, J=4.8, 1H), 8.30 (d, J=4.8, 2H).

Step B: 4-(N-Pyrimidin-2-yl-N-ethyl)amino Piperidine TFA

A solution of 117 mg (0.38 mmol) of 1-(t-butoxycarbonyl)-4-(N-pyrimidin-2-yl-N-ethyl)amino piperidine (from Step A) in 2 mL of $CH_2Cl_2$ at 0° C. was treated with 2 mL of trifluoroacetic acid (TFA). The resulting mixture was warmed to rt and stirred for 30 min. The mixture was concentrated. The residue was triturated with ether and the resulting solid was filtered and dried to afford 106 mg (86%) of the title compound: $^1$H NMR (500 MHz, $CD_3OD$) δ 1.19 (t, J=7.0, 3H), 1.97 (app d, J=12.5, 2H), 2.14 (dq, J=4.0, 13.5, 2H), 3.13 (dt, J=2.5, 13.5, 2H), 3.49–3.52 (m, 2H), 3.57 (q, J=7.0, 2H), 4.72–4.84 (m, 1H), 6.59 (app t, J=5.0, 1H), 8.31 (d, J=5.0, 2H).

Step C: 2-(R)-(3-(S)-(4-(N-Pyrimidin-2-yl-N-ethyl) aminopiperidin-1-yl)methyl-4-(S)-phenylpyrrolidin-1-yl)-2-(cyclohexyl)acetic Acid, Benzyl Ester A mixture of 38 mg (0.09 mmol) of 2-(R)-(3-(R)-formyl-4-(S)-phenylpyrrolidin-1-yl)-2-(cyclohexyl)acetic acid, benzyl ester (prepared above as Aldehyde 4) and 30 mg (0.09 mmol) of 4-(N-pyrimidin-2-yl-N-ethyl)amino piperidine TFA (from Step B) in 3 mL of $CH_2Cl_2$ was treated with 0.013 mL (0.9 mmol) of TEA and 65 mg (0.31 mmol) of sodium triacetoxyborohydride. The resulting mixture was stirred at rt for 1 h. The reaction mixture was partitioned between 30 mL of ether and 15 mL of 1.0 N NaOH and the layers were separated. The organic layer was ashed with 15 mL of sat'd NaCl, dried over $MgSO_4$ and concentrated. Flash chromatography on 3 g of silica gel using 3:1 v/v hexanes/EtOAc as the eluant afforded 42 mg (75%) of the title compound.

Step D: 2-(R)-(3-(S)-(4-(N-Pyrimidin-2-yl-N-ethyl) aminopiperidin-1-yl)methyl-4-(S)-phenylpyrrolidin-1-yl)-2-(cyclohexyl)acetic Acid A mixture of 42 mg (0.07 mmol) of 2-(R)-(3-(S)-(4-(N-pyrimidin-2-yl-N-ethyl)aminopiperidin-1-yl)-4-(S)-phenylpyrrolidin-1-yl)-2-(cyclohexyl) acetic acid, benzyl ester (from Step C) and 20 mg of 10% palladium on carbon in 5 mL of iPrOH was hydrogenated (40 psi) on a Paar shaker for 2 h. The catalyst was filtered and the filtrate was concentrated. Flash chromatography on 2 g of silica gel using 20:1:0.1 v/v/v $CH_2Cl_2$/MeOH/$NH_4OH$, then 10:1:0.1 v/v/v $CH_2Cl_2$/MeOH/$NH_4OH$ as the eluant afforded 34 mg (95%) of the title compound: $^1$H NMR (500 MHz, $CD_3OD$) δ 1.12 (t, J=7.0, 3H), 1.16–1.93 (16H), 2.08 (dt, J=2.5, 12.0, 1H), 2.34 (dd, J=5.0, 13.0, 1H), 2.49 (dd, J=10.0, 12.5, 1H), 2.75–2.85 (m, 2H), 2.97 (app d, J=11.5, 1H), 3.18 (app q, J=8.5, 1H), 3.46 (q, J=7.0, 2H), 3.49–3.65 (4H), 4.42–4.48 (m, 1H), 6.50 (app t, J=5.0, 1H), 7.28–7.38 (5H), 8.24 (d, J=5.0, 2H); ESI-MS 506 (M+H); HPLC B: 5.53 min.

EXAMPLE 42

2-(R)-(3-(S)-(4-(N-Pyrimidin-2-yl-N-methyl) aminopiperidin-1-yl)methyl-4-(S)-phenylpyrrolidin-1-yl)-2-(cyclohexyl)acetic Acid Step A: 4-(N-Pyrimidin-2-yl-N-methyl)amino Piperidine.TFA The title compound was prepared using procedures analogous to those described in EXAMPLE 41, Steps A and B, substituting methyl iodide for ethyl iodide in Step A. For the title compound: ¹H NMR (500 MHz, CD₃OD) δ 1.95 (app d, J=13.5, 2H), 2.08 (dq, J=4.0, 13.5, 2H), 3.06 (s, 3H), 3.15 (app t, J=12.0, 2H), 3.52 (app d, J=13.0, 2H), 4.88–4.95 (m, 1H), 6.67 (app t, J=5.5, 1H), 8.38 (d, J=5.5, 2H).

Step B: 2-(R)-(3-(S)-(4-(N-Pyrimidin-2-yl-N-methyl) aminopiperidin-1-yl)methyl-4-(S)-phenylpyrrolidin-1-yl)-2-(cyclohexyl)acetic Acid, (4-Methoxy)benzyl Ester The title compound was prepared from 2-(R)-(3-(R)-formyl-4-(S)-phenylpyrrolidin-1-yl)-2-(cyclohexyl)acetic acid, (4-methoxy)benzyl ester (Aldehyde 5) and 4-(N-pyrimidin-2-yl-N-methyl)amino piperidine.TFA (from Step A) using a procedure analogous to that described in EXAMPLE 41, Step C.

Step C: 2-(R)-(3-(S)-(4-(N-Pyrimidin-2-yl-N-methyl) aminopiperidin-1-yl)methyl-4-(S)-phenylpyrrolidin-1-yl)-2-(cyclohexyl)acetic Acid A solution of 35 mg (0.06 mmol) of 2-(R)-(3-(S)-(4-(N-pyrimidin-2-yl-N-methyl)aminopiperidin-1-yl)methyl-4-(S)-phenylpyrrolidin-1-yl)-2-(cyclohexyl)acetic acid, (4-methoxy)benzyl ester in 2 mL of 95% formic acid was stirred at 50° C. for 30 min. The solution was cooled and concentrated. Flash chromatography on 2.5 g of silica gel using 20:1:0.1 v/v/v CH₂Cl₂/MeOH/NH₄OH, then 10:1:0.1 v/v/v CH₂Cl₂/MeOH/NH₄OH as the eluant afforded 25 mg (89%) of the title compound: ESI-MS 492 (M+H); HPLC B: 5.27 min.

EXAMPLE 43

2-(R)-(3-(S)-(4-(N-Pyridin-2-yl-N-propyl) aminopiperidin-1-yl)methyl-4-(S)-phenylpyrrolidin-1-yl)-2-(cyclohexyl)acetic Acid The title compound was prepared using procedures analogous to those described in EXAMPLE 41, substituting 1-(t-butoxycarbonyl)-4-(N-pyridin-2-yl)aminopiperidine for 1-(t-butoxycarbonyl)-4-(N-pyrimidin-2-yl) aminopiperidine in Step A and propyl iodide for ethyl iodide in Step A. For the title compound: ESI-MS 520 (M+H).

EXAMPLE 44

2-(R)-(3-(S)-(4-(N-Pyrimidin-2-yl-N-propyl) aminopiperidin-1-yl)methyl-4-(S)-(3-thienyl) pyrrolidin-1-yl)-2-(cyclohexyl)acetic Acid Step A: 4-(N-Pyrimidin-2-yl-N-propyl) aminopiperidine.TFA The title compound was prepared using procedures analogous to those described in EXAMPLE 41, Steps A and B, substituting propyl iodide for ethyl iodide in Step A.

Step B: 2-(R)-(3-(S)-(4-(N-Pyrimidin-2-yl-N-propyl) aminopiperidin-1-yl)methyl-4-(S)-(3-thienyl)pyrrolidin-1-yl)-2-(cyclohexyl)acetic Acid, (4-Methoxy)benzyl Ester The title compound was prepared from 2-(R)-(3-(R)-formyl-4-(S)-(3-thienyl)pyrrolidin-1-yl)-2-(cyclohexyl) acetic acid, (4-methoxy)benzyl ester (Aldehyde 19; prepared by analogy to procedures given above for Aldehyde 13) and 4-(N-pyrimidin-2-yl-N-propyl)aminopiperidine.TFA (from Step A) using procedures analogous to those described in EXAMPLE 41, Step C.

Step C: 2-(R)-(3-(S)-(4-(N-Pyrimidin-2-yl-N-propyl) aminopiperidin-1-yl)methyl-4-(S)-(3-thienyl)pyrrolidin-1-yl)-2-(cyclohexyl)acetic Acid The title compound was prepared from 2-(R)-(3-(S)-(4-(N-pyrimidin-2-yl-N-propyl)aminopiperidin-1-yl)methyl-4-(S)-(3-thienyl)pyrrolidin-1-yl)-2-(cyclohexyl)acetic acid, (4-methoxy)benzyl ester (from Step B) using a procedure analogous to that described in EXAMPLE 42, Step C. For the title compound: ¹H NMR (500 MHz) δ 0.83–4.70 (36H), 6.46 (t, J=4.8, 1H), 7.17 (d, J=4.6, 1H), 7.23 (s, 1H), 7.34–7.35 (m, 1H), 8.25 (d, J=4.8, 2H), 8.59 (s, 1H); ESI-MS 526 (M+H).

EXAMPLE 45

2-(R)-(3-(S)-(4-(N-Pyrimidin-2-yl-N-propyl) aminopiperidin-1-yl)methyl-4-(S)-phenylpyrrolidin-1-yl)-3-methylbutanoic Acid The title compound was prepared from 2-(R)-(3-(R)-formyl-4-(S)-phenylpyrrolidin-1-yl)-3-methylpropionic acid, benzyl ester (prepared above as Aldehyde 8) and 4-(N-pyrimidin-2-yl-N-propyl)aminopiperidine.TFA (from EXAMPLE 44, Step A) using procedures analogous to those described in EXAMPLE 41, Steps C and D. For the title compound: ¹H NMR (500 MHz) δ 0.83–4.70 (32H), 6.43 (t, J=4.6, 1H), 7.25–7.32 (5H), 8.24 (d, J=4.5, 2H); ESI-MS 480 (M+H).

EXAMPLE 46

2-(R)-(3-(S)-(4-(N-Pyrazin-2-yl-N-propylamino) piperidin-1-yl)methyl-4-(S)-phenylpyrrolidin-1-yl)-2-(cyclohexyl)acetic Acid Step A: 1-(t-Butoxycarbonyl)-4-(N-pyrazin-2-yl) aminopiperidine The title compound was prepared using a procedure analogous to that described in Table 2, substituting 2-chloropyrazine for the heterocycles listed therein.

Step B: 2-(R)-(3-(S)-(4-(N-Pyrazin-2-yl-N-propyl) aminopiperidin-1-yl)methyl)-4-(S)-phenylpyrrolidin-1-yl)-2-(cyclohexyl)acetic Acid The title compound was prepared using procedures analogous to those described in EXAMPLE 41, Steps A–D, substituting 1-(t-butoxy-carbonyl)-4-(N-pyrazin-2-yl) aminopiperidine for 1-(t-butoxycarbonyl)-4-(N-pyrimidin-2-yl)aminopiperidine in Step A and propyl iodide for ethyl iodide in Step A. For the title compound: ¹H NMR (500 MHz) δ 0.83–4.43 (36H), 7.25–7.31 (5H), 7.75 (s, 1H), 7.90 (s, 1H), 7.97 (s, 1H); ESI-MS 520 (M+1).

EXAMPLE 47

2-(R)-(3-(S)-(4-(N-Pyrazin-2-yl-N-ethyl) aminopiperidin-1-yl)methyl-4-(S)-phenylpyrrolidin-1-yl)-2-(cyclohexyl)acetic Acid The title compound was prepared using procedures analogous to those described in EXAMPLE 41, Steps A–D, substituting 1-(t-butoxy-carbonyl)-4-(N-pyrazin-2-yl) aminopiperidine (from EXAMPLE 46, Step A) for 1-(t-butoxycarbonyl)-4-(N-pyrimidin-2-yl)aminopiperidine in Step A. For the title compound: ¹H NMR (500 MHz) δ 0.85–4.48 (34H), 7.26–7.32 (5H), 7.75 (d, J=2.4, 1H), 7.94 (s, 1H), 7.96 (s, J=2.4, 1H); ESI-MS 506 (M+H); HPLC A: 1.57 min.

EXAMPLE 48

2-(R)-(3-(S)-((4-(Benzyloxymethyl)piperidin-1-yl) methyl)-4-(S)-phenylpyrrolidin-1-yl)-cyclohexaneacetic Acid Step A: 1-(tert-Butoxycarbonyl)-4-(hydroxymethyl) piperidine Di-tert-butyl dicarbonate (4.69 g, 21.5 mmol) in CH₂Cl₂ (5 mL) was added over 10 min. to a solution of 4-(hydroxymethyl)piperidine (2.47 g, 21.4 mmol) in $CH_2Cl_2$ (16 mL). After stirring at RT for 1 h, the solution was diluted with ether (50 mL) and washed with 2 N aq. HCl, saturated aq. $NaHCO_3$, and saturated aq. NaCl (25 mL of each). The organic layer was dried ($Na_2SO_4$), decanted, and evaporated to give 4.57 g of the title compound as a crystalline solid. $^1H$ NMR (500 MHz, $CD_3OD$): δ 4.08 (d, J=14 Hz, 2H), 3.40 (d, J=6 Hz, 2H), 2.81–2.67 (m, 2H), 1.71 (d, J=13 Hz, 2H), 1.67–1.58 (m, 1H), 1.44 (s, 9H), 1.09 (qd, J=12, 4 Hz, 2H).

Step B: 4-(Benzyloxymethyl)piperidine Hydrochloride

NaH (60% oil dispersion, 53 mg, 1.3 mmol) was added in portions to a solution of 1-(tert-butoxycarbonyl)-4-(hydroxymethyl)piperidine (240 mg, 1.1 mmol) and benzyl bromide (0.40 mL, 0.58 g, 0.33 mmol) in DMF (2.0 mL). After 1 h, additional NaH (60% oil disperison, 15 mg, 0.38 mmol) was added. After a total of 2.25 h, the mixture was quenched with water and extracted with EtOAc. The organic layer was washed with saturated aq. NaCl, dried ($Na_2SO_4$), and evaporated. Purification by flash column chromatography on silica gel, eluting with 5–10% EtOAc in hexane gave 167 mg of 4-(benzyloxymethyl)-1-(tert-butoxycarbonyl)piperidine. A portion (160 mg, 0.55 mmol) of this intermediate was dissolved in $CH_3OH$ (2.0 mL) and a solution of HCl (2 N in ether, 2.0 mL, 4 mmol) was added. The mixture was stirred overnight at RT and evaporated to give the title compound as a white solid.

Step C: 2-(R)-(3-(S)-((4-(Benzyloxymethyl)piperidin-1-yl)methyl)-4-(S)-phenylpyrrolidin-1-yl)-cyclohexaneacetic Acid para-Methoxybenzyl Ester Molecular sieve pellets (3 Å) were added to a solution of 2-(R)-(3-(R)-formyl-4-(S)-phenylpyrrolidin-1-yl)-cyclohexaneacetic acid para-methoxybenzyl ester (32 mg, 0.074 mmol; prepared above as Aldehyde 5), 4-(benzyloxymethyl)piperidine hydrochloride (20 mg. 0.082 mmol), and N,N-diisopropylethylamine (0.014 mL, 10 mg, 0.080 mmol) in 1,2-dichloroethane (0.70 mL). The mixture was stirred for 30 min. at RT before the addition of sodium triacetoxyborohydride (24 mg, 0.11 mmol). After 3 h, the mixture was diluted with EtOAc (20 mL) and washed with saturated aq. $NaHCO_3$ (10 mL) followed by saturated aq. NaCl (10 mL). The organic layer was dried ($Na_2SO_4$), decanted, and evaporated. Purification by flash column chromatography on silica gel, eluting with 10–15% EtOAc/ 0.5% $CH_3OH/CH_2Cl_2$ gave 33 mg of the title compound as a colorless viscous oil. $^1H$ NMR (400 MHz, $CD_3OD$): δ 7.38 (d, J=8 Hz, 2H), 7.35–7.10 (m, 10H), 6.91 (d, J=8 Hz), 5.13 (s, 2H), 4.47 (s, 2H), 3.79 (s, 3H), 3.29 (d, J=6 Hz, 2H), 3.20 (dd, J=9, 7 Hz, 1H), 3.15–3.09 (m, 2H), 2.82–2.58 (m, 4H), 2.52 (dd, J=9, 7 Hz, 1H), 2.33–2.20 (m, 2H), 1.95 (bd, J=12 Hz, 1H), 1.85 (dd, J=12, 10 Hz, 1H), 1.80–1.47 (m, 10H), 1.30–1.11 (m, 5H), 1.05–0.91 (m, 2H); ESI-MS 625 (M+H).

Step D: 2-(R)-(3-(S)-((4-(Benzyloxymethyl)piperidin-1-yl)methyl)-4-(S)-phenylpyrrolidin-1-yl)-cyclohexaneacetic Acid A solution of α-(R)-(3-(S)-((4-(benzyloxymethyl) piperidin-1-yl)methyl)-4-(S)-phenylpyrrolidin-1-yl)-cyclohexaneacetic acid para-methoxybenzyl ester (30 mg, 0.048 mmol) in 96% formic acid (2.0 mL) was stirred at RT. After 2 h, the formic acid was evaporated at reduced pressure. Toluene was added and evaporated, and this was repeated with a second portion of toluene. The crude product was purified by flash column chromatography on silica gel packed in $CH_2Cl_2$. Elution with 5% $CH_3OH/1\%$ conc. aq. $NH_4OH/CH_2Cl_2$ followed by 10% $CH_3OH/2\%$ conc. aq. $NH_4OH/CH_2Cl_2$ gave 19 mg of the title compound as a colorless brittle glass. $^1H$ NMR (400 MHz, $CD_3OD$): δ 7.39–7.22 (m, 10H), 4.45 (s, 2H), 3.59 (dd, J=11, 8 Hz, 2H), 3.48 (d, J=4 Hz, 1H), 3.46–3.35 (m, 1H), 3.28 (d, J=6 Hz, 2H), 3.12 (td, J=10, 8 Hz, 1H), 2.93 (bd, J=11 Hz, 1H), 2.81–2.71 (m, 2H), 2.49 (dd, J=12, 10 Hz, 1H), 2.33 (dd, J=12, 3 Hz, 1H), 2.03 (bt, J=11 Hz, 1H), 1.92–1.12 (m, 18H); ESI-MS 505 (M+H).

EXAMPLE 49

2-(R)-(3-(S)-((4-(Benzyloxymethyl)-4-hydroxypiperidin-1-yl)methyl)-4-(S)-phenylpyrrolidin-1-yl)-cyclohexaneacetic Acid Step A: 5-(tert-Butoxycarbonyl)-5-aza-1-oxa-spiro[2.5]heptane A mixture of 5.50 g (25.0 mmol) of trimethylsulfoxonium iodide and 15 mL of DMSO was cooled to 5° C. and then was treated with 1.20 g (30.0 mmol) of sodium hydride (60 wt % in mineral oil). The cooling was removed and the mixture was stirred at for 30 min. The mixture was recooled to 5° C. and then was treated with 5.00 g (25.0 mmol) of 1-(tert-butoxycarbonyl)piperidin-4-one.

The resulting mixture was warmed to RT and then was stirred in an oil bath set at 50° C. for 30 min. The reaction was cooled and quenched with 100 mL of $H_2O$.

The quenched mixture was extracted with 300 mL of ether; the extract was washed with 3×100 mL of $H_2O$, dried over $MgSO_4$. Flash chromatography on 150 g of silica gel using 3:1 v/v hexanes/ether as the eluant afforded 2.84 g (53%) of the title compound: $^1H$ NMR (500 MHz, $CDCl_3$) δ–1.43–1.49 (m, 2H), 1.47 (s, 9H), 1.77–1.82 (m, 2H), 2.69 (s, 2H), 3.40–3.46 (m, 2H), 3.68–3.78 (m, 2H).

Step B: 4-(Benzyloxymethyl)-4-hydroxypiperidine

A solution of benzyl alcohol (0.775 mL, 7.5 mmol), 5-(tert-butoxycarbonyl)-5-aza-1-oxa-spiro[2.5]heptane (1.06 grams, 5 mmol) and KOH (0.84 g, 15 mmol) in DMSO (15 mL) was stirred at 30° C. overnight. The mixture was diluted with EtOAc (100 mL), and washed with 2 N aq. HCl, water, and saturated aq. NaCl (100 mL of each). The organic layer was dried ($MgSO_4$) and concentrated. Flash chromatography on silica gel, eluting with 25% EtOAc in hexane, afforded 4-(benzyloxymethyl)-1-(tert-butoxycarbonyl) piperidine which was suspended in 25 mL of 25% TFA in $CH_2Cl_2$ and stirred for 10 min. The solvent was removed and the residue was diluted with $CH_2Cl_2$ (100 mL) and washed with 1 M NaOH (100 mL). The organic phase was dried ($Na_2SO_4$)and concentrated to afford 510 mg of the title compound. $^1H$ NMR (300 MHz, $CDCl_3$): δ 1.6–1.8 (m, 4H), 2.9–3.16 (m, 6H), 3.36 (s, 2H), 4.58 (s, 2H), 7.25–7.4 (m, 5H).

Step C: 2-(R)-(3-(S)-((4-(Benzyloxymethyl)-4-hydroxypiperidin-1-yl)methyl)-4-(S)-phenylpyrrolidin-1-yl)-cyclohexaneacetic Acid para-Methoxybenzyl Ester Molecular sieve pellets (3 Å) were added to a solution of 2-(R)-(3-(R)-formyl-4-(S)-phenylpyrrolidin-1-yl)-cyclohexaneacetic acid para-methoxybenzyl ester (30 mg, 0.069 mmol; prepared above as Aldehyde 5) and 4-(benzyloxymethyl)-4-hydroxypiperidine (17 mg. 0.077 mmol) in 1,2-dichloroethane (0.60 mL). The mixture was stirred for 30 min. at RT before the addition of sodium triacetoxyborohydride (23 mg, 0.11 mmol). After 4 days, the mixture was diluted with EtOAc (20 mL) and washed with saturated aq. $NaHCO_3$ (10 mL) followed by saturated aq. NaCl (10 mL). The organic layer was dried ($Na_2SO_4$), decanted, and evaporated. Purification by flash column chromatography on silica gel, eluting with 15–20% EtOAc/ 0.5% $CH_3OH/CH_2Cl_2$ gave 21 mg of the title compound as a colorless film. $^1H$ NMR (400 MHz, $CD_3OD$): δ 7.36 (d, J=8 Hz, 2H), 7.35–7.21 (m, 7H), 7.16 (t, J=7 Hz, 1H), 7.11 (d, J=8 Hz, 2H), 6.91 (d, J=8 Hz, 1H), 5.12 (s, 2H), 4.52 (s, 2H), 3.78 (s, 3H), 3.25 (s, 2H), 3.20 (dd, J=9, 7 Hz, 1H), 3.13–3.07 (m, 2H), 2.70 (q, J=7 Hz, 1H), 2.60 (t, J=8 Hz, 1H), 2.56–2.45 (m, 2H), 2.39–2.23 (5H), 2.15 (td, J=11, 3 Hz, 1H), 1.95 (bd, J=12 Hz, 1H), 1.79–1.55 (m, 7H), 1.54–1.42 (m, 2H), 1.31–1.11 (m, 3H), 1.05–0.92 (m, 2H); ESI–MS 641 (M+H).

Step D: 2-(R)-(3-(S)-((4-(Benzyloxymethyl)-4-hydroxypiperidin-1-yl)methyl)-4-(S)-phenylpyrrolidin-1-yl)-cyclohexaneacetic Acid The title compound was prepared by a reaction analogous to Example 48, Step D, utilizing 2-(R)-(3-(S)-((4-(benzyloxymethyl)-4-hydroxypiperidin-1-yl)methyl)-4-(S)-phenylpyrrolidin-1-yl)-cyclohexaneacetic acid para-methoxybenzyl ester in place of α-(R)-(3-(S)-((4-(benzyloxymethyl)piperidin-1-yl)methyl)-4-(S)-phenylpyrrolidin-1-yl)-cyclohexaneacetic acid para-methoxybenzyl ester. $^1$H NMR (400 MHz, CD$_3$OD): δ 7.40–7.22 (m, 10H), 4.51 (s, 2H), 3.60 (dd, J=11, 8 Hz, 2H), 3.49 (d, J=4 Hz, 1H), 3.49–3.34 (m, 2H), 3.25 (s, 2H), 3.13 (td, J=10, 8 Hz, 1H), 2.82–2.71 (m, 1H), 2.65 (bd, J=10 Hz, 1H), 2.57–2.34 (m, 4H), 2.20 (bt, J=10 Hz, 1H), 1.92–1.74 (m, 5H), 1.72–1.61 (m, 3H), 1.56–1.41 (m, 3H), 1.39–1.10 (m, 4H); ESI–MS 521 (M+H).

EXAMPLE 50

2-(R)-(3-(S)-((4-(Naphthyl-2-oxy)piperidin-1-yl)methyl)-4-(S)-phenylpyrrolidin-1-yl)-cyclohexaneacetic Acid Step A: 1-Benzyl-4-(naphthyl-2-oxy)-piperidine To a solution of 1.03 g of 2-naphthol in 20 mL of methylene chloride was added 1-benzyl-4-hydroxypiperidine followed by 2.81 g of triphenylphosphine. After stirring at rt for 10 min., 1.35 mL of diethyl azodicarboxylate was added. After stirring at rt for 18 h, the reaction mixture was diluted with methylene chloride and washed with brine.

The organic layer was dried over anhydrous magnesium sulfate and concentrated under reduced pressure. The residue was purified by flash chromatography eluting with 20% EtOAc in hexane followed by 50% EtOAc in hexane to give a white solid. To the above solid was added 20% EtOAc in hexane and white impurity was filtered off. Concentration of the filtrate under reduced pressure afforded 1.4 g of the title compound as a white solid.

Step B: 4-(Naphthyl-2-oxy)-piperidine

To a solution of 500 mg of 1-benzyl-4-(naphthyl-2-oxy)-piperidine (from Step A) in 25 mL of MeOH was added 500 mg of ammonium formate followed by 500 mg of 10% palladium on carbon. After refluxing for 3 hours, the mixture was filtered through celite and concentrated. The residue was dissolved in EtOAc and washed with aqueous sodium bicarbonate followed by brine. The EtOAc layer was dried over magnesium sulfate and concentrated under reduced pressure to give 207 mg of the title compound as a viscous oil.

Step C: 2-(R)-(3-(S)-((4-(Naphthyl-2-oxy)piperidin-1-yl)methyl)-4-(S)-phenylpyrrolidin-1-yl)-cyclohexaneacetic Acid, 4-Methoxybenzyl Ester To a solution of 50 mg of 2-(R)-(3-(R)-formyl-4-(S)-phenylpyrrolidin-1-yl)-cyclohexaneacetic acid, benzyl ester (prepared above as Aldehyde 4) and 50 mg of 4-(naphthyl-2-oxy)-piperidine (from Step B) in 2 mL of THF was added one spatula tip of 3Å molecular sieves. After stirring at room temperature for 20 mim., 50 mg of sodium triacetoxyborohydride was added and the reaction was stirred at room temperature for 12 hours. The reaction was quenched with MeOH and diluted with EtOAc. After filtering molecular sieves, the filtrate was concentrated under reduced pressure. The residue was partitioned between EtOAc and water. The organic layer was washed with brine and dried over anhydrous magnesium sulfate. Concentration under reduced pressure followed by flash chromatography eluting with 20% EtOAc in hexane, 50% EtOAc in hexane and 100% EtOAc afforded 28 mg of the title compound as a viscous oil.

Step D: 2-(R)-(3-(S)-((4-(Naphthyl-2-oxy)piperidin-1-yl)methyl)-4-(S)-phenylpyrrolidin-1-yl)-cyclohexaneacetic Acid To a solution of 25 mg of 2-(R)-(3-(S)-((4-(Naphthyl-2-oxy)piperidin-1-yl)methyl)-4-(S)-phenylpyrrolidin-1-yl)-cyclohexaneacetic acid, 4-methoxybenzyl ester (from Step C) in 1.5 mL of anisole was added 1 mL of trifluoroacetic acid at room temperature. The reaction was stirred at room temperature for 3 hours. After concentration under reduced pressure, the residue was purified by flash chromatography eluting with CH$_2$Cl$_2$:MeOH:NH$_4$OH=90:5:0.5 and CHCl$_3$:MeOH:NH$_4$OH=80:15:1 to give 20 mg of the title compound as a white solid. $^1$H NMR (500 MHz, CD$_3$OD): δ 1.10–2.31 (m, 18H), 2.80–3.90 (m, 10H), 4.70 (m, 1H), 7.09 (d, J=8.8 Hz, 1H), 7.20–7.50 (m, 8H), 7,70 (d, J=8.4 Hz, 1H), 7.74 (d, J=8.9 Hz, 2H); Mass Spectrum (CH$_3$CN—TFA—NH$_4$HCO$_2$—ESI): 527 (M+1).

EXAMPLE 51

2-(R)-(3-(S)-((4-(Quinolin-6-yloxy)piperidin-1-yl)methyl)-4-(S)-phenylpyrrolidin-1-yl)-cyclohexaneacetic Acid The title compound was prepared using procedures analogous to those described in Example 50 except 6-hydroxyquinoline was employed in place of 2-naphthol in Step A. ESI–MS 528 (M+1); HPLC A: 1.71 min.

EXAMPLE 52

2-(R)-(3-(S)-((4-(N-(2-Benzyl-2H-tetrazol-5-yl)methyl-N-ethylamino)-piperidine-1-yl)methyl)-4-(S)-phenylpyrrolidin-1-yl)-cyclohexaneacetic Acid Step A: 1-t-Butyloxycarbonyl-4-ethylamino-piperidine To 5.0 g of N-Boc-4-piperidone were added 12.6 ml of titanium isopropoxide and 9.34 ml of triethylamine. This mixture was stirred for 1 hour, then 25 ml of EtOH (abs) and 1.056 g of sodium cyanoborohydride were added. The reaction was stirred for 48 hours at room temperature. EtOH and H$_s$O were added and the reaction mixture was filtered through Celite. The solvent was then evaporated under reduced pressure. The residue was purified by flash chromatography with 10% EtOAc in hexane to give 3.548 g of the title compound.

Step B: 1-t-Butyloxycarbonyl-4-(N-cyanomethyl-N-ethylamino)-piperidine

To a solution of 150 mg 1-t-butyloxycarbonyl-4-ethylamino-piperidine (from Step A) in 3 ml DCE were added 60 mg of chloroacetonitrile, 109 mg of potassium carbonate, and 11 mg of potassium iodide. The reaction was stirred at 60° C. overnight. Methylene chloride was added, and the solution was washed with 2×20 ml water, and 20 ml brine. The solvent was then evaporated under reduced pressure. The residue was purified by flash chromatography with 20% EtOAc in hexane to give 115 mg of the title compound.

Step C: 1-t-Butyloxy-4-(N-(2-benzyl-2H-tetrazol-5-yl)methyl-N-ethylamino)-piperidine To a solution of 224 mg of 1-t-butyloxycarbonyl-4-(N-cyanomethyl)ethylamino)-piperidine (from Step B) in 3 ml toluene was added 417 mg of azidotributyl tin. The reaction was stirred overnight at 110° C. 244 mg of benzyl bromide was added and the reaction was heated for another 3 hours. The solvent was evaporated under reduced pressure. The residue was purified by flash chromatography with 10% EtOAc in hexane followed by 30% EtOAc in hexane to give 204 mg of the title compound.

Step D: 4-(N-(2-Benzyl-2H-tetrazol-5-yl)methyl-N-ethylamino)piperidine Hydrochloride To 4 ml of a saturated solution of hydrogen chloride in EtOAc was added 204 mg of 1-t-butyloxy-4-(N-(2-benzyl-2H-tetrazol-5-yl)methyl-N-ethylamino)-piperidine (from Step C). After 40 minutes, the solvent was evaporated under reduced pressure to give 170 mg of the title compound.

Step E: 2-(R)-(3-(S)-((4-(N-(2-Benzyl-2H-tetrazol-5-yl) methyl-N-ethylamino)-piperidine-1-yl)methyl)-4-(S)-phenylpyrrolidin-1-yl)-cyclohexaneacetic Acid, 4-Methoxybenzyl Ester To a solution of 58 mg of 4-(N-(2-benzyl-2H-tetrazol-5-yl)methyl-N-ethylamino)-piperidine hydrochloride (from Step D) in 3 ml DCE was added 17 mg of triethylamine. After 20 minutes, 50 mg of 2-(R)-(3-(R)-Formyl-4-(S)-phenylpyrrolidin-1-yl)-cyclohexaneacetic acid, p-Methoxybenzyl ester (prepared above as Aldehyde 5), was added, followed by 36 mg of sodium triacetoxyborohydride. The reaction was stirred overnight at room temperature. The solvent was evaporated under reduced pressure. The residue was purified by flash chromatography with 50% EtOAc in hexane followed by 50% EtOAc+10% MeOH in hexane to give 54 mg of the title compound.

Step F: 2-(R)-(3-(S)-((4-(N-(2-Benzyl-2H-tetrazol-5-yl) methyl-N-ethylamino)-piperidine-1-yl)methyl)-4-(S)-phenylpyrrolidin-1-yl)-cyclohexaneacetic Acid To 54 mg of 2-(R)-(3-(S)-((4-(N-(2-Benzyl-2H-tetrazol-5-yl)methyl-N-ethylamino)-piperidine-1-yl)methyl)-4-(S)-phenylpyrrolidin-1-yl)-cyclohexaneacetic acid, 4-Methoxybenzyl ester (from Step E) were added 150 mg of anisole and 3 ml of triflouroacetic acid. The reaction was stirred at room temperature for 1 hour. The trifluoroacetic acid was evaporated under reduced pressure. The residue was purified by flash chromatography with 20% MeOH in EtOAc followed by 20% MeOH+2% NH$_4$OH in EtOAc to give 48 mg of the title compound. ESI–MS 601 (M+H).

EXAMPLE 53

2-(R)-(3-(S)-((3-(4-fluorobenzyl)-8-aza-1-oxa-spiro [4.5]decan-8-yl)methyl)-4-(S)-(3-fluorophenyl) pyrrolidin-1-yl)-3-cyclopropylpropionic Acid Step A: 5-(t-Butoxycarbonyl)-5-aza-1-oxa-spiro[2.5] heptane A solution of trimethylsulfoxonium iodide (22 grams, 100 mmol) in 100 mL dry DMSO was cooled to 0° C. and sodium hydride (4.4 grams, 60% dispersion in mineral oil, 110 mmol) was added slowly in portions. The resulting mixture was warmed to room temperature and stirred for 1 h. The solution was recooled to 0° C. and a solution of N-tert-butoxylcarbonyl-4-piperidone (20 grams, 100 mmol) in 100 mL DMSO was added dropwise using and addition funnel. The mixture was heated to 50° C. for 1 h then cooled and diluted with 400 mL water. The aqueous mixture was extracted with toluene (3×200 mL) and the combined organic portions were dried over sodium sulfate and concentrated. Flash chromatography (500 g silica, 5/1 hexane/ EtOAc) afforded 17 grams (80%)of the desired epoxide. $^1$H NMR (400 MHz, CDCl$_3$). δ 1.4–1.48 (m, 2H), 1.46 (s, 9H), 1.72–1.83 (m, 2H), 2.67 (s, 2H), 3.38–3.44 (m, 2H), 3.68–3.78 (m, 2H).

Step B: 2-oxo-8-(t-Butoxycarbonyl)-8-aza-1-oxaspiro[4.5] decane

A dry flask was charged with sodium hydride (1.1 grams, 60% dispersion in mineral oil, 27.5 mmol) and 25 mL THF. The mixture was cooled to 0° C. and diethylmalonate (4.2 mL, 27.5 mmol) was added. The mixture was warmed to room temperature and stirred for 30 min. A solution of 5-(t-Butoxycarbonyl)-5-aza-1-oxa-spiro[2.5]heptane (5.3 grams, 25 mmol, from Step A) in 5 mL THF was added via syringe and the mixture was refluxed overnight. The THF was removed in vacuo and the residue was dissolved in 35 mL ethanol/35 mL 1 N NaOH. The resulting mixture was refluxed overnight. The mixture was cooled to room temperature and acidified with conc. HCl then extracted with EtOAc. The organic portion was dried and concentrated to give a colorless oil. The oil was heated to 130° C. for 2 h then cooled and purified by flash chromatography (1/1 hexane/EtOAc) to give 4.7 grams (56%) of product. $^1$H NMR (400 MHz, CDCl$_3$). δ 1.46 (s, 9H), 1.62–1.72 (m, 2H), 1.8–1.84 (m, 2H), 2.06 (t, 2H), 2.66 (t, 2H), 3.22–3.32 (m, 2H), 3.8–3.9 (m, 2H).

Step C: 2-oxo-3-(4-Fluorobenzyl)-8-(t-butoxycarbonyl)-8-aza-1-oxa-spiro[4.5]decane A solution of diisopropyl amine (0.36 mL, 2.6 mmol) in 7.5 mL dry THF was cooled to −78° C. and n-butyllithium (1.5 mL, 1.6 M in hexane, 2.4 mmol) was added. The mixture was warmed to 0° C. for 15 min then recooled to −78° C. A solution of 2-oxo-8-(t-Butoxycarbonyl)-8-aza-1-oxaspiro[4.5]decane (510 mg, 2.0 mmol, from Step B) in 2 mL THF was added dropwise. After 30 min at −78° C. 4-fluorobenzyl bromide (0.32 mL, 2.6 mmol) was added and after 30 min the mixture was warmed to room temperature and quenched with sat'd ammonium chloride. The mixture was extracted with ethyl acetate and the organic portion was dried over sodium sulfate and concentrated. Flash chromatography (3/1 hexane/EtOAc) afforded 510 mg (70%) of the desired product. $^1$H NMR (400 MHz, CDCl$_3$). δ 1.44 (s, 9H), 1.51–1.81 (5H), 2.03–2.19 (m, 1H), 2.76–2.81 (dd, 1H), 2.99–3.04 (m, 1H), 3.18–3.3 (m, 3H), 3.72–3.81 (m, 2H), 6.97–7.03 (m, 2H), 7.11–7.18 (m, 2H). The lactone was separated into its enantiomers by semiprep chiral HPLC (chiralpak AD, 9/1 hexane/IPA→8/1 hexane/IPA) to afford the two enantiomers (enantiomer A, 92% ee and enantiomer B, 73% ee). The two enantiomers were converted to the spiro tetrahydrofuran derivatives as described below for enantiomer B.

Step D: 3-(4-Fluorobenzyl)-8-(t-butoxycarbonyl)-8-aza-1-oxa-spiro[4.5]decane

A solution of 3-(4-fluorobenzyl)-8-(t-Butoxycarbonyl)-8-aza-1-oxa-spiro[4.5]decane, enantiomer B (130 mg, 0.34 mmol, 73% ee, from Step C was dissolved in 1 mL THF and a solution of lithium borohydride (0.53 mL, 1.0 M in THF, 0.53 mmol) was added. The mixture was stirred overnight then diluted with EtOAc. The organic was washed with 1 N HCl and sat'd sodium chloride then dried over sodium sulfate and concentrated to provide the crude diol (125 mg, 95%). The diol was dissolved in 2 mL DCM and triphenylphosphine (133 mg, 0.51 mmol) was added. Diisopropylazodicarboxylate (0.1 mL, 0.51 mmol) was added and the mixture was stirred for 2 h. The reaction was quenched with 0.2 mL methanol and concentrated. Flash chromatography (4/1 hexane /EtOAc) afforded 100 mg (85%) of the desired product. Chiral HPLC analysis (Chiralpak AS, 99/1 hexane/ IPA). The product enantiomers were separated by semiprep chiral HPLC (Chiralpak AS, 99/1 hexane/IPA) to provide 60 mg (60%) of the pure enantiomer B. $^1$H NMR (400 MHz, CDCl$_3$). δ 1.38–1.48 (m, 2H), 1.44 (s, 9H), 1.58–1.1.65 (m, 3H), 1.88–1.93 (dd, 1H), 2.5–2.75 (m, 3H), 3.28–3.4 (m, 2H), 3.5–3.61 (m, 3H), 3.9–3.95 (m, 1H), 6.96–7.01 (m, 2H), 7.1–7.15 (m, 2H).

Step E: 2-(R)-(3-(S)-((3-(4-Fluorobenzyl)-8-aza-1-oxa-spiro[4.5]decan-8-yl)methyl)-4-(S)-(3-fluorophenyl)pyrrolidin-1-yl)-3-cyclopropylpropionic Acid A solution of 3-(4-fluorobenzyl)-8-(t-Butoxycarbonyl)-8-aza-1-oxa-spiro[4.5]decane, enantiomer B (37 mg, 0.105 mmol, from Step D) was dissolved in 2 mL methanol. 0.02 mL of conc. HCl was added and the mixture was heated to 50° C. for 2 h then concentrated to provide the HCl salt. Triethyl amine (0.017 mL, 0.122 mmol), sodium triacetoxy borohydride (34 mg, 0.162 mmol) and aldehyde 12 (32 mg, 0.081 mmol) were added. The mixture was stirred overnight then filtered through a plug of silica eluting with 19/1 DCM/MeOH. The solvent was removed and the residue was dissolved in 2 mL methanol. 10% Pd/C was added (30 mg, 0.03 mmol) and the mixture was stirred under 1 atm of hydrogen for 2 h. The catalyst was filtered off and the product was purified by flash chromatography (95/5 DCM/MeOH→95/5/0.5 DCM/MeOH/NH4OH) to afford 29 mg (67%) of the title compound. $^1$H NMR (500 MHz, CDCl$_3$). δ 0.18–0.21 (m, 2H), 0.5–0.53 (m, 2H), 0.8–0.86 (m, 1H), 1.33–1.36 (dd, 1H), 1.42–1.5 (m, 1H), 1.52–1.72 (m, 4H), 1.8–1.97 (m, 2H), 2.21–2.58 (m, 7H), 2.63–2.64 (d, 2H), 2.7–2.78 (m, 1H), 3.15–3.21 (q, 1H), 3.33–3.44 (m, 3H), 3.59–3.7 (m, 3H), 3.78–3.81 (t, 1H), 6.95–7.03 (m, 3H), 7.13–7.17 (m, 4H), 7.34–7.37 (m, 1H). ESI–MS, M/z; (M+H)=539.5 (obs), 539.67 (calc.).

EXAMPLES 54–66

Examples 54–66 in Table 6 were prepared according to the general procedure given in Example 53.

TABLE 6

| EXAMPLE # | R$^a$ | R$^b$ | ESI-MS M/z (M + H) |
|---|---|---|---|
| 54 | 3-benzyl-1-oxa-8-azaspiro[4.5]decan-8-yl, Isomer 1 | cyclopropylmethyl | 521.5 |
| 55 | 3-benzyl-1-oxa-8-azaspiro[4.5]decan-8-yl, Isomer 2 | cyclopropylmethyl | 521.5 |
| 56 | 3-(4-fluorobenzyl)-1-oxa-8-azaspiro[4.5]decan-8-yl, Isomer 1 | cyclopropylmethyl | 539.5 |
| 57 | 3-(4-fluorobenzyl)-1-oxa-8-azaspiro[4.5]decan-8-yl, Isomer 2 | cyclobutylmethyl | 553.3 |
| 58 | 2-benzyl-1-oxa-8-azaspiro[4.5]decan-8-yl, Racemic | cyclopropylmethyl | 521.3 |

TABLE 6-continued

| EXAMPLE # | Rᵃ | Rᵇ | ESI-MS M/z (M + H) |
|---|---|---|---|
| 59 | (4-fluorophenyl-substituted 1-oxa-8-azaspiro[4.5]decane) Racemic | cyclopropylmethyl | 525.3 |
| 60 | (4-fluorophenethyl-substituted 1-oxa-8-azaspiro[4.5]decane) Isomer 1 | cyclopropylmethyl | 553.5 |
| 61 | (4-fluorophenethyl-substituted 1-oxa-8-azaspiro[4.5]decane) Isomer 2 | cyclopropylmethyl | 553.5 |
| 62 | (4-fluorophenethyl-substituted 1-oxa-8-azaspiro[4.5]decane) Racemic | cyclopropylmethyl | 553.5 |
| 63 | 4-((2-(4-fluorophenylsulfonyl)ethyl)piperidinyl) | tert-butyl | 563.3 |
| 64 | 4-((2-(4-fluorophenylsulfonyl)ethyl)piperidinyl) | neopentyl | 577.4 |

TABLE 6-continued

| EXAMPLE # | R$^a$ | R$^b$ | ESI-MS M/z (M + H) |
|---|---|---|---|
| 65 | 4-F-C6H4-SO2-CH2CH2-(4-piperidinyl)- | -C(CH3)2-CF3 | 589.1 |
| 66 | 4-F-C6H4-SO2-CH2CH2-(4-piperidinyl)- | -C(CH3)2-OMe | 551.2 |

EXAMPLES 67–86

Examples 67–86 in Table 7 were prepared according to the general procedure given in Example 30, employing the appropriate commercially available thiophenols in Step D and the appropriate aldehyde whose syntheses are described above.

TABLE 7

| EXAMPLE # | R$_a$ | R$_b$ | MS m/Z (M + 1) | HPLC A (min.) |
|---|---|---|---|---|
| 67 | isopropyl | 2-pyrazinyl-SO2- | 533.4 | 2.27 |
| 68 | cyclopropylmethyl | 2-pyrazinyl-SO2- | 545.4 | 2.32 |

TABLE 7-continued
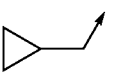
| EXAMPLE # | R$_a$ | R$_b$ | MS m/Z (M + 1) | HPLC A (min.) |
|---|---|---|---|---|
| 69 | 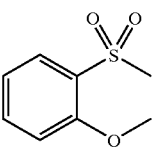 | 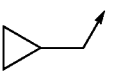 | 573.5 | 3.82 |
| 70 | 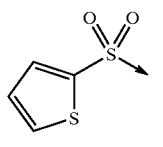 | 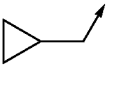 | 549.5 | 3.80 |
| 71 | 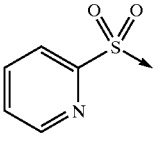 | 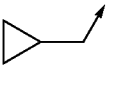 | 544.5 | 3.64 |
| 72 | 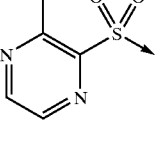 | 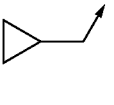 | 559.5 | 3.69 |
| 73 | 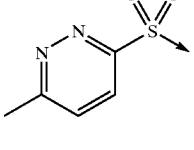 | 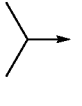 | 559.6 | 3.62 |
| 74 | 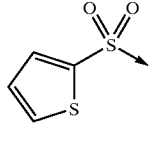 | 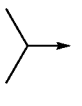 | 537.5 | 3.08 |
| 75 | 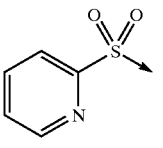 | 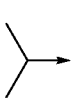 | 352.5 | 3.54 |
| 76 | | 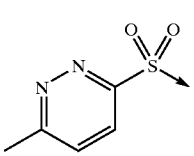 | 547.5 | 3.54 |

TABLE 7-continued
| EXAMPLE # | R$_a$ | R$_b$ | MS m/Z (M + 1) | HPLC A (min.) |
|---|---|---|---|---|
| 77 | 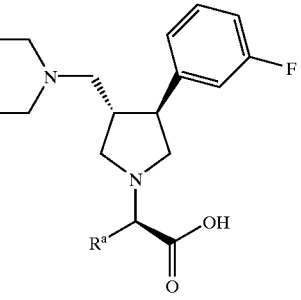 |  | 547.5 | 3.61 |
| 78 | 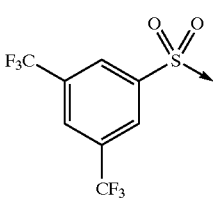 | 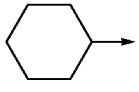 | 679.5 | 2.88 |
| 79 | 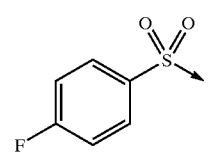 |  | 589.5 | 2.32 |
| 80 | 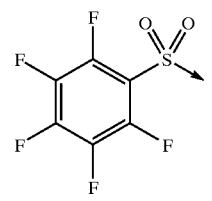 |  | 633.2 | 2.31 |
| 81 | 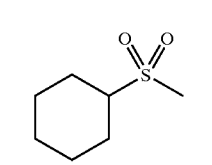 | 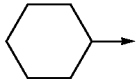 | 549.4 | 2.04 |
| 82 | 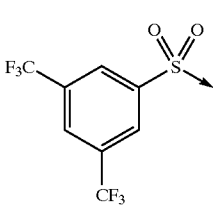 | | 707.4 | 2.92 |

TABLE 7-continued

| EXAMPLE # | $R_a$ | $R_b$ | MS m/Z (M + 1) | HPLC A (min.) |
|---|---|---|---|---|
| 83 | 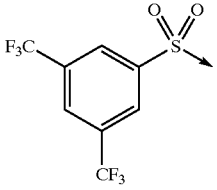 | 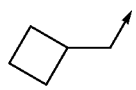 | 667.4 | 2.70 |
| 84 | 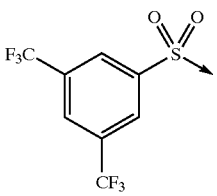 | 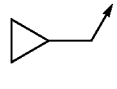 | 693.3 | 2.86 |
| 85 | 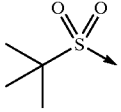 | 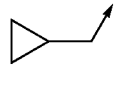 | 523.4 | 1.79 |
| 86 | | 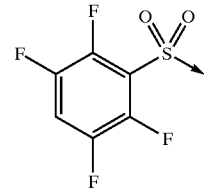 | 615.2 | 2.26 |

EXAMPLE 87

2-(R)-((3-(S)-(4-(N-((4-Fluorophenyl)sulfonyl)aminomethyl)-piperidine-1-yl)methyl)-4-(S)-(3-fluorophenyl)pyrrolidin-1-yl)-3-(cyclopropyl) propionic Acid Step A: 4-(N-((4-Fluorophenyl)sulfonyl)aminomethyl)-1-tert-butoxycarbonylpiperidine Diisopropylethylamine (DIEA, 0.7 mL, 2 mmol) was added to a solution of 4-(aminomethyl)-1-tert-butoxycarbonylpiperidine (200 mg, 0.93 mmol) in 5 mL of $CH_2Cl_2$ under nitrogen. (4-fluorophenyl)sulfonyl chloride (195 mg, 1 mmol) was then added, and the reaction mixture was stirred at room temperature for 30 min. The solution was diluted with diethyl ether, washed with 1N HCl, 1N NaOH, and brine, and then dried over $MgSO_4$. The solution was then concentrated to afford 284 mg (82% yield) of the title compound, which could be purified by recrystallization from diethyl ether. $^1$H NMR (300 MHz, $CDCl_3$). δ 1.00–1.13 (m, 1H), 1.42 (s, 9H), 1.61–1.70 (m, 3H), 2.58–2.70 (m, 2H), 2.80–2.84 (m, 2H), 4.02–4.16 (m, 2H), 4.46–4.52 (m, 1H), 7.17–7.22 (m, 2H), 7.82–7.90 (m, 2H).

Step B: 2-(R)-((3-(S)-(4-(N-((4-Fluorophenyl)sulfonyl) aminomethyl)-piperidine-1-yl)methyl)-4-(S)-(3-fluorophenyl)pyrrolidin-1-yl)-3-(cyclopropyl)propionic Acid A solution of 2-(R)-(3-(R)-formyl-4-(S)-(3-fluorophenyl) pyrrolidin-1-yl)-3-(cyclopropyl)propionic acid, benzyl ester (30 mg, 0.072 mmol; prepared above as Aldehyde 19) in 2 mL MeOH was stirred with 20 mg (0.019 mmol) 10% palladium on carbon under 1 atm of hydrogen using a balloon. Meanwhile, 4-(N-((4-fluorophenyl)sulfonyl)aminomethyl)-1-tert-butoxycarbonylpiperidine (37 mg, 0.1 mmol, from Step A) was dissolved in 1 mL of a solution of trifluoroacetic acid/CH$_2$Cl$_2$ (1:1). After 20 min., this solution was concentrated to provide the deprotected piperidine. After an additional 35 min., the palladium mixture was filtered through Celite, concentrated and redissolved in 1 mL 1,2-dichloroethane. The piperidine from above was then dissolved in 0.5 mL of 1,2-dichloroethane with diisopropylethylamine (0.021 mL, 0.122 mmol) and added to the aldehyde solution. Sodium triacetoxyborohydride (40 mg, 0.194 mmol) was added and the mixture was stirred for 1 h. The solvent was removed and the product was purified by preparative HPLC (column: YMC combiprep ODS-A 20×50 mm, gradient: 10% acetonitrile/water w/0.1% TFA to 100% acetonitrile/water/0.1% TFA over 8 min, then ramp to 10% acetonitrile/water w/0.1% TFA over 2 min, flow: 20 mL/min). The product was converted to a free base by loading onto a solid phase extraction cartridge (Varian SCX), eluting with 2M ammonia in MeOH, concentrating, then lyophilizing from acetonitrile/water to give 5.6 mg (14% yield) of the title compound. ESI–MS. M/z; (M+H)= 562.1.

EXAMPLE 88

2-(R)-((3-(S)-(4-((N-((4-Fluorophenyl)sulfonyl)-N-Methylamino)methyl)-piperidine-1-yl)methyl)-4-(S)-(3-fluorophenyl)pyrrolidin-1-yl)-3-(cyclopropyl)propionic Acid Step A: 4-((N-((4-Fluorophenyl)sulfonyl)-N-Methylamino)methyl)-1-tert-butoxycarbonylpiperidine 4-(N-((4-Fluorophenyl)sulfonyl)aminomethyl)-1-tert-butoxycarbonylpiperidine (100 mg, 0.27 mmol, from Example 87, Step A) was added to a slurry of sodium hydride (12 mg, 60% in mineral oil, 0.30 mmol) in 5 mL of dry tetrahydrofuran at 0° C. under nitrogen. Methyl iodide (0.022 mL, 0.35 mmol) was then added. The reaction mixture was then allowed to warm to room temperature overnight. The mixture was diluted with diethyl ether and washed with 1N NaOH and brine. The solution was dried over Na$_2$SO$_4$, filtered and concentrated to provide 98 mg (94% yield) of the title compound. ESI–MS. M/z; (M+H)= 387.0.

Step B: 2-(R)-((3-(S)-(4-((N-((4-Fluorophenyl)sulfonyl)-N-Methylamino)methyl)-piperidine-1-yl)methyl)-4-(S)-(3-fluorophenyl)pyrrolidin-1-yl)-3-(cyclopropyl)propionic Acid Aldehyde 19 (37 mg, 0.1 mmol) and 4-((N-((4-Fluorophenyl)sulfonyl)-N-Methylamino)methyl)-1-tert-butoxycarbonylpiperidine (30 mg, 0.072 mmol, from Step A) were reacted in a manner analogous to that described in Example 87, Step B to afford 30.9 mg (63% yield) of the title compound. ESI–MS. M/z; (M+H)=576.5.

EXAMPLES 89–90

Examples 89–90 in Table 8 were prepared according to the general procedure given in Example 87, employing the appropriate commercially available sulfonyl chlorides in Step A and the appropriate aldehydes, whose syntheses are described above.

TABLE 8

| EXAMPLE # | R$_a$ | R$_b$ | MS m/Z (M + 1) | HPLC A (min.) |
|---|---|---|---|---|
| 89 | cyclopropylmethyl | 3,5-bis(trifluoromethyl)phenyl | 680.1 | 2.58 |
| 90 | cyclopropylmethyl | pentafluorophenyl | 634.4 | 2.37 |

EXAMPLE 91

2-(R)-((3-(S)-(4-(2-Methyl-2-((4-fluorophenyl)sulfonyl)-1-propyl)piperidin-1-yl)methyl)-4-(S)-(3-fluorophenyl)-pyrrolidin-1-yl)-3-(cyclpropyl)propionic Acid Step A: 4-(2-Methyl-2-((4-fluorophenyl)sulfonyl)-1-propyl)-1-tert-butoxycarbonylpiperidine A solution of 4-(2-((4-fluorophenyl)sulfonyl)-1-ethyl)-1-tert-butoxycarbonylpiperidine (100 mg, 0.27 mmol, from Example 30, Step D) in 1 mL of THF was added to a solution of LiN(SiMe$_3$)$_2$ (1.0 M in THF, 0.54 mL, 0.54 mmol) in 5 mL of THF at –78° C. under nitrogen. Methyl iodide (0.038 mL, 0.6 mmol) was added and the reaction was stirred at –78° C. for 1 hour, followed by warming to room temperature. After 6 hours, the reaction was not complete by LC analysis, so an addition 0.54 mL of LiN(SiMe$_3$)$_2$ solution was added at –78° C., followed by more methyl iodide (0.038 mL, 0.6 mmol) and warming to room temperature overnight. The reaction mixture was then diluted with diethyl ether and washed with 1N NaOH, 1N HCl and brine. The solution was dried over MgSO$_4$, filtered, concentrated and purified by preparative HPLC (column: YMC combiprep ODS-A 20×50 mm, gradient: 10% acetonitrile/water w/0.1% TFA to 60% acetonitrile/water w/0.1% TFA over 20 min, then ramp to 10% acetonitrile/water w/0.1% TFA over 2 min, flow: 20 mL/min) to afford 17 mg (16% yield) of the desired product. ESI–MS. M/z; (M+H)=400.2.

Step B: 2-(R)-((3-(S)-(4-(2-Methyl-2-((4-fluorophenyl)sulfonyl)-1-propyl)piperidin-1-yl)methyl)-4-(S)-(3-fluorophenyl)-pyrrolidin-1-yl)-3-(cyclopropyl)propionic Acid Aldehyde 19 (13 mg, 0.03 mmol) and 4-(2-Methyl-2-((4-fluorophenyl)sulfonyl)-1-propyl)-1-tert-butoxycarbonylpiperidine (17 mg, 0.042 mmol, from Step A) were reacted in a manner analogous to that described in Example 87, Step B to afford 9.5 mg (54% yield) of the title compound. ESI–MS. M/z; (M+H)=589.4.

EXAMPLE 92

2-(R)-((3-(S)-(4-(2-((4-Fluorophenyl)sulfonyl)-1-ethyl)piperidin-1-yl)methyl)-4-(S)-(3-fluorophenyl)-pyrrolidin-1-yl)-3-(cyclopropyl)propionic Acid, Benzyl Ester Hydrochloide Aldehyde 19 (25 mg, 0.06 mmol) was dissolved in 1 mL of dioxane. Diisopropylethylamine (0.019 mL, 0.11 mmol) was added, followed by a solution of 4-(2-((4-Fluorophenyl)sulfonyl)-1-ethyl)piperidine trifluoroacetate (30 mg, 0.08 mmol, from Example 30, Step E) dissolved in 0.5 mL of dioxane. Sodium triacetoxyborohydride (25 mg, 0.12 mmol) was then added, and the reaction mixture was allowed to stand at room temperature overnight. The mixture was then concentrated and purified by preparative HPLC (column: YMC combiprep ODS-A 20×50 mm, gradient: 10% acetonitrile/water w/0.1% TFA to 100% acetonitrile/water w/0.1% TFA over 8 min, then ramp to 10% acetonitrile/water w/0.1% TFA over 2 min, flow: 20 mL/min) to afford 34.2 mg (83% yield) of the title compound. ESI–MS. M/z; (M+H)=651.5.

EXAMPLE 93

2-(R)-(3-(R or S)-((4-(2-((4-Fluorophenyl)sulfonyl)-1-ethyl)piperidin-1-yl)methyl)-4-(R or S)-(3-fluorophenyl)-pyrrolidin-1-yl)-3-cyclobutylpropionic Acid Step A: Methyl-(Z)-3'-fluorocinnamate To a solution of 6.6 mL (31.2 mmol) of bis(2, 2, 2-trifluoroethyl) (methoxycarbonyl methyl)phosphonate and 40.01 g (151 mmol) of 18-crown-6 in 300 mL of THF at −78° C. was added 60 mL (30.0 mmol) of 0.5 M KHMDS in toluene (NOTE: Temperature maintained <−70° C.). After stirring for 10 minutes, a solution of 3.4 mL (32.0 mmol) of 3-flurobenzaldehyde in 25 mL of THF was added. The reaction was stirred for 2.5 hours and quenched with 200 mL of saturated $NH_4Cl$. After warming to room temperature, the reaction was partitioned between 400 mL of $Et_2O$ and 300 mL of $H_2O$. The phases were separated and the aqueous layer was extracted with 200 mL of $Et_2O$. The combined organic phases were washed with 400 mL of brine, dried over $MgSO_4$ and concentrated under reduced pressure. The residue was purified by flash chromatography eluting with 9:1 v/v hexanes/EtOAc to yield 5.7 g (>100%) of the title compound: $R_f$: 0.33 (9:1 v/v hexanes/EtOAc); $^1$H NMR (500 MHz, $CDCl_3$) δ 3.74 (s, 3H), 6.01 (d, J=12.6 Hz, 1H), 6.92 (d, J=12.6 Hz, 1H), 7.05 (m, 1H), 7.27–7.40 (m, 3H).

Step B: (Z)-3'-Fluorocinnamic Acid

To a solution of methyl-(Z)-3'-fluorocinnamate (approximately 30 mmol; from Step A) in 100 mL of EtOH at 0° C. was added 12 mL (60 mmol) of 5 N NaOH. After stirring at room temperature for 4 hours, volatiles were removed under reduced pressure. The residue was dissolved in 250 mL of $H_2O$ and washed with 50 mL of $Et_2O$. After separating phases, the aqueous layer was acidified to pH 1–2 using 2 N HCl, extracted with 2×250 mL $CH_2Cl_2$, dried over $Na_2SO_4$ and concentrated under reduced pressure to yield 4.79 g (96% over two steps) of the title compound, which was used without further purification. $^1$H NMR (500 MHz, $CDCl_3$) δ 6.02 (d, J=12.6 Hz, 1H), 7.02–7.08 (m, 2H), 7.28–7.40 (m, 3H).

Step C: 3-(Z)-(3'-Fluorocinnamoyl)-4-(S)-benzyl Oxazolidin-2-one

To a solution of 4.75 g (28.5 mmol) of (Z)-(3'-fluoro)-cinnamic acid (from Step B) in 200 mL of THF at −20° C. was added 10 L (71.7 mmol) of TEA and 3.5 mL (28.4 mmol) of pivaloyl chloride. After stirring for 2.5 hours at −20° C. and adding 1.53 g (36 mmol) of LiCl and 5.05 g (28.4 mmol) of 4-(S)-benzyl oxazolidin-2-one, the reaction was warmed to room temperature and stirred for 5 hours. Volatiles were removed under reduced pressure. The residue was dissolved in 500 mL of EtOAc and washed with 2×500 mL of 0.5 N $KHSO_4$, 500 mL of brine, 500 mL of 1 N $NaHCO_3$, and 500 mL of brine. The oraganic phase was dried over $Na_2SO_4$ and concentrated under reduced pressure. The residue was preabsorbed onto silica gel and purified by flash chromatography eluting with 4:1 v/v hexanes/EtOAc to yield 7.56 g, which was recrystallized from 150 mL of with 9:1 v/v hexanes/EtOAc to yield 6.23 g (67%) of the title compound: $R_f$: 0.21 (4:1 v/v hexanes/EtOAc); $^1$H NMR (500 MHz, $CDCl_3$) δ 2.81 (dd, J=13.3, 9.6 Hz, 1H), 3.38 (dd, J=13.3, 3.4 Hz, 1H), 4.19–4.26 (m, 2H), 4.75 (m, 1H), 6.96–7.08 (m, 3H), 7.23–7.38 (m, 6H).

Step D: 3-(1-Benzyl-4-(R or S)-(3-fluorophenyl) pyrrolidine-3-(R or S)-carbonyl)-4-(S)-benzyl Oxazolidin-2-one and 3-(1-Benzyl-4-(S or -R)-(3-fluoro) phenylpyrrolidine-3-(S or R)-carbonyl)-4-(S)-benzyl Oxazolidin-2-one The title compounds were prepared using a procedure analogous to that described for 3-(1-benzyl-4-(R)-(3-fluorophenyl)pyrrolidine-3-(S)-carbonyl)-4-(S)-benzyl oxazolidin-2-one (prepared above as Pyrrolidine 1), except that 3-(Z)-(3'-fluorocinnamoyl)-4-(S)-benzyl oxazolidin-2-one (from Example 93, Step C) was substituted for 3-(E)-(3'-fluorocinnamoyl)-4-(S)-benzyl oxazolidin-2-one in Step B. The residue was purified by flash chromatography eluting with 7:2:1 v/v/v hexanes/$CH_2Cl_2$/EtOAc to yield 4.0 g (46%) of the less polar diastereomer (Diastereomer 1) and 2.54 g (29%) of the more polar diastereomer (Diastereomer 2). For Diastereomer 1: $R_f$: 0.53 (9:1 v/v $CH_2Cl_2$/$Et_2O$); $^1$H NMR (500 MHz, $CDCl_3$) δ 2.58 (dd, J=13.3, 9.8 Hz, 1H), 2.70 (dd, J=9.1, 7.1 Hz, 1H), 2.92 (t, J=8.6 Hz, 1H), 3.06–3.14 (m, 2H), 3.25 (t, J=8.2 Hz, 1H), 3.40 (dd, J=9.5, 2.8 Hz, 1H), 3.74–3.92 (m, 5H), 4.63 (m, 1H), 6.88 (m, 1H), 7.07–7.44 (m, 13H). For Diastereomer 2: $R_f$: 0.38 (9:1 v/v $CH_2Cl_2$/$Et_2O$); $^1$H NMR (500 MHz, $CDCl_3$) δ 1.41 (dd, J=13.3, 11.4 Hz, 1H), 2.45 (dd, J=13.3, 3.1 Hz, 1H), 2.76 (dd, J=9.3, 6.3 Hz, 1H), 2.87 (t, J=8.7 Hz, 1H), 3.11 (dd, J=9.2, 7.6 Hz, 1H), 3.40 (dd, J=9.4, 7.1 Hz, 1H), 3.77 (Abq, J=12.9 Hz, 2H), 3.88 (dd, J=9.1, 2.6 Hz, 1H), 3.99 (t, J=8.5 Hz, 1H), 4.07 (m, 1H), 4.36 (m, 1H), 4.48 (m, 1H), 6.88 (m, 1H), 7.03 (d, J=7.1 Hz, 2H), 7.17–7.44 (m, 11H).

Step E: 3-(4-(R or S)-(3-Flurophenyl)pyrrolidine-3-(R or S)-carbonyl)-4-(S)-benzyl Oxazolidin-2-one The title compound was prepared using a procedure analogous to that described for Pyrrolidine 1, Step E, where 3-(1-benzyl-4-(S)-(3-fluorophenyl)pyrrolidine-3-(R or S)-carbonyl)-4-(R or S)-benzyl oxazolidin-2-one (Diastereomer 1 from EXAMPLE 93, Step D) was substituted for 1-benzyl-3-(R)-(t-butyldimethylsilyloxymethyl)-4-(S)-phenyl pyrrolidine, to yield the title compound, which was used without further purification: $^1$H NMR (500 MHz, $CDCl_3$) δ 1.55 (dd, J=13.5, 11.2 Hz, 1H), 2.52 (dd, J=13.5, 3.2 Hz, 1H), 3.20 (dd, J=11.7, 7.8 Hz, 1H), 3.32 (m, 1H), 3.56 (dd, J=11.7, 7.8 Hz, 1H), 3.63 (dd, J=11.7, 7.8 Hz, 1H), 3.89–4.03 (m, 3H), 4.37–4.49 (m, 2H), 6.87–7.34 (m, 9H).

Step F: 3-(1-tert-Butoxycarbonyl-4-(R or S)-(3-fluorophenyl)pyrrolidine-3-(R or S)-carbonyl)-4-(S)-benzyl Oxazolidin-2-one A solution of 1.18 g (3.2 mmol) of 3-(4-(R or S)-(3-fluorophenyl)pyrrolidine-3-(R or S)-carbonyl)-4-(S)-benzyl oxazolidin-2-one (from EXAMPLE 93, Step E) in 8 mL of $CH_2Cl_2$ at room temperature was treated with 780 mg (3.6 mmol) of Boc$_2$O. After stirring at room temperature overnight, the reaction was diluted with 150 mL of CH$_2$Cl$_2$ and washed with 1 N NaHCO$_3$. After separating phases, the aqueous layer was extracted with 100 mL of CH$_2$Cl$_2$. The combined organic layers were washed with 200 mL of brine, dried over Na$_2$SO$_4$ and concentrated under reduced pressure. The residue was purified using a 40M Biotage column eluting with 7:3 v/v hexanes/EtOAc to yield 1.14 g (79%) of the title compound: R$_f$: 0.28 (7:3 v/v hexanes/EtOAc); $^1$H NMR (500 MHz, CDCl$_3$) δ 1.53 (s, 9H), 2.06 (m, 1H), 2.72 (m, 1H), 3.71–4.16 (m, 7H), 4.50 (1H), 4.63 (m, 1H), 6.92–7.07 (m, 5H), 7.23–7.31 (m, 4H).

Step G: 1-tert-Butoxycarbonyl-3-(R or S)-carboxy-4-(R or S)-(3-fluorophenyl)pyrrolidine To a solution of 1.14 g (2.4 mmol) of 3-(1-tert-butoxycarbonyl4-(R or S)-(3-fluorophenyl)pyrrolidine-3-(R or S)-carbonyl)-4-(S)-benzyl oxazolidin-2-one (from EXAMPLE 93, Step F) at 0° C. in 48 mL of THF and 12 mL of H$_2$O was added 1.23 mL (12.4 mmol) of 32% H$_2$O$_2$ and 265 mg (6.3 mmol) of LiOH.H$_2$O. After stirring for 4 hours, 11 mL of 1.25 M Na$_2$SO$_3$ and 34 mL of 0.5 N NaHCO$_3$ were added and volatiles were removed under reduced pressure. The residue was diluted with 200 mL of H$_2$O and washed with 4×200 mL of CH$_2$Cl$_2$. The aqueous layer was acidified to pH 1 using 2 N HCl, extracted with 4×200 mL of EtOAc, dried over Na$_2$SO$_4$ and concentrated under reduced pressure to yield 720 mg (96%) of the title compound, which was used without further purification: $^1$H NMR (500 MHz, CDCl$_3$) δ 1.50 (s, 9H), 3.37 (m, 1H), 3.63–3.78 (m, 5H), 6.87–6.97 (m, 3H), 7.25 (m, 1H).

Step H: 1-tert-Butoxycarbonyl-3-(R or S)-hydroxymethyl-4-(R or S)-(3-fluorophenyl)pyrrolidine To a solution of 720 mg (2.3 mmol) of 1-tert-butoxycarbonyl-3-(R or S)-carboxy-4-(R or S)-(3-fluorophenyl)pyrrolidine (from EXAMPLE 93, Step G) in 21 mL of dioxane at room temperature was added 5.9 mL of 2 M borane-Methylsulfide in THF. An ice bath was used to control the temperature of the reaction. After stirring at room temperature for 2.5 hours, MeOH was added. After removing volatiles under reduced pressure, the residue was reconcentrated 2× using MeOH. The residue was purified using a 40S Biotage column eluting with 96:4 v/v CH$_2$Cl$_2$/MeOH to yield 636 mg (92%) of the title compound: R$_f$: 0.36 (95:5 v/v CH$_2$Cl$_2$/MeOH); $^1$H NMR (500 MHz, CDCl$_3$) δ 1.49 (s, 9H), 2.10 (br, 1H), 2.68 (m, 1H), 3.28–3.46 (m, 2H), 3.50–3.72 (m, 5H), 6.87–6.95 (m, 3H), 7.27 (m, 1H).

Step I: 1-tert-Butoxycarbonyl-3-(R or S)-iodomethyl-4-(R or S)-(3-fluorophenyl)pyrrolidine To a solution of 161 mg (0.61 mmol) triphenylphosphine in 3 mL of CH$_2$Cl$_2$ under argon was added 52 mg (0.77 mmol) of imidazole and 155 mg (0.61 mmol) of iodine. A solution of 150 mg (0.51 mmol) of 1-tert-butoxycarbonyl-3-(R or S)-hydroxymethyl-4-(R or S)-(3-fluorophenyl)pyrrolidine (from EXAMPLE 93, Step H) was added. After stirring 2 hours at room temperature, the reaction was absorbed onto silica gel and purified by flash chromatography eluting with 9:1 v/v hexanes/EtOAc to yield 102 mg (49%) of the title compound: R$_f$: 0.69 (3:2 v/v hexanes/EtOAc); $^1$H NMR (500 MHz, CDCl$_3$) δ 1.51 (s, 9H), 2.71–2.76 (m, 2H), 2.91 (m, 1H), 3.23 (m, 1H), 3.50 (m, 1H), 3.70–3.81 (m, 3H), 6.91–7.00 (m, 3H), 7.29 (m, 1H).

Step J: 1-tert-Butoxycarbonyl-(3-(R or S)-(4-(2-((4-fluorophenyl)sulfonyl)-1-ethyl)piperidin-1-yl)methyl)-4-(R or S)-(3-fluorophenyl)-pyrrolidine A solution of 102 mg (0.25 mmol) of 1-tert-butoxycarbonyl-3-(R or S)-iodomethyl4-(R or S)-phenylpyrrolidine (from EXAMPLE 93, Step I) and 129 mg (0.48 mmol) of 4-(2-((4-fluorophenyl)sulfonyl)-1-ethyl) piperidine (from Example 30, Step E) in 1 mL of CH$_3$CN was heated at 80° C. for 10 hours. The reaction was diluted with 25 mL of CH$_2$Cl$_2$ and washed with 25 mL of 1 N NaHCO$_3$. After separating phases, the aqueous layer was extracted with 25 mL of CH$_2$Cl$_2$. The combined organic phases were dried over Na$_2$SO$_4$ and concentrated under reduced pressure. The residue was purified by flash chromatography eluting with 4:1 v/v hexanes/acetone to yield 35 mg (26%) of the title compound: R$_f$: 0.23 (4:1 v/v hexanes/acetone); $^1$H NMR (500 MHz, CDCl$_3$) δ 1.50–1.85 (m, 16H), 2.59–2.77 (m, 4H), 3.07–3.14 (m, 4H), 3.42–3.73 (m, 6H), 6.86–6.93 (m, 3H), 7.22–7.28 (m, 3H), 7.90–7.94 (m, 2H).

Step K: (3-(R or S)-(4-(2-((4-Fluorophenyl)sulfonyl)-1-ethyl)piperidin-1-yl)methyl)-4-(R or S)-(3-fluorophenyl)-pyrrolidine, Trifluoroacetate Salt A solution of 35 mg (0.065 mmol) of 1-tert-butoxycarbonyl-(3-(R or S)-(4-(2-((4-fluorophenyl)sulfonyl)-1-ethyl)piperidin-1-yl)methyl)-4-(R or S)-(3-fluorophenyl)-pyrrolidine (from EXAMPLE 93, Step J) in 0.5 mL of CH$_2$Cl$_2$ was treated with 0.5 mL of TFA. After 1 hour, the volatiles were removed under reduced pressure. The residue was reconcentrated 2× using CH$_2$Cl$_2$ and 2× using Et$_2$O to yield the title compound, which was used without further purification. $^1$H NMR (500 MHz, CDCl$_3$) δ 1.59–1.83 (m, 6H), 2.50–2.79 (m, 2H), 3.06–4.20 (m, 13H), 6.94–7.04 (m, 3H), 7.22–7.36 (m, 3H), 7.86–7.88 (m, 2H).

Step L: 2-(S)-Trifluoromethanesulfonoxy-3-(cyclobutyl) propanoic Acid, (4-Methoxy)benzyl Ester To a solution of 100 mg (0.38 mmol) of 2-(S)-hydroxy-3-(cyclobutyl)propanoic acid, (4-methoxy) benzyl ester (prepared as Hydroxy ester 4 above) in 1.5 mL of CH$_2$Cl$_2$ at −78° C. was added 0.11 mL (0.61 mmol) of 2,6-lutidine. After 5 minutes, 0.096 mL (0.57 mmol) of Tf$_2$O was added. The reaction was stirred at −78° C. for 30 minutes and 20 minutes at 0° C. The reaction mixture was absorbed onto silica gel and purified by flash chromatography eluting with 9:1 v/v hexanes/EtOAc to yield 135 mg (89%) of the title compound: R$_f$: 0.55 (4:1 v/v hexanes/EtOAc); $^1$H NMR (500 MHz, CDCl$_3$) δ 1.63–2.18 (m, 8H), 2.44 (m, 1H), 3.83 (s, 3H), 5.04 (m, 1H), 5.19 (s, 2H), 6.92 (d, J=8.6 Hz, 2H), 7.32 (d, J=8.6 Hz, 2H).

Step M: 2-(R)-(3-(R or S)-(4-(2-((4-Fluorophenyl)sulfonyl)-1-ethyl)piperidin-1-yl)methyl)-4-(R or S)-(3-fluorophenyl)-pyrrolidin-1-yl)-3-cyclobutylpropionic Acid, (4-Methoxy)benzyl Ester To a solution of 44 mg (0.065 mmol) (3-(R or S)-(4-(2-((4-fluorophenyl)sulfonyl)-1-ethyl)piperidin-1-yl)methyl)-4-(R or S)-(3-fluorophenyl)-pyrrolidine, trifluoroacetate salt (from EXAMPLE 93, Step K) and 50 mg (0.12 mmol) of 2-(S)-trifluoromethanesulfonoxy-3-(cyclobutyl)propanoic acid, (4-methoxy) benzyl ester (from Example 93, Step L) in 1 mL CH$_3$CN at 0° C. was added 0.034 mL (0.2 mmol) of DIEA. The reaction was warmed to room temperature and stirred overnight. An additional 16 mg of triflate was added and stirred for 4 hours. The reaction was partitioned between 25 mL of CH$_2$Cl$_2$ and 25 mL 1 N NaHCO$_3$. After separating phases, the aqueous layer was extracted with 25 mL CH$_2$Cl$_2$. The organic phases were combined, dried over Na$_2$SO$_4$ and concentrated under reduced pressure. The residue was purified by flash chromatography eluting with 85:15 v/v hexanes/EtOAc to yield 14 mg (31%) of the title compound: R$_f$: 0.20 (85:15 v/v hexanes/EtOAc); $^1$H NMR (500 MHz, CDCl$_3$) δ 1.08–3.34 (m, 31H), 3.81 (s, 3H), 5.10 (s, 2H), 6.86–7.33 (m, 10H), 7.91–7.94 (m, 2H).

Step N: 2-(R)-(3-(R or S)-(4-(2-((4-Fluorophenyl)sulfonyl)-1-ethyl)piperidin-1-yl)methyl)-4-(R or S)-(3-fluorophenyl)-pyrrolidin-1-yl)-3-cyclobutylpropionic Acid A mixture of 14 mg (0.02 mmol) of 2-(R)-(3-(R or S)-(4-(2-((4-fluorophenyl)sulfonyl)-1-ethyl)piperidin-1-yl)methyl)-4-(R or S)-(3-fluorophenyl)-pyrrolidin-1-yl)-3-cyclobutylpropionic acid, (4-methoxy) benzyl ester (from EXAMPLE 93, Step M) and 5.5 mg of 10% palladium on carbon in 2 mL of MeOH was hydrogenated at room temperature under 1 atmosphere of hydrogen. After 2 hours the reaction was filtered through a pad of celite and concentrated under reduced pressure. The residue was purified by flash chromatography eluting with a gradient of 95:5 v/v $CH_2Cl_2$/MeOH, 95/5/0.5 v/v/v $CH_2Cl_2$/MeOH/$NH_4OH$ and 90:10:1 v/v/v $CH_2Cl_2$/MeOH/$NH_4OH$ to yield 9 mg (80%) of the title compound: $R_f$: 0.29 (90:10:1 v/v/v $CH_2Cl_2$/MeOH/$NH_4OH$); $^1H$ NMR (500 MHz, $CD_3OD$) δ 1.03–2.20 (m, 16H), 2.49 (m, 1H), 2.71–2.90 (m, 3H), 3.17–3.82 (m, 11H), 6.98–7.09 (m, 3H), 7.32–7.38 (m, 3H), 7.93–7.97 (m, 2H). ESI-MS 575 (M+1); HPLC A: 2.19.

EXAMPLE 94

2-(R)-(3-(S or R)-((4-(2-((4-Fluorophenyl)sulfonyl)-1-ethyl)piperidin-1-yl)methyl)-4-(S or R)-(3-fluorophenyl)-pyrrolidin-1-yl)-3-cyclobutylpropionic Acid The title compound was prepared from 3-(1-benzyl-4-(S or R)-(3-fluoro)phenylpyrrolidine-3-(S or R)-carbonyl)-4-(S)-benzyl oxazolidin-2-one (Diastereomer 2 from EXAMPLE 93, Step D) using procedures analogous to those described in EXAMPLE 93, Steps E–N: ESI-MS 575 (M+1); HPLC A: 2.11.

EXAMPLE 95

2-(R)-((3-(S)-((1'-(3H-Pyrimid-4-one-6-yl)-4,4'-bipiperidin)-1-yl)methyl)-4-(S)-(3-fluorophenyl)pyrrolidin-1-yl)-3-(cyclopropyl)propanoic Acid Step A: 6-((1'-tert-Butoxycarbonyl-4,4'-bipiperidin)-1-yl)-2-chloro-3H-pyrimid-4-one A solution of 100 mg (0.61 mmol) of 2,6-dichloropyrimid-4-one (Helv. Chim. Acta 1989, 72, 738) and 246 mg (0.92 mmol) of 1-tert-butoxycarbonyl-4,4'-bipiperidine in 6 mL of EtOH was refluxed for 2.25 hours. After cooling the reaction with an ice bath, the resulting solid was filtered and dried to yield 126 mg (52%) of the title compound: $R_f$: 0.77 (90:10:1 v/v/v $CH_2Cl_2$/MeOH/$NH_4OH$); $^1H$ NMR (500 MHz, $CD_3OD$) δ 1.12–1.85 (m, 19H), 2.62–2.67 (m, 2H), 2.87–2.92 (m, 2H), 4.13–4.15 (m, 2H), 4.53–4.55 (m, 2H), 5.74 (s, 1H).

Step B: 6-((1'-tert-Butoxycarbonyl-4,4'-bipiperidin)-1-yl)-3H-pyrimid-4-one

A suspension of Raney nickel was added to 60 mg (0.15 mmol) of 6-((1'-tert-butoxycarbonyl-4,4'-bipiperidin)-1-yl)-2-chloro-3H-pyrimid-4-one (from Step A) in 1.5 mL of $H_2O$, 3 mL MeOH and 1.5 mL of EtOAc. The reaction was heated to reflux for a total of 12.5 hours (periodically more Ra—Ni would be added to maintain the reaction). The reaction mixture was filtered through a pad of celite. The filtrate was diluted with 25 mL of $H_2O$ and extracted with 2×25 ml of $CH_2Cl_2$. The combined organic layers were dried over $Na_2SO_4$ and concentrated under reduced pressure to yield 12 mg (23%) of the title compound: $R_f$: 0.67 (90:10:1 v/v/v $CH_2Cl_2$/MeOH/$NH_4OH$); $^1H$ NMR (500 MHz, $CD_3OD$) δ 1.14–1.84 (m, 19H), 2.59–2.64 (m, 2H), 2.87–2.99 (m, 2H), 4.13–4.15 (m, 2H), 4.46–4.48 (m, 2H), 5.71 (d, J=6.2 Hz, 1H), 7.74 (d, J=6.2 Hz, 1H).

Step C: 6-(4,4'-Bipiperidin-1-yl)-3H-pyrimid-4-one, Hydrochloride Salt

To 1 mL of MeOH at 0° C. was added 0.028 mL (0.4 mmol) of acetyl chloride. After 20 minutes a solution of 12 mg (0.033 mmol) 6-((1'-tert-butoxycarbonyl-4,4'-bipiperidin)-1-yl)-3H-pyrimid-4-one (from Step B) in $CH_2Cl_2$ and MeOH was added. The reaction was stirred for 4 hours at room temperature. Volatiles were removed under reduced pressure to yield the title compound, which was used without further purification.

Step D: 2-(R)-((3-(S)-((1'-(3H-Pyrimid-4-one-6-yl)-4,4'-bipiperidin)-1-yl)methyl)-4-(S)-(3-fluorophenyl)pyrrolidin-1-yl)-3-(cyclopropyl)propanoic Acid The title compound was prepared using procedures analogous to those described in Example 41, Step C, and Example 42, Step C, using 6-(4,4'-bipiperidin-1-yl)-3H-pyrimid-4-one, hydrochloride salt (Example 95, Step C) and 2-(R)-(3-(R)-formyl-4-(S)-(3-fluorophenyl)pyrrolidin-1-yl)-3-(cyclopropyl)propionic acid, (4-methoxy)benzyl ester (prepared as Aldehyde 12 above). $R_f$: 0.11 (90:10:1 v/v/v $CH_2Cl_2$/MeOH/$NH_4OH$); $^1H$ NMR (500 MHz, $CD_3OD$) δ 0.19–0.21 (m, 2H), 0.52–0.55 (m, 2H), 0.84 (s, 1H), 1.14–1.42 (m, 7H), 1.67–1.77 (m, 5H), 1.94 (m, 1H), 2.18 (m, 1H), 2.41 (m, 1H), 2.62 (m, 1H), 2.86–2.90 (m, 4H), 3.10–3.75 (m, 7H), 4.32–4.34 (m, 2H), 5.71 (d, J=6.7 Hz, 1H), 7.05 (m, 1H), 7.18–7.21 (m, 2H), 7.40 (m, 1H), 7.56 (d, J=6.7 Hz, 1H). ESI-MS 552 (M+1); HPLC A: 1.52.

EXAMPLE 96

2-(R)-((3-(S)-((1'-(5-Cyanopyridine-2-yl)-4,4'-bipiperidin)-1-yl)methyl)-4-(S)-(3-fluorophenyl)pyrrolidin-1-yl)-3-(cyclopropyl)propanoic Acid Step A: 2-((1'-tert-Butoxycarbonyl-4,4'-bipiperidin)-1-yl)-5-cyanopyridine A solution of 103 mg (0.38 mmol) 1-tert-butoxycarbonyl-4,4'-bipiperidine, 45 mg (0.32 mmol) of 2-chloro-5-cyanopyridine (J. Org. Chem. 1979, 44, 2693), 44.5 mg (0.46 mmol) of sodium tert-butoxide and 9 mg (0.014 mmol) of racemic BINAP in 3 mL of toluene was degassed 3× under vacuum using argon. After the addition of 3 mg (0.014) mmol) of Pd(OAc)$_2$, the reaction was degassed 3× under vacuum using argon. The reaction was stirred at 80° C. for 16 hours, cooled to room temperature and partitioned between 50 mL of Et$_2$O and 50 mL of H$_2$O. After separating phases, the organic layer was dried over MgSO$_4$ and concentrated under reduced pressure. The residue was purified by flash chromatography eluting with 7:3 v/v hexanes/EtOAc to yield 32 mg (26%) of the title compound: $R_f$: 0.40 (3:2 v/v hexanes/EtOAc); $^1H$ NMR (300 MHz, CDCl$_3$) δ 1.12–1.45 (m, 15H), 1.65–1.83 (m, 4H), 2.59–2.67 (m, 2H), 2.82–2.92 (m, 2H), 4.10–4.14 (m, 2H), 4.42–4.48 (m, 2H), 6.60 (d, J=9.1 Hz, 1H), 7.57 (dd, J=2.3 Hz, 1H), 8.38 (d, J=2.3 Hz, 1H).

Step B: 2-(4,4'-Bipiperidin-1-yl)-5-cyanopyridine, Trifluoroacetate Salt

To a solution of 32 mg (0.086 mmol) of 2-((1'-tert-butoxycarbonyl-4,4'-bipiperidin)-1-yl)-5-cyanopyridine (from Step A) and 0.015 mL of anisole in 1 mL of CH$_2$Cl$_2$ was added 0.5 mL of TFA. After 3 hours, volatiles were removed under reduced pressure to yield the title compound, which was used without further purification.

Step C: 2-(R)-((3-(S)-((1'-(5-Cyanopyridine-2-yl)-4,4'-bipiperidin)-1-yl)methyl)-4-(S)-(3-fluorophenyl)pyrrolidin-1-yl)-3-(cyclopropyl)propanoic Acid The title compound was prepared using procedures analogous to those described in Example 41, Step C, and Example 42, Step C, using 2-(4,4'-bipiperidin-1-yl)-5-cyanopyridine, trifluoroacetate salt (Example 96, Step B) and 2-(R)-(3-(R)-formyl-4-(S)-(3-fluorophenyl)pyrrolidin-1-yl)-3-(cyclopropyl)propionic acid, (4-methoxy)benzyl ester (prepared as Aldehyde 12 above). $R_f$: 0.16 (90:10:1 v/v/v $CH_2Cl_2$/MeOH/$NH_4H$); $^1$H NMR (500 MHz, $CD_3OD$) δ 0.16–0.19 (m, 2H), 0.50–0.54 (m, 2H), 0.84 (m, 1H), 1.04–1.37 (m, 6H), 1.61–2.01 (m, 8H), 2.37 (m, 1H), 2.53 (m, 1H), 2.72–2.98 (m, 5H), 3.17 (m, 1H), 3.29–3.37 (m, 2H), 3.58–3.67 (m, 3H), 4.46–4.49 (m, 2H), 6.78 (d, J=9.1 Hz, 1H), 7.00 (m, 1H), 7.14–7.17 (m, 2H), 7.35 (m, 1H), 7.63 (dd, J=9.1, 2.3 Hz, 1H), 8.32 (d, J=2.3 Hz, 1H). ESI–MS 560 (M+1); HPLC A: 2.13.

EXAMPLES 97–105

The following compounds were prepared using analogous procedures described in EXAMPLE 96 by substituting the appropriate aryl halide in EXAMPLE 96, Step A.

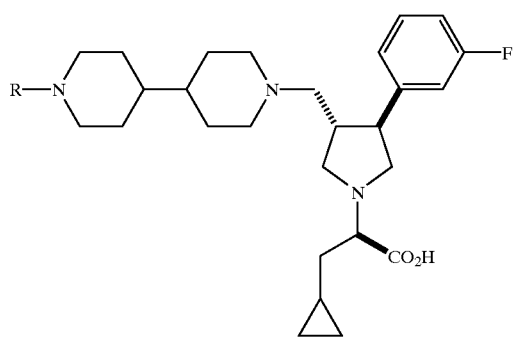

| EXAMPLE # | R | ESI-MS (M + H) | HPLC A |
|---|---|---|---|
| 97 | 5-nitro-pyridin-2-yl | 580 | 2.35 |
| 98 | 2-pyridyl | 535 | 1.49 |
| 99 | 3-pyridyl | 535 | 1.57 |
| 100 | 4-pyridyl | 535 | 2.19 |
| 101 | 2-naphthyl | 584 | 2.44 |
| 102 | 1-naphthyl | 584 | 2.56 |
| 103 | 4-fluorophenyl | 552 | 1.82 |
| 104 | 5-$CF_3$-pyridin-2-yl | 603 | 2.32 |
| 105 | 5-methyl-pyridin-2-yl | 549 | 1.69 |

EXAMPLE 106

2-(R)-(3-(S)-(4-(3-(N-(5-Trifluoromethylpyridin-2-yl)-N-methyl)aminoprop-1-piperidin-1-yl)methyl)-4-(S)-(3-fluorophenyl)pyrrolidin-1-yl)-3-cyclopropyl) propanoic Acid Step A: 4-(3-(Methylamino)-1-propyl)-1-tert-butoxycarbonyl-piperidine A solution of 4-(3-iodoprop-1-yl)-1-tert-butoxycarbonyl-piperidine (728 mg, 2.06 mmol,) in 5.0 mL of THF was treated with 5.0 mL of methylamine (70% in water) and the resulting mixture was stirred at rt for 18 h. The mixture was partitioned between diethyl ether (50 mL) and water (50 mL) and the layers were separated. The organic layer was washed with 50 mL of sat'd NaCl, dried and concentrated to afford 457 mg (83%) of the title compound: $^1$H NMR (500 MHz, $CDCl_3$): δ 1.05–1.68 (19H), 1.47 (s, 9H), 2.45 (s, 3H), 2.56–2.68 (4H), 4.00–4.15 (2H).

Step B: 4-(3-(N-(5-Trifluoromethylpyridin-2-yl)-N-methyl)aminoprop-1-yl)1-tert-butoxycarbonylpiperidine 2-Bromo-5-trifluoromethyl pyridine (91 mg, 0.40 mmol), 4-(3-(methylamino)-1-propyl)-1-tert-butoxycarbonyl piperidine (140 mg, 0.52 mmol from Example 106, Step A), sodium tert-butoxide (54 mg, 0.56 mmol), palladium(II) acetate (4 mg, 0.02 mmol) and 2,2'-bis(diphenylphosphino)-1,1'-binaphthyl (10 mg, 0.02 mmol) were combined in 4 mL dry toluene under argon. The mixture was heated to 70° C. for 4 h then cooled to rt and diluted with 50 mL ether. The solution was washed with water and sat'd NaCl, dried and concentrated. Flash chromatography on 14 g silica gel using 9:1 then 4:1 v/v hexane/$Et_2O$ as the eluant afforded 25 mg (15%) of the title compound: $^1$H NMR (500 MHz, $CDCl_3$): δ 1.06–1.68 (18H), 1.47 (s, 9H), 2.60–2.75 (2H), 3.09 (s, 3H), 3.56 (t, J=7.5 Hz, 2H), 4.00–4.15 (2H), 6.47 (d, J=8.9 Hz, 1H), 7.59 (dd, J=8.9, 2.5 Hz, 1H), 6.47 (d, J=2.5 Hz, 1H).

Step C: 2-(R)-((3-(S)-(4-(3-(N-(5-Trifluoromethylpyridin-2-yl)-N-methyl)aminoprop-1-yl)piperidin-1-yl)methyl)-4-(S)-(3-fluorophenyl)pyrrolidin-1-yl)-3-(cyclopropyl) propanoic Acid The title compound was prepared using procedures analogous to those described in EXAMPLE 95, Steps C and D starting from 4-(3-(N-(5-trifluoromethylpyridin-2-yl)-N-methyl)aminoprop-1-yl)-1-tert-butoxycarbonyl piperidine (from EXAMPLE 106, Step B): $^1$H NMR (500 MHz, $CDCl_3$): δ 0.13–3.90 (34H), 3.04 (s, 3H), 6.43 (d, J=9.0 Hz, 1H), 6.92–7.29 (4H), 7.57 (dd, J=9.0, 2.4 Hz, 1H), 8.34 (s, 1H). Mass Spectrum (EI): 591.2 (M+1). HPLC A: 2.16 min.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula I:

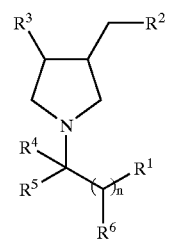

wherein:
  $R^1$ is selected from:
    (1) —$CO_2H$,
    (2) —$NO_2$,
    (3) -hydroxyisoxazole,
    (4) —$SO_2NH$—($C_{0-3}$ alkyl)—$R^9$, wherein $R^9$ is independently selected from: hydrogen, $C_{1-6}$ alkyl, $C_{5-6}$ cycloalkyl, benzyl or phenyl, which is unsubstituted or substituted with 1–3 substituents where the substituents are independently selected from: halo, $C_{1-3}$ alkyl, $C_{1-3}$ alkoxy and trifluoromethyl,
(5) —$SO_2NHCO$—($C_{0-3}$ alkyl)—$R^9$, wherein $R^9$ is independently selected from: hydrogen, $C_{1-6}$ alkyl, $C_{5-6}$ cycloalkyl, benzyl or phenyl, which is unsubstituted or substituted with 1–3 substituents where the substituents are independently selected from: halo, $C_{1-3}$ alkyl, $C_{1-3}$ alkoxy and trifluoromethyl, and
(6) —$P(O)(OH)_2$;

$R^2$ is selected from the group consisting of:

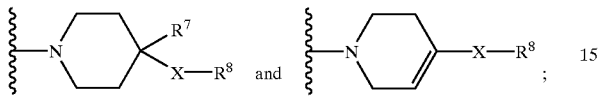

wherein $R^7$ is selected from:
(1) hydrogen,
(2) $C_{1-6}$ alkyl, which is unsubstituted or substituted with 1–4 substituents where the substituents are independently selected from: hydroxy, cyano, and halo,
(3) cyano,
(4) hydroxy, and
(5) halo;
wherein X is —($C_{0-6}$ alkyl)—Y—($C_{0-6}$ alkyl)—,
where the alkyl is unsubstituted, or substituted with 1–7 substituents where the substituents are independently selected from:
(a) halo,
(b) hydroxy,
(c) —O—$C_{1-3}$ alkyl, and
(d) trifluoromethyl,
and where Y is selected from:
—$SO_2$—, —$NR^{10}$—, —S—, —O—, —SO—, —$SO_2N(R^{10})$—, —$N(R^{10})SO_2$—, and —$PO_2$—;
and where $R^{10}$ is independently selected from: hydrogen, $C_{1-6}$ alkyl, benzyl, phenyl, $(CO)C_{1-6}$ alkyl, —$SO_2$—$C_{1-6}$ alkyl, —$SO_2$-phenyl, —$SO_2$-heterocycle, and $C_{1-6}$ alkyl-$C_{3-6}$ cycloalkyl,
which is unsubstituted or substituted with 1–3 substituents where the substituents are independently selected from: halo, $C_{1-3}$ alkyl, $C_{1-3}$ alkoxy and trifluoromethyl;
or X is

and wherein $R^8$ is selected from:
t-butyl, cyclohexyl, phenyl, naphthyl, biphenyl, and heterocycle,
which is unsubstituted or substituted with 1–7 of $R^{11}$ where $R^{11}$ is independently selected from:
(a) halo,
(b) cyano,
(c) hydroxy,
(d) $C_{1-6}$ alkyl, which is unsubstituted or substituted with 1–5 of $R^{12}$ where $R^{12}$ is independently selected from: halo, cyano, hydroxy, $C_{1-6}$ alkoxy, —$CO_2H$, —$CO_2(C_{1-6}$ alkyl), phenyl, trifluoromethyl, and —$NR^9R^{10}$,
(e) —O—$C_{1-6}$ alkyl, which is unsubstituted or substituted with 1–5 of $R^{12}$, (f) —$CF_3$,
(g) —$CHF_2$,
(h) —$CH_2F$,
(i) —$NO_2$,
(j) phenyl,
(k) —$CO_2R^9$,
(l) tetrazolyl,
(m) —$NR^9R^{10}$,
(n) —$NR^9$—$COR^{10}$,
(o) —$NR^9$—$CO_2R^{10}$,
(p) —CO—$NR^9R^{10}$,
(q) —OCO—$NR^9R^{10}$,
(r) —$NR^9CO$—$NR^9R^{10}$,
(s) —$S(O)_m$—$R^9$, wherein m is an integer selected from 0, 1 and 2,
(t) —$S(O)_2$—$NR^9R^{10}$,
(u) —$NR^9S(O)_2$—$R^{10}$, and
(v) —$NR^9S(O)_2$—$NR^9R^{10}$;

$R^3$ is selected from the group consisting of:
phenyl and heterocycle,
which is unsubstituted or substituted with 1–7 substituents where the substituents are independently selected from:
(a) halo,
(b) trifluoromethyl,
(c) hydroxy,
(d) $C_{1-3}$ alkyl,
(e) —O—$C_{1-3}$ alkyl,
(f) —$CO_2R^9$,
(g) —$NR^9R^{10}$, and
(h) —$CONR^9R^{10}$;

$R^4$ is selected from:
$C_{1-10}$ alkyl, $C_{3-8}$ cycloalkyl, —($C_{1-3}$ alkyl)—$C_{3-8}$ cycloalkyl, $C_{2-10}$ alkenyl, $C_{2-10}$ alkynyl, phenyl, —($C_{1-6}$ alkyl)-phenyl, naphthyl, biphenyl, heterocycle, hydrogen, cyclohexenyl, dihydronaphthyl, tetrahydronaphthyl, and octahydronaphthyl,
which is unsubstituted or substituted with 1–7 of $R^{11}$ where $R^{11}$ is independently as defined above;

$R^5$ is selected from:
hydrogen or $C_{1-6}$ alkyl, wherein the alkyl is unsubstituted or substituted with 1–7 substituents where the substituents are independently selected from:
(a) halo,
(b) trifluoromethyl,
(c) hydroxy,
(d) $C_{1-3}$ alkyl
(e) —O—$C_{1-3}$ alkyl,
(f) —$CO_2R^9$,
(g) —$NR^9R^{10}$, and
(h) —$CONR^9R^{10}$,
or where $R^4$ and $R^5$ may be joined together to form a $C_{3-8}$cycloalkyl ring which may be unsubstituted or substituted with 1–7 of $R^{11}$;

$R^6$ is independently selected from:
hydrogen or $C_{1-6}$ alkyl, wherein the alkyl is unsubstituted or substituted with 1–7 substituents where the substituents are independently selected from:
(a) halo,
(b) thifluoromethyl,
(c) hydroxy,
(d) $C_{1-3}$ alkyl,
(e) —O—$C_{1-3}$ alkyl,
(f) —$CO_2R^9$,
(g) —$NR^9R^{10}$, and
(h) —$CONR^9R^{10}$;

n is an integer selected from 0, 1, 2 and 3;
and pharmaceutically acceptable salts thereof and individual diastereomers thereof.

2. The compound of claim 1, wherein
R$^1$ is selected from:
  (1) —CO$_2$H,
  (2) —NO$_2$,
  (3) -hydroxyisoxazole,
  (4) —SO$_2$NH—(C$_{0-3}$ alkyl)—R$^9$, wherein R$^9$ is independently selected from: hydrogen, C$_{1-6}$ alkyl, C$_{5-6}$ cycloalkyl, benzyl or phenyl, which is unsubstituted or substituted with 1–3 substituents where the substituents are independently selected from: halo, C$_{1-3}$ alkyl, C$_{1-3}$ alkoxy and trifluoromethyl, and
  (5) —P(O)(OH)$_2$;
R$^2$ is selected from the group consisting of:

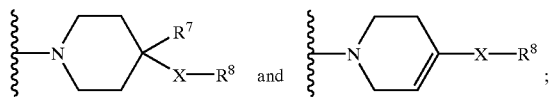

wherein R$^7$ is selected from:
  (1) hydrogen,.
  (2) C$_{1-6}$ alkyl, which is unsubstituted or substituted with 1–4 substituents where the substituents are independently selected from: hydroxy, cyano, and halo,
  (3) cyano,
  (4) hydroxy, and
  (5) halo,
wherein X is —(C$_{0-6}$ alkyl)—Y—(C$_{0-6}$ alkyl)—,
  where the alkyl is unsubstituted or substituted with 1–7 substituents where the substituents are independently selected from:
    (a) halo,
    (b) hydroxy,
    (c) —O—C$_{1-3}$ alkyl, and
    (d) trifluoromethyl,
  and where Y is selected from:
    —SO$_2$—, —NR$^{10}$—, —S—, —O—, and —SO—,
  and where R$^{10}$ is independently selected from: hydrogen, C$_{1-6}$ alkyl, benzyl, phenyl, (CO)C$_{1-6}$ alkyl, —SO$_2$—C$_{1-6}$ alkyl, —SO$_2$-phenyl, —SO$_2$-heterocycle, and C$_{1-6}$ alkyl-C$_{3-6}$ cycloalkyl,
    which is unsubstituted or substituted with 1–3 substituents where the substituents are independently selected from: halo, C$_{1-3}$ alkyl, C$_{1-3}$ alkoxy and trifluoromethyl; and
wherein R$^8$ is selected from:
  phenyl, naphthyl, biphenyl, and heterocycle, which is unsubstituted or substituted with 1–7 of R$^{11}$ where R$^{11}$ is independently selected from:
    (a) halo,
    (b) cyano,
    (c) hydroxy,
    (d) C$_{1-6}$ alkyl, which is unsubstituted or substituted with 1–5 of R$^{12}$ where R$^{12}$ is independently selected from: halo, cyano, hydroxy, C$_{1-6}$ alkoxy, —CO$_2$H, —CO$_2$(C$_{1-6}$ alkyl), phenyl, trifluoromethyl, and —NR$^9$R$^{10}$—,
    (e) —O—C$_{1-6}$ alkyl, which is unsubstituted or substituted with 1–5 of R$^{12}$,
    (f) —CF$_3$,
    (g) —CHF$_2$,
    (h) —CH$_2$F,
    (i) —NO$_2$,
    (j) phenyl,
    (k) —CO$_2$R$^9$,
    (l) tetrazolyl,
    (m) —NR$^9$R$^{10}$;
    (n) —NR$^9$—COR$^{10}$,
    (o) —NR$^9$—CO$_2$R$^{10}$,
    (p) —CO—NR$^9$R$^{10}$,
    (q) —OCO—NR$^9$R$^{10}$,
    (r) —NR$^9$CO—NR$^9$R$^{10}$,
    (s) —S(O)$_m$—R$^9$, wherein m is an integer selected from 0, 1 and 2,
    (t) —S(O)$_2$—NR$^9$R$^{10}$,
    (u) —NR$^9$S(O)$_2$—R$^{10}$, and
    (v) —NR$^9$S(O)$_2$—NR$^9$R$^{10}$.

3. The compound of claim 1 wherein R$^1$ is —CO$_2$H or —P(O)(OH)$_2$.

4. The compound of claim 1 wherein R$^1$ is —CO$_2$H.

5. The compound of claim 2 wherein R$^1$ is —CO$_2$H.

6. The compound of claim 1 wherein R$^3$ is selected from the group consisting of:
  phenyl and thienyl,
    which may be unsubstituted or substituted with 1–5 substituents where the substituents are independently selected from:
    (a) halo,
    (b) trifluoromethyl,
    (c) hydroxy,
    (d) C$_{1-3}$ alkyl, and
    (e) —O—C$_{1-3}$ alkyl.

7. The compound of claim 1 wherein R$^3$ is selected from the group consisting of:
  phenyl and thienyl,
    which may be unsubstituted or substituted with 1–5 substituents where the substituents are independently selected from:
    (a) fluoro,
    (b) chloro,
    (c) trifluoromethyl,
    (d) hydroxy, and
    (e) C$_{1-3}$ alkyl.

8. The compound of claim 1 wherein R$^3$ is selected from the group consisting of:
  phenyl, which may be unsubstituted or substituted with 1–5 substituents
    where the substituents are independently selected from:
    (a) fluoro, and
    (b) chloro; and
  unsubstituted thienyl.

9. The compound of claim 1 wherein R$^3$ is unsubstituted phenyl, (3-fluoro)phenyl or 3-thienyl.

10. The compound of claim 2 wherein R$^3$ is unsubstituted phenyl, (3-fluoro)phenyl or 3-thienyl.

11. The compound of claim 1 wherein R$^4$ is C$_{1-10}$ alkyl, C$_{3-8}$ cycloalkyl, or —(C$_{1-3}$ alkyl)-C$_{3-8}$ cycloalkyl,
  which is unsubstituted or substituted with 1–5 substituents where the substituents are independently selected from:
    (a) halo,
    (b) hydroxy,
    (c) —C$_{1-6}$ alkyl, which is unsubstituted or substituted with halo, cyano, —CO$_2$H, hydroxy or trifluoromethyl,
    (d) —O—C$_{1-6}$ alkyl, which is unsubstituted or substituted halo, cyano, —CO$_2$H, hydroxy or trifluoromethyl,
    (e) —CF$_3$,
    (f) —CHF$_2$,
    (g) —CH$_2$F, and
    (h) —CO$_2$H.

12. The compound of claim 1 wherein $R^4$ is selected from: isopropyl, isobutyl, sec-butyl, t-butyl, cyclohexyl, cyclopentyl, cyclobutyl, cyclopropyl, —$CH_2$-cyclohexyl, —$CH_2$-cyclopentyl, —$CH_2$-cyclobutyl, and —$CH_2$-cyclopropyl.

13. The compound of claim 1 wherein $R^4$ is selected from: isopropyl, sec-butyl, t-butyl, cyclohexyl, cyclopentyl, cyclobutyl, cyclopropyl, —$CH_2$-cyclobutyl, and —$CH_2$-cyclopropyl.

14. The compound of claim 1 wherein $R^4$ is selected from: cyclohexyl, isopropyl, sec-butyl, t-butyl, —$CH_2$-cyclobutyl and —$CH_2$-cyclopropyl.

15. The compound of claim 2 wherein $R^4$ is selected from: cyclohexyl, isopropyl, —$CH_2$-cyclobutyl and —$CH_2$-cyclopropyl.

16. The compound of claim 1 wherein $R^5$ is hydrogen.

17. The compound of claim 1 wherein $R^6$ is hydrogen or unsubstituted $C_{1-6}$ alkyl.

18. The compound of claim 1 wherein $R^6$ is hydrogen.

19. The compound of claim 1 wherein $R^7$ is hydrogen, fluoro, hydroxy or $C_{1-6}$ alkyl.

20. The compound of claim 1 wherein $R^7$ is hydrogen or fluoro.

21. The compound of claim 1 wherein $R^7$ is hydrogen.

22. The compound of claim 1 wherein X is:

—($C_{0-4}$ alkyl)—Y—($C_{0-4}$ alkyl)—, where the alkyl is unsubstituted or substituted with 1–4 substituents where the substituents are independently selected from:
(a) halo,
(b) hydroxy,
(c) —O—$C_{1-3}$ alkyl, and
(d) trifluoromethyl, and where Y is selected from:
—$SO_2$—, —$NR^{10}$—, —S—, —O—, and —SO—, and where $R^{10}$ is independently selected from:
hydrogen, unsubstituted $C_{1-6}$ alkyl, and unsubstituted $C_{1-6}$ alkyl-$C_{3-6}$ cycloalkyl.

23. The compound of claim 1 wherein X is:

—($C_{0-2}$ alkyl)—Y—($C_{0-2}$ alkyl)—, where the alkyl is unsubstituted, and where Y is selected from:
—$SO_2$—, —SO—, —$NR^{10}$—, —S—, and —O—, and where $R^{10}$ is independently selected from:
unsubstituted $C_{1-4}$ alkyl, and unsubstituted $C_{1-3}$ alkyl-$C_{3-6}$ cycloalkyl.

24. The compound of claim 1 wherein X is selected from:

—($C_{0-2}$ alkyl)—$SO_2$—($C_{0-2}$ alkyl)—,
—($C_{0-2}$ alkyl)—SO—($C_{0-2}$ alkyl)—,
—($C_{0-2}$ alkyl)—S—($C_{0-2}$ alkyl)—,
—($C_{0-2}$ alkyl)—O—($C_{0-2}$ alkyl)—, and
—($C_{0-2}$ alkyl)—$NR^{10}$—($C_{0-2}$ alkyl)—,
where $R^{10}$ is independently selected from:
unsubstituted $C_{2-4}$ alkyl, and unsubstituted $C_{1-2}$ alkyl-$C_3$ cycloalkyl.

25. The compound of claim 1 wherein X is selected from:
(1) —$CH_2CH_2$—$SO_2$—,
(2) —$CH_2CH_2$—SO—,
(3) —$CH_2CH_2$—S—,
(4) —$CH_2$—O—$CH_2$—.
(5) —$N(CH_2CH_3)$—,
(6) —$N(CH_2CH_2CH_3)$—, and
(7) —$N(CH_2$-cyclopropyl)-.

26. The compound of claim 1 wherein $R^8$ is selected from: phenyl, naphthyl, benzoimidazolyl, benzofurazanyl, isoxazolyl, pyrazinyl, pyridazinyl, pyridyl, pyrimidyl, and tetrazolopyridyl, which is unsubstituted or substituted with 1–7 substituents where the substituents are independently selected from:
(a) halo,
(b) cyano,
(c) hydroxy,
(d) $C_{1-6}$ alkyl, which is unsubstituted or substituted with 1–5 of $R^{12}$ where $R^{12}$ is independently selected from: halo, cyano, hydroxy, $C_{1-6}$ alkoxy, —$CO_2H$, phenyl, —$CO_2(C_{1-6}$ alkyl), trifluoromethyl, and —$NR^9R^{10}$, wherein $R^9$ and $R^{10}$ are independently selected from: hydrogen, $C_{1-6}$ alkyl, $C_{5-6}$ cycloalkyl, benzyl or phenyl, which is unsubstituted or substituted with 1–3 substituents where the substituents are independently selected from: halo, $C_{1-3}$ alkyl, $C_{1-3}$ alkoxy and trifluoromethyl;
(e) —O—$C_{1-6}$ alkyl, which is unsubstituted or substituted with 1–5 of $R^{12}$,
(f) —$CF_3$,
(g) —$CHF_2$,
(h) —$CH_2F$,
(i) —$NO_2$,
(j) phenyl,
(k) —$CO_2R^9$,
(l) tetrazolyl,
(m) —$NR^9R^{10}$,
(n) —$NR^9$—$COR^{10}$,
(o) —$NR^9$—$CO_2R^{10}$,
(p) —CO—$NR^9R^{10}$,
(q) —OCO—$NR^9R^{10}$,
(r) —$NR^9CO$—$NR^9R^{10}$,
(s) —$S(O)_m$—$R^9$, wherein m is an integer selected from 0, 1 and 2,
(t) —$S(O)_2$—$NR^9R^{10}$,
(u) —$NR^9S(O)_2$—$R^{10}$, and
(v) —$NR^9S(O)_2$—$NR^9R^{10}$.

27. The compound of claim 1 wherein $R^8$ is selected from: phenyl, benzofurazanyl, pyridyl, pyrimidyl, pyrazyl, and pyridazyl;

which is unsubstituted or substituted with 1–5 substituents where the substituents are independently selected from:
(a) halo,
(b) cyano,
(c) —$NO_2$,
(d) —$CF_3$,
(e) —$CHF_2$,
(f) —$CH_2F$,
(g) tetrazolyl,
(h) $C_{1-6}$ alkyl, which is unsubstituted or substituted with phenyl, and
(i) —O—$C_{1-6}$ alkyl.

28. The compound of claim 1 wherein $R^8$ is selected from: phenyl, benzofurazanyl, pyridyl, pyrimidyl, pyrazyl, and pyridazyl;

which is unsubstituted or substituted with 1–3 substituents where the substituents are independently selected from:
(a) fluoro,
(b) chloro,
(c) cyano,
(d) —$NO_2$, and
(e) —$CF_3$.

29. The compound of claim 1 wherein $R^8$ is selected from: phenyl, benzofurazanyl, pyridyl, pyrimidyl, pyrazyl, and pyridazyl.

30. The compound of claim 1 wherein n is an integer selected from 0 and 1.

31. The compound of claim 1 wherein n is an integer which is 0.

32. The compound of claim 1 which is of the stereochemical configuration:

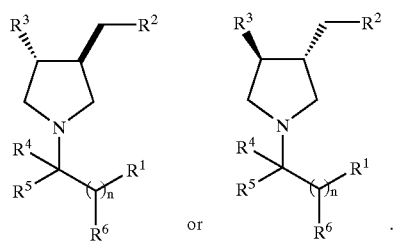

33. The compound of claim 1, which is a compound of formula (II):

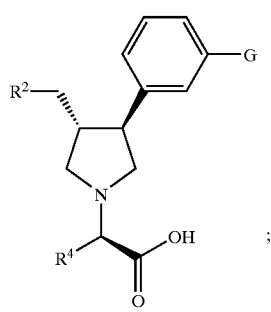

(II)

wherein $R^2$ is selected from the group consisting of

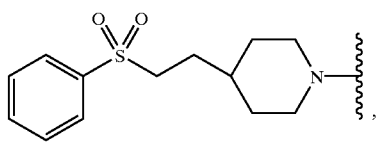

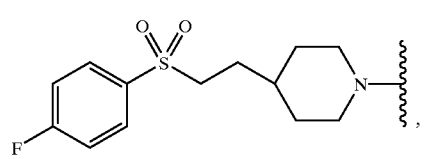

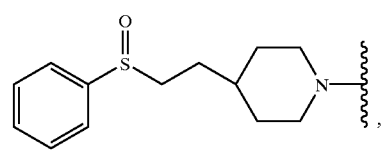

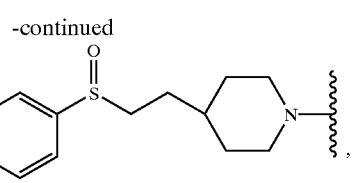

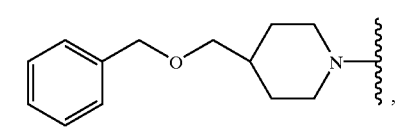

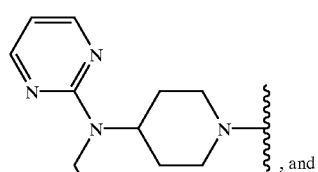

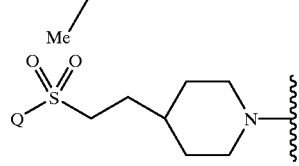

$R^4$ is selected from the group consisting of

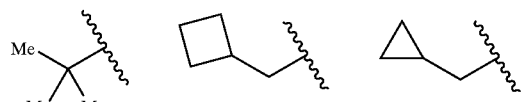

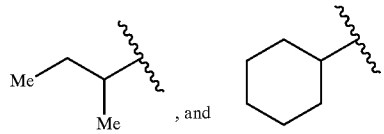

Q is pyridyl, pyrazinyl, pyrimidinyl, or thienyl, any one of which is unsubstituted or substituted with methyl or trifluoromethyl; and G is hydrogen or fluoro;

and pharmaceutically acceptable salts thereof and individual diastereomers thereof.

34. A compound selected from the group consisting of

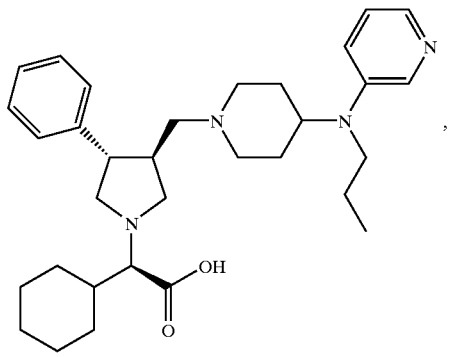

145
-continued
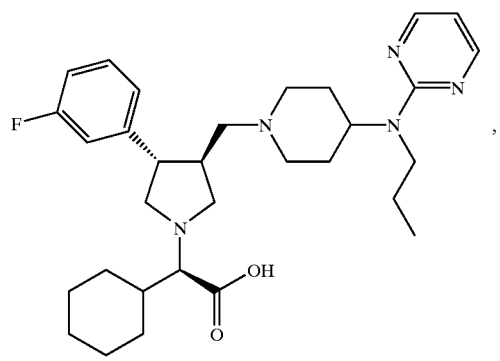
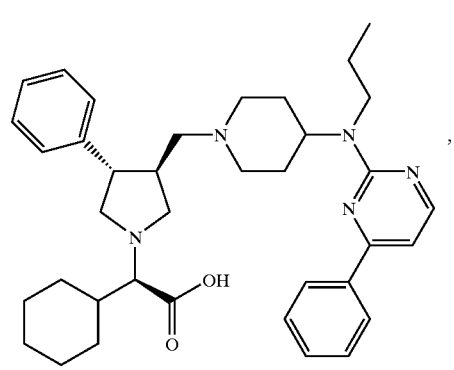
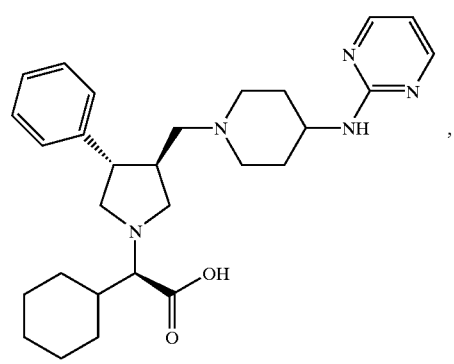
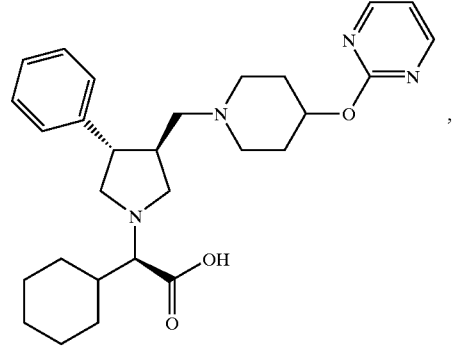
146
-continued
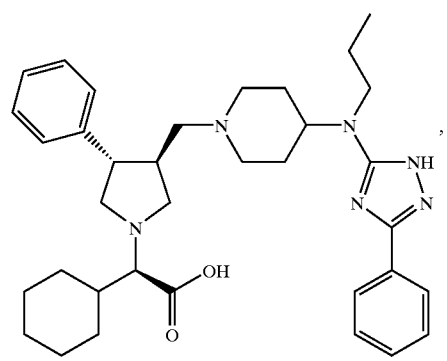
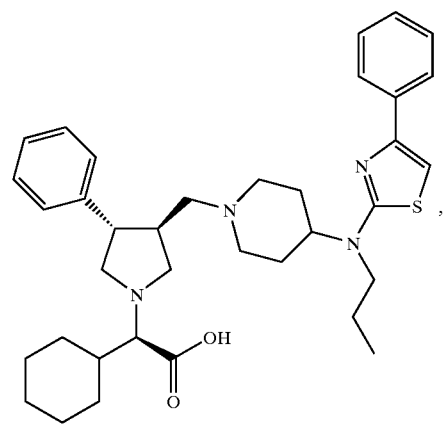
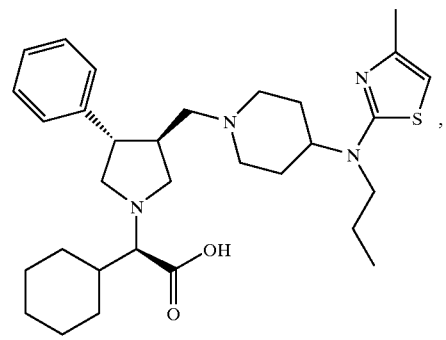
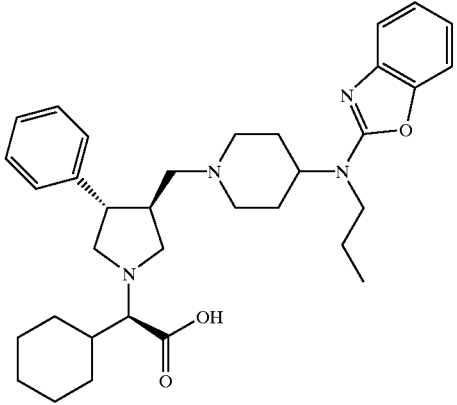

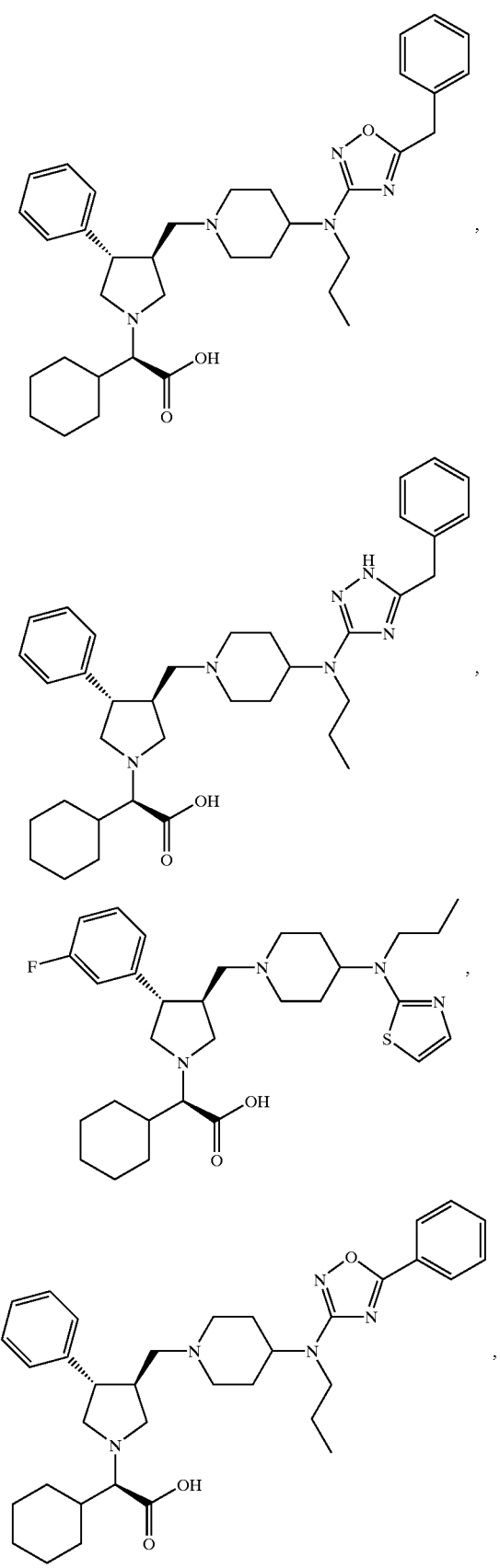
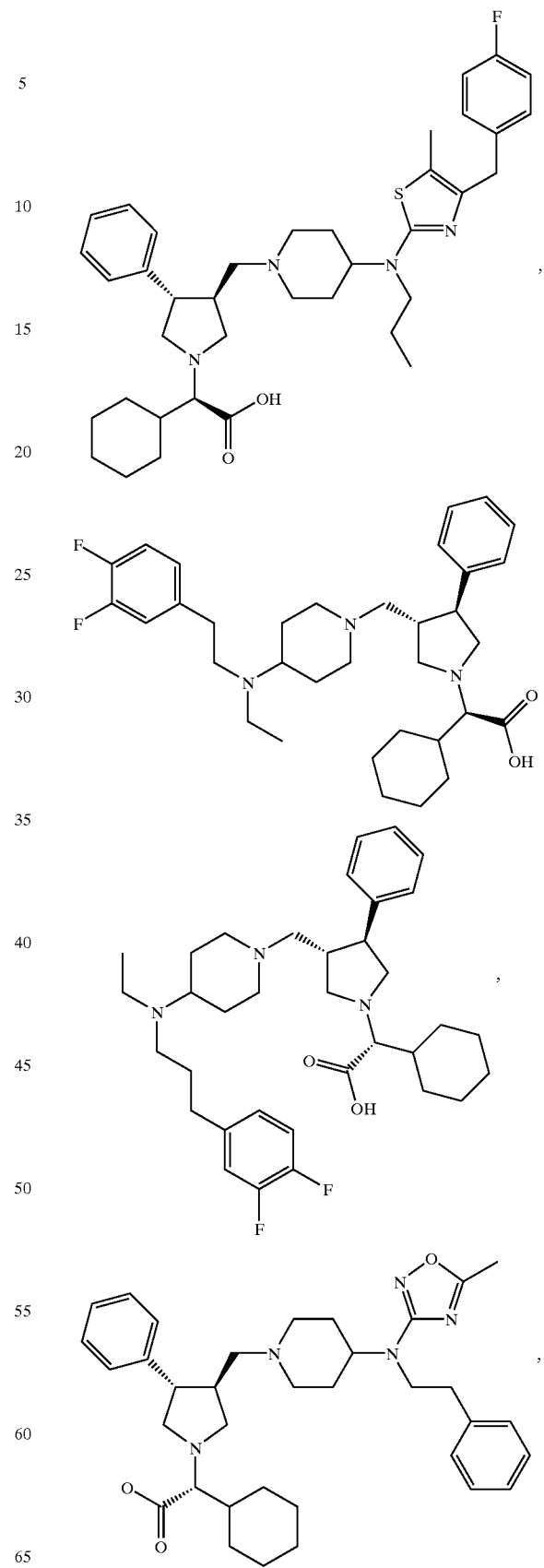

149
-continued
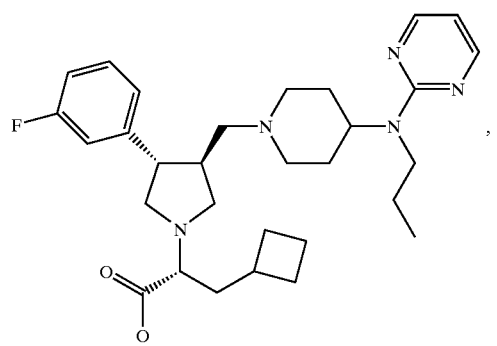
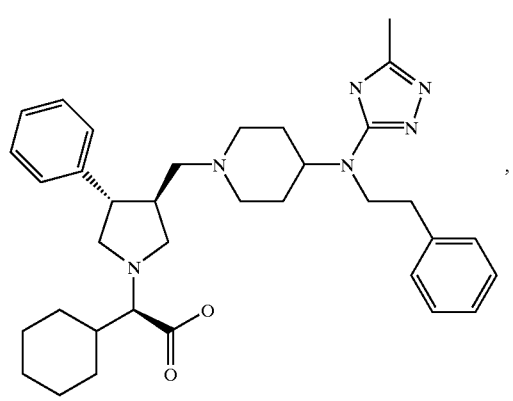
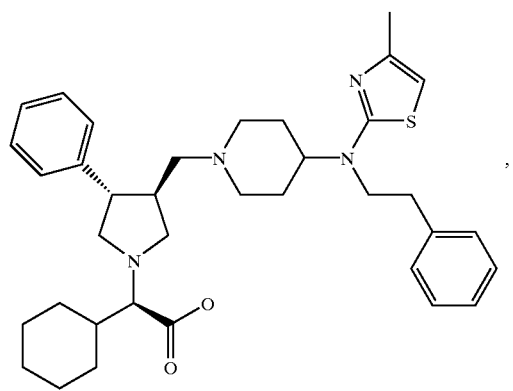
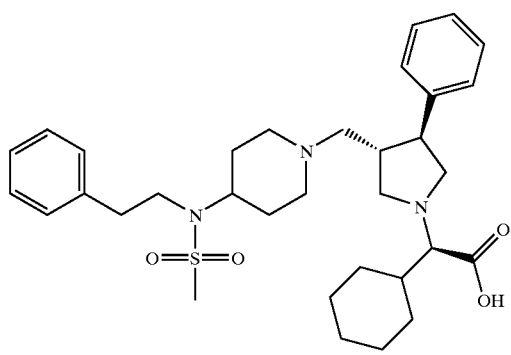
150
-continued
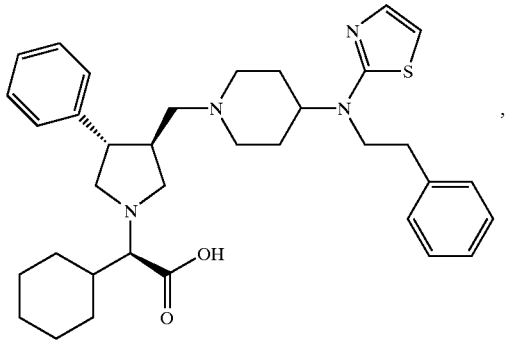
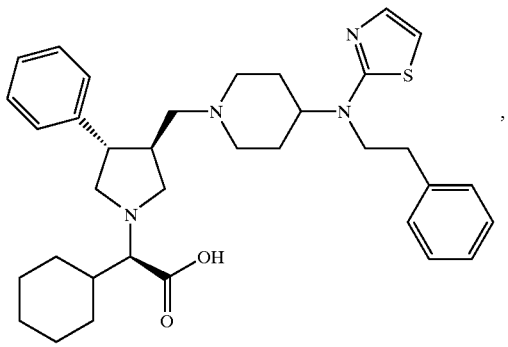
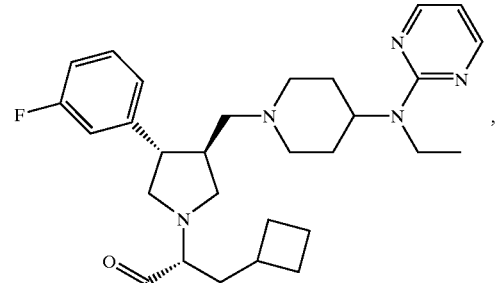
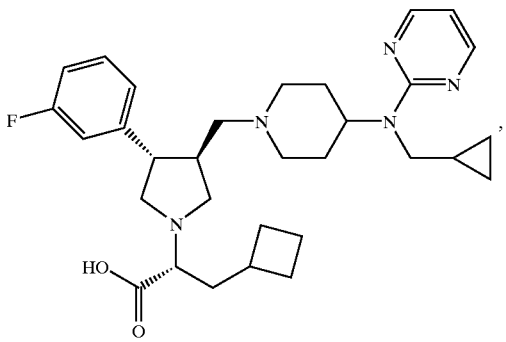
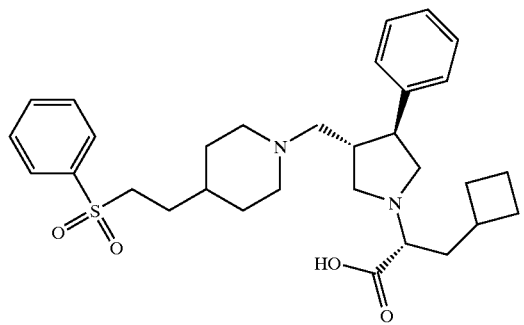

151
-continued
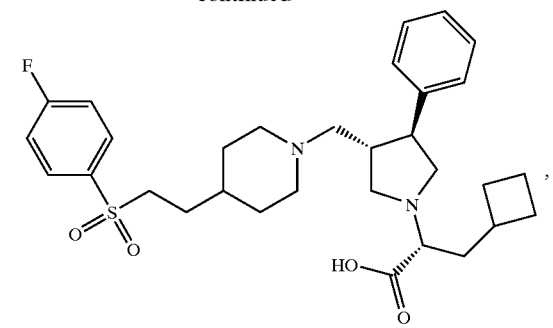
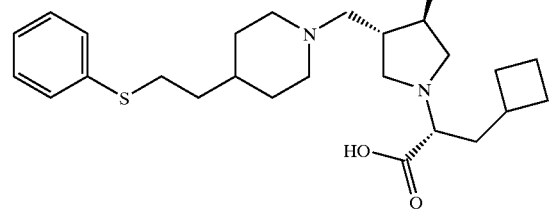
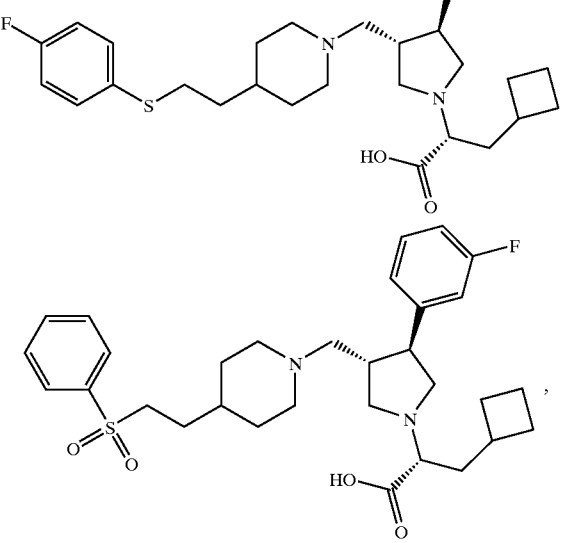
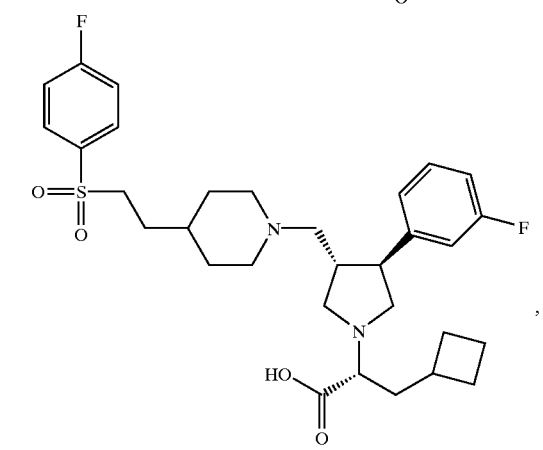
152
-continued
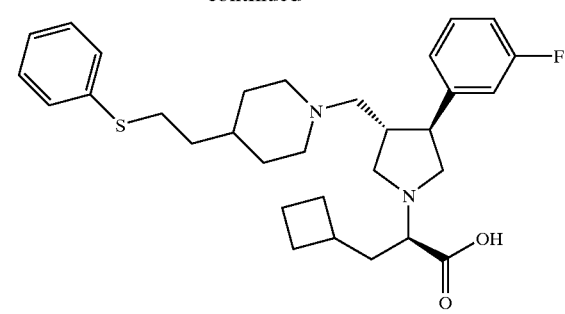
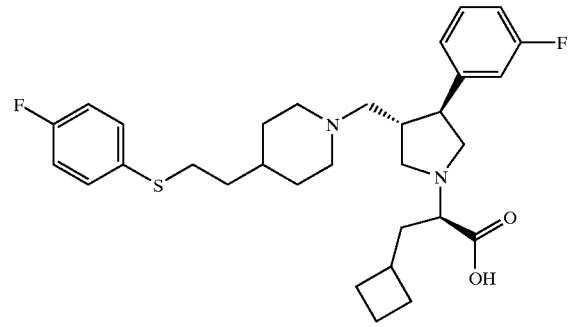
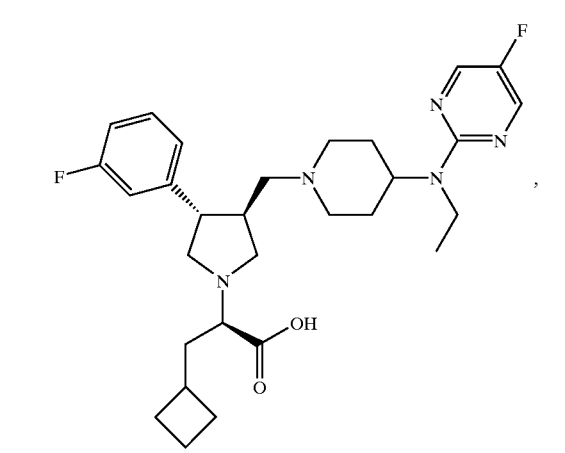
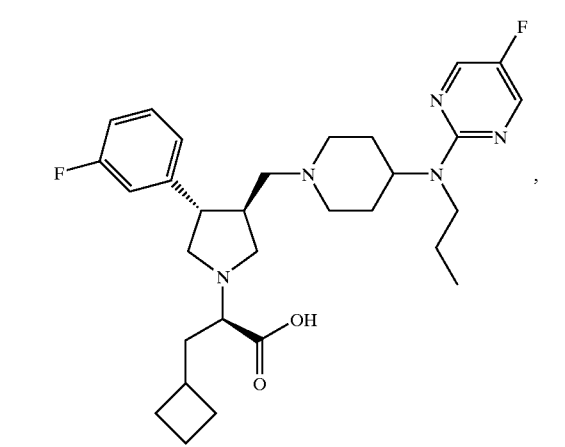

153
-continued
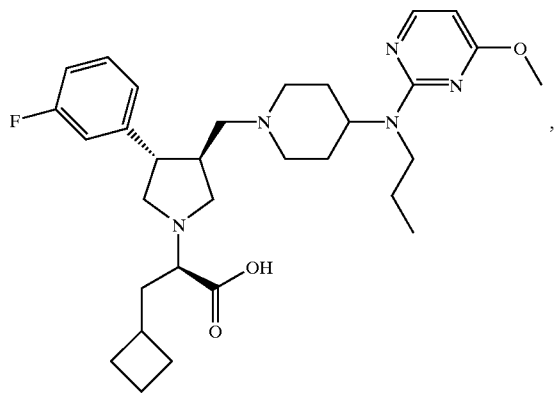
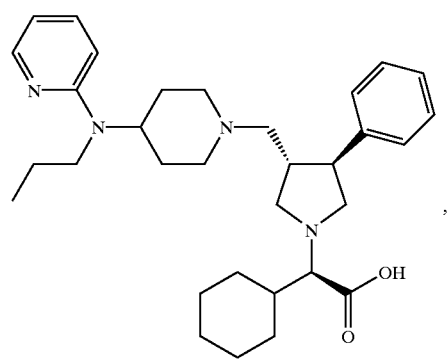
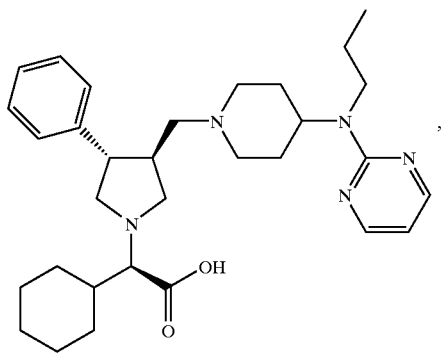
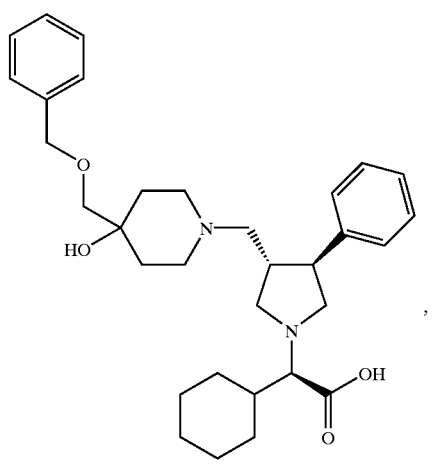
154
-continued
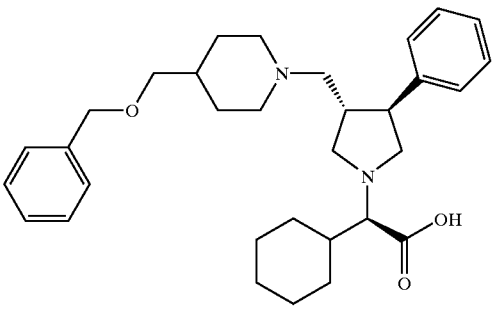
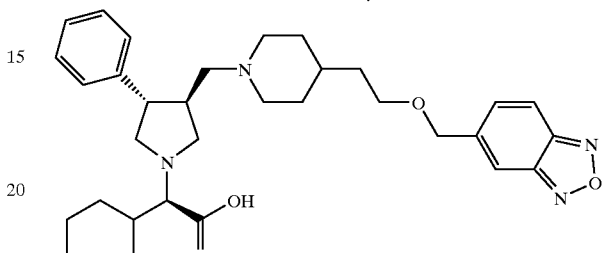
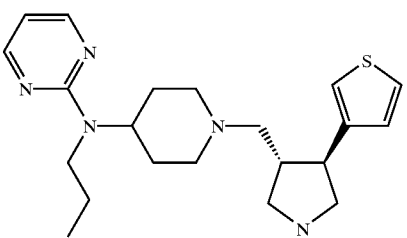
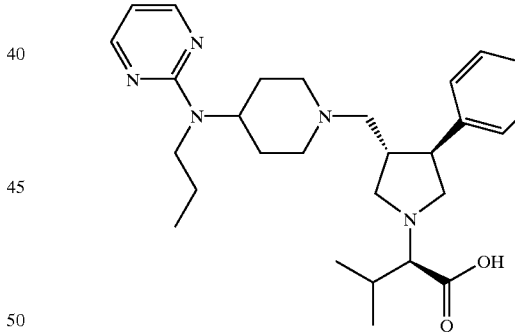
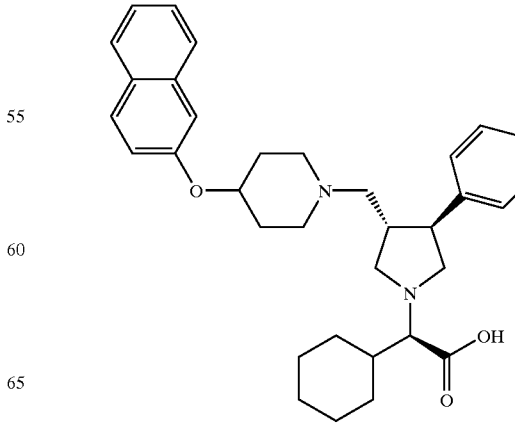

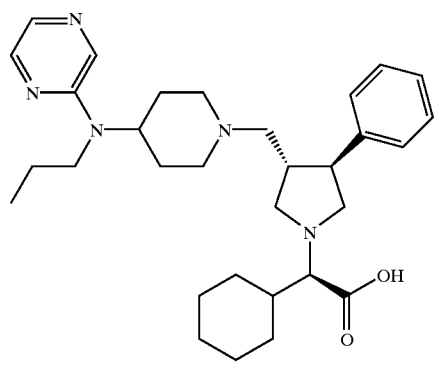
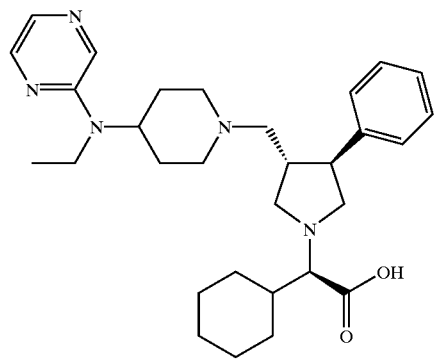
,
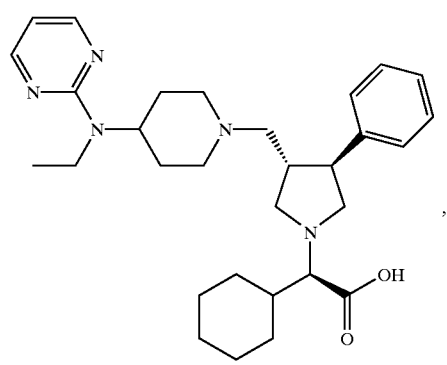
,
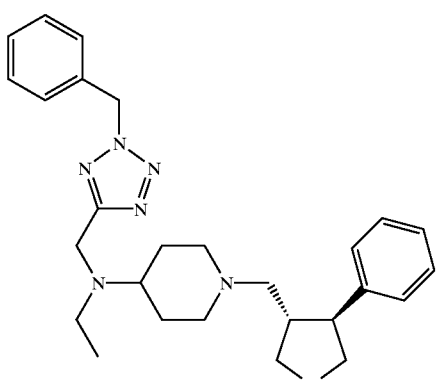
,
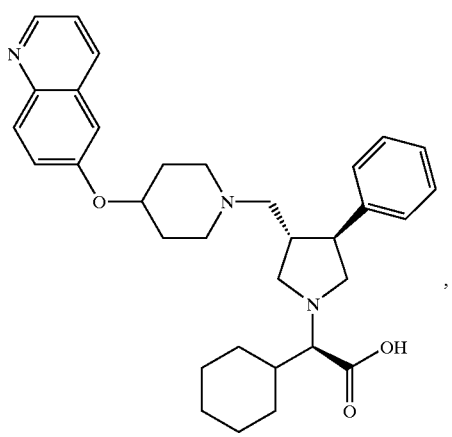
,
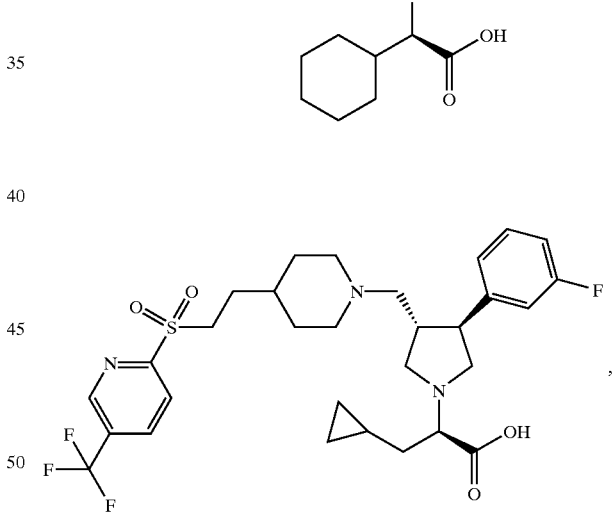
,
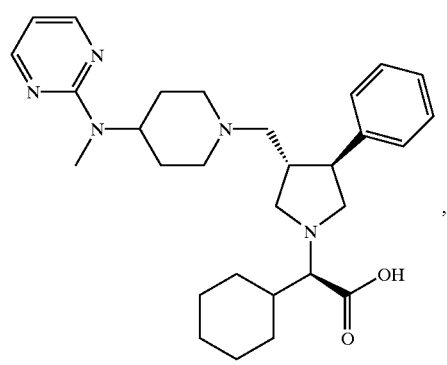
,
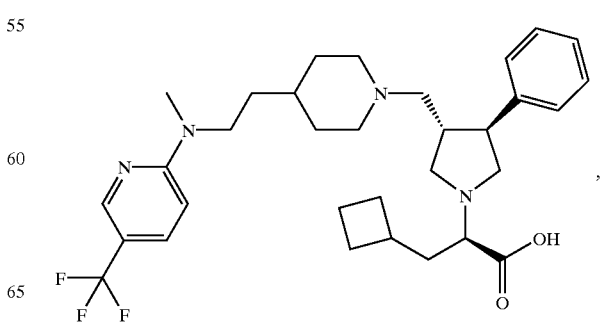
,

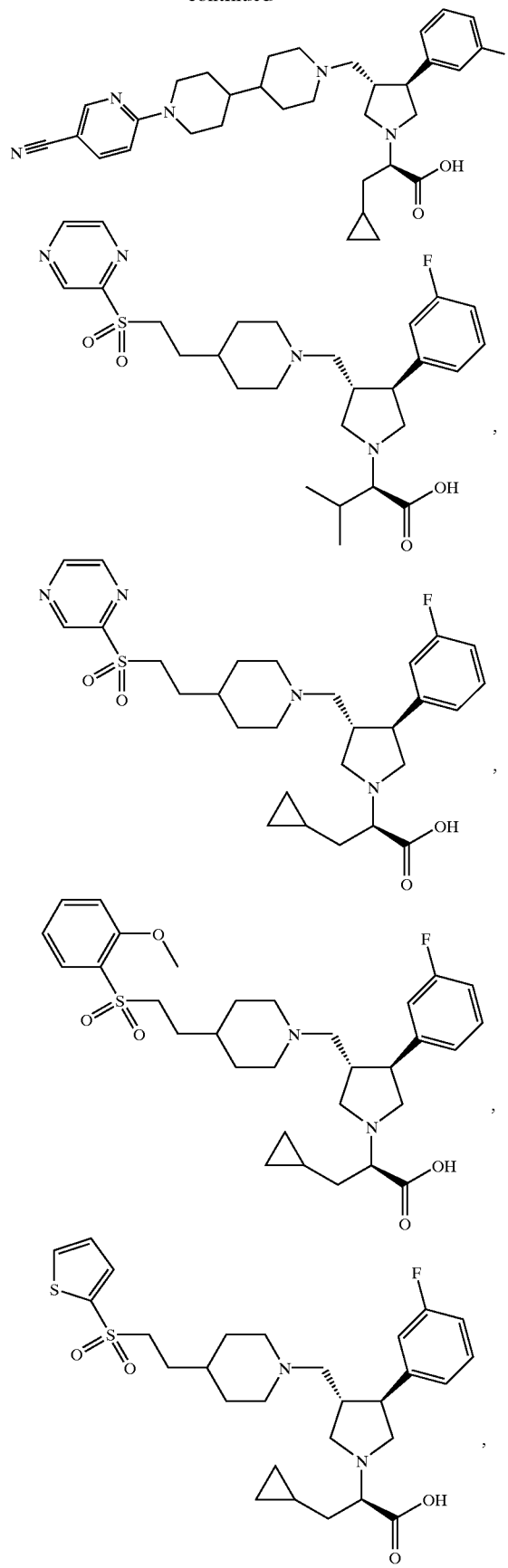
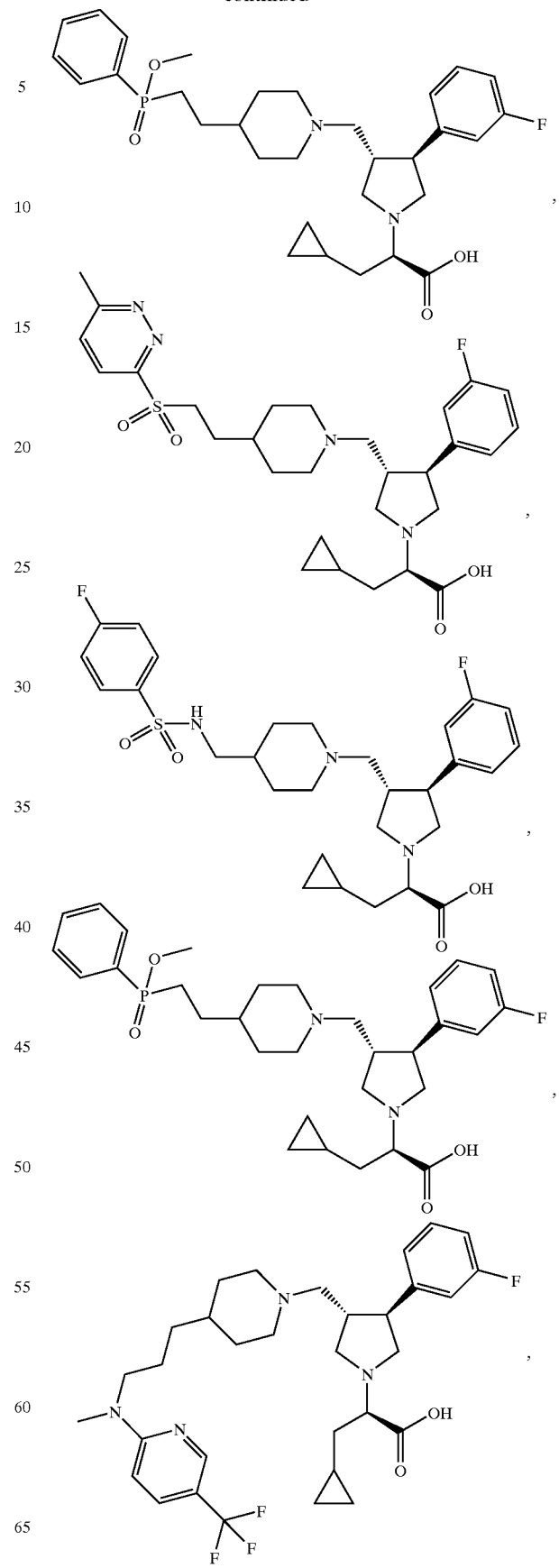

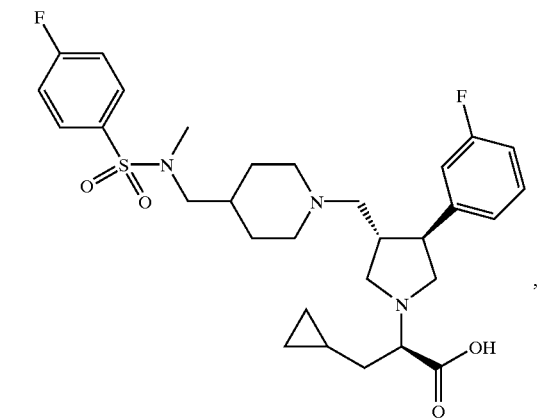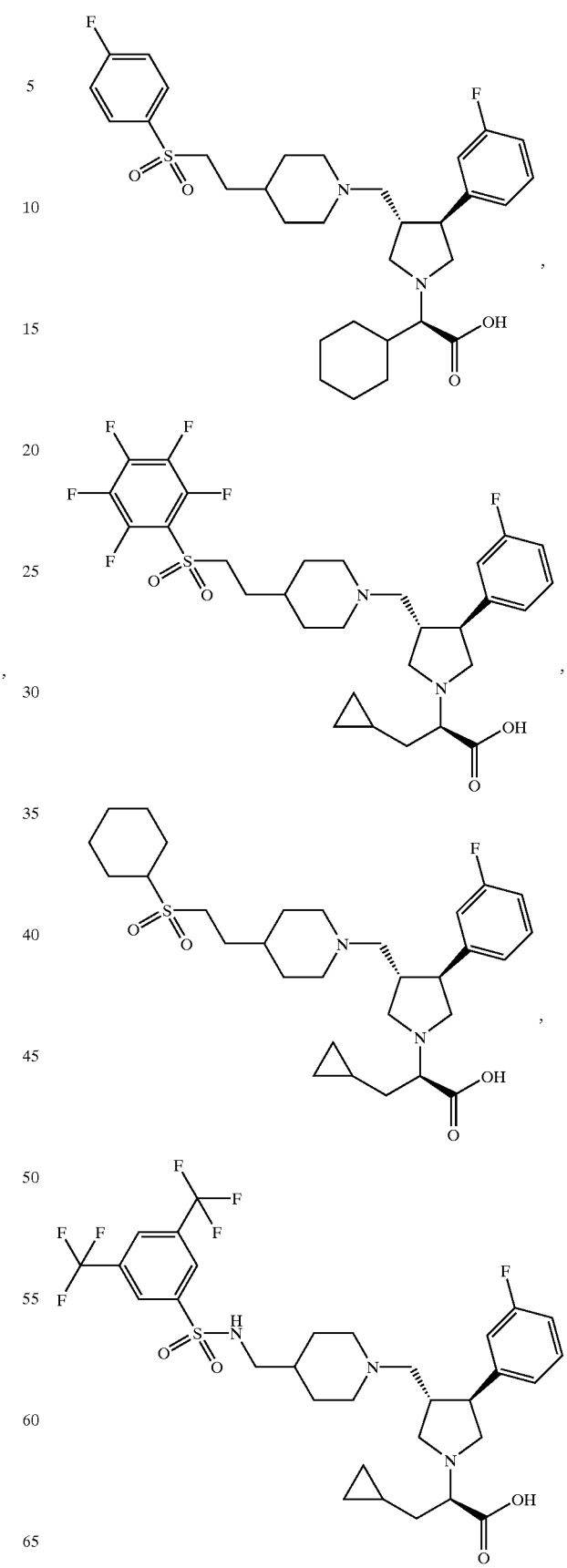

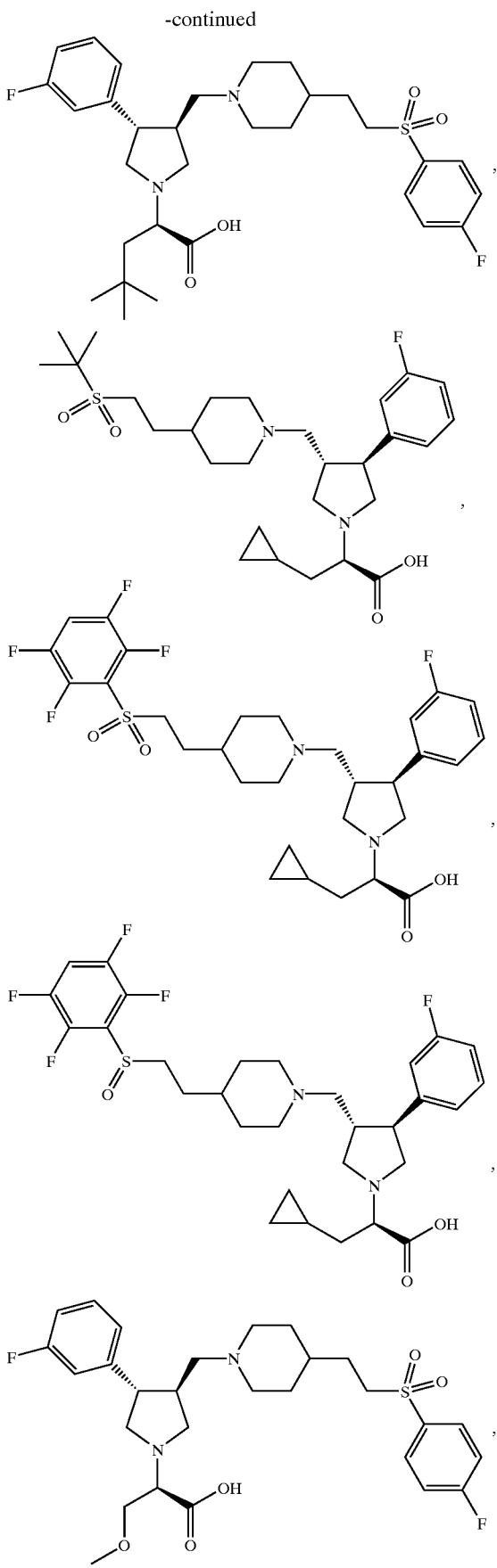

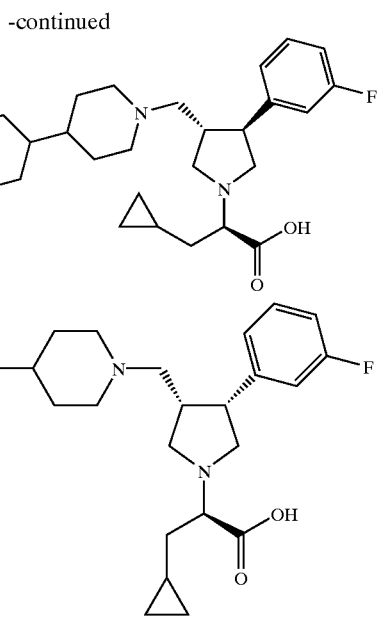

and pharmaceutically acceptable salts thereof.

35. A pharmaceutical composition which comprises an inert carrier and a compound of claim 1.

36. A method for modulation of CCR-3 or CCR-5 chemokine receptor activity in a mammal which comprises the administration of an effective amount of the compound of claim 1 or a pharmaceutically acceptable salt or an individual diastereomer thereof.

37. A method for treating infection by HIV, delaying of the onset of AIDS, or treating AIDS comprising the administration to a patient of an effective amount of the compound of claim 1 or a pharmaceutically acceptable salt or an individual diastereomer thereof.

38. A method for the treatment of asthma, allergic rhinitis, dermatitis, conjunctivitis, atherosclerosis or rheumatoid arthritis which comprises the administration to a patient of an effective amount of the compound of claim 1 or a pharmaceutically acceptable salt or an individual diastereomer thereof.

39. A method for blocking the entry of HIV into target cells of a patient, the target cells having a CCR-3 receptor or a CCR-5 receptor which is a co-receptor for HIV, which comprises administering to the patient in need thereof the compound of claim 1, or a pharmaceutically acceptable; salt or an individual diastereomer thereof, in an amount effective to block HIV from binding to the CCR-3 or CCR-5 co-receptors of the target cells.

40. The method according to claim 39, wherein blocking the entry of HIV into target cells delays the onset of AIDS in the patient.

41. The method according to claim 39, wherein blocking the entry of HIV into target cells treats the pathological conditions of AIDS in the patient.

42. The method according to claim 39, wherein blocking the entry of HIV into target cells treats infection of the patient by HIV.

43. The method according to claim 39, wherein blocking the entry of HIV into target cells treats infectious spread of HIV in the patient.

* * * * *